(12) United States Patent
Fukuzaki

(10) Patent No.: US 9,062,084 B2
(45) Date of Patent: Jun. 23, 2015

(54) METHOD OF FORMING METAL COMPLEX COMPOUND, AND ORGANIC ELECTROLUMINESCENCE DEVICE

(75) Inventor: Eiji Fukuzaki, Kanagawa (JP)

(73) Assignee: UDC Ireland, Dublin (IE)

( * ) Notice: Subject to any disclaimer, the term of this patent is extended or adjusted under 35 U.S.C. 154(b) by 935 days.

(21) Appl. No.: 12/872,356

(22) Filed: Aug. 31, 2010

(65) Prior Publication Data

US 2011/0050093 A1 Mar. 3, 2011

(30) Foreign Application Priority Data

Aug. 31, 2009 (JP) ................. 2009-201148
Mar. 29, 2010 (JP) ................. 2010-076448

(51) Int. Cl.
| | | |
|---|---|---|
| C07F 15/00 | (2006.01) | |
| C09K 11/06 | (2006.01) | |
| H05B 33/14 | (2006.01) | |
| H05B 33/20 | (2006.01) | |
| H01L 51/00 | (2006.01) | |
| H01L 51/50 | (2006.01) | |

(52) U.S. Cl.
CPC ......... *C07F 15/0033* (2013.01); *C07F 15/0086* (2013.01); *C09K 11/06* (2013.01); *C09K 2211/1029* (2013.01); *C09K 2211/1044* (2013.01); *C09K 2211/1059* (2013.01); *C09K 2211/185* (2013.01); *H01L 51/0081* (2013.01); *H01L 51/0085* (2013.01); *H01L 51/0087* (2013.01); *H01L 51/5012* (2013.01); *H01L 2251/308* (2013.01); *H05B 33/14* (2013.01); *H05B 33/20* (2013.01)

(58) Field of Classification Search
CPC .................. C07F 15/0033; C07F 15/0086
USPC ........................................... 548/101
See application file for complete search history.

(56) References Cited

U.S. PATENT DOCUMENTS

| 6,835,835 B1 | 12/2004 | Huo | |
|---|---|---|---|
| 8,586,204 B2 * | 11/2013 | Xia et al. ............... | 428/690 |
| 2002/0068190 A1 | 6/2002 | Tsuboyama et al. | |
| 2006/0008670 A1 | 1/2006 | Lin et al. | |
| 2008/0297033 A1 | 12/2008 | Knowles et al. | |
| 2010/0141125 A1 * | 6/2010 | Otsu et al. ............... | 313/504 |

FOREIGN PATENT DOCUMENTS

| JP | 2001-247859 A | 9/2001 | | |
|---|---|---|---|---|
| JP | 2002-175884 A | 6/2002 | | |
| JP | 2005531590 | 10/2005 | | |
| JP | 2002540572 | 1/2006 | | |
| JP | 2007-019462 A | 1/2007 | | |
| JP | 2007051243 | 3/2007 | | |
| JP | 2007-509872 A | 4/2007 | | |
| JP | 2007509872 | 4/2007 | | |
| JP | 2007-513158 A | 5/2007 | | |
| JP | 2007513158 | 5/2007 | | |
| JP | 2009021336 | 1/2009 | | |
| JP | 2009102533 A | * 5/2009 | ............ | C09K 11/06 |
| JP | 2009-149655 A | 7/2009 | | |
| JP | 2009526071 | 7/2009 | | |
| JP | 2010120893 A | * 6/2010 | ............ | C07D 471/04 |
| WO | 2008/101842 A1 | 8/2008 | | |
| WO | WO-2008/140115 A1 | * 11/2008 | ............ | H01L 51/50 |

OTHER PUBLICATIONS

Colombo, et al., "Facial Tris Cyclometalated Rh and IR Complexes: Their Synthesis, Structure, and Optical Spectroscopic Properties", American Chemical Society, Inorganic Chemistry, vol. 33, No. 3, 1994, 545-550.

Beeby, et al., "Tuning the emission of cyclometalated iridium complexes by simple ligand modification", The Royal Society of Chemistry 2003, J. Mater. Chem., 2003, 13, 80-83.

Lamansky, et al., "Synthesis and Characterization of Phosphorescent Cyclometalated Iridium Complexes", American Chemical Society, Inorganic Chemistry, vol. 40, No. 7, 2001, 1704-1711.

Zhang, et al., "A New Synthetic Route to the Preparation of a Series of Strong Photoreducing Agents: *fac* Tris-Ortho-Metalated Complexes of Iridium (III) with Substituted 2-Phenylpyridines", American Chemical Society, Inorganic Chemistry, vol. 30, No. 8, 1991, 1685-1687.

Lipshutz, et al., "Protection of Imidazoles As Their β-Trimethylsilylethoxymethyl (SEM) Derivatives", Pergamon Journals Ltd., Tetrahedron Letters, vol. 27, No. 35, pp. 4095-4098, 1986.

Dedeian, et al., "Photophysical and Electrochemical Properties of Heteroleptic Tris-Cyclometalated Iridium (III) Complexes", Inorganic Chemistry, vol. 44, No. 13, 2005, 4445-4447.

Jikken Kagaku Koza (Experiments in Chemistry) 25, Yuki Gosei (Organic Synthesis) VII—Yuki Kinzoku Shiyaku ni yoru Gosei (Synthesis by Organometallic Reagents), edited by the Chemical Society of Japan, 1991, Fourth Edition, pp. 9 to 10.

(Continued)

*Primary Examiner* — Joseph Kosack
(74) *Attorney, Agent, or Firm* — Riverside Law LLP

(57) ABSTRACT

To provide methods of forming fluorescence-producing organometallic complexes which can ensure high durability when used in organic electroluminescence devices. For example, a compound 106 is prepared in accordance with the following reaction scheme.

(8d)

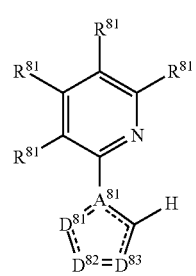

19 Claims, 1 Drawing Sheet

(56) References Cited

OTHER PUBLICATIONS

Jikken Kagaku Koza (Experiments in Chemistry) 18, Yuki Gosei (Organic Synthesis) VI—Kinzoku wo mochiiru Yuki Gosei (Synthesis using Metals), edited by the Chemical Society of Japan, 2004, Fifth Edition, p. 14.

Office Action dated Nov. 25, 2009 from the Japanese Patent Office in Japanese counterpart application No. 2009-201148.

* cited by examiner

METHOD OF FORMING METAL COMPLEX COMPOUND, AND ORGANIC ELECTROLUMINESCENCE DEVICE

CROSS-REFERENCE TO RELATED APPLICATION(S)

The present application claims priority from Japanese Patent Application Nos. 2009-201148 filed on Aug. 31, 2009, and 2010-076448 filed on Mar. 29, 2010, the entire content of which is incorporated herein by reference.

BACKGROUND

1. Field

The present invention relates to methods of forming metal complex compounds, and to organic electroluminescence devices. More specifically, the invention relates to methods of forming fluorescent organic metal complexes, especially methods of forming fluorescent organic metal complexes for use in organic electroluminescence devices (light emitting devices, or EL devices), and with organic electroluminescence devices made by using such the organic metal complexes.

2. Description of the Related Art

In recent years, organic metal complexes have received attention as functional materials such as new display materials, memory materials, photosensitizing dyes and chemical sensor dyes. By using fluorescent organic metal complexes in particular in organic electroluminescence devices, the device efficiency has improved and performance enhancement has been achieved.

Organic electroluminescence (EL) devices can produce light emission of high intensity through the application of low voltage, and therefore attention has been given to them as promising display devices. One of important characteristic values of such an organic electroluminescence device is power consumption. The power consumption is expressed as the product of voltage and electric current, and the lower the voltage required for the device to attain a desired brightness and the smaller value the electric current is reduced to, the lower the power consumption of the device can be made.

Fluorescent materials have been used for the purpose of reducing the power consumption of such devices, and thereby improvements in device efficiency have been underway. As the fluorescent materials, iridium complexes and platinum complexes have been known (see e.g. JP-A-2001-247859 and JP-A-2007-19462), but they haven't allowed development of devices having compatibility between high efficiency and high durability yet.

In order to incorporate fluorescent materials into organic electroluminescence devices, there is a necessity to establish methods of chemically preparing metal complexes, notably fluorescent iridium complexes and platinum complexes, with high yield and high purity.

As methods for synthesizing iridium complexes and platinum complexes, there are the method of synthesizing them by allowing chlorine-bridged metal dimers and ligands to react with each other in the presence of a silver salt (*Inorg. Chem.*, 1994, 33, 545-550 and J. Mater. Chem., 2003, 13, 80-83), the method of synthesizing them from chlorine-bridged metal dimers by way of β-diketoner containing complexes (*Inorg. Chem.*, 2001, 40, 1704-1711), the method of synthesizing them by allowing tris(β-diketonato) complexes and ligands to react with each other (*Inorg. Chem.*, 1991, 30, 1685-1687), and so on. However, decomposition products resulting from high-temperature reaction and impurities of starting material origin were included in the products obtained by using those synthesis methods, and they constituted a factor causing deterioration in durability of devices.

Complexes having 5-membered nitrogen-containing heterocyclic rings as partial structures of ligands, notably blue-fluorescent material-oriented complexes, tend to cause decomposition reaction at high temperatures, and a minute quantity of decomposed matter resulting from the reaction is apt to get mixed in devices. In addition, by-products tend to be formed (tend to take coordination forms other than intended ones). Therefore their yields are low, and besides, there were cases in which products themselves were not obtained.

Alternatively, methods of forming complexes by metal-metal exchange reaction have been also proposed. As to complexes having 5-membered nitrogen-containing heterocyclic rings as partial structures of ligands, however, high-acidity hydrogen atoms of the 5-membered nitrogen-containing heterocyclic rings cause exchange reaction with metals (*Tetrahedron Letters*, 1996, 27, 4095-4098), and therefore it has been difficult to synthesize complexes having intended coordination forms.

SUMMARY

With respect to the problem in *Tetrahedron Letters*, 1996, 27, 4095-4098, hydrogen atoms in 5-membered nitrogen-containing heterocyclic rings cause no exchange reaction with metals so long as the syntheses are conducted by way of the invention's proposed compounds of structure represented by the formula (1a), and therefore it becomes possible to synthesize complexes in intended coordination forms by metal-metal exchange reaction.

Although compounds represented by the following formula (1a) are generally prepared from halogen-substituted compounds thereof, the invention proposes a synthesis method using halogen-free ligands as starting materials, and metal complexes prepared according to the present synthesis method resist being contaminated with halogen as impurity. It has been suggested that halogen impurity is a factor responsible for the lowered durability of devices, and therefore the use of metal complexes prepared in the invention is expected to bring about an improvement in device durability.

Objects of the invention are to provide methods of synthesizing metal complexes which, when used in organic electroluminescence devices, ensure improvements in device durability, and to provide organic electroluminescence devices using such metal complexes.

These objects are attained with embodiments of the invention as described below.

[1]

A method of forming a compound having a nitrogen-containing heterocyclic 5-membered ring as a partial structure of a ligand through the use of metal-metal exchange reaction, wherein the compound is represented by the following formula (1) and formed by allowing a compound represented by the following formula (1a) to react with a compound represented by the following formula (1b).

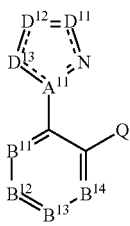

(1a)

In formula (1a), Q represents an alkali metal, an alkaline earth metal, an alkaline earth metal halide, a trialkyltin, zinc or a zinc halide, which each may further have an arbitrary organic group as a substituent; $A^{11}$, $B^{11}$ to $B^{14}$ and $D^{11}$ to $D^{13}$ have the same meanings as $A^{11}$, $B^{11}$ to $B^{14}$ and $D^{11}$ to $D^{13}$ in the formula (1), respectively.

$$[L^{11}{}_k M^{11}(\mu\text{-}Y)]_2 \quad (1b)$$

Formula (1b) stands for a bridged metal dimmer; Y is F, Cl, Br, I, $OR^{13}$, $R^{13}COO$, $SR^{13}$ or $N(R^{13})_2$; each of $R^{13}$s is independently a hydrogen atom, an aliphatic hydrocarbon group having 1 to 20 carbon atoms or an aromatic hydrocarbon group; k is 2 when $M^{11}$ is Ir, while k is 1 when $M^{11}$ is Pt; $L^{11}$ and $M^{11}$ have the same meanings as $L^{11}$ and $M^{11}$ in the formula (1), respectively.

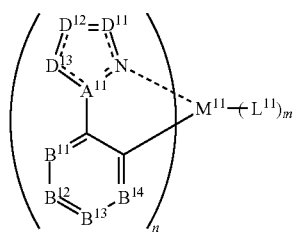

(1)

In formula (1), $M^{11}$ represents Ir or Pt; each of $A^{11}$s independently represents a nitrogen atom or a carbon atom; each of $B^{11}$ to $B^{14}$ independently represents a nitrogen atom or $C\text{—}R^{11}$, $R^{11}$ represents a hydrogen atom or a substituent and each $R^{11}$ may be the same as or different from every other $R^{11}$; each of $D^{11}$ to $D^{13}$ independently represents an atom selected from carbon, nitrogen, oxygen, sulfur and silicon; each of the bonds between atoms in the 5-membered ring formed from $D^{11}$ to $D^{13}$, $A^{11}$ and an N atom represents a single bond or a double bond; each of $D^{11}$ to $D^{13}$ may have a substituent as long as it can undergo further substitution; $L^{11}$ represents atoms forming a bidentate ligand; n represents an integer of 1 to 3 and m represents an integer of 0 to 2, provided that n+m is 2 or 3.

[2]

The forming method according to [1], wherein the compound represented by the formula (1a) is a compound represented by the following formula (2a), the compound represented by the formula (1b) is a compound represented by the following formula (2b) and the compound represented by the formula (1) is a compound represented by the following formula (2).

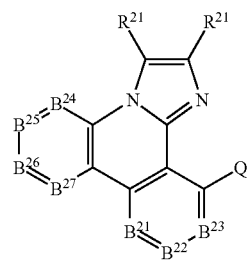

(2a)

In formula (2a), Q represents an alkali metal, an alkaline earth metal, an alkaline earth metal halide, a trialkyltin, zinc or a zinc halide, which each may further have an arbitrary organic group as a substituent; $R^{21}$ and $B^{21}$ to $B^{27}$ have the same meanings as $R^{21}$ and $B^{21}$ to $B^{27}$ in the formula (2), respectively.

$$[L^{21}{}_k M^{21}(\mu\text{-}Y)]_2 \quad (2b)$$

Formula (2b) stands for a bridged metal dimmer; Y is F, Cl, Br, I, $OR^{23}$, $R^{23}COO$, $SR^{23}$ or $N(R^{23})_2$, each of $R^{23}$s is independently a hydrogen atom, an aliphatic hydrocarbon group having 1 to 20 carbon atoms or an aromatic hydrocarbon group; k is 2 when $M^{21}$ is Ir, while k is 1 when $M^{21}$ is Pt; $L^{21}$ and $M^{21}$ have the same meanings as $L^{21}$ and $M^{21}$ in the formula (2), respectively.

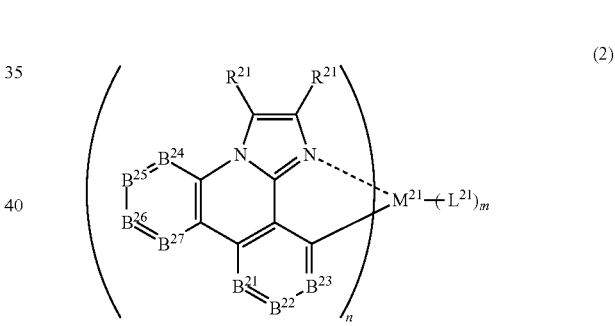

(2)

In formula (2), $M^{21}$ represents Ir or Pt; $R^{21}$ represents a hydrogen atom or a substituent and each $R^{21}$ may be the same as or different from every other $R^{21}$; each of $B^{21}$ to $B^{27}$ independently represents a nitrogen atom or $C\text{—}R^{22}$, $R^{22}$ represents a hydrogen atom or a substituent and each $R^{22}$ may be the same as or different from every other $R^{22}$; $L^{21}$ represents atoms forming a bidentate ligand; n represents an integer of 1 to 3 and m represents an integer of 0 to 2, provided that n+m is 2 or 3.

[3]

The forming method according to [1], wherein the compound represented by the formula (1a) is a compound represented by the following formula (3a), the compound represented by the formula (1b) is a compound represented by the following formula (3b) and the compound represented by the formula (1) is a compound represented by the following formula (3).

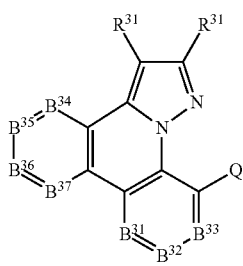
(3a)

In formula (3a), Q represents an alkali metal, an alkaline earth metal, an alkaline earth metal halide, a trialkyltin, zinc or a zinc halide, which each may further have an arbitrary organic group as a substituent; $R^{31}$ and $B^{31}$ to $B^{37}$ have the same meanings as $R^{31}$ and $B^{31}$ to $B^{37}$ in the formula (3), respectively.

(3b)

In formula (3b), Y is F, Cl, Br, I, $OR^{33}$, $R^{33}COO$, $SR^{33}$ or $N(R^{33})_2$; each of $R^{33}$s is independently a hydrogen atom, an aliphatic hydrocarbon group having 1 to 20 carbon atoms or an aromatic hydrocarbon group; k is 2 when $M^{31}$ is Ir, while k is 1 when $M^{31}$ is Pt; $L^{31}$ and $M^{31}$ have the same meanings as $L^{31}$ and $M^{31}$ in the formula (3), respectively.

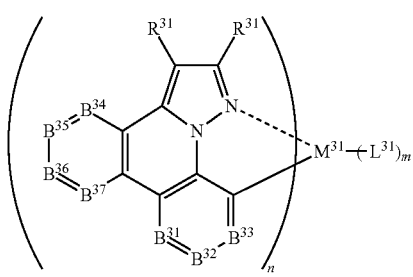
(3)

In formula (3), $M^{31}$ represents Ir or Pt; $R^{31}$ represents a hydrogen atom or a substituent and each $R^{31}$ may be the same as or different from every other $R^{31}$; each of $B^{31}$ to $B^{37}$ independently represents a nitrogen atom or $C-R^{32}$, $R^{32}$ represents a hydrogen atom or a substituent and each $R^{32}$ may be the same as or different from every other $R^{32}$; $L^{31}$ represents atoms forming a bidentate ligand; n represents an integer of 1 to 3 and m represents an integer of 0 to 2, provided that n+m is 2 or 3.

[4]
The forming method according to [1], wherein the compound represented by the formula (1a) is a compound prepared by reaction between a compound represented by the following formula (1c) and at least one reactant selected from the group consisting of alkali metals, organolithium compounds, alkaline earth metals and alkylmagnesium halides.

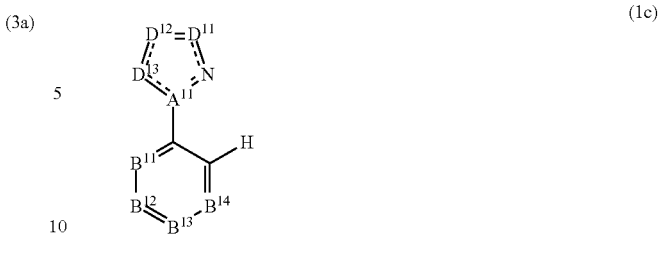
(1c)

In formula (1c), $A^{11}$, $B^{11}$ to $B^{14}$ and $D^{11}$ to $D^{13}$ have the same meanings as $A^{11}$, $B^{11}$ to $B^{14}$ and $D^{11}$ to $D^{13}$ in the formula (1a), respectively.

[5]
The forming method according to [2], wherein the compound represented by the formula (2a) is a compound prepared by reaction between a compound represented by the following formula (2c) and at least one reactant selected from the group consisting of alkali metals, organolithium compounds, alkaline earth metals and alkylmagnesium halides.

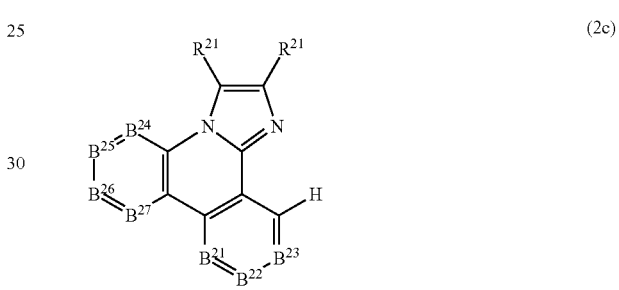
(2c)

In formula (2c), $R^{21}$ and $B^{21}$ to $B^{27}$ have the same meanings as $R^{21}$ and $B^{21}$ to $B^{27}$ in the formula (2a), respectively.

[6]
The forming method according to [3], wherein the compound represented by the formula (3a) is a compound prepared by reaction between a compound represented by the following formula (3c) and at least one reactant selected from the group consisting of alkali metals, organolithium compounds, alkaline earth metals and alkylmagnesium halides.

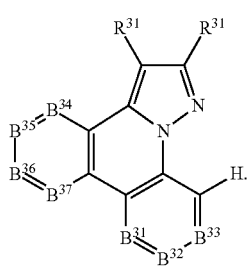
(3c)

In formula (3c), $R^{31}$ and $B^{31}$ to $B^{37}$ have the same meanings as $R^{31}$ and $B^{31}$ to $B^{37}$ in the formula (3a), respectively.

[7]
A method of forming a compound having a nitrogen-containing heterocyclic 5-membered ring as a partial structure of a ligand through the use of metal-metal exchange reaction, wherein the compound is represented by the following formula (4) and formed by allowing a compound represented by the following formula (4a) to react with a compound represented by the following formula (4b).

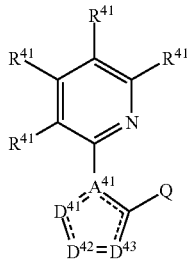
(4a)

In formula (4a), Q represents an alkali metal, an alkaline earth metal, an alkaline earth metal halide, a trialkyltin, zinc or a zinc halide, which each may further have an arbitrary organic group as a substituent; $R^{41}$, $A^{41}$ and $D^{41}$ to $D^{43}$ have the same meanings as $R^{41}$, $A^{41}$ and $D^{41}$ to $D^{43}$ in the formula (4), respectively.

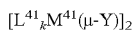
(4b)

Formula (4b) stands for a bridged metal dimmer; Y is F, Cl, Br, I, $OR^{42}$, $R^{42}COO$, $SR^{42}$ or $N(R^{42})_2$; each of $R^{42}$s is independently a hydrogen atom, an aliphatic hydrocarbon group having 1 to 20 carbon atoms or an aromatic hydrocarbon group; k is 2 when $M^{41}$ is Ir, while k is 1 when $M^{41}$ is Pt; $L^{41}$ and $M^{41}$ have the same meanings as $L^{41}$ and $M^{41}$ in the formula (4), respectively.

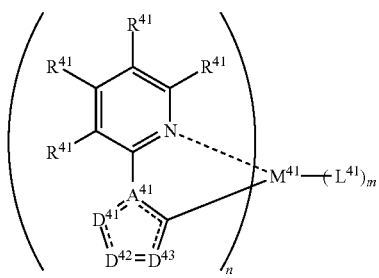
(4)

In formula (4), $M^{41}$ represents Ir or Pt; each of $R^{41}$s independently represents a hydrogen atom or a substituent; each of $A^{41}$s represents a nitrogen atom or a carbon atom; each of $D^{41}$ to $D^{43}$ independently represents an atom selected from the group consisting of carbon, nitrogen, oxygen, sulfur and silicon; each of the bonds between atoms in the 5-membered ring formed from $D^{41}$ to $D^{43}$, $A^{41}$ and a C atom represents a single bond or a double bond; each of $D^{41}$ to $D^{43}$ may have a substituent as long as it can undergo further substitution; $L^{41}$ represents atoms forming a bidentate ligand; n represents an integer of 1 to 3 and m represents an integer of 0 to 2, provided that n+m is 2 or 3.

[8]
The forming method according to [7], wherein the compound represented by the formula (4a) is a compound prepared by reaction between a compound represented by the following formula (4c) and at least one reactant chosen from alkali metals, organolithium compounds, alkaline earth metals or alkylmagnesium halides.

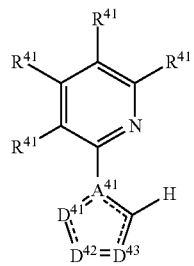
(4c)

In formula (4c), $R^{41}$, $A^{41}$ and $D^{41}$ to $D^{43}$ have the same meanings as $R^{41}$, $A^{41}$ and $D^{41}$ to $D^{43}$ in the formula (4a), respectively.

[9]
A method of forming a compound having a nitrogen-containing heterocyclic 5-membered ring as a partial structure of a ligand through the use of metal-metal exchange reaction wherein the compound is represented by the following formula (5) and formed by allowing a compound represented by the following formula (5a) to react with a compound represented by the following formula (5b) or (5c).

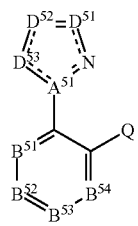
(5a)

In formula (5a), Q represents an alkali metal, an alkaline earth metal, an alkaline earth metal halide, a trialkyltin, zinc or a zinc halide, which each may further have an arbitrary organic group as a substituent; $A^{51}$, $B^{51}$ to $B^{54}$ and $D^{51}$ to $D^{53}$ have the same meanings as $A^{51}$, $B^{51}$ to $B^{54}$ and $D^{51}$ to $D^{53}$ in the formula (5), respectively.

$$M^{51}(ZR^{52}_2)_m X_m \quad (5b)$$

In formula (5b), X is Cl, Br, or I; Z is an O atom or an S atom; each of $R^{52}$s is independently a hydrogen atom or a substituent; $M^{51}$ has the same meaning as $M^{51}$ in the formula (5); m is 3 when $M^{51}$ is Ir, while m is 2 when $M^{51}$ is Pt.

(5c)

In formula (5c), X is Cl, Br or I; each of $R^{53}$s independently represents a hydrogen atom or a substituent; $M^{51}$ has the same meaning as $M^{51}$ in the formula (5); m is 3 when $M^{51}$ is Ir, while m is 2 when $M^{51}$ is Pt.

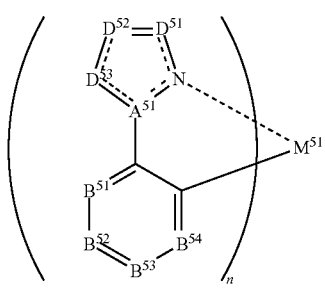

(5)

In formula (5), $M^{51}$ represents Ir or Pt; each of $A^{51}$'s independently represents a nitrogen atom or a carbon atom; each of $B^{51}$ to $B^{54}$ independently represents a nitrogen atom or C—$R^{51}$, $R^{51}$ represents a hydrogen atom or a substituent and each $R^{51}$ may be the same as or different from every other $R^{51}$; each of $D^{51}$ to $D^{53}$ independently represents an atom selected from the group consisting of carbon, nitrogen, oxygen, sulfur or silicon; each of the bonds between atoms in the 5-membered ring formed from $D^{51}$ to $D^{53}$, $A^{51}$ and an N atom represents a single bond or a double bond; each of $D^{51}$ to $D^{53}$ may have a substituent as long as it can undergo further substitution; n is 3 when $M^{51}$ is Ir, while n is 2 when $M^{51}$ is Pt.

The forming method according to [9], wherein the compound represented by the formula (5a) is a compound represented by the following formula (6a), the compound represented by the formula (5b) is a compound represented by the following formula (6b), the compound represented by the formula (5c) is a compound represented by the following formula (6c) and the compound represented by the formula (5) is a compound represented by the following formula (6).

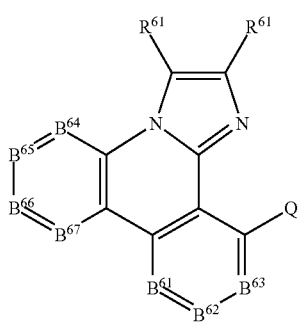

(6a)

In formula (6a), Q represents an alkali metal, an alkaline earth metal, an alkaline earth metal halide, a trialkyltin, zinc or a zinc halide, which each may further have an arbitrary organic group as a substituent; $R^{61}$ and $B^{61}$ to $B^{67}$ have the same meanings as $R^{61}$ and $B^{61}$ to $B^{67}$ in the formula (6), respectively.

$M^{61}(ZR^{63}_2)_m X_m$ (6b)

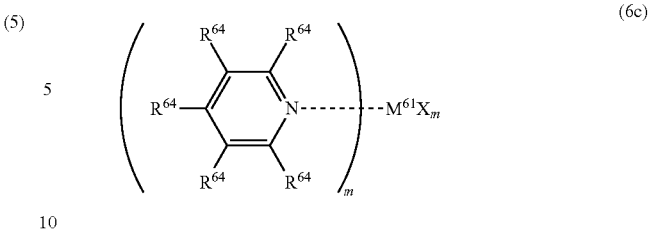

(6c)

In formula (6b), X is Cl, Br, or I; Z is an O atom or an S atom; each of $R^{63}$'s is independently a hydrogen atom or a substituent; $M^{61}$ has the same meaning as $M^{61}$ in the formula (6); m is 3 when $M^{61}$ is Ir, while m is 2 when $M^{61}$ is Pt.

In formula (6c), X is Cl, Br or I; each of $R^{64}$'s independently represents a hydrogen atom or a substituent; $M^{61}$ has the same meaning as $M^{61}$ in the formula (6); m is 3 when $M^{61}$ is Ir, while m is 2 when $M^{61}$ is Pt.

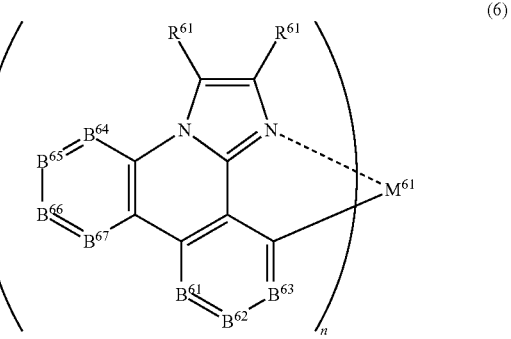

(6)

In formula (6), $M^{61}$ represents Ir or Pt; each of $R^{61}$'s independently represents a hydrogen atom or a substituent and each $R^{61}$ may be the same as or different from every other $R^{61}$; each of $B^{61}$ to $B^{67}$ independently represents a nitrogen atom or C—$R^{62}$, $R^{62}$ represents a hydrogen atom or a substituent and each $R^{62}$ may be the same as or different from every other $R^{62}$; n is 3 when $M^{61}$ is Ir, while n is 2 when $M^{61}$ is Pt.

[11]

The forming method according to [9], wherein the compound represented by the formula (5a) is a compound represented by the following formula (7a), the compound represented by the formula (5b) is a compound represented by the following formula (7b), the compound represented by the formula (5c) is a compound represented by the following formula (7c) and the compound represented by the formula (5) is a compound represented by the following formula (7).

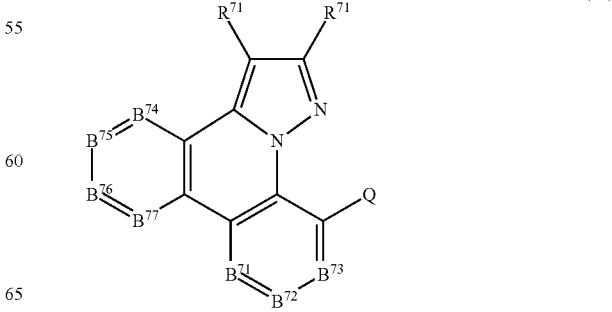

(7a)

In formula (7a), Q represents an alkali metal, an alkaline earth metal, an alkaline earth metal halide, a trialkyltin, zinc or a zinc halide, which each may further have an arbitrary organic group as a substituent; $R^{71}$ and $B^{71}$ to $B^{77}$ have the same meanings as $R^{71}$ and $B^{71}$ to $B^{77}$ in the formula (7), respectively.

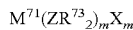
(7b)

In formula (7b), X is Cl, Br, or I; Z is an O atom or an S atom; each of $R^{73}$s is independently a hydrogen atom or a substituent; $M^{71}$ has the same meaning as $M^{71}$ in the formula (7); m is 3 when $M^{71}$ is Ir, while m is 2 when $M^{71}$ is Pt.

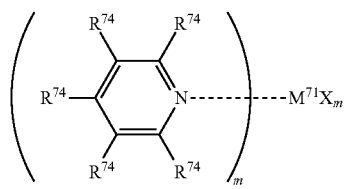
(7c)

In formula (7c), X is Cl, Br or I; each of $R^{74}$s independently represents a hydrogen atom or a substituent; $M^{71}$ has the same meaning as $M^{71}$ in the formula (7); m is 3 when $M^{71}$ is Ir, while m is 2 when $M^{71}$ is Pt.

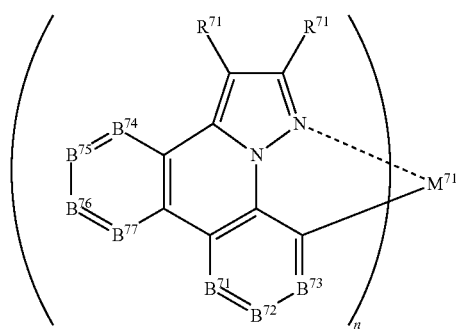
(7)

In formula (7), $M^{71}$ represents Ir or Pt; each of $R^{71}$s independently represents a hydrogen atom or a substituent and each $R^{71}$ may be the same or different from every other $R^{71}$; each of $B^{71}$ to $B^{77}$ independently represents a nitrogen atom or C—$R^{72}$, $R^{72}$ represents a hydrogen atom or a substituent and each $R^{72}$ may be the same as or different from every other $R^{72}$; n is 3 when $M^{71}$ is Ir, while n is 2 when $M^{71}$ is Pt.

[12]

The forming method according to [9], wherein the compound represented by the formula (5a) is a compound prepared by reaction between a compound represented by the following formula (5d) and at least one reactant selected from the group consisting of alkali metals, organolithium compounds, alkaline earth metals or alkylmagnesium halides.

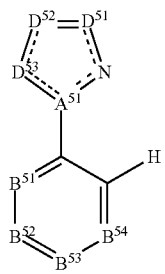
(5d)

In formula (5d), $A^{51}$, $B^{51}$ to $B^{54}$ and $D^{51}$ to $D^{53}$ have the same meanings as $A^{51}$, $B^{51}$ to $B^{54}$ and $D^{51}$ to $D^{53}$ in the formula (5a), respectively.

[13]

The forming method according to [10], wherein the compound represented by the formula (6a) is a compound prepared by reaction between a compound represented by the following formula (6d) and at least one reactant selected from the group consisting of alkali metals, organolithium compounds, alkaline earth metals or alkylmagnesium halides.

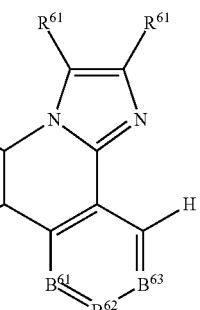
(6d)

In formula (6d), $R^{61}$ and $B^{61}$ to $B^{67}$ have the same meanings as $R^{61}$ and $B^{61}$ to $B^{67}$ in the formula (6a), respectively.

[14]

The forming method according to [11], wherein the compound represented by the formula (7a) is a compound prepared by reaction between a compound represented by the following formula (7d) and at least one reactant chosen from alkali metals, organolithium compounds, alkaline earth metals or alkylmagnesium halides.

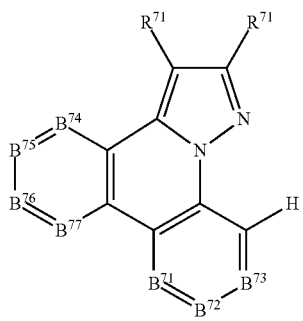
(7d)

In formula (7d), $R^{71}$ and $B^{71}$ to $B^{77}$ have the same meanings as $R^{71}$ and $B^{71}$ to $B^{77}$ in the formula (7a), respectively.

[15]

A method of forming a compound having a nitrogen-containing heterocyclic 5-membered ring as a partial structure of a ligand through the use of metal-metal exchange reaction, wherein the compound is represented by the following formula (8) and manufactured by allowing a compound represented by the following formula (8a) to react with a compound represented by the following formula (8b) or (8c).

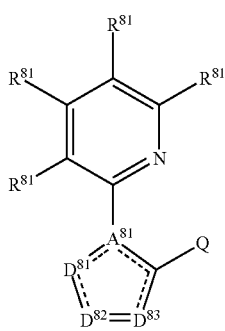
(8a)

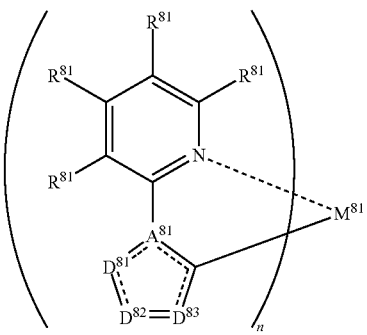
(8)

In formula (8), $M^{81}$ represents Ir or Pt; each of $R^{81}$s independently represents a hydrogen atom or a substituent; each of $A^{81}$s independently represents a nitrogen atom or a carbon atom, each of $D^{81}$ to $D^{83}$ independently represents an atom chosen from carbon, nitrogen, oxygen, sulfur or silicon; each of the bonds between in the 5-membered ring formed from $D^{81}$ to $D^{83}$, $A^{81}$ and a C atom represents a single bond or a double bond; each of $D^{81}$ to $D^{83}$ may have a substituent as long as it can undergo further substitution; n is 3 when $M^{81}$ is Ir, while n is 2 when $M^{81}$ is Pt.

[16]

The forming method according to [15], wherein the compound represented by the formula (8a) is a compound prepared by reaction between a compound represented by the following formula (8d) and at least one reactant selected from the group consisting of alkali metals, organolithium compounds, alkaline earth metals or alkylmagnesium halides.

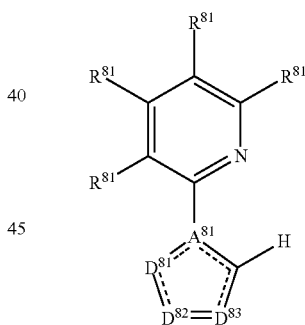
(8d)

In formula (8a), Q represents an alkali metal, an alkaline earth metal, an alkaline earth metal halide, a trialkyltin, zinc or a zinc halide, which each may further have an arbitrary organic group as a substituent; $R^{81}$, $A^{81}$ and $D^{81}$ to $D^{83}$ have the same meanings as $R^{81}$, $A^{81}$ and $D^{81}$ to $D^{83}$ in the formula (8), respectively.

(8b)

In formula (8b), X is Cl, Br, or I; Z is an O atom or an S atom; each of $R^{82}$s is independently a hydrogen atom or a substituent; $M^{81}$ has the same meaning as $M^{81}$ in the formula (8); m is 3 when $M^{81}$ is Ir, while m is 2 when $M^{81}$ is Pt.

In formula (8d), $R^{81}$, $A^{81}$ and $D^{81}$ to $D^{83}$ have the same meanings as $R^{81}$, $A^{81}$ and $D^{81}$ to $D^{83}$ in the formula (8a), respectively.

[17]

A compound formed by the forming method according to any one of [1] to [16] and represented by any one of the formulae (1) to (8).

[18]

An organic electroluminescence device material, which is a compound formed by the forming method according to any one of [1] to [16] and represented by any one of the formulae (1) to (8), wherein the compound has a Li atom and ion content of 0.1 ppm to 50 ppm.

[19]

An organic electroluminescence device material, which is a compound manufactured by the forming method according to any one of [1] to [16] and represented by any one of the

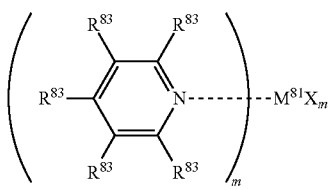
(8c)

In formula (8c), X is Cl, Br or I; each of $R^{83}$s independently represents a hydrogen atom or a substituent; $M^{81}$ has the same meaning as $M^{81}$ in the formula (8), and m is 3 when $M^{81}$ is Ir, while m is 2 when $M^{81}$ is Pt.

formulae (1) to (8), wherein the compound has an Mg atom and ion content of 0.1 ppm to 50 ppm.

[20]

An organic electroluminescence device having: a pair of electrodes; and at least one organic layer provided between the pair of electrodes, which includes a light emitting layer, wherein at least one layer included in the organic layer contains a compound formed by the forming method according to any one of claims 1 to 16 and represented by any one of the formulae (1) to (8).

[21]

An organic electroluminescence device having: a pair of electrodes; and at least one organic layer provided between a pair of electrodes, which includes a light emitting layer, wherein the light emitting layer contains a compound formed by the forming method according to any one of [1] to [16] and represented by any one of the formulae (1) to (8).

[22]

A light emission apparatus using the organic electroluminescence devices according to [20] or [21].

[23]

A display apparatus using the organic electroluminescence devices according to [20] or [21].

[24]

An illumination apparatus using the organic electroluminescence devices according to [20] or [21].

Embodiments of the invention are methods of forming compounds represented by the formulae (1) to (8) which have nitrogen-containing heterocyclic 5-membered rings as partial structures of ligands thereof through the use of metal-metal exchange reaction. By carrying out the reaction at a low temperature in particular, decomposition reaction and side reaction of the 5-membered nitrogen-containing heterocyclic rings are retarded, and thus the decomposed-matter contents in light emitting materials are reduced and the yields can be enhanced. In addition, it becomes possible to provide organic EL devices of excellent durability.

BRIEF DESCRIPTION OF DRAWINGS

A general configuration that implements the various features of the invention will be described with reference to the drawings. The drawings and the associated descriptions are provided to illustrate embodiments of the invention and not to limit the scope of the invention.

DETAILED DESCRIPTION OF EXEMPLARY EMBODIMENTS

Figure 1:
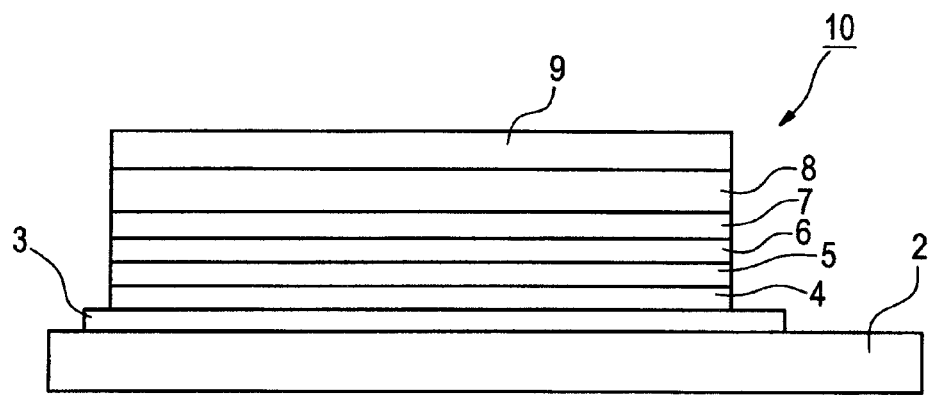
FIG. 1 is a schematic diagram showing one example of the layer structure of an organic EL device relating to the invention (a first embodiment of the invention)

Embodiments of the invention are methods of forming compounds represented by the following formulae (1) to (8) which have nitrogen-containing heterocyclic 5-membered rings as partial structures of ligands thereof through the use of metal-metal exchange reaction.

According to the present forming methods, light emitting materials reduced in impurity and decomposed-matter contents can be obtained.

The light emitting materials reduced in impurity and decomposed-matter contents are restrained from causing photoemission quench traceable to impurities and decomposed matter, and therefore it is surmised that the devices using the metal complexes produced in accordance with the present forming methods deliver improved durability.

Moreover, the light emitting materials synthesized from halogen-free ligands yield further improvement in device durability. Since there is a suggestion that halogen impurity is a cause of a drop in device durability, it is surmised that the use of light emitting materials prepared in the invention suppresses photoemission quench caused by halogen impurity and contributes to improvement in device durability.

In addition, it is preferred that metal complexes produced by the present methods contain Li and Mg atoms and Li and Mg ions in minute quantities, preferably in quantities ranging from 0.1 ppm to 50 ppm. These minute quantities of Li and Mg atoms and Li and Mg ions react with impurities and decomposed matter (e.g. halogen, moisture, detached ligands) included in the metal complexes and precipitate out in the form of lithium salts and magnesium salts. Thus they can be deactivated. Although, when metal complexes are stored as they are contaminated with impurities and decomposed matter, there is apprehension that photoemission quenchers are formed by reaction of metal complexes with the impurities and the decomposed matter, the presence of minute quantities of Li and Mg atoms and Li and Mg ions is thought to restrain the formation of photoemission quenchers and thereby to enhance the device durability. However, because Li and Mg ions as well as Li and Mg atoms are hygroscopic, it is preferred that their content in each metal complex be 50 ppm or below. Additionally, ppm is by mass.

[Compounds Represented by Formula (1)]

One forming method according to the invention is a method of forming compounds having nitrogen-containing heterocyclic 5-membered rings as partial structures of ligands thereof through the use of metal-metal exchange reaction, and more specifically, a method of forming compounds represented by the formula (1) by allowing compounds represented by the formula (1a) to react with compounds represented by the formula (1b).

The compounds represented by the formula (1) are illustrated below in detail.

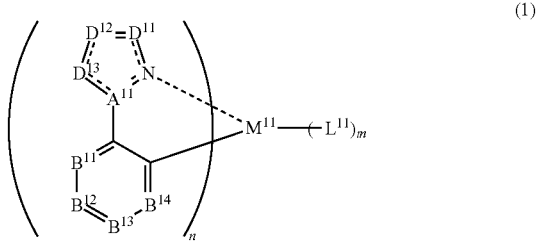

(1)

In the formula (1), $M^{11}$ represents Ir or Pt, each of $A^{11}$s independently represents a nitrogen atom or a carbon atom, each of $B^{11}$ to $B^{14}$ independently represents a nitrogen atom or C—$R^{11}$, and $R^{11}$ represents a hydrogen atom or a substituent, wherein each $R^{11}$ may be the same as or different from every other $R^{11}$. And each of $D^{11}$ to $D^{13}$ independently represents an atom chosen from carbon, nitrogen, oxygen, sulfur or silicon. Each of bonds between atoms in the 5-membered ring formed from $D^{11}$ to $D^{13}$, $A^{11}$ and an N atom represents a single bond or a double bond. Each of $D^{11}$ to $D^{13}$ may have a substituent as long as it can undergo further substitution. And $L^{11}$ represents atoms forming a bidentate ligand. n represents an integer of 1 to 3 and m represents an integer of 0 to 2, provided that n+m is 2 or 3.

$A^{11}$ represents a nitrogen atom or a carbon atom and, together with $D^{11}$ to $D^{13}$ and a nitrogen atom, forms a nitrogen-containing heterocyclic 5-membered ring.

Each of $D^{11}$ to $D^{13}$ independently represents an atom chosen from carbon, nitrogen, oxygen, sulfur or silicon. The bonds between atoms in the 5-membered ring formed from $D^{11}$ to $D^{13}$, $A^{11}$ and a nitrogen atom, though not particularly restricted, may be any of varying combinations of single and double bonds. Each of $D^{11}$ to $D^{13}$ is preferably a carbon or nitrogen atom.

The number of nitrogen atoms in the 5-membered ring formed from $D^{11}$ to $D^{13}$, $A^{11}$ and a nitrogen atom is preferably from 1 to 3, far preferably 1 or 2, particularly preferably 2.

The 5-membered ring formed from $D^{11}$ to $D^{13}$, $A^{11}$ and a nitrogen atom is preferably an aromatic ring.

When each of $D^{11}$ to $D^{13}$ can further undergo substitution, it may have a substituent selected from among the following substituent group A.

[Substituent Group A]

An alkyl group (preferably having a carbon number of 1 to 30, more preferably from 1 to 20, still more preferably from 1 to 10, e.g., methyl, ethyl, isopropyl, tert-butyl, n-octyl, n-decyl, n-hexadecyl, trifluoromethyl, pentafluoroethyl), a cycloalkyl group (preferably having a carbon number of 3 to 30, more preferably from 3 to 20, still more preferably from 3 to 10, e.g., cyclopropyl, cyclopentyl, cyclohexyl), an alkenyl group (preferably having a carbon number of 2 to 30, more preferably from 2 to 20, still more preferably from 2 to 10, e.g., vinyl, allyl, 2-butenyl, 3-pentenyl), an alkynyl group (preferably having a carbon number of 2 to 30, more preferably from 2 to 20, still more preferably from 2 to 10, e.g., propargyl, 3-pentynyl), an aryl group (preferably having a carbon number of 6 to 30, more preferably from 6 to 20, still more preferably from 6 to 12, e.g., phenyl, p-methylphenyl, naphthyl, anthranyl), an amino group (preferably having a carbon number of 0 to 30, more preferably from 0 to 20, still more preferably from 0 to 10, e.g., amino, methylamino, dimethylamino, diethylamino, dibenzylamino, diphenylamino, ditolylamino), an alkoxy group (preferably having a carbon number of 1 to 30, more preferably from 1 to 20, still more preferably from 1 to 10, e.g., methoxy, ethoxy, butoxy, 2-ethylhexyloxy), an aryloxy group (preferably having a carbon number of 6 to 30, more preferably from 6 to 20, still more preferably from 6 to 12, e.g., phenyloxy, 1-naphthyloxy, 2-naphthyloxy), a heterocyclic oxy group (preferably having a carbon number of 1 to 30, more preferably from 1 to 20, still more preferably from 1 to 12, e.g., pyridyloxy, pyrazyloxy, pyrimidyloxy, quinolyloxy), an acyl group (preferably having a carbon number of 1 to 30, more preferably from 1 to 20, still more preferably from 1 to 12, e.g., acetyl, benzoyl, formyl, pivaloyl), an alkoxycarbonyl group (preferably having a carbon number of 2 to 30, more preferably from 2 to 20, still more preferably from 2 to 12, e.g., methoxycarbonyl, ethoxycarbonyl), an aryloxycarbonyl group (preferably having a carbon number of 7 to 30, more preferably from 7 to 20, still more preferably from 7 to 12, e.g., phenyloxycarbonyl), an acyloxy group (preferably having a carbon number of 2 to 30, more preferably from 2 to 20, still more preferably from 2 to 10, e.g., acetoxy, benzoyloxy), an acylamino group (preferably having a carbon number of 2 to 30, more preferably from 2 to 20, still more preferably from 2 to 10, e.g., acetylamino, benzoylamino), an alkoxycarbonylamino group (preferably having a carbon number of 2 to 30, more preferably from 2 to 20, still more preferably from 2 to 12, e.g., methoxycarbonylamino), an aryloxycarbonylamino group (preferably having a carbon number of 7 to 30, more preferably from 7 to 20, still more preferably from 7 to 12, e.g., phenyloxycarbonylamino), a sulfonylamino group (preferably having a carbon number of 1 to 30, more preferably from 1 to 20, still more preferably from 1 to 12, e.g., methanesulfonylamino, benzenesulfonylamino), a sulfamoyl group (preferably having a carbon number of 0 to 30, more preferably from 0 to 20, still more preferably from 0 to 12, e.g., sulfamoyl, methylsulfamoyl, dimethylsulfamoyl, phenylsulfamoyl), a carbamoyl group (preferably having a carbon number of 1 to 30, more preferably from 1 to 20, still more preferably from 1 to 12, e.g., carbamoyl, methylcarbamoyl, diethylcarbamoyl, phenylcarbamoyl), an alkylthio group (preferably having a carbon number of 1 to 30, more preferably from 1 to 20, still more preferably from 1 to 12, e.g., methylthio, ethylthio), an arylthio group (preferably having a carbon number of 6 to 30, more preferably from 6 to 20, still more preferably from 6 to 12, e.g., phenylthio), a heterocyclic thio group (preferably having a carbon number of 1 to 30, more preferably from 1 to 20, still more preferably from 1 to 12, e.g., pyridylthio, 2-benzimizolylthio, 2-benzoxazolylthio, 2-benzothiazolylthio), a sulfonyl group (preferably having a carbon number of 1 to 30, more preferably from 1 to 20, still more preferably from 1 to 12, e.g., mesyl, tosyl), a sulfinyl group (preferably having a carbon number of 1 to 30, more preferably from 1 to 20, still more preferably from 1 to 12, e.g., methanesulfinyl, benzenesulfinyl), an ureido group (preferably having a carbon number of 1 to 30, more preferably from 1 to 20, still more preferably from 1 to 12, e.g., ureido, methylureido, phenylureido), a phosphoric acid amido group (preferably having a carbon number of 1 to 30, more preferably from 1 to 20, still more preferably from 1 to 12, e.g., diethylphosphoric acid amido, phenylphosphoric acid amido), a hydroxy group, a mercapto group, a halogen atom (for example, a fluorine atom, a chlorine atom, a bromine atom and an iodine atom, preferably a fluorine atom), a cyano group, a sulfo group, a carboxyl group, a nitro group, a hydroxamic acid group, a sulfino group, a hydrazino group, an imino group, a heterocyclic group (preferably having a carbon number of 1 to 30, more preferably from 1 to 12; examples of the heteroatom include a nitrogen atom, an oxygen atom and a sulfur atom; specifically an imidazolyl group, a pyridyl group, a quinolyl group, a furyl group, a thienyl group, a piperidyl group, a morpholino group, a benzoxazolyl group, a benzimidazolyl group, a benzothiazolyl group, a carbazolyl group, an azepinyl group and the like), a silyl group (preferably having a carbon number of 3 to 40, more preferably from 3 to 30, still more preferably from 3 to 24, e.g., trimethylsilyl, triphenylsilyl), and a silyloxy group (preferably having a carbon number of 3 to 40, more preferably from 3 to 30, still more preferably from 3 to 24, e.g., trimethylsilyloxy, triphenylsilyloxy). These substituents may be further substituted.

In addition, two or more of those substituents may combine with each other to form a ring.

Of those substituents, an alkyl group, a cycloalkyl group, an aryl group, an amino group, an alkoxy group, an aryloxy group, an acyl group, an alkoxycarbonyl group, an aryloxy group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfonyl group, an ureido group, a phosphorylamido group, a hydroxyl group, a mercapto group, a halogen atom, a sulfo group, a carboxyl group, a nitro group, a sulfino group, a heterocyclic group and a silyl group are preferable to the others. Among these substituents, it is far preferred that a substituted or unsubstituted alkyl group, a cycloalkyl group, an aryl group, an amino group, an alkoxy group, an aryloxy group, a cyano group, a fluorine atom and a heterocyclic group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Some of these substituents may also combine with each other and complete a condensed ring, and examples of a ring formed from them include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

As to the 5-membered ring formed from $D^{11}$ to $D^{13}$, $A^{11}$ and a nitrogen atom, especially preferred combinations are a case where $D^{13}$ is a nitrogen atom and $D^{11}$, $D^{12}$ and $A^{11}$ are carbon atoms and a case where $A^{11}$ is a nitrogen atom and $D^{11}$ to $D^{13}$ are carbon atoms. These cases are expressed as the following partial structures in the concrete. When the 5-membered ring formed from $D^{11}$ to $D^{13}$, $A^{11}$ and a nitrogen atom has either of the following partial structures, the acidity of hydrogen atoms in $R^{1a}$ to $R^{1e}$ is low, and therefore the hydrogen atoms in $R^{1a}$ to $R^{1e}$ resist undergoing hydrogen-metal exchange reaction, and it becomes easy to derive the compound represented by the formula (1a) from a starting material at a high yield. In addition, when either of the following partial structures is present in a compound represented by the formula (1), the lowest excited triplet-state energy level of the compound is heightened. Therefore it is favorable for preparation of a shortwave fluorescent material to have such partial structure in the compound.

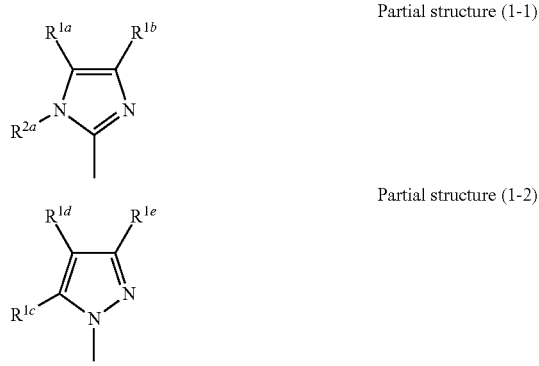

Partial structure (1-1)

Partial structure (1-2)

Each of $R^{1a}$ to $R^{1e}$ independently represents a hydrogen atom or a substituent. The substituent represented by each of $R^{1a}$ to $R^{1e}$ may further have a substituent and can be chosen from the substituent group A.

Suitable examples of a substituent of the substituent represented by each of $R^{1a}$ to $R^{1e}$ include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfonyl group, an ureido group, a phosphorylamido group, a hydroxyl group, a mercapto group, a halogen atom, a sulfo group, a carboxyl group, a nitro group, a sulfino group, a heterocyclic group and a silyl group. Of these substituents, an alkyl group, a cycloalkyl group, an aryl group, an amino group, an alkoxy group, an aryloxy group, a cyano group, a fluorine atom and a heterocyclic group are preferable to the others, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

Alternatively, $R^{1a}$ and $R^{1b}$, or adjacent two of $R^{1c}$ to $R^{1e}$ may combine with each other and complete a condensed ring, and examples of a ring formed from them include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

Examples of a substituent suitable as each of $R^{1a}$ to $R^{1e}$ include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group and a silyl group. Among them, a substituted or unsubstituted alkyl group, a cycloalkyl group, an amino group, an alkoxy group, an aryloxy group, a cyano group, a fluorine atom and a heterocyclic ring are preferable to the others, and more preferably a substituted or unsubstituted alkyl group, a fluorine atom, a methoxy group and an aryl group, and the best ones are a substituted or unsubstituted alkyl group (preferably an alkyl group having 1 to 6 carbon atoms and a cycloalkyl group having 5 to 10 carbon atoms, far preferably a methyl group, an ethyl group, a propyl group, an iso-propyl group, a butyl group, a tert-butyl group, a cycloheptyl group, a cyclohexyl group and an adamantyl group, more preferably a methyl group, an iso-propyl group, a tert-butyl group, a cyclohexyl group and an adamantly group, and still more preferably a methyl group and a tert-butyl group) and an aryl group (preferably an aryl group having 6 to 12 carbon atoms, far preferably phenyl, p-methylphenyl, o-methylphenyl, 2,6-dimethylphenyl, 2,4,6-trimethoxyphenyl, naphthyl and anthranyl, further preferably phenyl, o-methylphenyl, 2,6-dimethylphenyl and 2,4,6-trimethoxyphenyl, particularly preferably phenyl and 2,6-dimethylphenyl). It is preferable that at least either of $R^{1a}$ and $R^{1b}$ or at least any one of $R^{1c}$ to $R^{1e}$ is not a hydrogen atom but a substituent. In such cases, the tendency of $R^{1a}$ to $R^{1e}$ to cause hydrogen-metal exchange reaction is reduced, and therefore it becomes easy to derive the compounds represented by the formula (1a) from starting materials at good yields.

It is appropriate that at least either of $R^{1a}$ and $R^{1b}$ be an alkyl group or an aryl group, and that $R^{1a}$ in particular be an alkyl group or an aryl group. As the aryl group, a 2,6-dialkyl-substituted aryl group is suitable.

The 2,6-disubstituted aryl group is preferably a 2,6-dimethylphenyl group, a 2,4,6-trimethylphenyl group, a 2,6-diisopropylphenyl group, a 2,4,6-triisopropylphenyl group, a 2,6-dimethyl-4-phenylphenyl group, a 2,6-dimethyl-4-(2,6-dimethylpyridine-4-yl)phenyl group, a 2,6-diphenylphenyl group, a 2,6-diphenyl-4-isopropylphenyl group, a 2,4,6-triphenylphenyl group, a 2,6-diisopropyl-4-(4-isopropylphenyl)phenyl group, 2,6-diisopropyl-4-(3,5-dimethylphenyl)phenyl group, a 2,6-diisopropyl-4-(pyridine-4-yl)phenyl group or a 2,6-di(3,5-dimethylphenyl)phenyl group, far preferably a 2,6-dimethylphenyl group, a 2,4,6-trimethylphenyl group, a 2,6-diisopropylphenyl group or a 2,4,6-triisopropylphenyl group, further preferably a 2,6-dimethylphenyl group or a 2,4,6-trimethylphenyl group, particularly preferably a 2,6-dimethylphenyl group.

At least one of $R^{1c}$ to $R^{1e}$ is preferably an alkyl group or an aryl group. It is far preferable that either $R^{1c}$ or $R^{1e}$ is an alkyl group or an aryl group, and it is particularly preferable that $R^{1c}$ is an alkyl group or an aryl group. As the aryl group, a 2,6-dialkyl-substituted aryl group is suitable.

The 2,6-disubstituted aryl group is preferably a 2,6-dimethylphenyl group, a 2,4,6-trimethylphenyl group, a 2,6-diisopropylphenyl group, a 2,4,6-triisopropylphenyl group, a 2,6-dimethyl-4-phenylphenyl group, a 2,6-dimethyl-4-(2,6-dimethylpyridine-4-yl)phenyl group, a 2,6-diphenylphenyl group, a 2,6-diphenyl-4-isopropylphenyl group, a 2,4,6-triphenylphenyl group, a 2,6-diisopropyl-4-(4-isopropylphenyl)phenyl group, 2,6-diisopropyl-4-(3,5-dimethylphenyl)phenyl group, a 2,6-diisopropyl-4-(pyridine-4-yl)phenyl group or a 2,6-di(3,5-dimethylphenyl)phenyl group, far preferably a 2,6-dimethylphenyl group, a 2,4,6-trimethylphenyl group, a 2,6-diisopropylphenyl group or a 2,4,6-triisopropylphenyl group, further preferably a 2,6-dimethylphenyl group or a 2,4,6-trimethylphenyl group, particularly preferably a 2,6-dimethylphenyl group.

$R^{2a}$ represents a hydrogen atom or a substituent chosen from substituents including the substituent group A. Examples of the substituent suitable as $R^{2a}$ include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group and a silyl group. Of these substituents, a substituted or unsubstituted alkyl group, a cycloalkyl group, an aryl group, an alkoxy group, an aryloxy group, a cyano group, a fluorine atom and a heterocyclic ring are preferable to the others, and an alkyl group, a cycloalkyl group and aryl group are far preferred.

Alternatively, $R^{2a}$ may combine with either $R^{1a}$ or $R^{1b}$ and complete a condensed ring. Examples of a ring formed from these substituents include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

Each of $B^{11}$ to $B^{14}$ independently represents a nitrogen atom or C—$R^{11}$, and $R^{11}$ represents a hydrogen atom or a substituent. $B^{11}$ to $B^{14}$ are not particularly restricted as to the combination thereof, but the number of nitrogen atoms in the combination is preferably from 0 to 2, far preferably 0 or 1.

As the substituent represented by $R^{11}$, any of those recited as the substituent group A can be adopted.

Each $R^{11}$ may be the same as or different from every other $R^{11}$. And $R^{11}$ may further have a substituent, and the substituent can be chosen from those recited as the substituent group A. Alternatively, neighboring $R^{11}$s may combine with each other and complete a condensed ring, and examples of a ring formed from them include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

When $R^{11}$ further has a substituent, suitable examples of the substituent include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group and a silyl group. Of these substituents, a substituted or unsubstituted alkyl group, preferably a methyl group or trifluoromethyl group, a cycloalkyl group, an aryl group, an amino group, an alkoxy group, an aryloxy group, a cyano group, a fluorine atom and a heterocyclic group are preferable to the others, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The substituent suitable as $R^{11}$ is an alkyl group, a cycloalkyl group, an aryl group, an amino group, an alkoxy group, an aryloxy group, an acyl group, an alkoxycarbonyl group, an aryloxycarbonyl group, an aryloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group or a silyl group. Of these substituents, a substituted or unsubstituted alkyl group, a cycloalkyl group, an aryl group, an amino group, an alkoxy group, an aryloxy group, a cyano group, a fluorine atom and a heterocyclic ring are preferable to the others, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

$L^{11}$ represents atoms forming a bidentate ligand. The bidentate ligand represented by $L^{11}$ has no particular restriction, but it is preferably a bidentate ligand that $L^{11}$, together with $M^{11}$, forms a coordinate bond via its nitrogen atom, and besides, one of its carbon, oxygen and nitrogen atoms and $M^{11}$ form a covalent bond. And the bidentate ligand far preferred as $L^{11}$ is a bidentate ligand whose nitrogen atom and $M^{11}$ form a coordinate bond, and besides, whose carbon atom and $M^{11}$ form a covalent bond. Examples of such a bidentate ligand include substituted or unsubstituted phenylpyridine, phenylpyrazole, phenylimidazole, pyridylimidazole, phenyltriazole, phenyltetrazole, pyridiylpyridine, imidazolylpyridine, pyrazolylpyridine and triazolylpyridine. Of these ligands, phenylpyridine, phenylpyrazole, phenylimidazole, pyridylimidazole, pyridylpyridine and pyrazolylpyridine are preferable to the others. Additionally, these ligands may further have substituents chosen from the substituent group A.

It is further preferred that $L^{11}$ have a structure chosen from the following bidentate-ligand group L. In the group L, L-a to L-d are preferred, L-a and L-b are far preferred, and L-a in particular is still far preferred.

Bidentate-ligand Group L

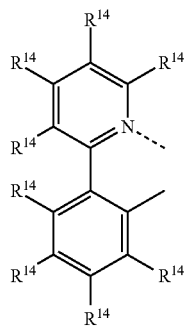

L-a

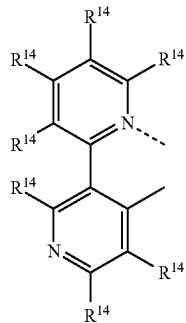

L-b

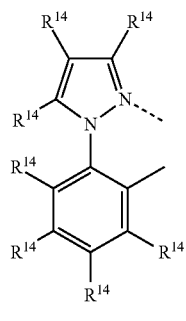

L-c

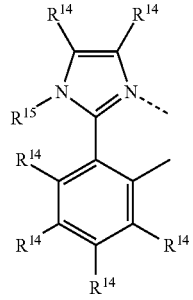

L-d

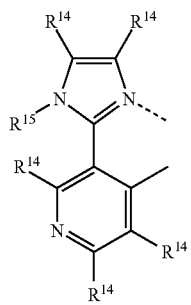

L-e

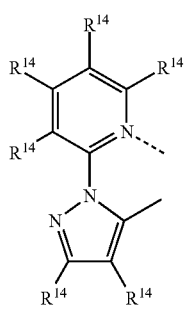

L-f

Each of $R^{14}$s independently represents a hydrogen atom or a substituent. Each $R^{14}$ may be the same as or different from every other $R^{14}$. In addition, $R^{14}$ may further have a substituent, and the substituent can be chosen from the substituent group A.

Alternatively, neighboring $R^{14}$s may combine with each other and complete a condensed ring, and examples of a ring formed from them include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

Suitable examples of $R^{14}$ include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group and a silyl group. Of these substituents, a substituted or unsubstituted alkyl group, a cycloalkyl group, an aryl group, an amino group, an alkoxy group, an aryloxy group, a cyano group, a fluorine atom and a heterocyclic group are preferable to the others, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

$R^{15}$ represents a hydrogen atom or a substituent chosen from substituents including the substituent group A. Suitable examples of the substituent include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group and a silyl group. Of these substituents, a substituted or unsubstituted alkyl group, a cycloalkyl group, an aryl group, an alkoxy group, an aryloxy group, a cyano group, a fluorine atom and a heterocyclic group are preferable to the others, and far preferred ones are an alkyl group, a cycloalkyl group and an aryl group.

Alternatively, $R^{15}$ and a neighboring $R^{14}$ may combine with each other and complete a condensed ring, and examples of a ring formed from them include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

n represents an integer of 1 to 3, and when $M^{11}$ is Ir, n is 3 or 1, preferably 3. When $M^{11}$ is Pt, n is 2 or 1, preferably 2.

m represents an integer of 0 to 2, and when $M^{11}$ is Ir, m is 0 or 2, preferably 0. When $M^{11}$ is Pt, m is 0 or 1, preferably 0.

n+m is 3 when $M^{11}$ is Ir, while it is 2 when $M^{11}$ is Pt.

The compounds represented by the formula (1a) are illustrated below.

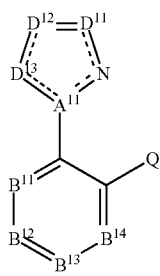

(1a)

In the formula (1a), Q represents an alkali metal, an alkaline earth metal, an alkaline earth metal halide, a trialkyltin, zinc or a zinc halide, which each may further have an arbitrary organic group as a substituent, and $A^{11}$, $B^{11}$ to $B^{14}$ and $D^{11}$ to $D^{13}$ have the same meanings as $A^{11}$, $B^{11}$ to $B^{14}$ and $D^{11}$ to $D^{13}$ in the formula (1), respectively, and their preferred ranges are also the same as those in the formula (1), respectively.

The organometallic compounds (1a) according to the invention are compounds each containing an alkali metal, an alkaline earth metal, tin or zinc attached to the carbon atom to combine with the central atom ($M^{11}$) of a complex represented by the formula (1). These metals each may further have an arbitrary organic group. Such an organic group may be chosen from the substituent group A, and it is preferably an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group or a silyl group, far preferably an alkyl group, a cycloalkyl group, an aryl group, an amino group, an alkoxy group, an aryloxy group, a cyano group, a fluorine atom or a heterocyclic group, and particularly preferably an alkyl group and an aryl group. Examples of these organic groups include a methyl group, an ethyl group, a propyl group, an isopropyl group, an n-butyl group, a sec-butyl group, a tert-butyl group, a pentyl group, a hexyl group, a heptyl group, an octyl group, a cycloheptyl group, a cyclohexyl group, a cyclopentyl group, a cyclopropyl group, an adamantly group, a benzyl group, an allyl group, a vinyl group, an acetyl group, a trimethylsilylmethyl group, a phenyl group, an o-tolyl group, an m-tolyl group, an o-tolyl group, a p-tolyl group, a biphenyl group, a naphthyl group, an anthryl group, a diisopropylamido group, bis(trimethylsilyl)amido group, a bis(trifluoromethanesulfonyl) imido group, a 2,2,6,6-tetramethylpiperidido group. Of these groups, a methyl group, an ethyl group, a propyl group, an isopropyl group, an n-butyl group, a sec-butyl group, a tert-butyl group, a trimethylsilyl group, a phenyl group, a diisopropylamido group and a 2,2,6,6-tetramethylpiperidido group are preferable to the others. And far preferred ones are a methyl group, an ethyl group, an isopropyl group, an n-butyl group, a sec-butyl group, a tert-butyl group, a phenyl group, a diisopropylamido group and a 2,2,6,6-tetramethylpiperidido group, further preferred ones are an ethyl group, an isopropyl group, an n-butyl group, a tert-butyl group, a phenyl group, a diisopropylamido group and a 2,2,6,6-tetramethylpiperidido group, particularly preferred ones are an ethyl group, an n-butyl group, a tert-butyl group, a phenyl group, a diisopropylamido group and a 2,2,6,6-tetramethylpiperidido group, and infinitely preferred ones are an n-butyl group, a tert-butyl group, a phenyl group, a diisopropylamido group and a 2,2, 6,6-tetramethylpiperidido group. Of these groups, an n-butyl group, a tert-butyl group and a phenyl group are preferable to the others, and the best ones are an n-butyl group and a tert-butyl group.

In addition, those metals each may further have an inorganic group such as halide.

Q represents an alkali metal, an alkaline earth metal, an alkaline earth metal halide, a trialkyltin, zinc or a zinc halide, preferably an alkali metal, an alkaline earth metal or zinc, far preferably lithium, sodium, magnesium or zinc, further preferably magnesium or zinc. As an organomagnesium compound, the so-called Grignard compound is suitable. This compound is a compound having a halide in addition to a magnesium-aryl bond, namely a compound of aryl-Mg halide type.

Examples of compounds represented by the formula (1a) are illustrated below, but these examples should not be construed as limiting the scope of the invention.

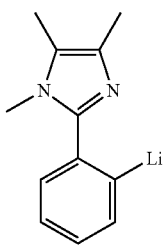

1

-continued
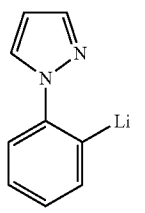
2
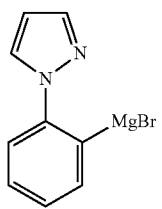
3
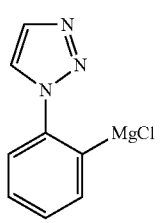
4
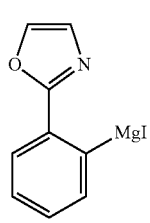
5
6
7
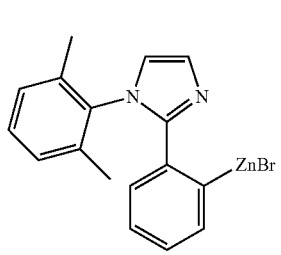
8
-continued
9
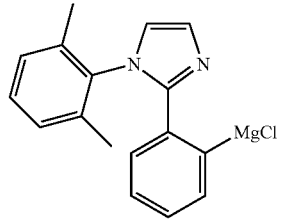
10
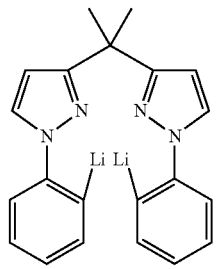
11
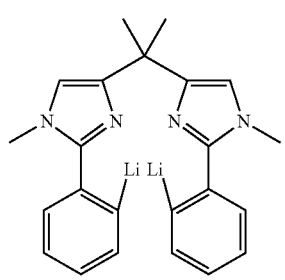
12
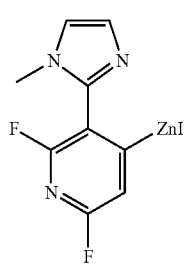
13
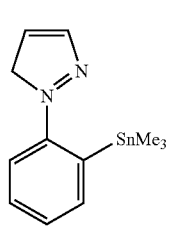
14

-continued
15
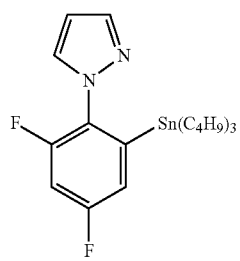
16
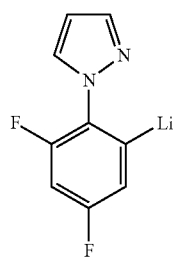
17
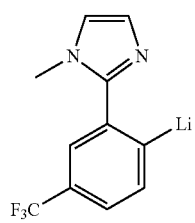
18
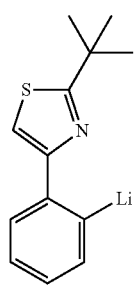
19
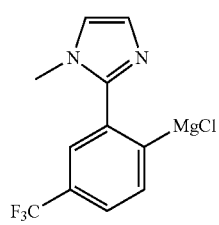
20
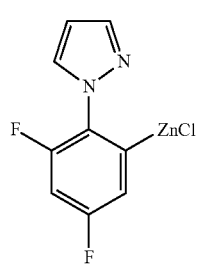
-continued
15
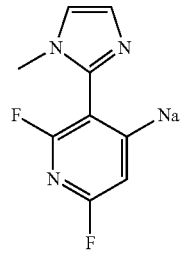
16
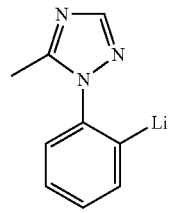
17
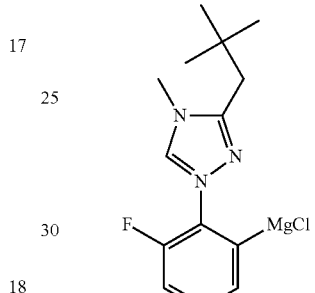
18
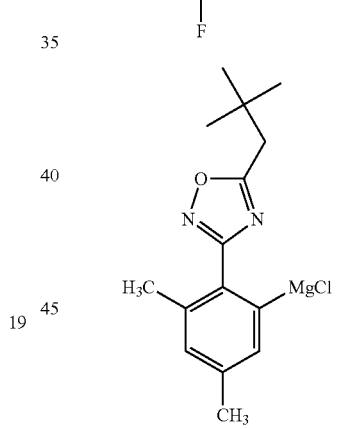
19
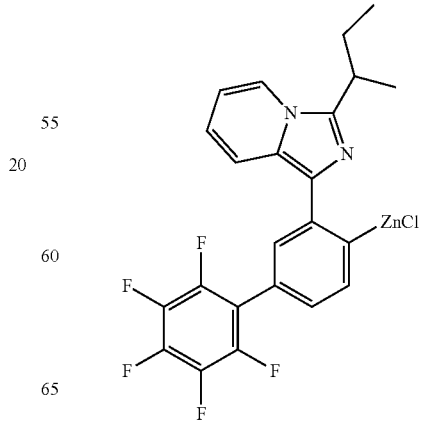

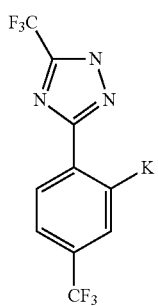
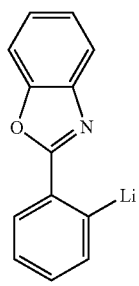
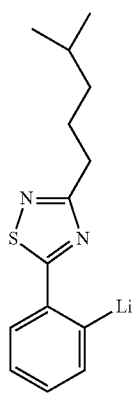
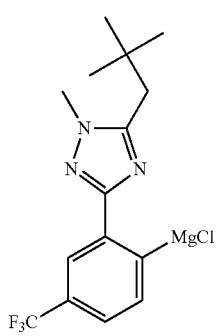
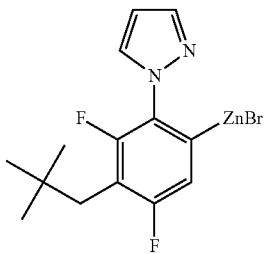
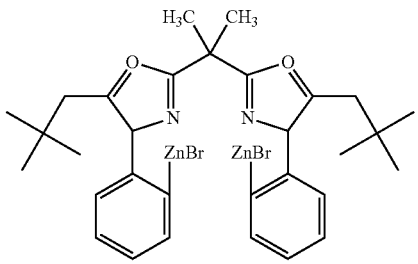
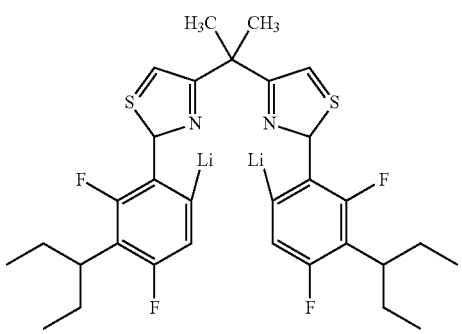
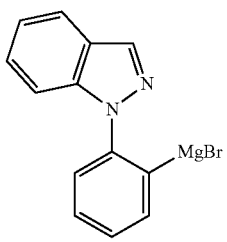
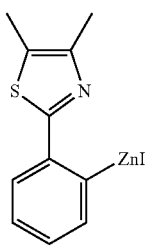
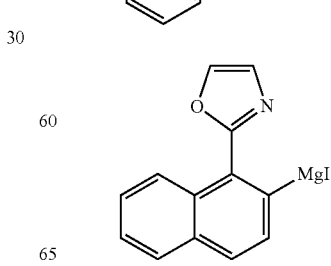

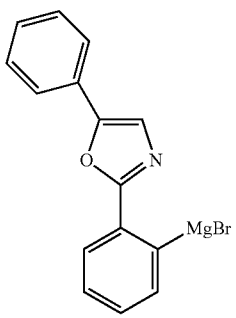
37
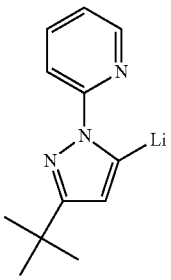
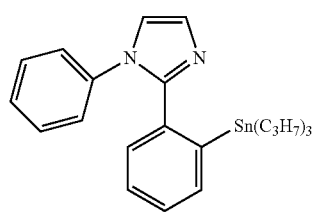
38
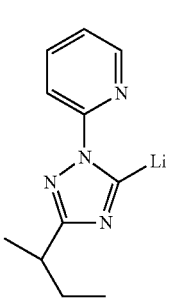
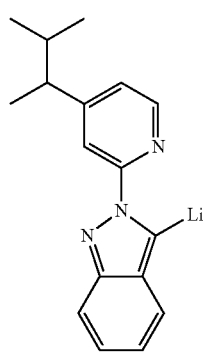
39
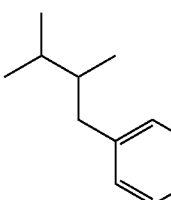
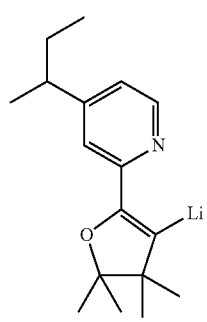
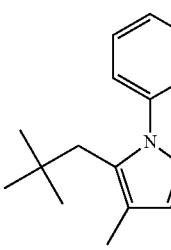
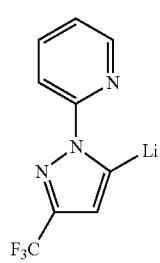
41
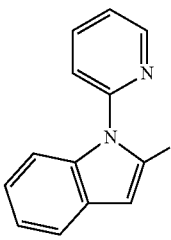

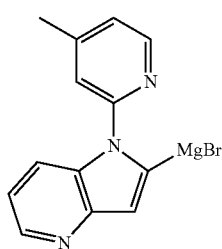
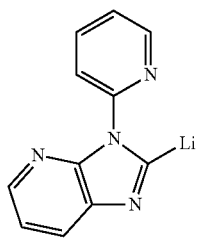
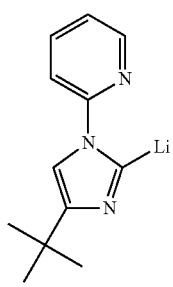
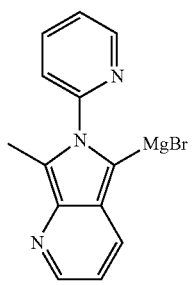
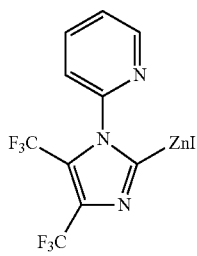
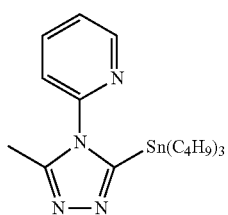
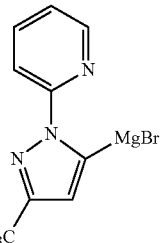
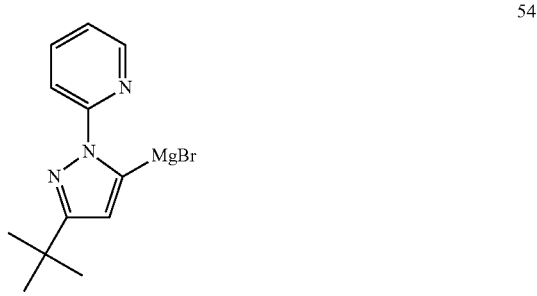
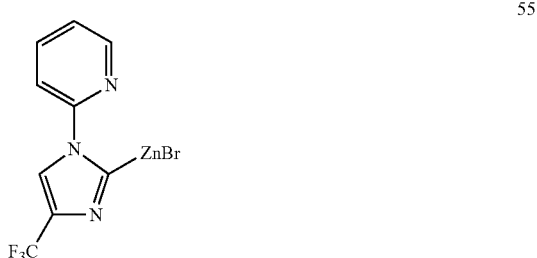
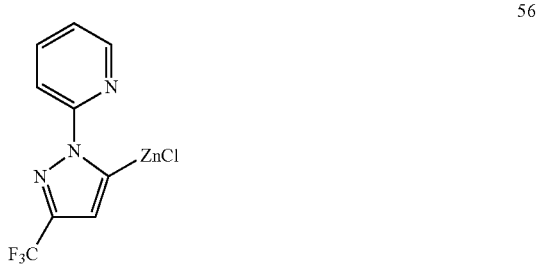
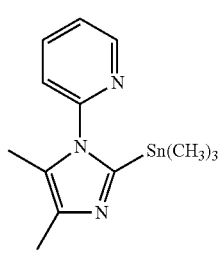

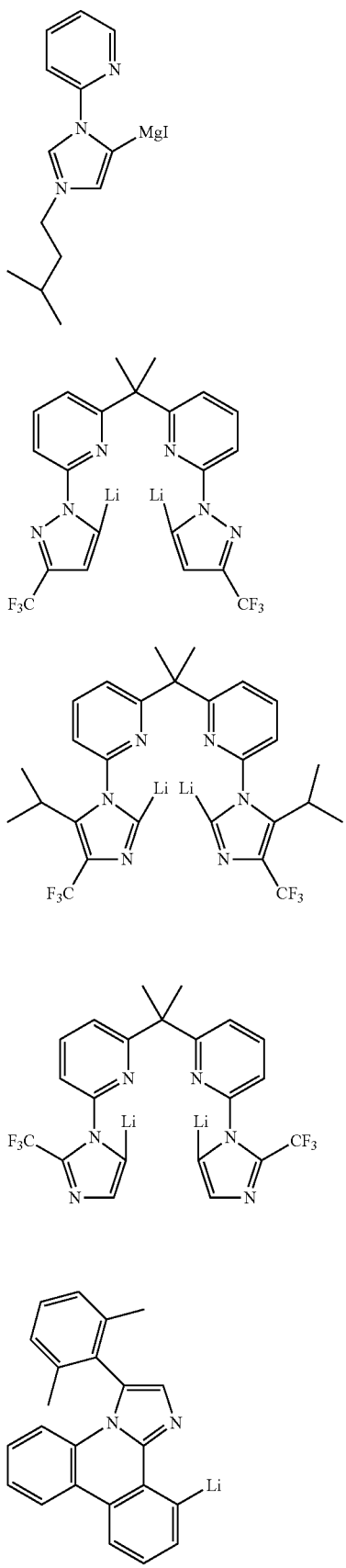
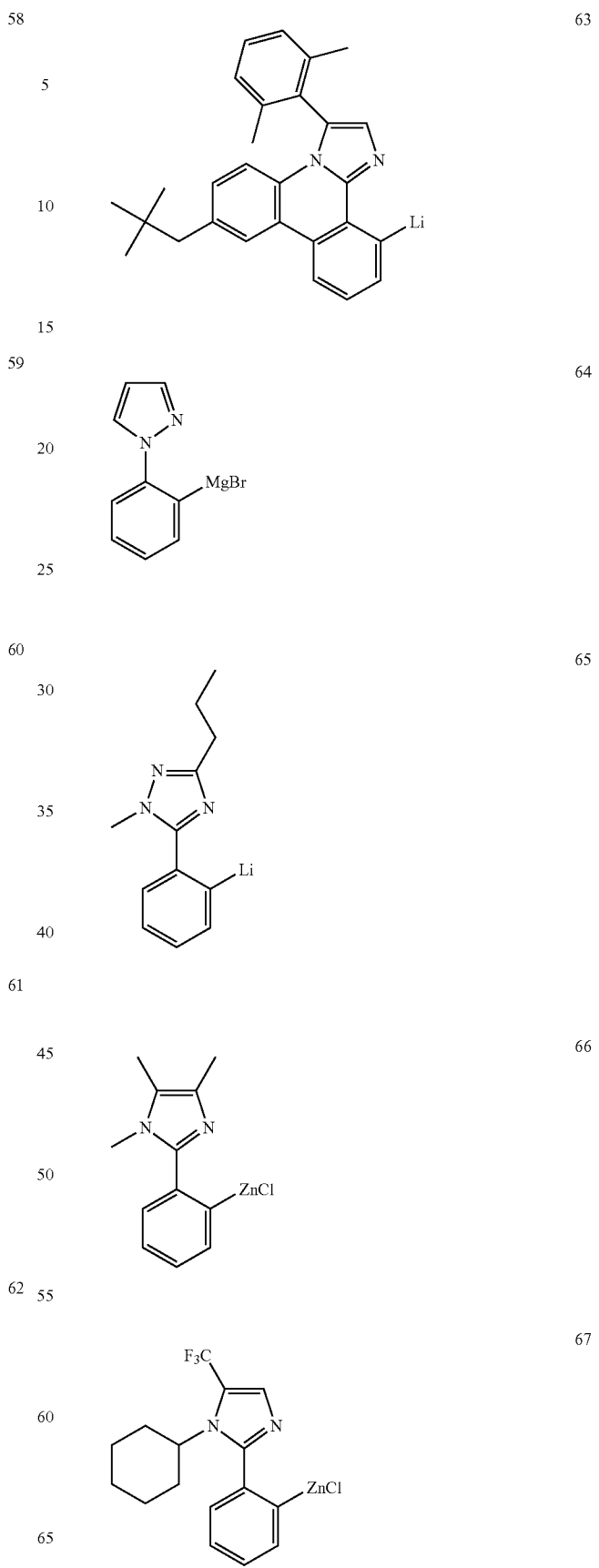

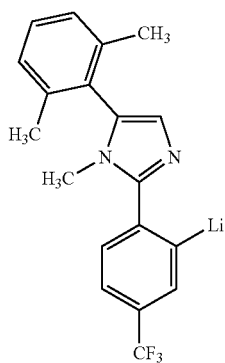

68

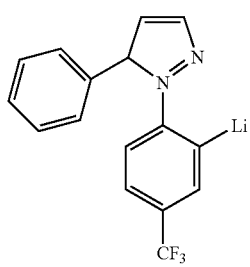

69

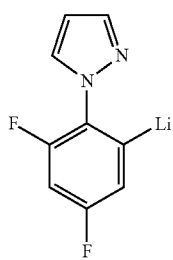

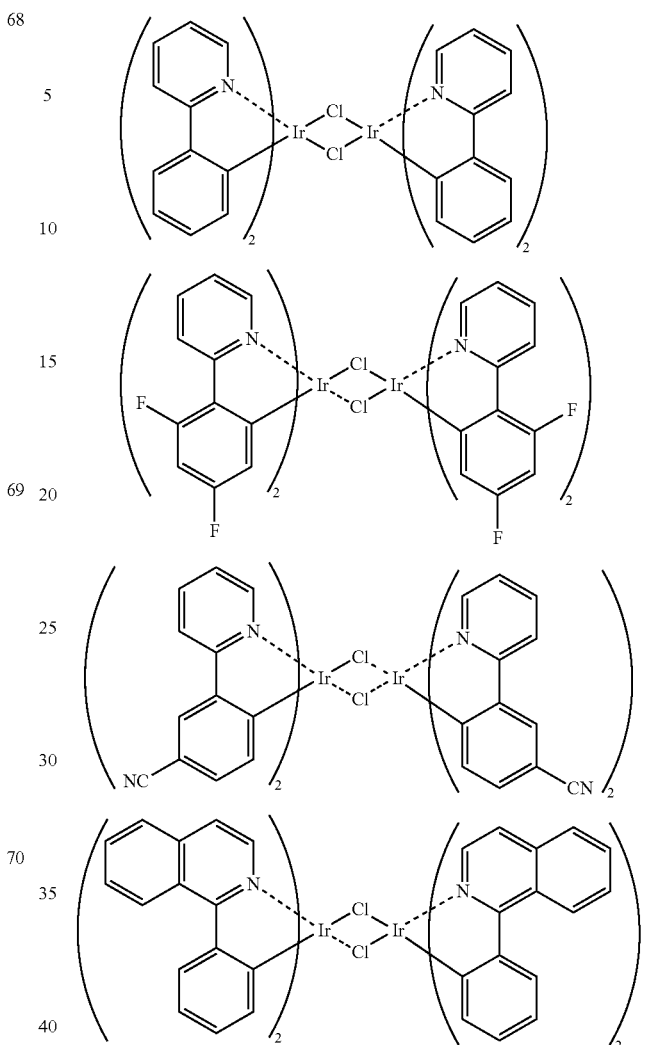

The formula (1b) is described below.

$$[L^{11}{}_kM^{11}(\mu\text{-}Y)]_2 \qquad (1b)$$

The formula (1b) stands for a bridged metal dimer, Y is F, Cl, Br, I, $OR^{13}$, $R^{13}COO$, $SR^{13}$ or $N(R^{13})_2$, and each of $R^{13}$s is independently a hydrogen atom, an aliphatic hydrocarbon group having 1 to 20 carbon atoms or an aromatic hydrocarbon group. k is 2 when $M^{11}$ is Ir, while k is 1 when $M^{11}$ is Pt. $L^{11}$ and $M^{11}$ have the same meanings as $L^{11}$ and $M^{11}$ in the formula (1), respectively, and their preferred ranges are also the same as those in the formula (1), respectively.

μ is a symbol standing for a bridging ligand, and the formula (1b) stands for a binuclear metal complex bridged via the ligand Y. Herein, Y is preferably Cl or Br, particularly preferably Cl. Syntheses of such compounds are described e.g. in *Inorg. Chem.*, 1994, 33, 545, *J. Mater. Chem.*, 2003, 13, 80, and *J. Am. Chem. Soc.*, 1984, 106, 6647.

Examples of compounds represented by the formula (1b) are illustrated below, but these examples should not be construed as limiting the scope of the invention.

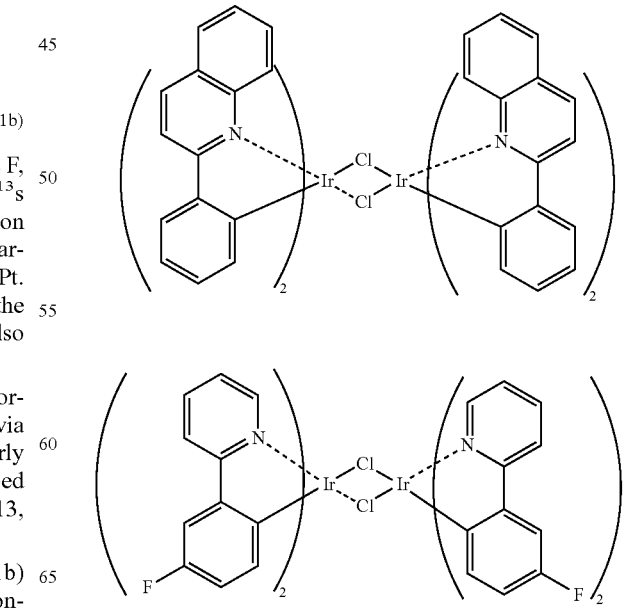

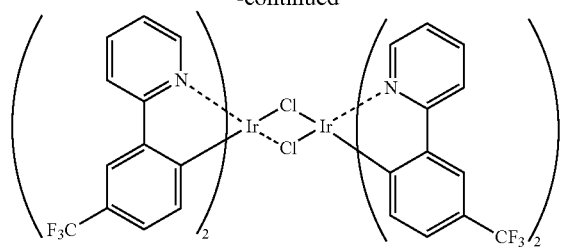
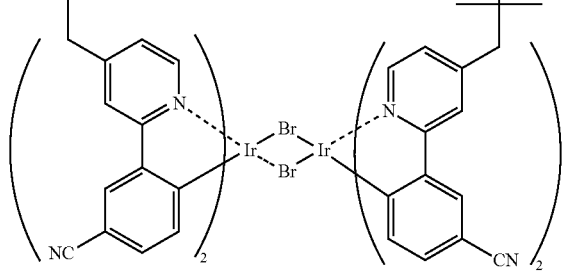
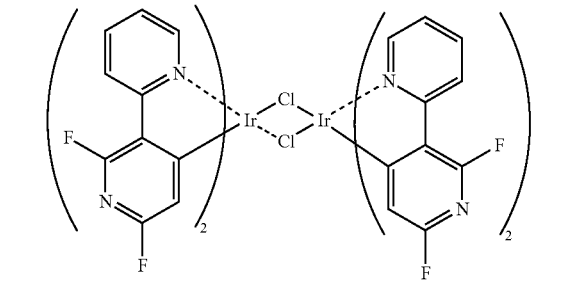
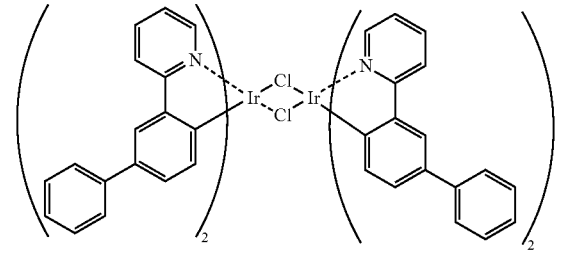
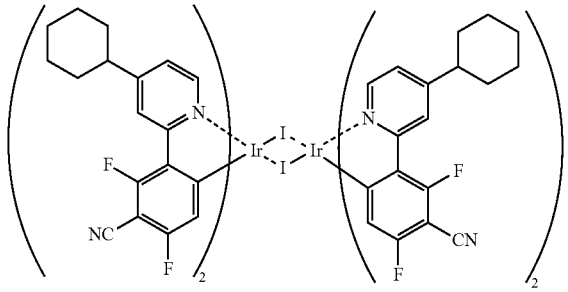
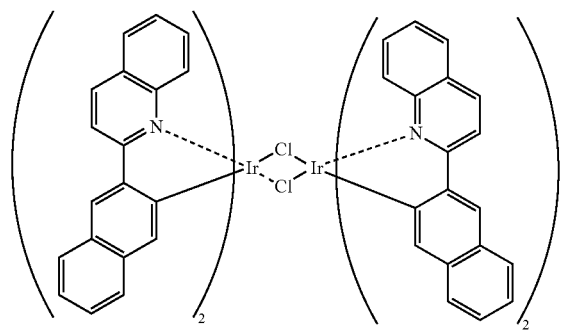
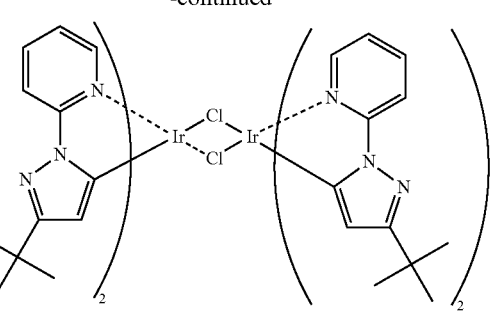
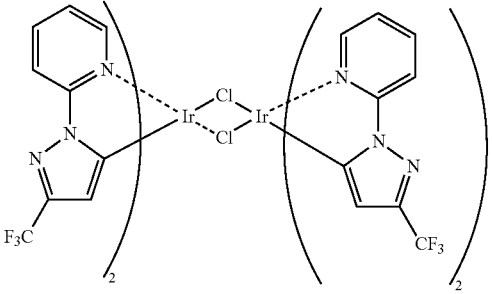
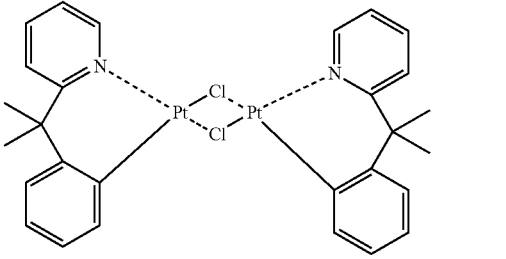
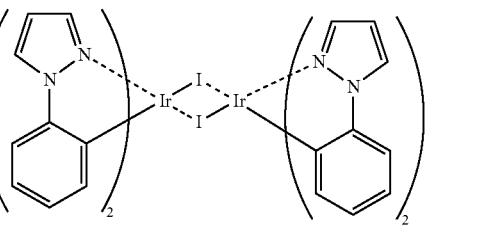
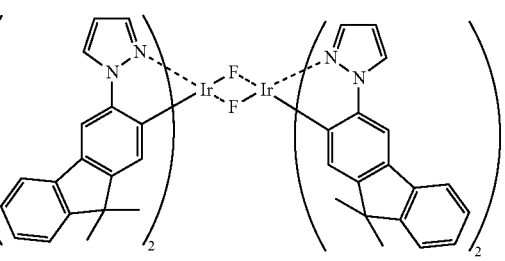
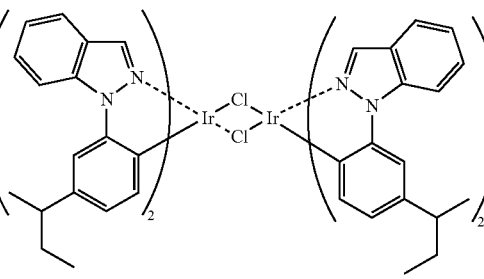

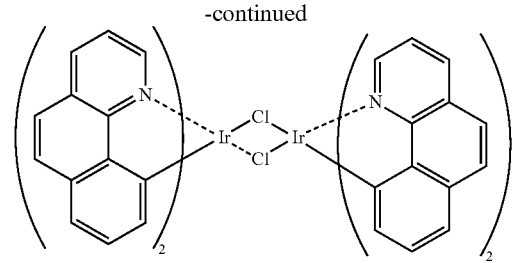
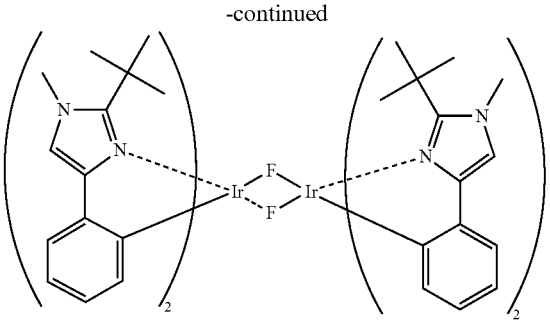
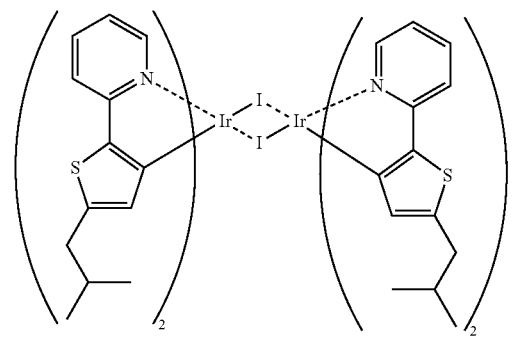
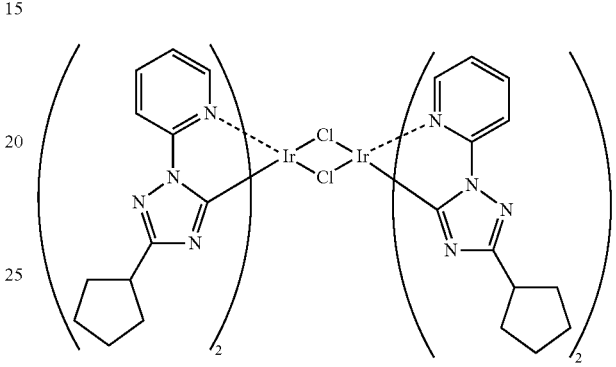
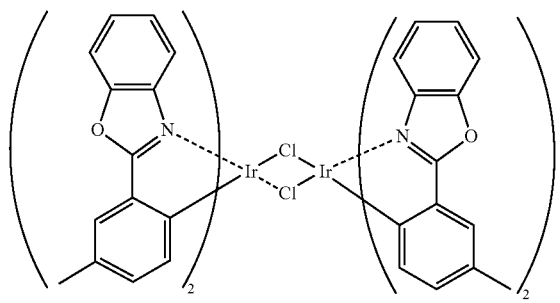
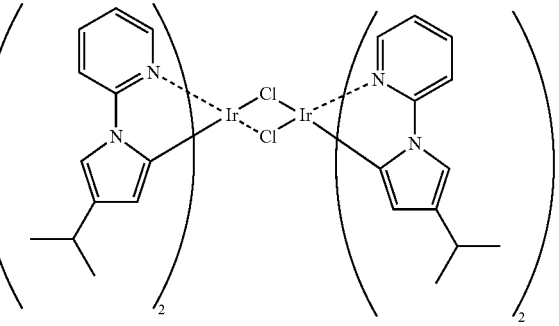
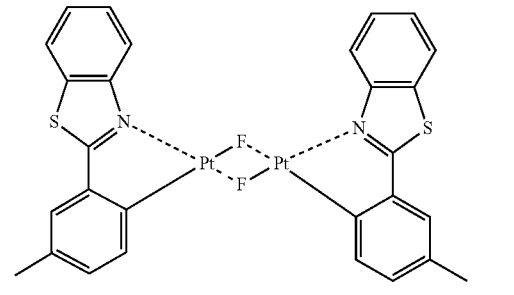
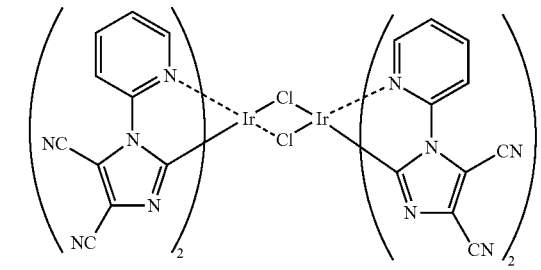
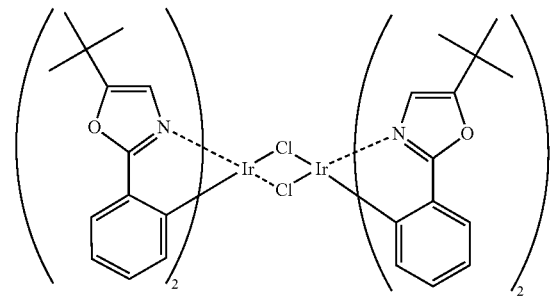
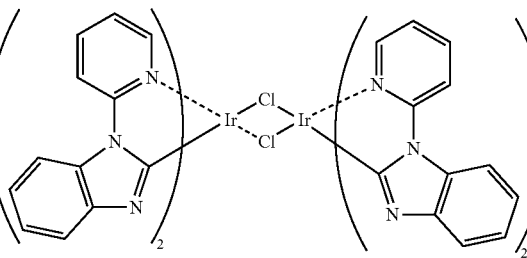

-continued
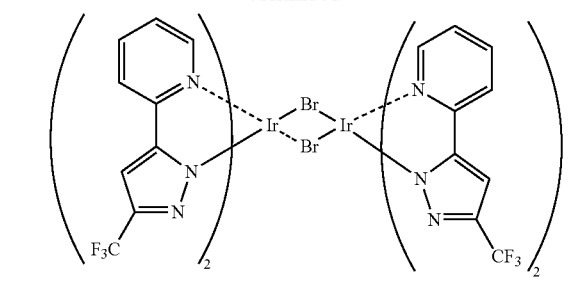
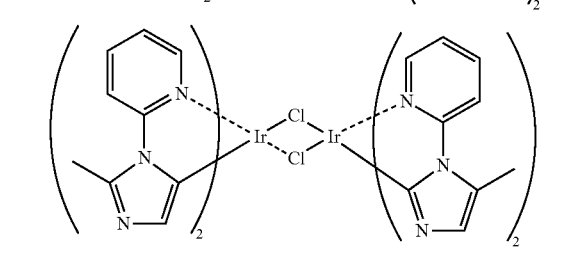
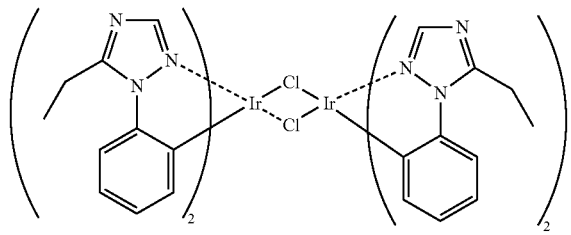
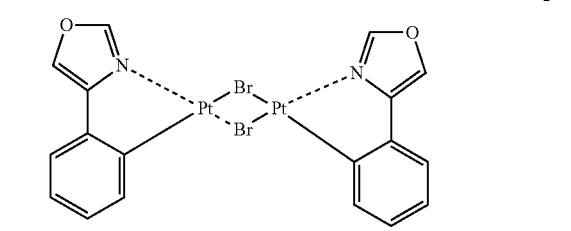
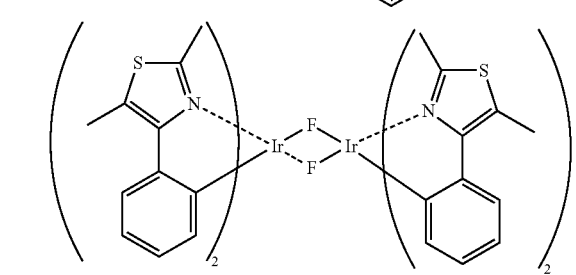
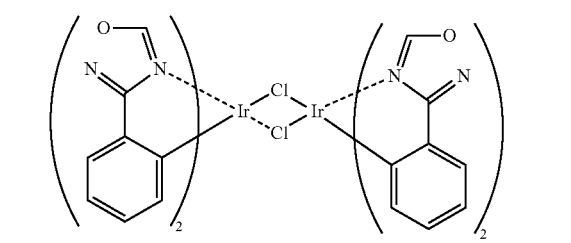
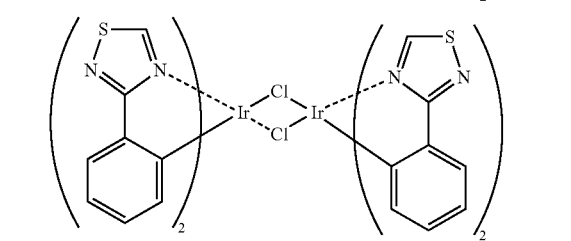
-continued
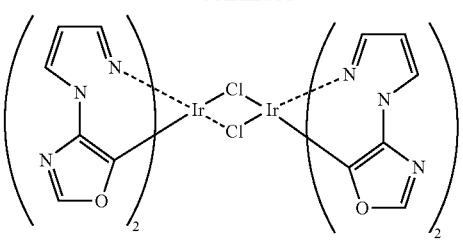
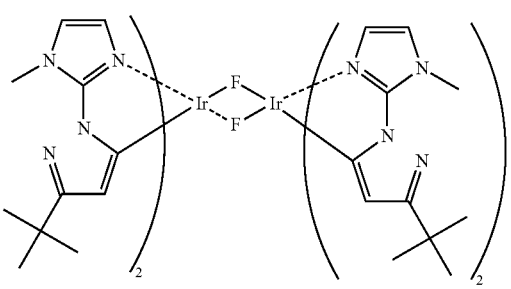
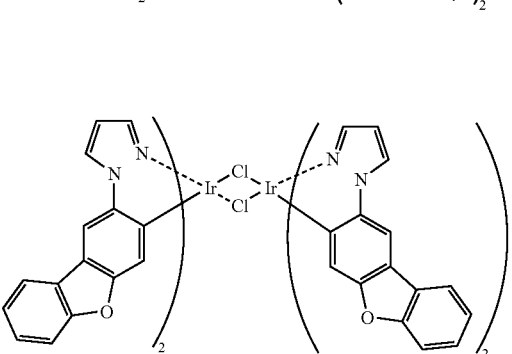
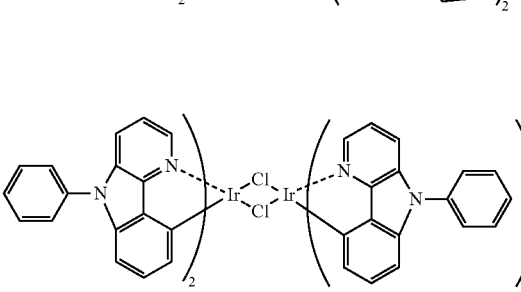
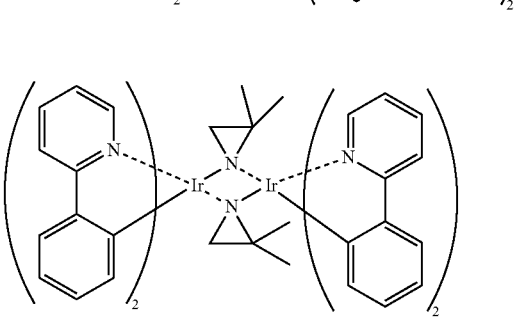
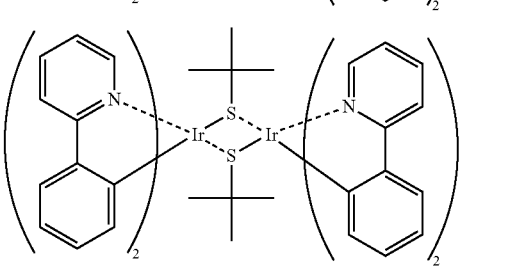

-continued

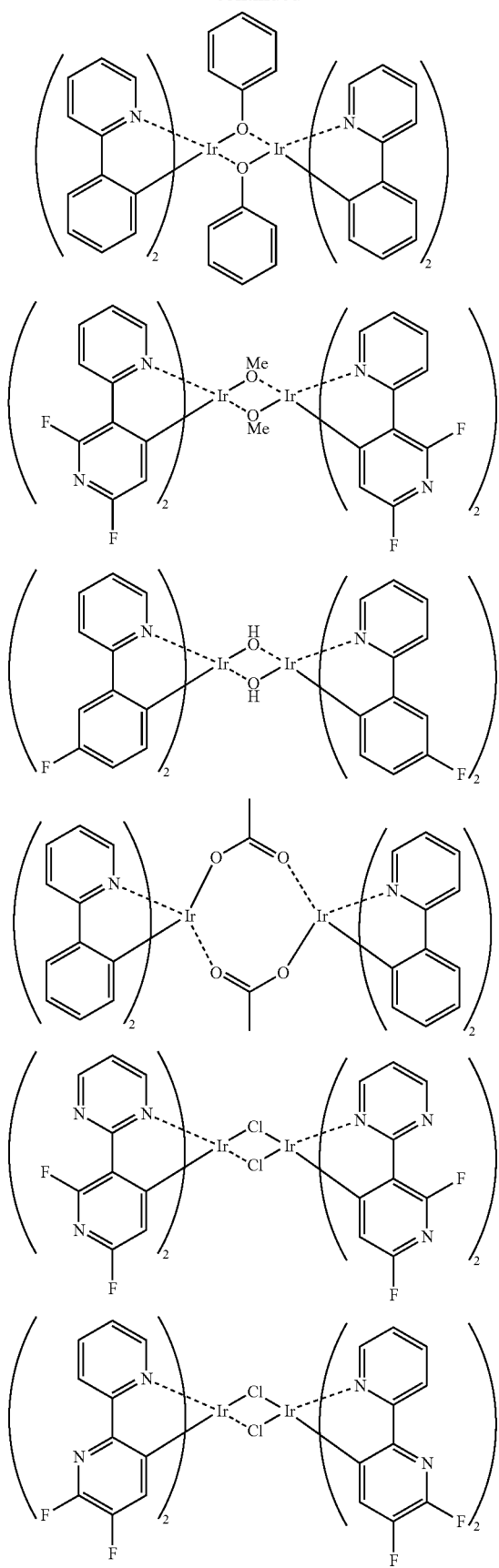

In the present forming method, the mole ratio between the compound (1b) which is a bridged metal dimer and the compound (1a) which is a ligand rendered functional by an organic metal, that is (1b):(1a), is preferably from 1:2 to 1:50, far preferably from 1:2 to 1:25, particularly preferably from 1:2 to 1:10.

Examples of a reaction medium which can be used suitably in the reaction between a compound represented by the formula (1a) and a compound represented by the formula (1b) include linear or cyclic ethers, preferably diethyl ether, methyl tert-butyl ether, tetrahydrofuran (THF), dioxane and tetrahydropyran, oligoethers or polyethers such as poly(ethylene glycol) diethyl ether, linear or cyclic dialkylureas such as hexamethylphosphoric acid amide (HMPA), N,N'-dimethylpropyleneurea (DMPU) and N,N'-dimethylethyleneurea(1,3-dimethylimidazolidine-2-one), aromatic hydrocarbons such as benzene, toluene and xylene, and halogenated hydrocarbons such as dichloromethane and chloroform. These reaction solvents are preferably dehydrated (anhydrous) solvents.

In the invention, it is appropriate that the reaction be carried out in a temperature range of −78° C. to 150° C., preferably in a temperature range of −78° C. to 70° C.

In the invention, it is appropriate that the reaction be pursued over 0.5 to 48 hours, preferably over 1 to 24 hours. So long as the reaction time is in such a range, sufficient conversion of a metal-containing starting material used becomes possible, and yield loss and contamination of the product can be prevented.

Additionally, reactions described hereinafter, namely reaction between a compound represented by the formula (2a) and a compound represented by the formula (2b), reaction between a compound represented by the formula (3a) and a compound represented by the formula (3b), and reaction between a compound represented by the formula (4a) and a compound represented by the formula (4b), are performed under the same conditions as specified above.

Among the compounds represented by the formula (1), compounds represented by the following formula (2) are preferred. By taking on a condensed arene ring structure, positions at which a metal ($M^{21}$)-carbon bond and a metal ($M^{21}$)-nitrogen bond are to be formed become limited (because $D^{13}$ and $B^{11}$ in the formula (1) have undergone substitution), and therefore compounds represented by the formula (2) become easy to synthesize. The compounds represented by the formula (2) can be prepared by allowing compounds represented by the formula (2a) to react with compounds represented by the formula (2b).

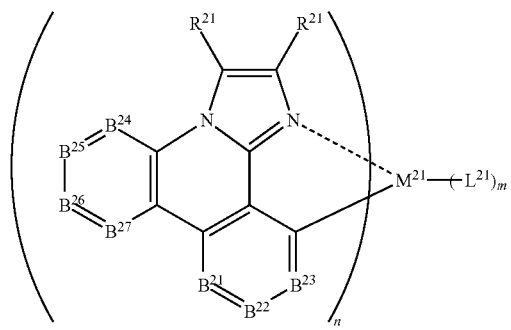

(2)

In the formula (2), $M^{21}$ represents Ir or Pt, each of $R^{21}$s independently represents a hydrogen atom or a substituent and each $R^{21}$ may be the same as or different from every other $R^{21}$, each of $B^{21}$ to $B^{27}$ independently represents a nitrogen atom or C—$R^{22}$, and $R^{22}$ represents a hydrogen atom or a substituent and each $R^{22}$ may be the same as or different from every other $R^{22}$.

In the formula (2), $M^{21}$, $L^{21}$, n and m have the same meanings as $M^{11}$, $L^{11}$, n and m in the formula (1), respectively, and their preferred ranges are also the same as the ranges preferred as $M^{11}$, $L^{11}$, n and m in the formula (1), respectively.

Each of $B^{21}$ to $B^{27}$ independently represents a nitrogen atom or C—$R^{22}$, and $R^{22}$ represents a hydrogen atom or a substituent. $B^{21}$ to $B^{27}$ have no particular restriction as to their combination, but the number of nitrogen atoms in the combination is preferably from 0 to 2, far preferably 0 or 1.

The preferred range of each $R^{21}$ is the same as that of $R^{1a}$ and $R^{1b}$ each in the partial structure (1-1). It is preferable that at least one of $R^{21}$s is not a hydrogen atom, but a substituent. This is because the tendency of $R^{21}$s to cause hydrogen-metal exchange reaction is reduced, and thereby it becomes easy to derive compounds represented by the formula (2a) from starting materials at high yields.

The preferred range of $R^{22}$ is the same as that of $R^{11}$ in the formula (1).

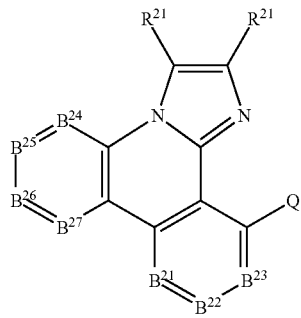

(2a)

In the formula (2a), Q represents an alkali metal, an alkaline earth metal, an alkaline earth metal halide, a trialkyltin, zinc or a zinc halide, which each may further have an arbitrary organic group as a substituent. $R^{21}$ and $B^{21}$ to $B^{27}$ have the same meanings as $R^{21}$ and $B^{21}$ to $B^{27}$ in the formula (2), respectively.

$$[L^{21}{}_k M^{21}(\mu\text{-}Y)]_2 \quad (2b)$$

The formula (2b) stands for a bridged metal dimer, Y is F, Cl, Br, I, $OR^{23}$, $R^{23}COO$, $SR^{23}$ or $N(R^{23})_2$, and each of $R^{23}$s is independently a hydrogen atom, an aliphatic hydrocarbon group having 1 to 20 carbon atoms or an aromatic hydrocarbon group. k is 2 when $M^{21}$ is Ir, while k is 1 when $M^{21}$ is Pt. $L^{21}$, $M^{21}$, Y and $R^{23}$ have the same meanings as $L^{11}$, $M^{11}$, Y and $R^{13}$ in the formula (1b), respectively, and their preferred ranges are also the same as the ranges preferred as $L^{11}$, $M^{11}$, Y and $R^{13}$ in the formula (1b), respectively. μ is a symbol standing for a bridging ligand.

Among the compounds represented by the formula (1), compounds represented by the following formula (3) are also preferred. By taking on a condensed arene ring structure, positions at which a metal ($M^{31}$)-carbon bond and a metal ($M^{31}$)-nitrogen bond are to be formed become limited (because $D^{13}$ and $B^{11}$ in the formula (1) have undergone substitution), and therefore compounds represented by the formula (3) become easy to synthesize. The compounds represented by the formula (3) can be prepared by allowing compounds represented by the formula (3a) to react with compounds represented by the formula (3b).

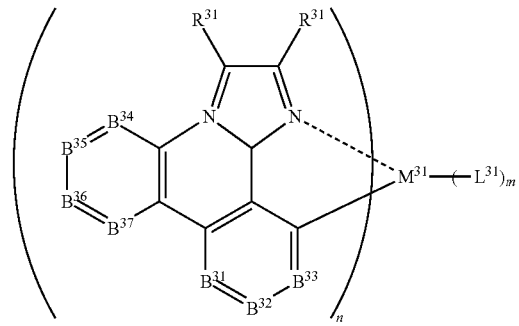

(3)

In the formula (3), $M^{31}$ represents Ir or Pt, each of $R^{31}$s independently represents a hydrogen atom or a substituent and each $R^{31}$ may be the same as or different from every other $R^{31}$, each of $B^{31}$ to $B^{37}$ independently represents a nitrogen atom or C—$R^{32}$, and $R^{32}$ represents a hydrogen atom or a substituent and each $R^{32}$ may be the same as or different from every other $R^{32}$. $L^{31}$ represents atoms forming a bidentate ligand. n represents an integer of 1 to 3 and m represents an integer of 0 to 2, provided that n+m is 2 or 3.

In the formula (3), $M^{31}$, $L^{31}$, $R^{32}$, n and m have the same meanings as $M^{11}$, $L^{11}$, $R^{11}$, n and m in the formula (1), respectively, and their preferred ranges are also the same as the ranges preferred as $M^{11}$, $L^{11}$, $R^{11}$, n and m in the formula (1), respectively.

Each of $B^{31}$ to $B^{37}$ independently represents a nitrogen atom or C—$R^{32}$, and $R^{32}$ represents a hydrogen atom or a substituent. $B^{31}$ to $B^{37}$ have no particular restriction as to their combination, but the number of nitrogen atoms in the combination is preferably from 0 to 2, far preferably 0 or 1.

The preferred range of each $R^{31}$ is the same as that of $R^{1c}$ and $R^{1e}$ each in the partial structure (1-2). It is preferable that at least one of $R^{31}$s is not a hydrogen atom, but a substituent. This is because the tendency of $R^{31}$s to cause hydrogen-metal exchange reaction is reduced, and thereby it becomes easy to derive compounds represented by the formula (3a) from starting materials at high yields.

The preferred range of $R^{32}$ is the same as that of $R^{11}$ in the formula (1).

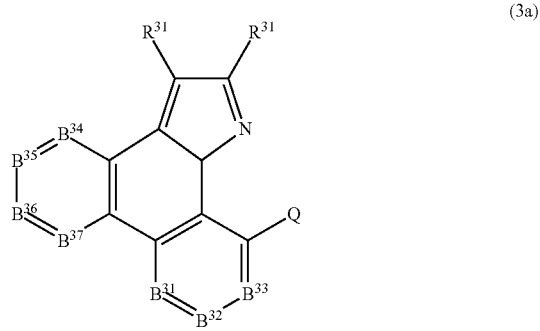

(3a)

In the formula (3a), Q represents an alkali metal, an alkaline earth metal, an alkaline earth metal halide, a trialkyltin, zinc or a zinc halide, which each may further have an arbitrary organic group as a substituent. And $R^{31}$ and $B^{31}$ to $B^{37}$ have the same meanings as $R^{31}$ and $B^{31}$ to $B^{37}$ in the formula (3), respectively.

$$[L^{31}{}_k M^{31}(\mu\text{-}Y)]_2$$ (3b)

In the formula (3b), Y is F, Cl, Br, I, $OR^{33}$, $R^{33}COO$, $SR^{33}$ or $N(R^{33})_2$, and each of $R^{33}$s is independently a hydrogen atom, an aliphatic hydrocarbon group having 1 to 20 carbon atoms or an aromatic hydrocarbon group. k is 2 when $M^{31}$ is Ir, while k is 1 when $M^{31}$ is Pt. $L^{31}$, $M^{31}$, Y and $R^{33}$ have the same meanings as $L^{11}$, $M^{11}$, Y and $R^{13}$ in the formula (1b), respectively, and their preferred ranges are the same as the ranges preferred as $L^{11}$, $M^{11}$, Y and $R^{13}$ in the formula (1b), respectively. μ is a symbol standing for a bridging ligand.

The compounds represented by the formula (1a) are preferably prepared by reaction between compounds represented by the following formula (1c) and at least one reactant selected from alkali metals, organolithium compounds, alkaline earth metals or alkylmagnesium halides.

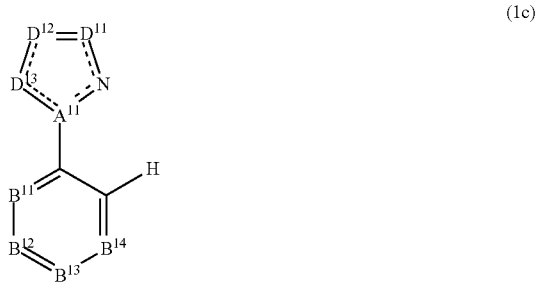

(1c)

In the formula (1c), $A^{11}$, $B^{11}$ to $B^{14}$, and $D^{11}$ to $D^{13}$ have the same meanings as $A^{11}$, $B^{11}$, to $B^{14}$, and $D^{11}$ to $D^{13}$ in the formula (1a), respectively.

Examples of an alkali metal, an organolithium compound, an alkaline earth metal and an alkylmagnesium halide which are usable in the reaction include lithium, n-butyl lithium, s-butyl lithium, t-butyl lithium, lithium naphthalenide, lithium biphenylide, phenyl lithium, lithium diisopropylamide, lithium 2,2,6,6-tetramethylpiperidide, magnesium, methylmagnesium bromide, methylmagnesium chloride, ethylmagnesium bromide, ethylmagnesium chloride, propylmagnesium bromide and propylmagnesium chloride. Of these reactants, n-butyl lithium, t-butyl lithium, lithium diisopropylamide, lithium 2,2,6,6-tetramethylpiperidide, magnesium, ethylmagnesium bromide, ethylmagnesium chloride, propylmagnesium bromide and propylmagnesium chloride are preferable to the others, and far preferred ones are n-butyl lithium, ethylmagnesium bromide, ethylmagnesium chloride, propylmagnesium bromide and propylmagnesium chloride.

When an organolithium compound is used, a co-solvent or a base (e.g. potassium tert-butoxide) for activating the organolithium compound may be added. And examples of the co-solvent include amine compounds, such as tetramethylethylenediamine (TMEDA), 1,4-diazabicyclo[2.2.2]octane (DABCO) and sparteine, and amide compounds, such as hexamethylphosphoric acid triamide (HMPA) and N,N'-dimethylpropyleneurea (DMPU).

When an alkaline earth metal is used, iodine or an alkyl halide (e.g. methyl iodide, dibromoethane, ethyl bromide) for activating the alkaline earth metal may be added.

When an alkylmagnesium halide is used, a lithium salt (e.g. lithium chloride, lithium bromide), zinc chloride or an alkyl lithium (e.g. n-butyl lithium) for activating the alkylmagnesium halide may be added.

Additionally, reactions of compounds represented by the formula (2c) or compounds represented by the formula (3c) or compounds represented by the formula (4c) with any one kind of reactant chosen from alkali metals, organolithium compounds, alkaline earth metals, or alkylmagnesium halides are conducted under the same conditions as mentioned hereinbefore.

The compounds represented by the formula (2a) are preferably prepared by reaction between compounds represented by the following formula (2c) and at least one reactant selected from alkali metals, organolithium compounds, alkaline earth metals or alkylmagnesium halides.

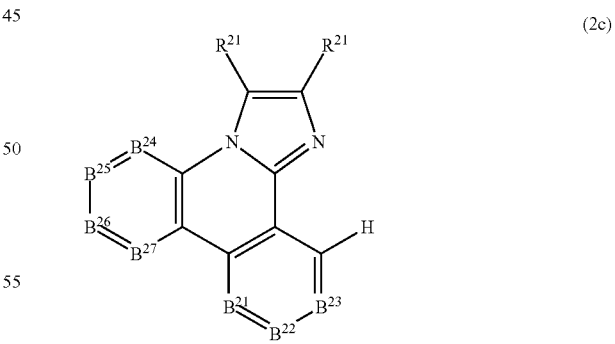

(2c)

In the formula (2c), $R^{21}$ and $B^{21}$ to $B^{27}$ have the same meanings as $R^{21}$ and $B^{21}$ to $B^{27}$ in the formula (2a), respectively.

The compounds represented by the formula (3a) are preferably prepared by reaction between compounds represented by the following formula (3c) and at least one reactant selected from alkali metals, organolithium compounds, alkaline earth metals or alkylmagnesium halides.

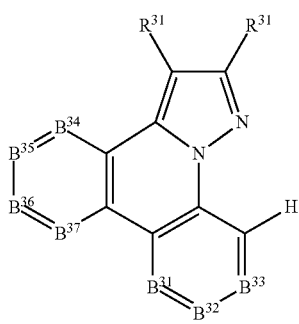

(3c)

In the formula (3c), $R^{31}$ and $B^{31}$ to $B^{37}$ have the same meanings as $R^{31}$ and $B^{31}$ to $B^{37}$ in the formula (3a), respectively.

[Compounds Represented by Formula (4)]

Another forming method according to the invention is a method of forming compounds having nitrogen-containing heterocyclic 5-membered rings as partial structures of ligands thereof through the use of metal-metal exchange reaction, and more specifically, a method of forming compounds represented by the formula (4) by allowing compounds represented by the formula (4a) to react with compounds represented by the formula (4b).

The compounds represented by the formula (4) are illustrated below in detail.

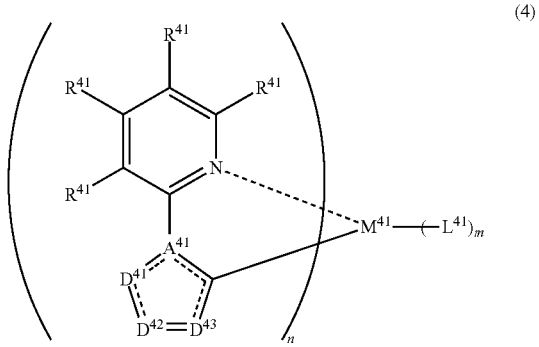

(4)

In the formula (4), $M^{41}$ represents Ir or Pt, each of $R^{41}$s independently represents a hydrogen atom or a substituent, each of $A^{41}$s independently represents a nitrogen atom or a carbon atom, and each of $D^{41}$ to $D^{43}$ independently represents an atom chosen from carbon, nitrogen, oxygen, sulfur or silicon. Each of the atom-atom bonds in the 5-membered ring formed from $D^{41}$ to $D^{43}$, $A^{41}$ and a C atom is a single bond or a double bond. When $D^{41}$ to $D^{43}$ have the possibility of further undergoing substitution, they each may have a substituent. $L^{41}$ represents atoms forming a bidentate ligand. n represents an integer of 1 to 3 and m represents an integer of 0 to 2, provided that n+m is 2 or 3.

$A^{41}$ represents a nitrogen atom or a carbon atom and, together with $D^{41}$ to $D^{43}$ and a carbon atom, forms a nitrogen-containing 5-membered heterocyclic ring.

Each of $D^{41}$ to $D^{43}$ independently represents an atom chosen from carbon, nitrogen, oxygen, sulfur or silicon. The atom-atom bonds in the 5-membered ring formed from $D^{41}$ to $D^{43}$, $A^{41}$ and a carbon atom are not particularly restricted, and may make any combinations of single and double bonds. Each of $D^{41}$ to $D^{43}$ is preferably a carbon atom or a nitrogen atom.

The number of nitrogen atoms in the 5-membered ring formed from $D^{41}$ to $D^{43}$, $A^{41}$ and a nitrogen atom is preferably from 1 to 3, far preferably 1 or 2.

The 5-membered ring formed from $D^{41}$ to $D^{43}$, $A^{41}$ and a carbon atom is preferably an aromatic ring.

When $D^{41}$ to $D^{43}$ have the possibility of further undergoing substitution, they each may have a substituent chosen from the substituent group A.

Suitable examples of the substituent include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group and a silyl group. Of these substituents, a substituted or unsubstituted alkyl group, a cycloalkyl group, an aryl group, an amino group, an alkoxy group, an aryloxy group, a cyano group, a fluorine atom and a heterocyclic group are preferable to the others, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

The substituents may combine with each other and complete a condensed ring. Examples of a ring formed from such substituents include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

As to the 5-membered ring formed from $D^{41}$ to $D^{43}$, $A^{41}$ and a carbon atom, the especially preferred combination is a case where $A^{41}$ and $D^{41}$ are nitrogen atoms and $D^{42}$ and $D^{43}$ are carbon atoms. This case is expressed as the following partial structure in the concrete. When the 5-membered ring formed from $D^{41}$ to $D^{43}$, $A^{41}$ and a carbon atom has the following partial structure, the acidity of hydrogen atoms in $R^4$ is low, and therefore the hydrogen atoms in $R^4$ resist undergoing hydrogen-metal exchange reaction, and it becomes easy to derive the compound represented by the formula (4a) from a starting material at a high yield. In addition, when the following partial structure is present in a compound represented by the formula (4), the lowest excited triplet-state energy level of the compound is heightened. Therefore it is favorable for preparation of a shortwave phosphorescent material to have such partial structure in the compound.

Partial structure (4-1)

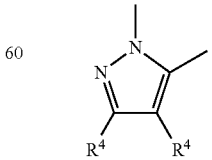

Each of $R^4$s independently represents a hydrogen atom or a substituent. Each $R^4$ may be the same as or different from the other $R^4$. Each $R^4$ may further have a substituent, and the substituent can be chosen from the substituent group A.

Alternatively, the two $R^4$s may combine with each other and complete a condensed ring, and examples of a ring formed from them include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

Suitable examples of $R^4$ include an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group and a silyl group. Of these substituents, a substituted or unsubstituted alkyl group, a cycloalkyl group, an aryl group, an amino group, an alkoxy group, an aryloxy group, a cyano group, a fluorine atom and a heterocyclic group are preferable to the others, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group.

As the substituent represented by $R^{41}$, any one included in the substituent group A can be adopted.

Each $R^{41}$ may be the same as or different from every other $R^{41}$. In addition, each $R^{41}$ may further have a substituent, and the substituent can be chosen from the substituent group A. Alternatively, any pair of adjacent $R^{41}$s may combine with each other and complete a condensed ring, and examples of a ring formed from them include a benzene ring, a pyridine ring, a pyrazine ring, a pyrimidine ring, a triazine ring, a pyridazine ring, a pyrrole ring, a pyrazole ring, an imidazole ring, a triazole ring, an oxazole ring, an oxadiazole ring, a thiazole ring, a thiadiazole ring, a furan ring, a thiophene ring, a selenophene ring, a silole ring, a germole ring and a phosphole ring.

The substituent preferable as $R^4$ is an alkyl group, a cycloalkyl group, an aryl group, an amino group, an alkoxy group, an aryloxy group, an acyl group, an alkoxycarbonyl group, an aryloxycarbonyl group, an acyloxy group, a sulfonylamino group, a sulfamoyl group, a carbamoyl group, an alkylthio group, an arylthio group, a heterocyclylthio group, a sulfonyl group, a sulfinyl group, an ureido group, a phosphorylamido group, a hydroxyl group, a mercapto group, a halogen atom, a sulfo group, a carboxyl group, a nitro group, a sulfino group, a heterocyclic group or a silyl group, still more preferably a substituted or unsubstituted alkyl group, a fluorine atom, a methoxy group, an aryl group or a cyano group. In particular, the substituent is preferably a substituted or unsubstituted alkyl group, a fluorine atom or a cyano group, and most preferably a methyl group, a trifluoromethyl group, a fluorine atom or a cyano group. It is preferable that at least one of $R^4$s is not a hydrogen atom, but a substituent. This is because the tendency of $R^{41}$s to cause hydrogen-metal exchange reaction is reduced, and thereby it becomes easy to derive compounds represented by the formula (4a) from starting materials at good yields.

$L^{41}$ represents atoms forming a bidentate ligand. The bidentate ligand represented by $L^{41}$ has no particular restriction, but it is preferably a bidentate ligand that $L^{41}$, together with $M^{41}$, forms a coordinate bond via its nitrogen atom, and besides, one of its carbon, oxygen and nitrogen atoms and $M^{41}$ form a covalent bond. And the bidentate ligand far preferred as $L^{41}$ is a bidentate ligand whose nitrogen atom and $M^{41}$ form a coordinate bond, and besides, whose carbon atom and $M^{41}$ form a covalent bond. Examples of such a bidentate ligand include substituted or unsubstituted phenylpyridine, phenylpyrazole, phenylimidazole, pyridylimidazole, phenyltriazole, phenyltetrazole, pyridiylpyridine, imidazolylpyridine, pyrazolylpyridine and triazolylpyridine. Of these ligands, phenylpyridine, phenylpyrazole, phenylimidazole, pyridylimidazole, pyridylpyridine and pyrazolylpyridine are preferable to the others. Additionally, these ligands may further have substituents as recited above.

It is further preferred that $L^{41}$ have a structure chosen from the foregoing bidentate-ligand group L. In the group L, L-a to L-d are preferred, L-a and L-b are far preferred, and L-a in particular is preferred.

n represents an integer of 1 to 3, and when $M^{41}$ is Ir, n is 3 or 1, preferably 3. When $M^{41}$ is Pt, n is 2 or 1, preferably 2.

m represents an integer of 0 to 2, and when $M^{41}$ is Ir, m is 0 or 2, preferably 0. When $M^{41}$ is Pt, m is 0 or 1, preferably 0.

n+m is 3 when $M^{41}$ is Ir, while it is 2 when $M^{41}$ is Pt.

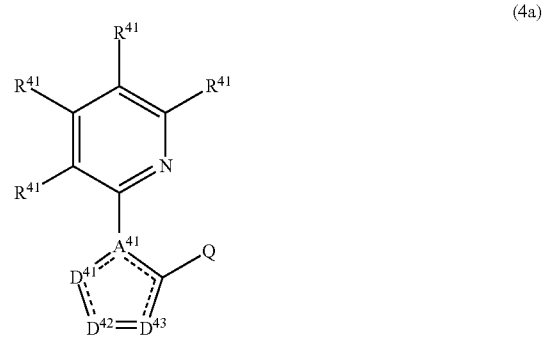

(4a)

In the formula (4a), Q represents an alkali metal, an alkaline earth metal, an alkaline earth metal halide, a trialkyltin, zinc or a zinc halide, which each may further have an arbitrary organic group as a substituent. $R^{41}$s, $A^{41}$ and $D^{41}$ to $D^{43}$ have the same meanings as $R^{41}$s, $A^{41}$ and $D^{41}$ to $D^{43}$ in the formula (4), respectively.

$$[L^{41}{}_kM^{41}(\mu\text{-}Y)]_2 \qquad (4b)$$

The formula (4b) stands for a bridged metal dimer, Y is F, Cl, Br, I, $OR^{42}$, $R^{42}COO$, $SR^{42}$ or $N(R^{42})_2$, and each of $R^{42}$s is independently a hydrogen atom, an aliphatic hydrocarbon group having 1 to 20 carbon atoms or an aromatic hydrocarbon group. k is 2 when $M^{41}$ is Ir, while k is 1 when $M^{31}$ is Pt. The preferred ranges of $L^{41}$, $M^{41}$, Y and $R^{42}$ are the same as the ranges preferred as $L^{11}$, $M^{11}$, Y and $R^{13}$ in the formula (1b), respectively. μ is a symbol standing for a bridging ligand.

The compounds represented by the formula (4a) are preferably prepared by reaction between compounds represented by the following formula (4c) and at least one reactant selected from alkali metals, organolithium compounds, alkaline earth metals or alkylmagnesium halides.

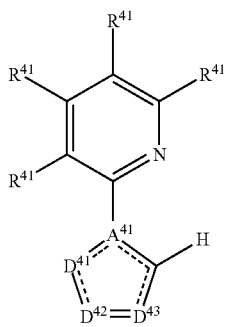

(4c)

In the formula (4c), $R^{41}$s, $A^{41}$ and $D^{41}$ to $D^{43}$ have the same meanings as $R^{41}$s, $A^{41}$ and $D^{41}$ to $D^{43}$ in the formula (4a), respectively.

Conditions under which the reaction between each of the compounds represented by the formula (1c), (2c), (3c) or (4c) and an alkali metal, an organolithium compound, an alkaline earth metal or an alkylmagnesium halide is conducted are described below.

Examples of a solvent usable in the reaction include linear or cyclic ethers such as diethyl ether, methyl tert-butyl ether, THF, dioxane and tetrahydropyran, aromatic hydrocarbons such as benzene, toluene and xylene, and aliphatic hydrocarbons such as petroleum ether, n-hexane and n-pentane.

The range of temperatures at which the reaction is conducted is preferably from −100° C. to 150° C., far preferably from −78° C. to 70° C., further preferably from −78° C. to 10° C.

The reaction is conducted over 0.5 to 48 hours, preferably over 3 to 24 hours.

[Compounds Represented by Formula (5)]

Still another forming method according to the invention is a method of forming compounds having nitrogen-containing heterocyclic 5-membered rings as partial structures of ligands thereof through the use of metal-metal exchange reaction, and more specifically, a method of forming compounds represented by the formula (5) by allowing compounds represented by the formula (5a) to react with compounds represented by the formula (5b) or (5c).

The compounds represented by each of the formulae (5), (5a), (5b) and (5c) are illustrated below in detail.

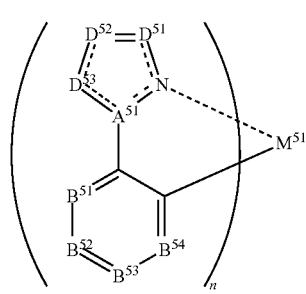

(5)

In the formula (5), $M^{51}$ represents Ir or Pt, each of $A^{51}$s independently represents a nitrogen atom or a carbon atom, each of $B^{51}$ to $B^{54}$ independently represents a nitrogen atom or C—$R^{51}$, and $R^{51}$ represents a hydrogen atom or a substituent. Each $R^{51}$ may be the same as or different from every other $R^{51}$. And each of $D^{51}$ to $D^{53}$ independently represents an atom chosen from carbon, nitrogen, oxygen, sulfur or silicon. Each of the atom-atom bonds in the 5-membered ring formed from $D^{51}$ to $D^{53}$, $A^{51}$ and an N atom is a single bond or a double bond. When $D^{51}$ to $D^{53}$ have the possibility of further undergoing substitution, they each may have a substituent. n is 3 when $M^{51}$ is Ir, while it is 2 when $M^{51}$ is Pt.

In the formula (5), $A^{51}$, $B^{51}$ to $B^{54}$, $D^{51}$ to $D^{53}$ and $R^{51}$ have the same meanings as $A^{11}$, $B^{11}$ to $B^{14}$, $D^{11}$ to $D^{13}$ and $R^{11}$ in the formula (1), respectively, and their preferred ranges are also the same as the ranges preferred as $A^{11}$, $B^{11}$ to $B^{14}$, $D^{11}$ to $D^{13}$ and $R^{11}$ in the formula (1), respectively.

The 5-membered ring formed from $A^{51}$, $D^{51}$ to $D^{53}$ and a nitrogen atom is preferably an aromatic ring.

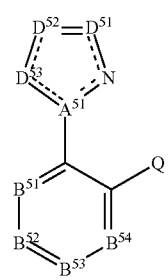

(5a)

In the formula (5a), Q represents an alkali metal, an alkaline earth metal, an alkaline earth metal halide, a trialkyltin, zinc or a zinc halide, which each may further have an arbitrary organic group as a substituent. $A^{51}$, $B^{51}$ to $B^{54}$ and $D^{51}$ to $D^{53}$ have the same meanings as $A^{51}$, $B^{51}$ to $B^{54}$ and $D^{51}$ to $D^{53}$ in the formula (5), respectively.

$$M^{51}(ZR^{52}_2)_m X_m \quad (5b)$$

In the formula (5b), X is Cl, Br or I, Z is an O atom or an S atom, and each of $R^{52}$s is independently a hydrogen atom or a substituent. $M^{51}$ has the same meaning as $M^{51}$ in the formula (5). m is 3 when $M^{51}$ is Ir, while it is 2 when $M^{51}$ is Pt.

Z is an O atom or an S atom, preferably an S atom.

X is preferably Br or Cl, particularly preferably Cl.

As a substituent represented by each $R^{52}$, any substituent in the substituent group A can be adopted.

Of the two $R^{52}$s, one may be the same as or different from the other. In addition, each $R^{52}$ may further have a substituent, and the substituent can be chosen from the substituent group A.

Each $R^{52}$ is preferably an alkyl group, a cycloalkyl group, an aryl group or a heterocyclic group, far preferably a substituted or unsubstituted alkyl, cycloalkyl or aryl group.

Alternatively, the two $R^{52}$s may combine with each other and form a ring. Examples of the ring formed include a tetrahydrothiophene ring, a pentamethylenesulfide ring, a dithian ring, a tetrahydrofuran ring, a dioxane ring and a tetrahydropyran ring.

When Z is an S atom and $R^{52}$ is a substituted or unsubstituted alkyl group, the total number of carbon atoms in the two $R^{52}$s is preferably from 4 to 20, far preferably from 6 to 20, particularly preferably from 8 to 20. This is because, when the number of carbon atoms is increased, the sulfide as decomposed matter comes to resist causing an odor leak, which is advantageous from a production viewpoint.

Examples of compounds represented by the formula (5b) are illustrated below, but these examples should not be construed as limiting the scope of the invention.

Ir(C₂H₅—S—C₂H₅)₃Cl₃   Ir(C₂H₅—S—C₂H₅)₃I₃
Ir(C₄H₉—S—C₄H₉)₃I₃   Ir(CH₃—S—C₁₂H₂₅)₃Cl₃
Ir(CH₃—S—C₁₂H₂₅)₃Br₃   Pt(C₃H₇—S—C₃H₇)₂Cl₂
Ir(C₆H₁₃—S—C₆H₁₃)₃Br₃   Pt(C₂H₅—S—C₅H₁₁)₃Cl₃
Pt(C₃H₇—O—C₃H₇)₂Cl₂   Pt(CH₃—S—CH₃)₂Cl₂
Ir(CH₃—S—CH₃)₂Cl₂

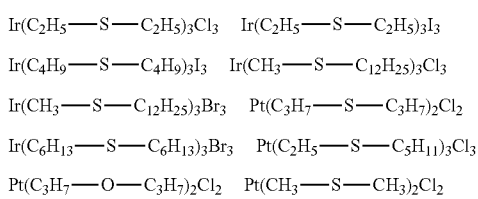
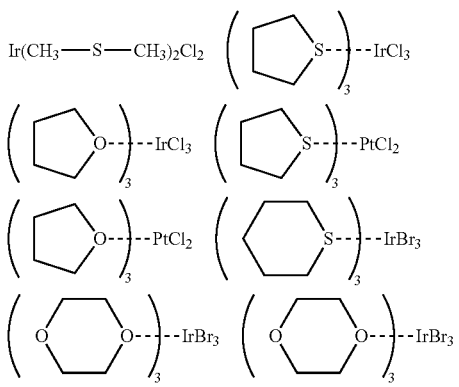
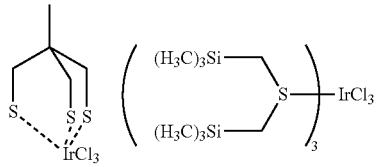
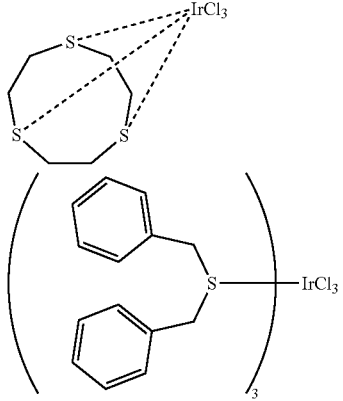
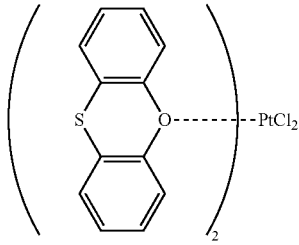
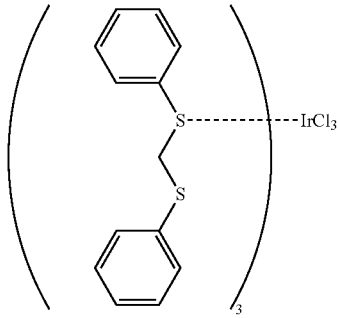

-continued

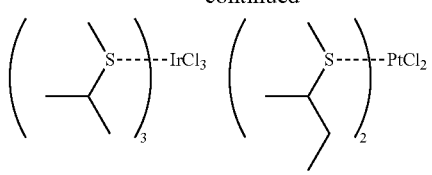
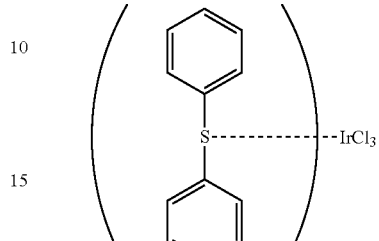

Syntheses of compounds represented by the formula (5b) are described e.g. in *Inorg. Synth.*, 1960, 6, 21, and *J. Chem. Soc. Dalton Trans.*, 1972, 613.

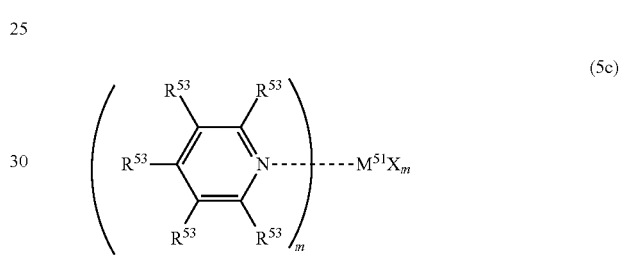

(5c)

In the formula (5c), X is Cl, Br or I, and each of $R^{53}$s is independently a hydrogen atom or a substituent. $M^{51}$ has the same meaning as $M^{51}$ in the formula (5). m is 3 when $M^{51}$ is Ir, while it is 2 when $M^{51}$ is Pt.

As a substituent represented by each $R^{53}$, any substituent in the substituent group A can be adopted.

Each $R^{53}$ may be the same as or different from every other $R^{53}$. In addition, each $R^{53}$ may further have a substituent, and the substituent can be chosen from the substituent group A.

Each $R^{53}$ is preferably a hydrogen atom, an alkyl group, a cycloalkyl group, an aryl group or a heterocyclic group, far preferably a hydrogen atom or a substituted or unsubstituted alkyl, cycloalkyl or aryl group, further preferably a hydrogen atom or a substituted or unsubstituted alkyl or aryl group, particularly preferably a hydrogen atom.

Examples of compounds represented by the formula (5c) are illustrated below, but these examples should not be construed as limiting the scope of the invention.

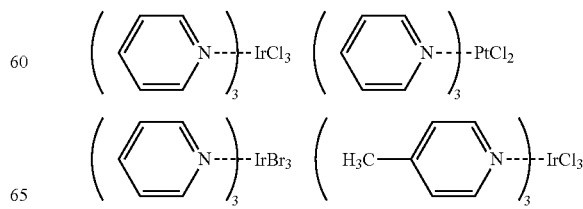

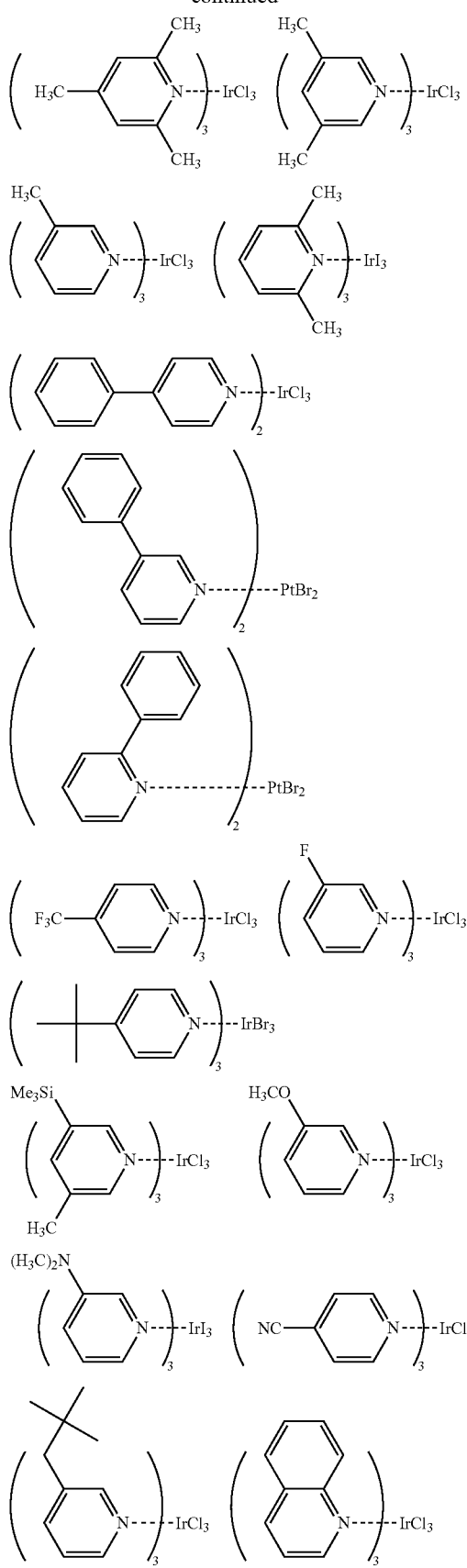

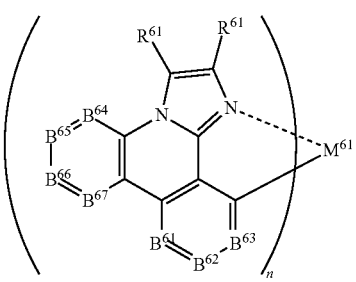

In the reaction between a compound of the formula (5a) and a compound of the formula (5b) or (5c), the mole ratio of the compound of the formula (5b) or (5c) to the compound of the formula (5a) is from 1:3 to 1:50, preferably from 1:3 to 1:25, particularly preferably from 1:3 to 1:10.

Examples of a suitable reaction medium include linear or cyclic ethers, such as diethyl ether, methyl tert-butyl ether, THF, dioxane and tetrahydropyran, oligoethers or polyethers such as poly(ethylene glycol) diethyl ether, hexamethylphosphoric acid triamide (HMPA), linear or cyclic dialkylureas such as N,N'-dimethylpropyleneurea (DMPU) and N,N'-dimethylethyleneurea (1,3-dimethylimidazolidine-2-one), aromatic hydrocarbons such as benzene, toluene and xylene, and halogenated hydrocarbons such as dichloromethane and chloroform. Of these reaction media, linear or cyclic ethers such as diethyl ether, methyl tert-butyl ether, THF, dioxane and tetrahydropyran are preferred over the others.

In the invention, the reaction is carried out in a temperature range of $-78°$ C. to $150°$ C., preferably in a temperature range of $-78°$ C. to $70°$ C.

In the invention, the reaction is conducted over 0.5 to 48 hours, preferably over 3 to 24 hours. So long as the reaction time is in such a range, sufficient conversion of a metal-containing starting material used becomes possible, and yield loss and contamination of the product can be prevented.

Additionally, reactions between compounds explained below, namely reaction between a compound represented by the following formula (6a) and a compound represented by the following formula (6b) or (6c), reaction between a compound represented by the following formula (7a) and a compound represented by the following formula (7b) or (7c) and reaction between a compound represented by the following formula (8a) and a compound represented by the following formula (8b) or (8c), are conducted under the same conditions as described above.

The compounds represented by the formula (5) are preferably compounds represented by the following formula (6). The compounds represented by the formula (6) are obtained by allowing compounds represented by the following formula (6a) to react with compounds represented by the following formula (6b) or (6c).

(6)

In the formula (6), $M^{61}$ represents Ir or Pt, each of $R^{61}$'s independently represents a hydrogen atom or a substituent and each $R^{61}$ may be the same as or different from every other $R^{61}$, each of $B^{61}$ to $B^{67}$ independently represents a nitrogen atom or C—$R^{62}$, and $R^{62}$ represents a hydrogen atom or a substituent. Each $R^{62}$ may be the same as or different from every other $R^{62}$. n is 3 when $M^{61}$ is Ir, while it is 2 when $M^{61}$ is Pt.

In the formula (6), $M^{61}$, $R^{62}$ and n have the same meanings as $M^{51}$, $R^{51}$ and n in the formula (5), respectively, and their preferred ranges are also the same as the ranges preferred as $M^{51}$, $R^{51}$ and n in the formula (5), respectively.

Each of $B^{61}$ to $B^{67}$ independently represents a nitrogen atom or C—$R^{62}$, and $R^{62}$ represents a hydrogen atom or a substituent. $B^{61}$ to $B^{67}$ are not particularly restricted as to the combination thereof, but the number of nitrogen atoms in the combination is preferably from 0 to 2, far preferably 0 or 1.

The preferred range of $R^{61}$ is the same as that of $R^{1a}$ or $R^{1b}$ in the partial structure (1-1).

The preferred range of $R^{62}$ is the same as that of $R^{51}$ in the formula (5).

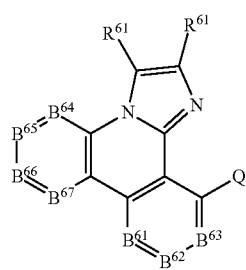
(6a)

In the formula (6a), Q represents an alkali metal, an alkaline earth metal, an alkaline earth metal halide, a trialkyltin, zinc or a zinc halide, which each may further have an arbitrary organic group as a substituent. And $R^{61}$ and $B^{61}$ to $B^{67}$ have the same meanings as $R^{61}$ and $B^{61}$ to $B^{67}$ in the formula (6), respectively.

(6b)

In the formula (6b), $M^{61}$, X, Z, $R^{63}$ and m have the same meanings as $M^{51}$, X, Z, $R^{52}$ and m in the formula (5b), respectively, and their preferred ranges are also the same as the ranges preferred as $M^{51}$, X, Z, $R^{52}$ and m in the formula (5b), respectively.

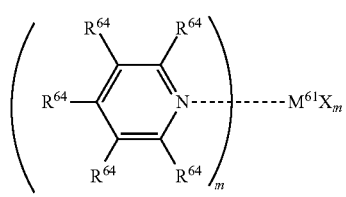
(6c)

In the formula (6c), $M^{61}$, X, $R^{64}$ and m have the same meanings as $M^{51}$, X, $R^{53}$ and m in the formula (5c), respectively, and their preferred ranges are also the same as the ranges preferred as $M^{51}$, X, $R^{53}$ and m in the formula (5c), respectively.

The compounds represented by the formula (5) are preferably compounds represented by the following formula (7). The compounds represented by the formula (7) are obtained by allowing compounds represented by the following formula (7a) to react with compounds represented by the following formula (7b) or (7c).

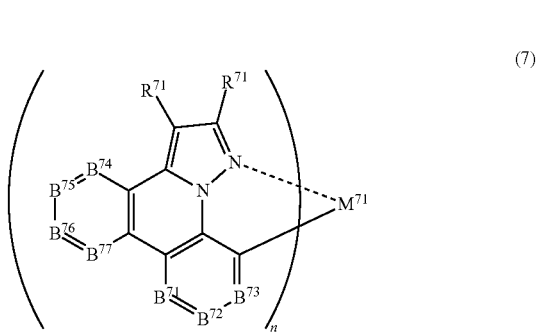
(7)

In the formula (7), $M^{71}$ represents Ir or Pt, each of $R^{71}$s independently represents a hydrogen atom or a substituent and each $R^{71}$ may be the same as or different from every other $R^{71}$, each of $B^{71}$ to $B^{77}$ independently represents a nitrogen atom or C—$R^{72}$, and $R^{72}$ represents a hydrogen atom or a substituent. Each $R^{72}$ may be the same as or different from every other $R^{72}$. n is 3 when $M^{71}$ is Ir, while it is 2 when $M^{71}$ is Pt.

In the formula (7), $M^{71}$, $R^{71}$ and n have the same meanings as $M^{51}$, $R^{51}$ and n in the formula (5), respectively, and their preferred ranges are also the same as the ranges preferred as $M^{51}$, $R^{51}$ and n in the formula (5), respectively.

Each of $B^{71}$ to $B^{77}$ independently represents a nitrogen atom or C—$R^{72}$, and $R^{72}$ represents a hydrogen atom or a substituent. $B^{71}$ to $B^{77}$ are not particularly restricted as to the combination thereof, but the number of nitrogen atoms in the combination is preferably from 0 to 2, far preferably 0 or 1.

The preferred range of $R^{71}$ is the same as that of $R^{1d}$ or $R^{1e}$ in the partial structure (1-2).

The preferred range of $R^{72}$ is the same as that of $R^{51}$ in the formula (5).

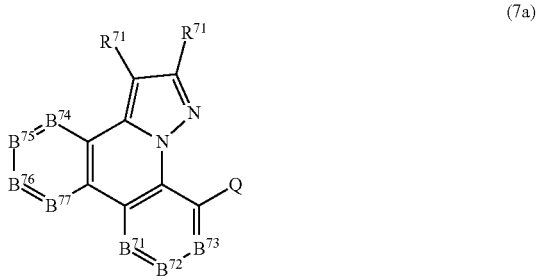
(7a)

In the formula (7a), Q represents an alkali metal, an alkaline earth metal, an alkaline earth metal halide, a trialkyltin, zinc or a zinc halide, which each may further have an arbitrary organic group as a substituent. $R^{71}$ and $B^{71}$ to $B^{77}$ have the same meanings as $R^{71}$ and $B^{71}$ to $B^{77}$ in the formula (7), respectively.

(7b)

In the formula (7b), $M^{71}$, X, Z, $R^{73}$ and m have the same meanings as $M^{51}$, X, Z, $R^{52}$ and m in the formula (5b), respectively, and their preferred ranges are also the same as the ranges preferred as $M^{51}$, X, Z, $R^{52}$ and m in the formula (5b), respectively.

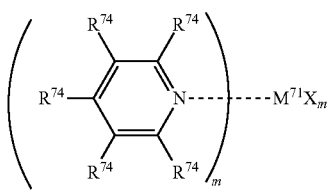
(7c)

In the formula (7c), $M^{71}$, X, $R^{74}$ and m have the same meanings as $M^{51}$, X, $R^{53}$ and m in the formula (5c), respectively, and their preferred ranges are also the same as the ranges preferred as $M^{51}$, X, $R^{53}$ and m in the formula (5c), respectively.

The compounds represented by the formula (5a) are preferably prepared by reaction between compounds represented by the following formula (5d) and at least one reactant selected from alkali metals, organolithium compounds, alkaline earth metals or alkylmagnesium halides.

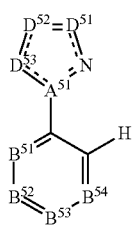
(5d)

In the formula (5d), $A^{51}$, $B^{51}$ to $B^{54}$ and $D^{51}$ to $D^{53}$ have the same meanings as $A^{51}$, $B^{51}$ to $B^{54}$ and $D^{51}$ to $D^{53}$ in the formula (5a), respectively.

The compounds represented by the formula (6a) are preferably prepared by reaction between compounds represented by the following formula (6d) and at least one reactant selected from alkali metals, organolithium compounds, alkaline earth metals or alkylmagnesium halides.

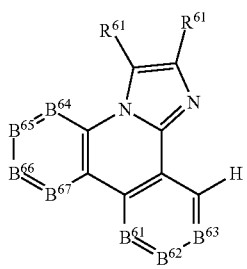
(6d)

In the formula (6d), $R^{61}$ and $B^{61}$ to $B^{67}$ have the same meanings as $R^{61}$ and $B^{61}$ to $B^{67}$ in the formula (6a), respectively.

The compounds represented by the formula (7a) are preferably prepared by reaction between compounds represented by the following formula (7d) and at least one reactant selected from alkali metals, organolithium compounds, alkaline earth metals or alkylmagnesium halides.

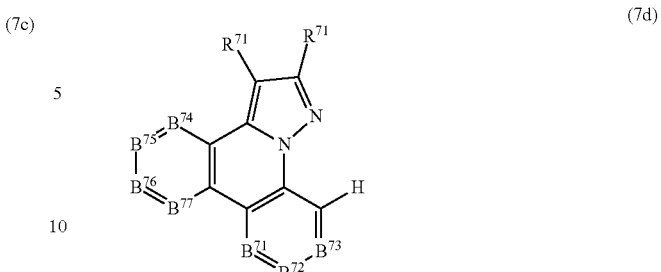
(7d)

In the formula (7d), $R^{71}$ and $B^{71}$ to $B^{77}$ have the same meanings as $R^{71}$ and $B^{71}$ to $B^{77}$ in the formula (7a), respectively.

[Compounds Represented by Formula (8)]

A further forming method according to the invention is a method of forming compounds having nitrogen-containing heterocyclic 5-membered rings as partial structures of ligands thereof through the use of metal-metal exchange reaction, and more specifically, a method of forming compounds represented by the formula (8) by allowing compounds represented by the formula (8a) to react with compounds represented by the formula (8b) or (8c).

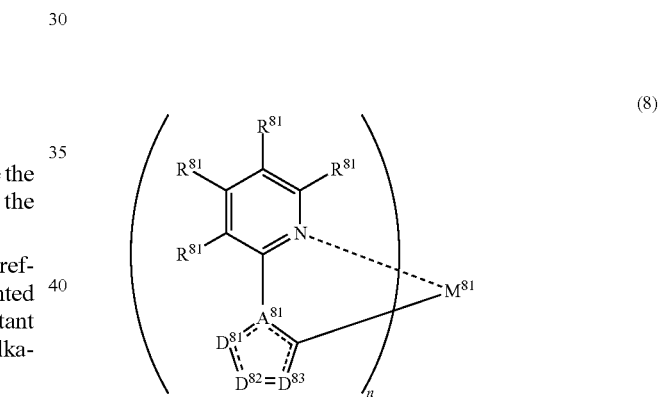
(8)

In the formula (8), $M^{81}$ represents Ir or Pt, each of $R^{81}$s independently represents a hydrogen atom or a substituent, each of $A^{81}$s independently represents a nitrogen atom or a carbon atom, and each of $D^{81}$ to $D^{83}$ independently represents an atom chosen from carbon, nitrogen, oxygen, sulfur or silicon. Each of the atom-atom bonds in the 5-membered ring formed from $D^{81}$ to $D^{83}$, $A^{81}$ and a C atom is a single bond or a double bond. When $D^{81}$ to $D^{83}$ have the possibility of further undergoing substitution, they each may have a substituent. n is 3 when $M^{81}$ is Ir, while it is 2 when $M^{81}$ is Pt.

In the formula (8), $A^{81}$, $D^{81}$ to $D^{83}$ and $R^{81}$ have the same meanings as $A^{41}$, $D^{41}$ to $D^{43}$ and $R^{41}$ in the formula (4), respectively, and their preferred ranges are also the same as the ranges preferred as $A^{41}$, $D^{41}$ to $D^{43}$ and $R^{41}$ in the formula (4), respectively.

The 5-membered ring formed from $A^{81}$, $D^{81}$ to $D^{83}$ and a carbon atom is preferably an aromatic ring.

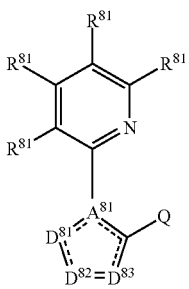
(8a)

In the formula (8a), Q represents an alkali metal, an alkaline earth metal, an alkaline earth metal halide, a trialkyltin, zinc or a zinc halide, which each may further have an arbitrary organic group as a substituent. And $R^{81}$, $A^{81}$ and $D^{81}$ to $D^{83}$ have the same meanings as $R^{81}$, $A^{81}$ and $D^{81}$ to $D^{83}$ in the formula (8), respectively.

$$M^{81}(ZR^{82}{}_2)_m X_m \tag{8b}$$

In the formula (8b), $M^{81}$, X, Z, $R^{82}$ and m have the same meanings as $M^{51}$, X, Z, $R^{52}$ and m in the formula (5b), respectively, and their preferred ranges are also the same as the ranges preferred as $M^{51}$, X, Z, $R^{52}$ and m in the formula (5b), respectively.

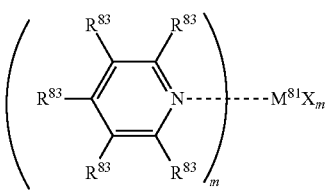
(8c)

In the formula (8c), $M^{81}$, X, $R^{83}$ and m have the same meanings as $M^{51}$, X, $R^{53}$ and m in the formula (5c), respectively, and their preferred ranges are also the same as the ranges preferred as $M^{51}$, X, $R^{53}$ and m in the formula (5c), respectively.

The compounds represented by the formula (8a) are preferably prepared by reaction between compounds represented by the following formula (8d) and at least one reactant selected from alkali metals, organolithium compounds, alkaline earth metals or alkylmagnesium halides.

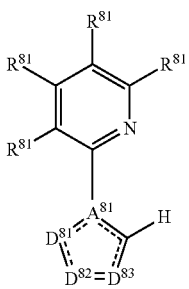
(8d)

In the formula (8d), $R^{81}$, $A^{81}$ and $D^{81}$ to $D^{83}$ have the same meanings as $R^{81}$, $A^{81}$ and $D^{81}$ to $D^{83}$ in the formula (8a), respectively.

Conditions under which the reaction between each of the compounds represented by the formulae (5d), (6d), (7d) or (8d) and at least one reactant chosen from alkali metals, organolithium compounds, alkaline earth metals or alkylmagnesium halides is conducted are described below.

Examples of a solvent usable in the reaction include linear or cyclic ethers such as diethyl ether, methyl tert-butyl ether, THF, dioxane and tetrahydropyran, aromatic hydrocarbons such as benzene, toluene and xylene, and aliphatic hydrocarbons such as petroleum ether, n-hexane and n-pentane.

The range of temperatures at which the reaction is conducted is preferably from −100° C. to 150° C., far preferably from −78° C. to 70° C., further preferably from −78° C. to 10° C.

The reaction is conducted over 0.5 to 48 hours, preferably over 3 to 24 hours.

[Compounds]

The compounds according to the invention are compounds formed by the present forming methods and represented by any of the formulae (1) to (8).

Compounds represented by the formula (1) are as follows.

(1a)

In the formula (1a), Q represents an alkali metal, an alkaline earth metal, an alkaline earth metal halide, a trialkyltin, zinc or a zinc halide, which each may further have an arbitrary organic group as a substituent, and $A^{11}$, $B^{11}$ to $B^{14}$ and $D^{11}$ to $D^{13}$ have the same meanings as $A^{11}$, $B^{11}$ to $B^{14}$ and $D^{11}$ to $D^{13}$ in the formula (1), respectively.

$$[L^{11}{}_k M^{11}(\mu\text{-}Y)]_2 \tag{1b}$$

The formula (1b) stands for a bridged metal dimer, Y is F, Cl, Br, I, $OR^{13}$, $R^{13}COO$, $SR^{13}$ or $N(R^{13})_2$, and each of $R^{13}$s is independently a hydrogen atom, an aliphatic hydrocarbon group having 1 to 20 carbon atoms or an aromatic hydrocarbon group. k is 2 when $M^{11}$ is Ir, while k is 1 when $M^{11}$ is Pt. $L^{11}$ and $M^{11}$ have the same meanings as $L^{11}$ and $M^{11}$ in the formula (1), respectively.

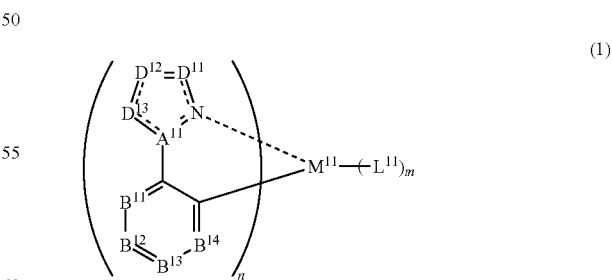
(1)

In the formula (1), $M^{11}$ represents Ir or Pt, each of $A^{11}$s independently represents a nitrogen atom or a carbon atom, each of $B^{11}$ to $B^{14}$ independently represents a nitrogen atom or C—$R^{11}$, and $R^{11}$ represents a hydrogen atom or a substituent, wherein each $R^{11}$ may be the same as or different from every other $R^{11}$. And each of $D^{11}$ to $D^{13}$ independently represents an atom chosen from carbon, nitrogen, oxygen, sulfur or silicon. Each of the bonds between atoms in the 5-membered ring formed from $D^{11}$ to $D^{13}$, $A^{11}$ and an N atom represents a single bond or a double bond. Each of $D^{11}$ to $D^{13}$ may have a substituent as long as it can undergo further substitution. And $L^{11}$ represents atoms forming a bidentate ligand. n represents an integer of 1 to 3 and m represents an integer of 0 to 2, provided that n+m is 2 or 3.

Formulae and preferred ranges of the compounds represented by the formulae (1) to (8) are the same as described hereinbefore.

Examples of the compounds represented by the formulae (1) to (8) are illustrated below, but these examples should not be construed as limiting the scope of the invention.

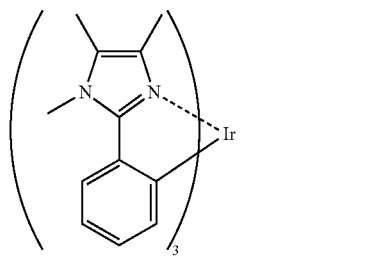

1

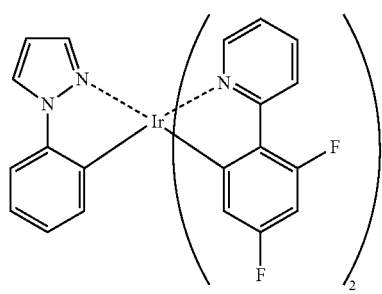

2

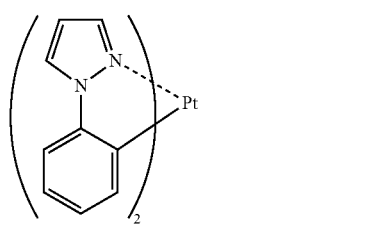

3

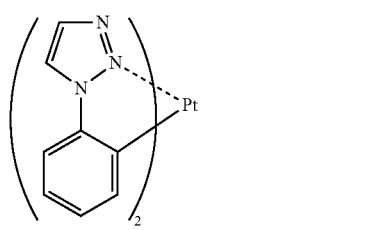

4

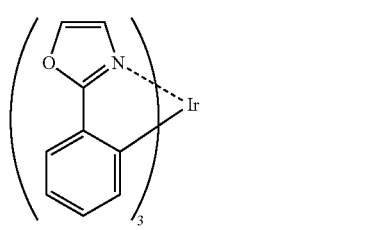

5

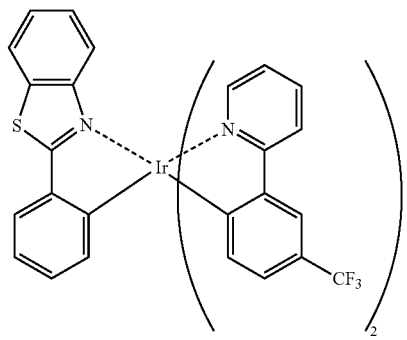

6

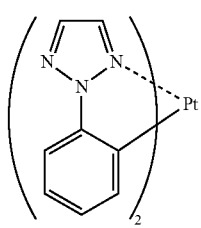

7

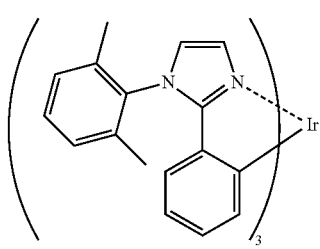

8

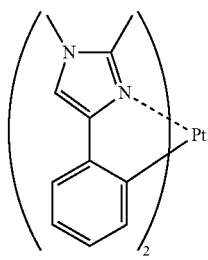

9

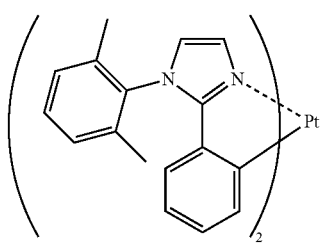

10

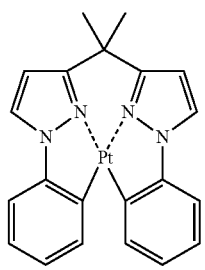

11

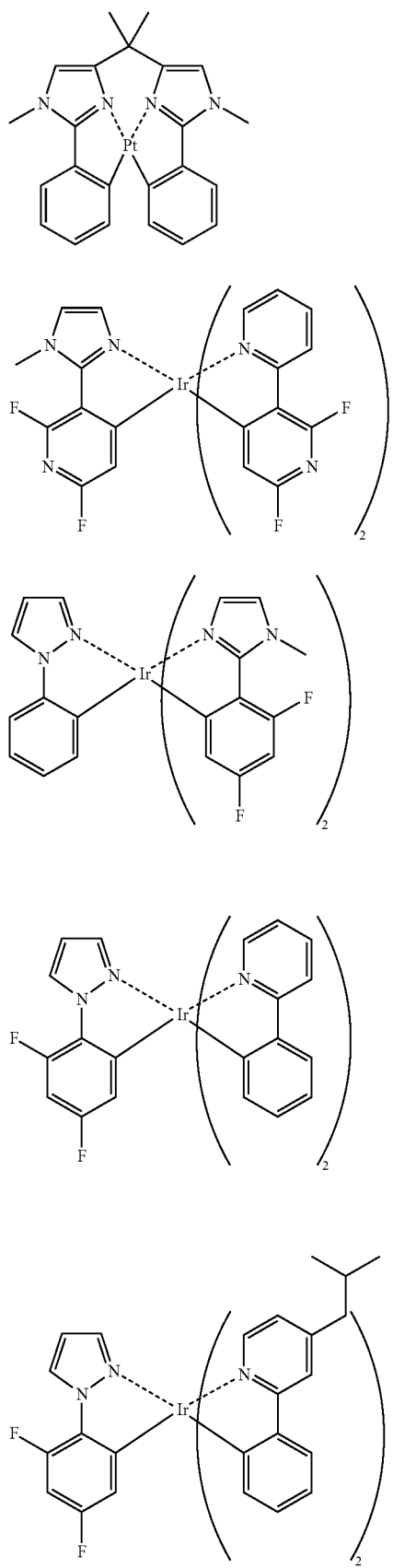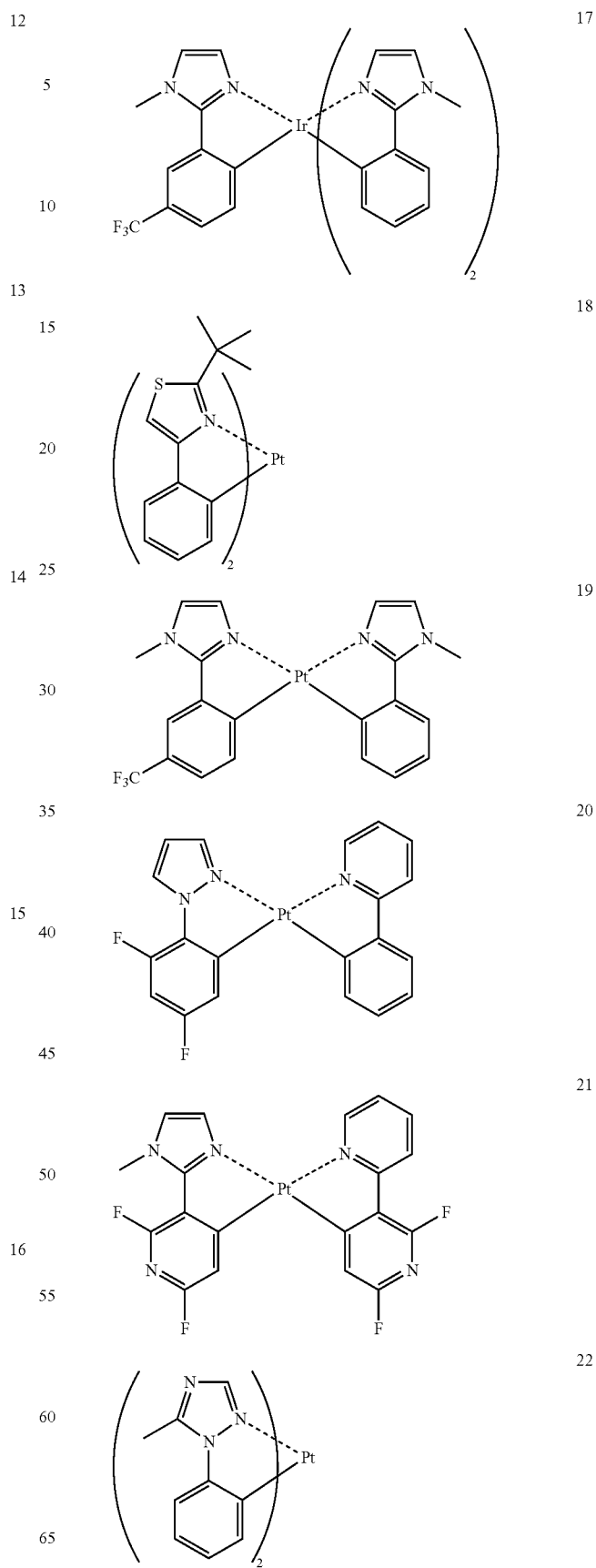

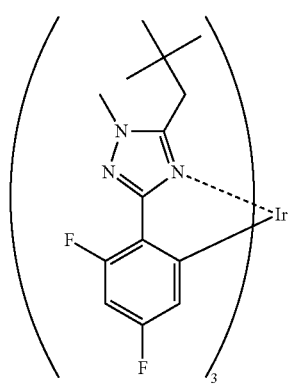
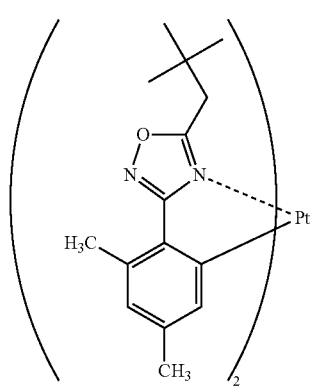
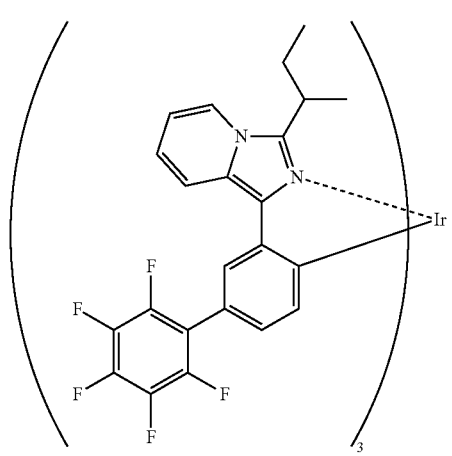
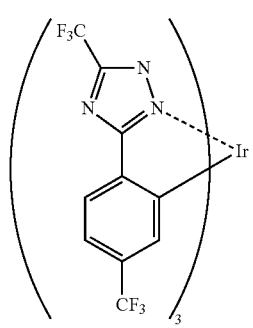
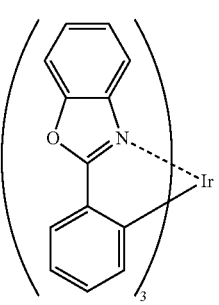
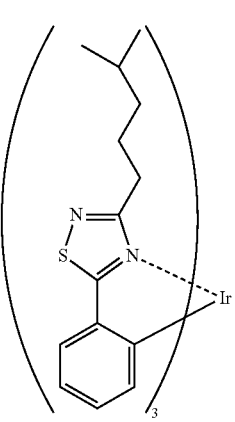
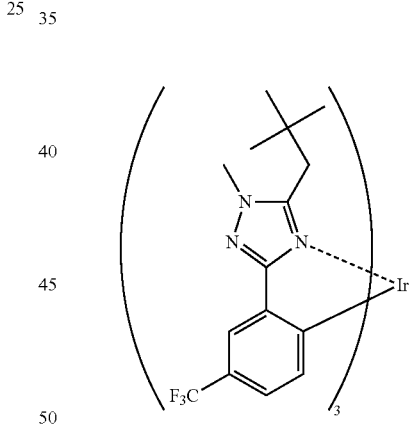
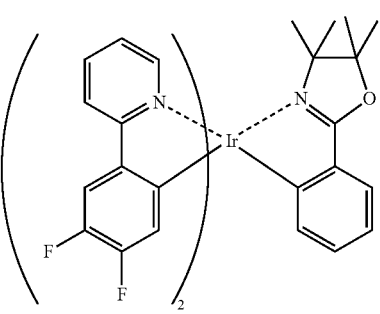

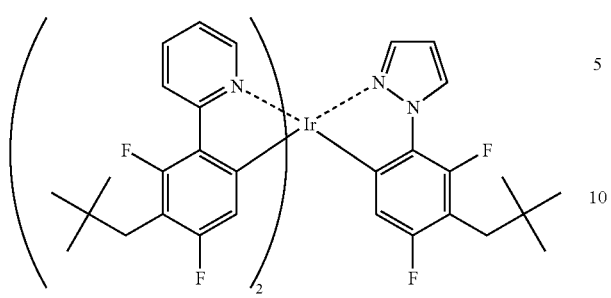
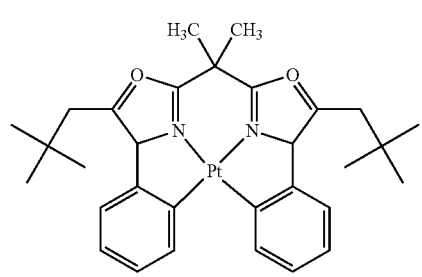
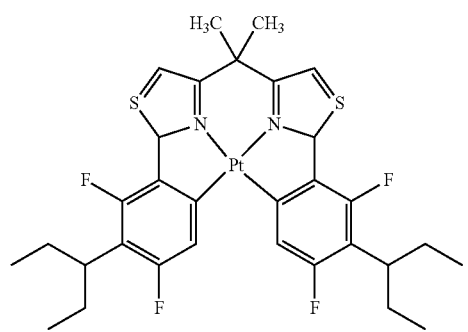
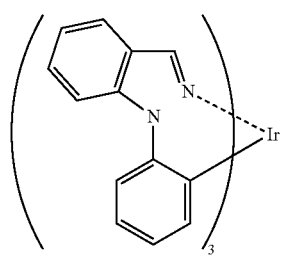
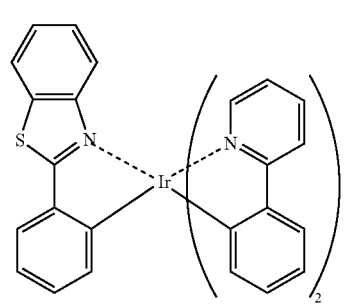
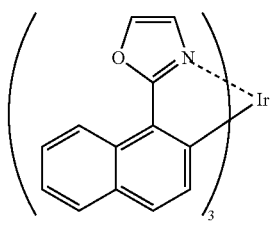
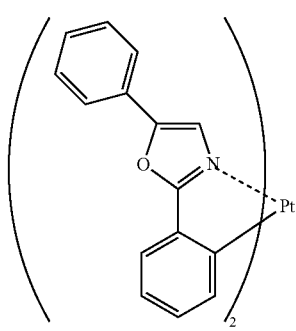
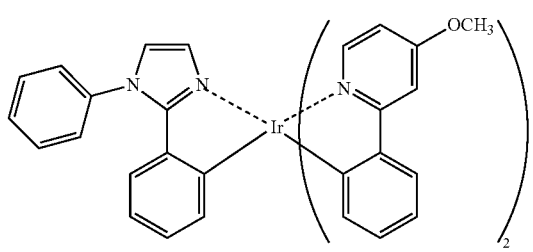

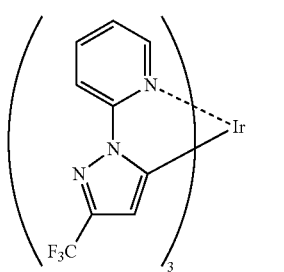
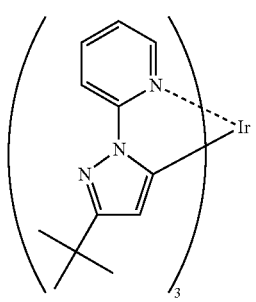
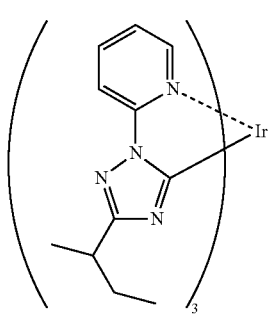
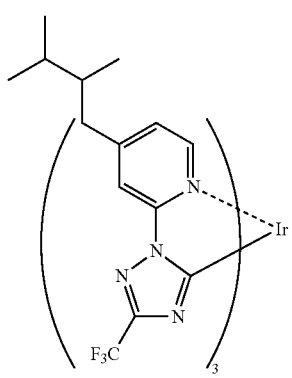
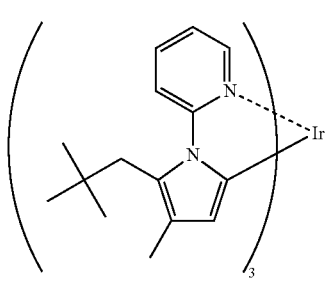
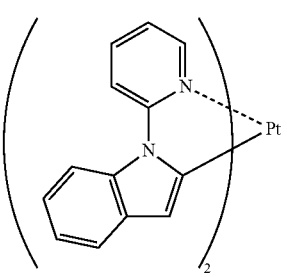
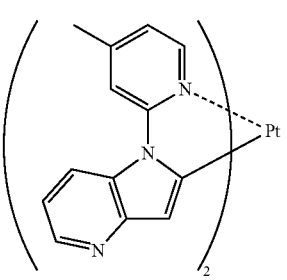
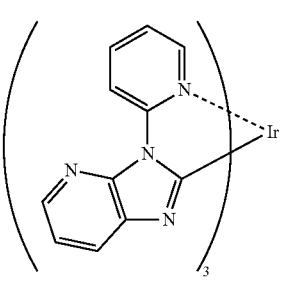
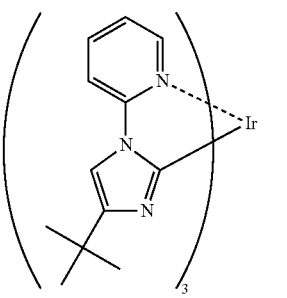
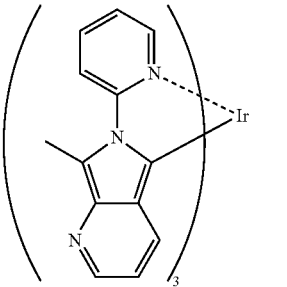

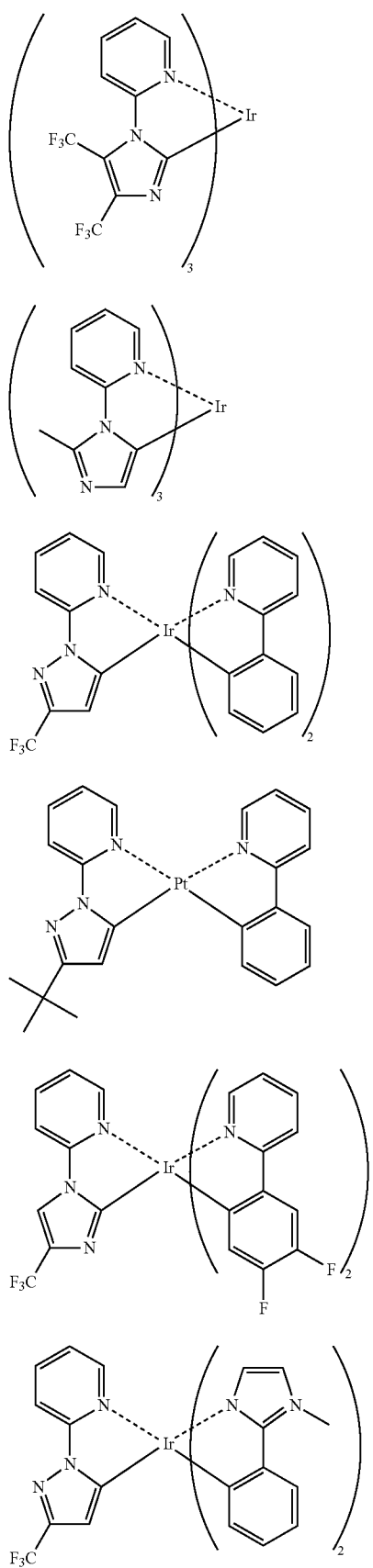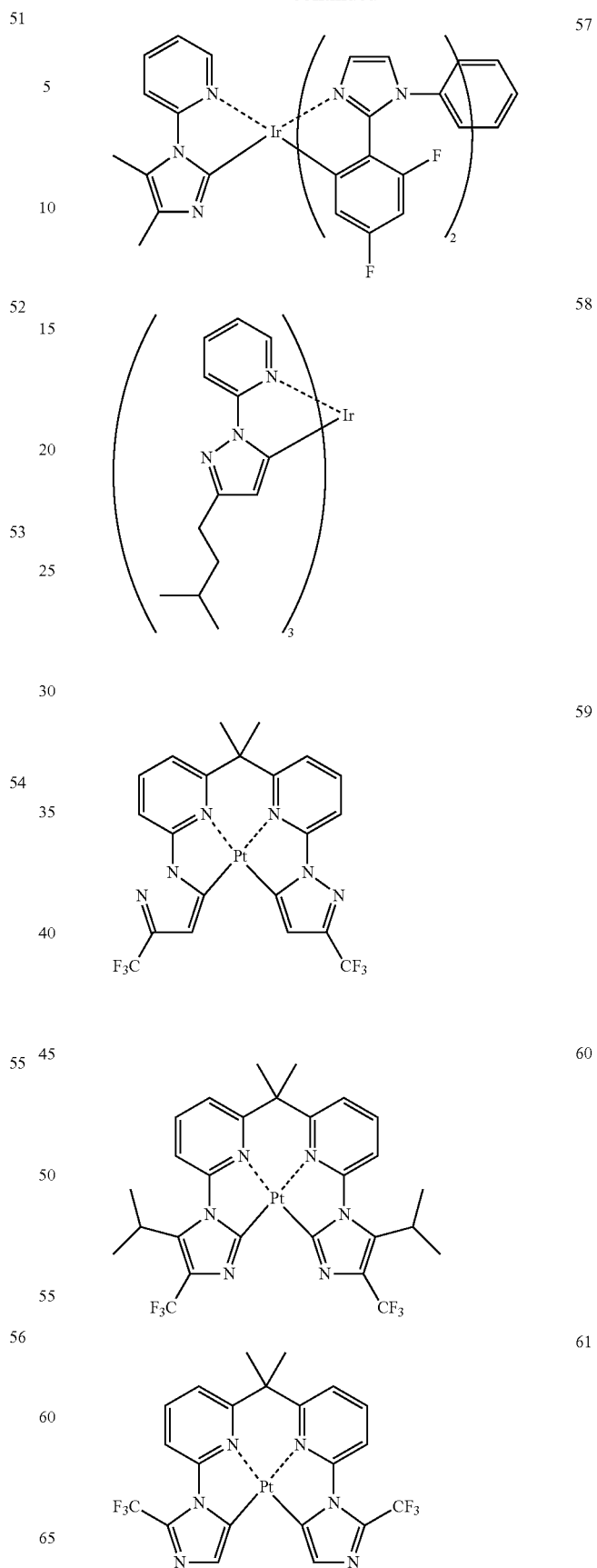

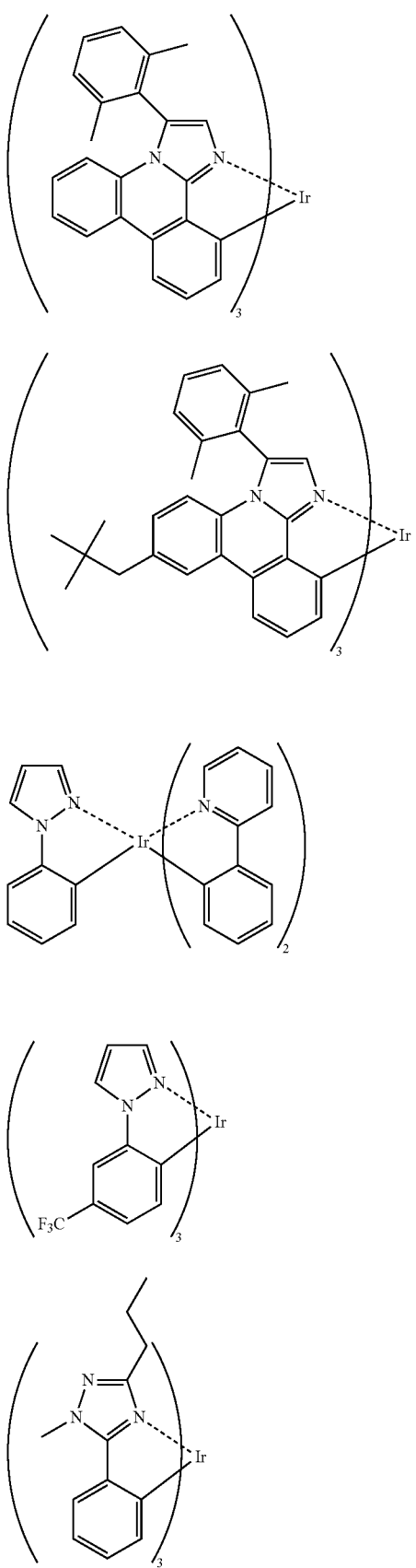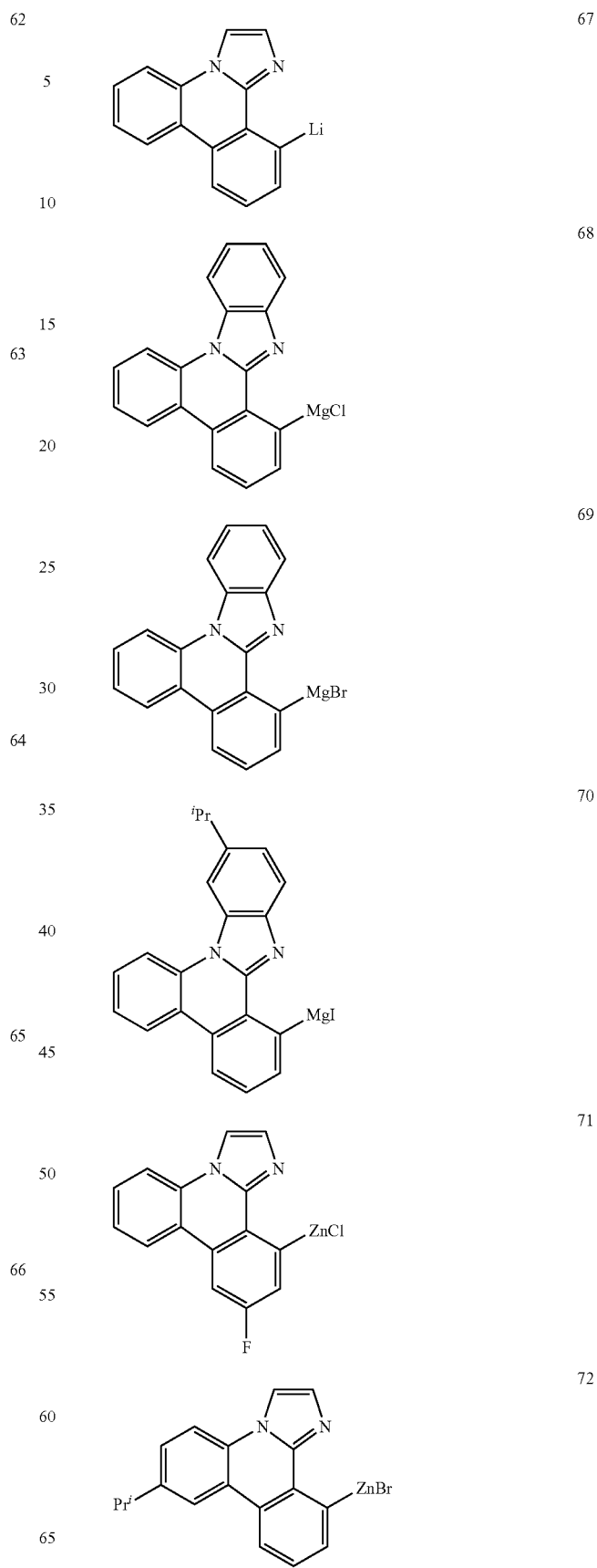

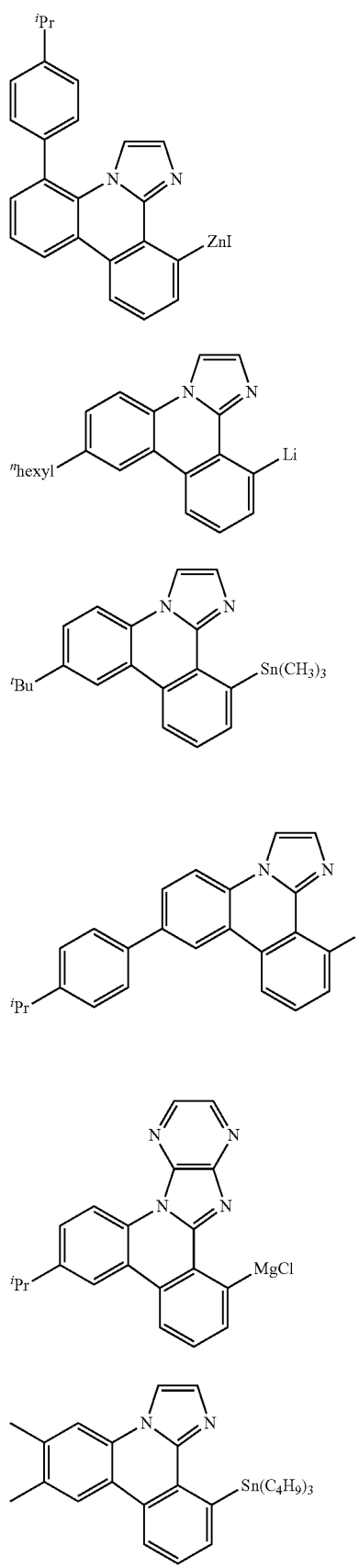
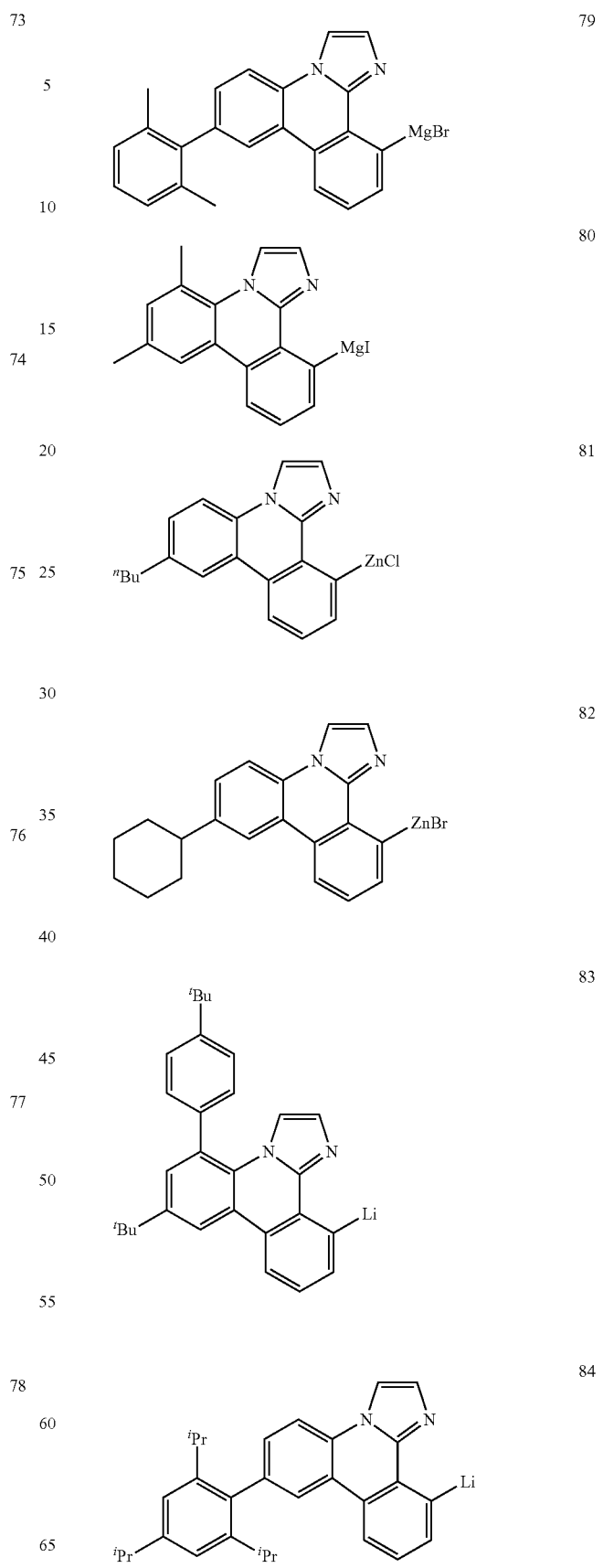

-continued
85
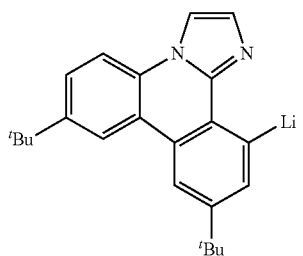
86
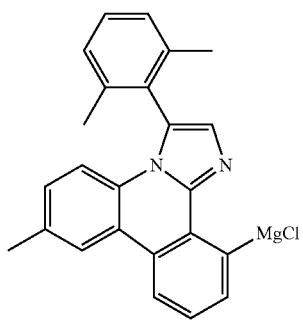
87
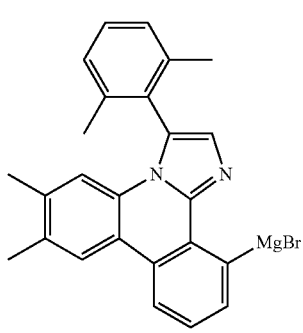
88
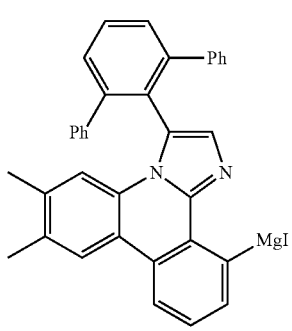
89
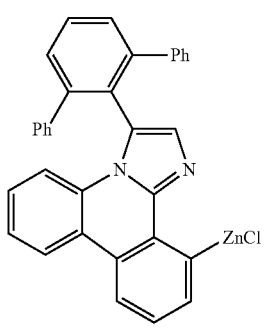
90
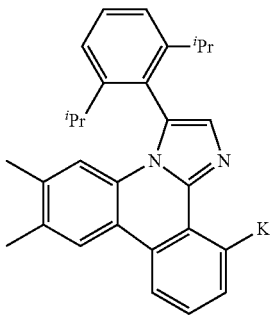
91
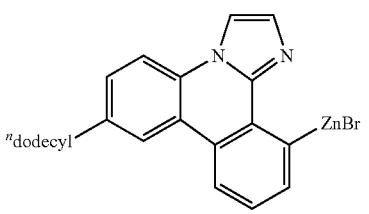
92
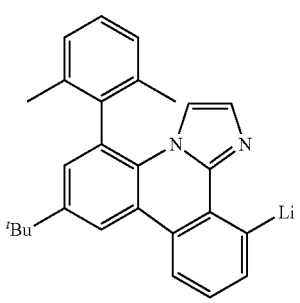
93
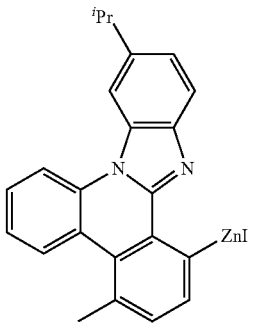
94
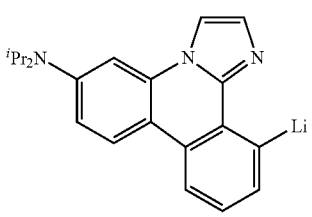

-continued
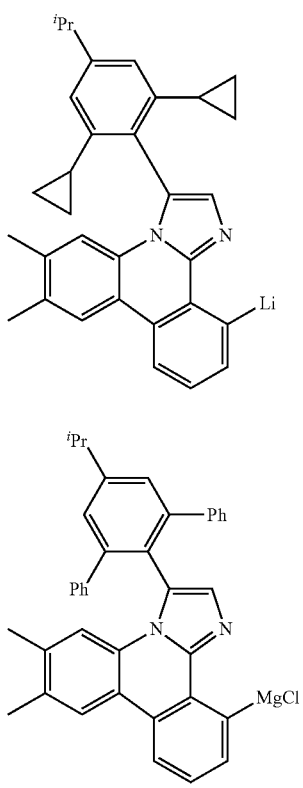
87
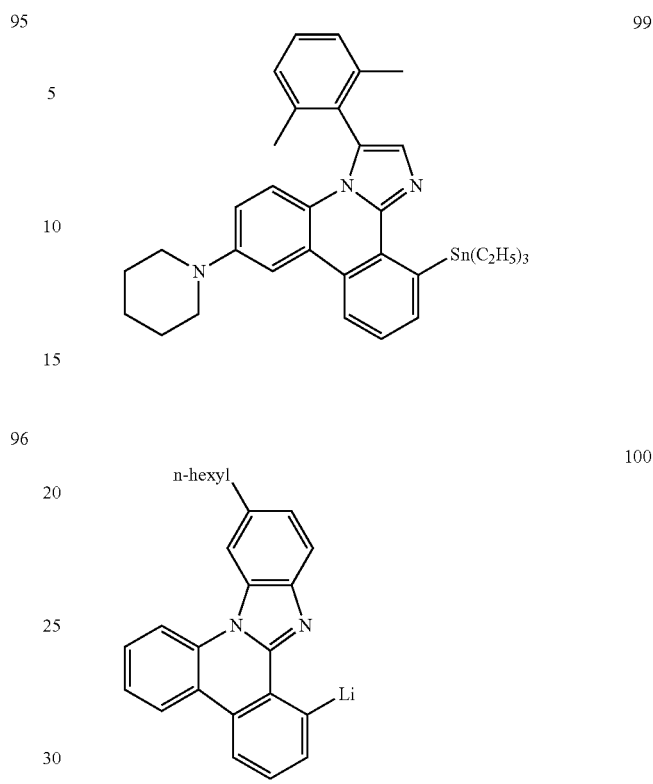
95
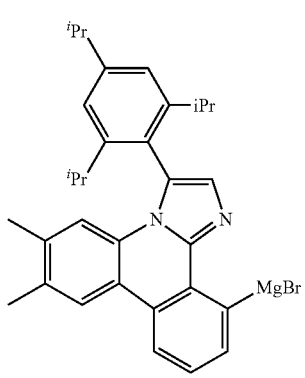
96
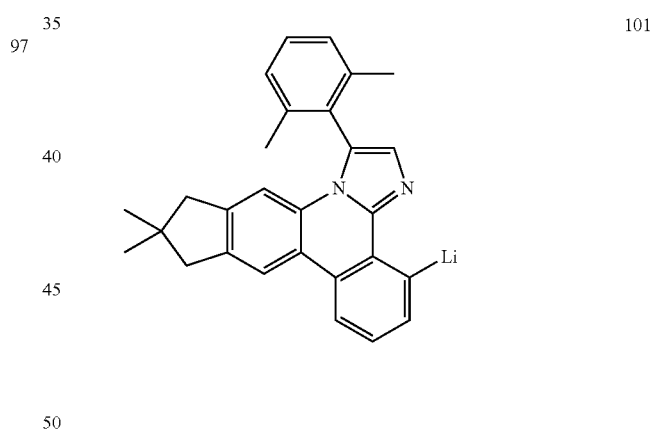
99
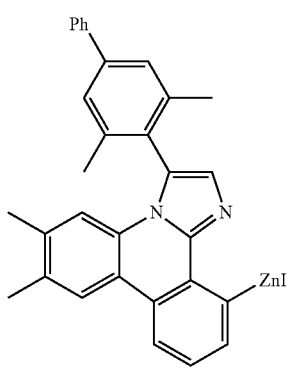
97
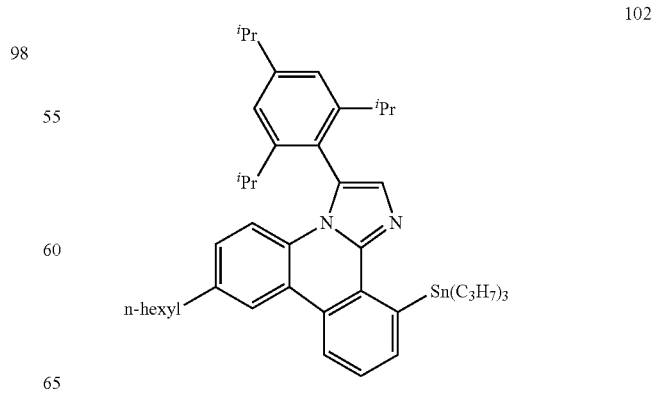
100
98
101
102

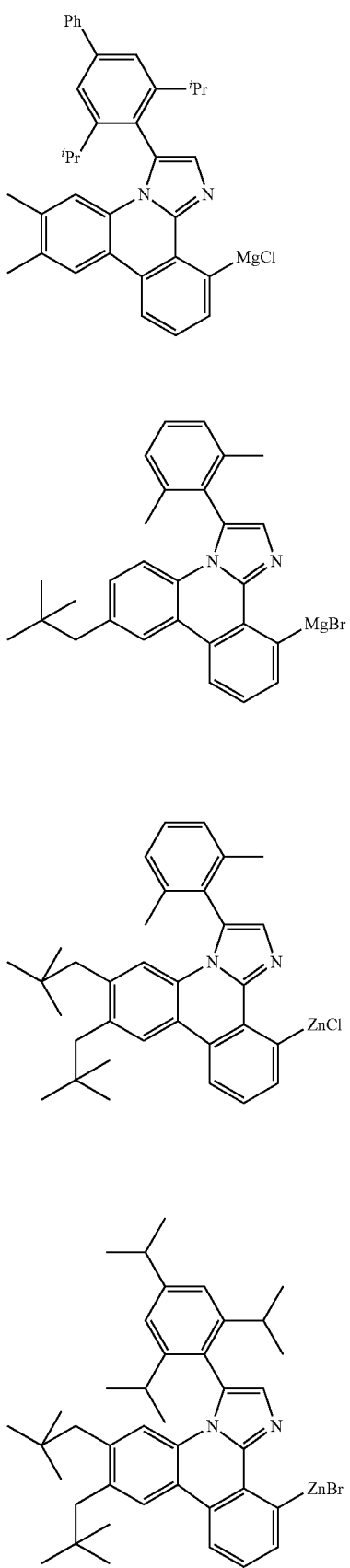
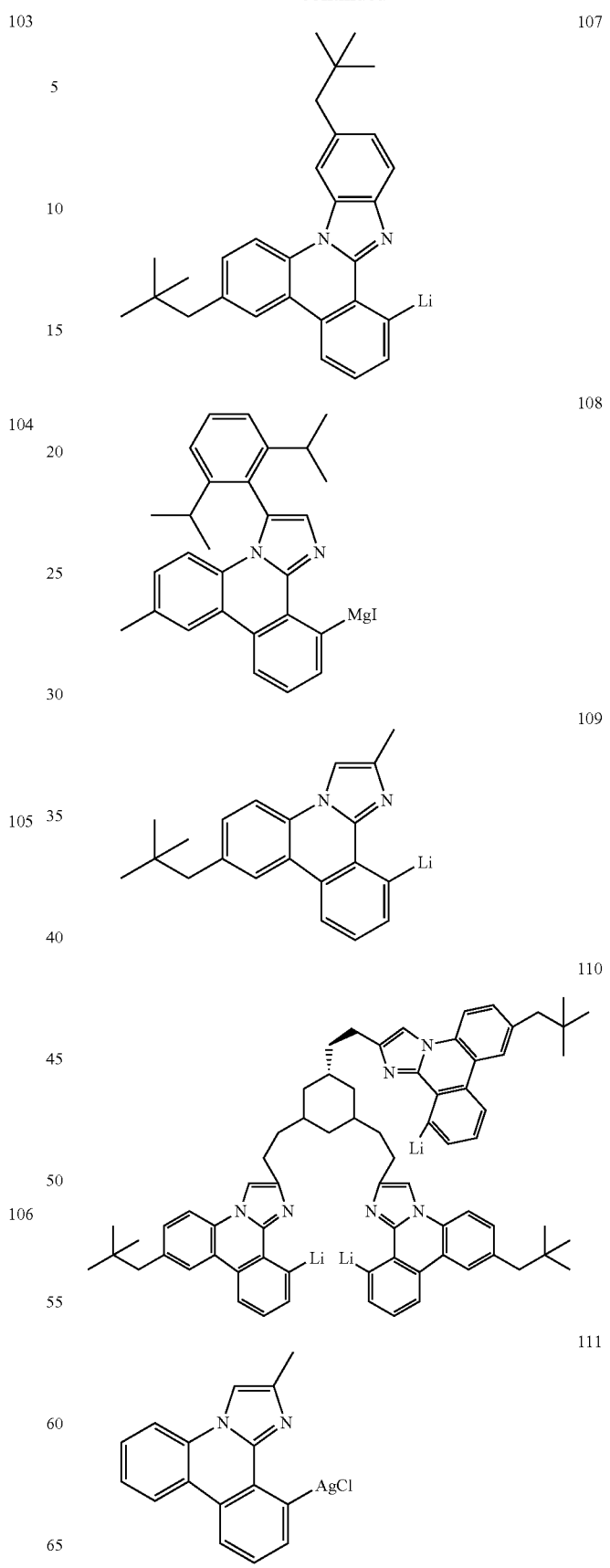

| 112 | 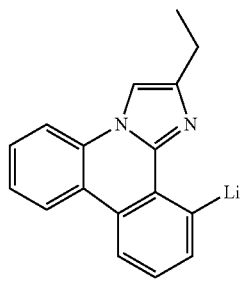 | 118 |
| --- | --- | --- |
| 114 | 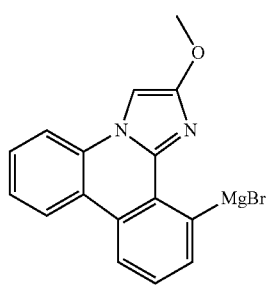 | 119 |
| 115 | 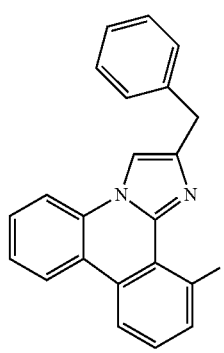 | 120 |
| 116 | 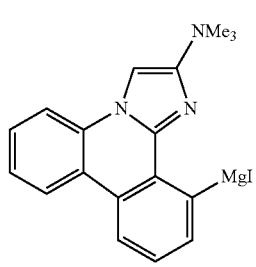 | 121 |
| 117 | 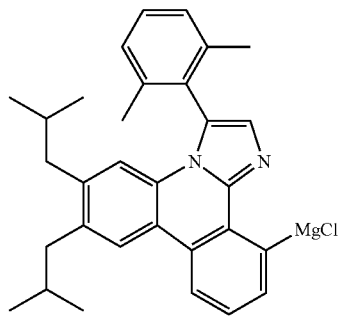 | 122 |
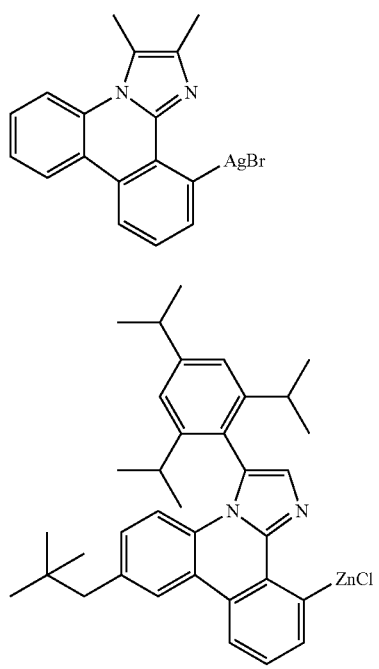
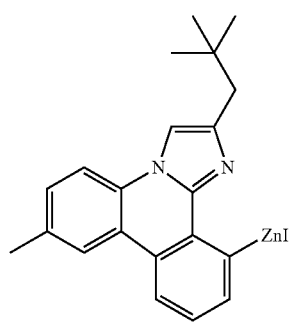
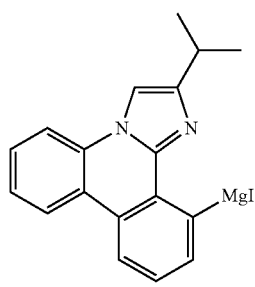
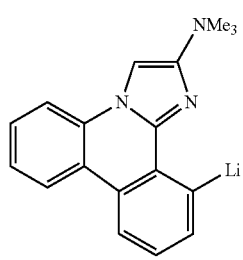

-continued
123 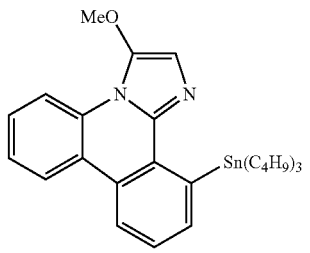
124 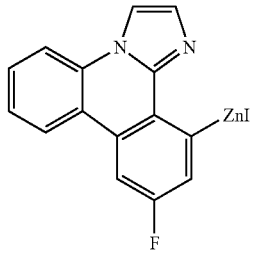
125 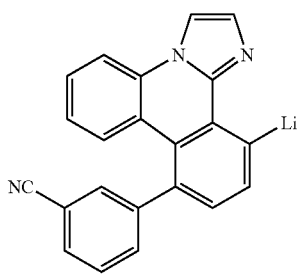
126 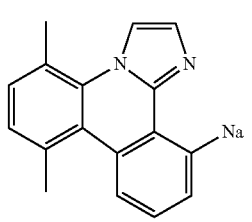
127 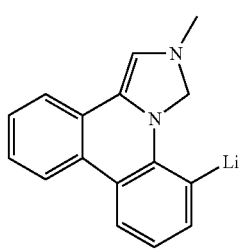
128 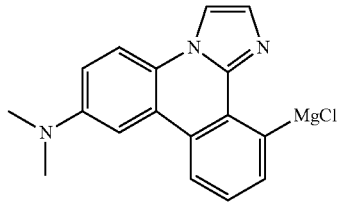
-continued
129 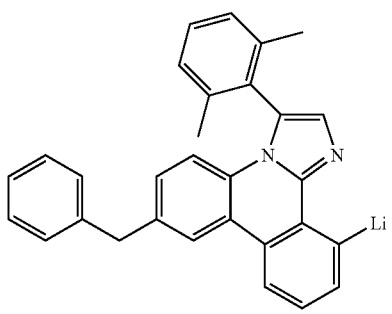
130 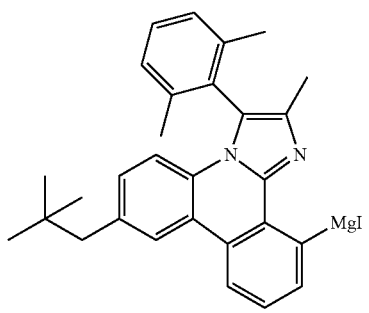
131 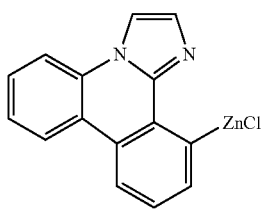
132 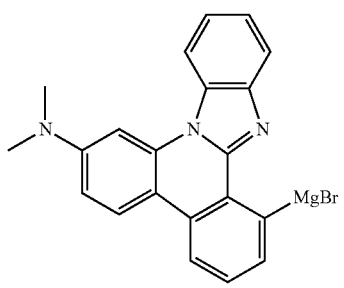
133 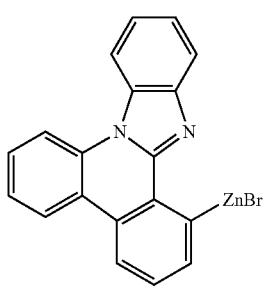
134 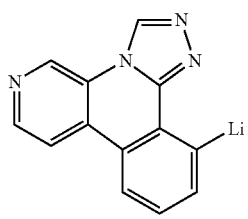

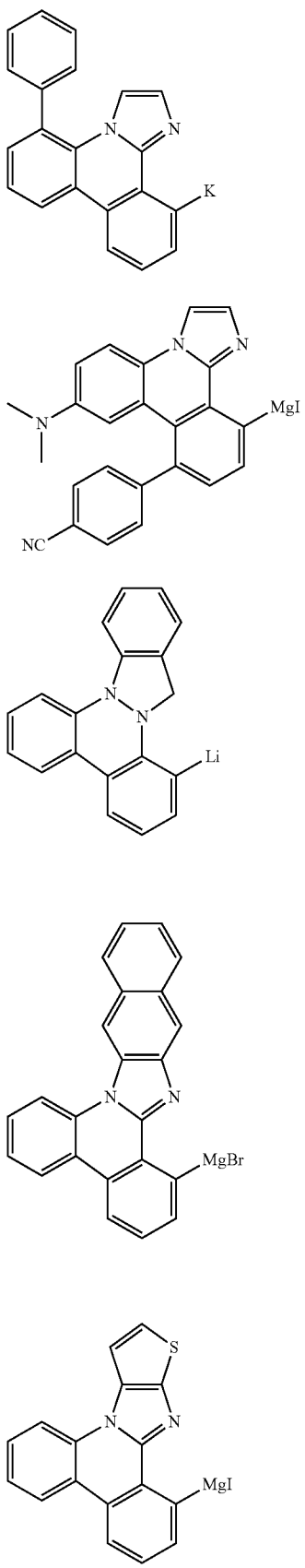
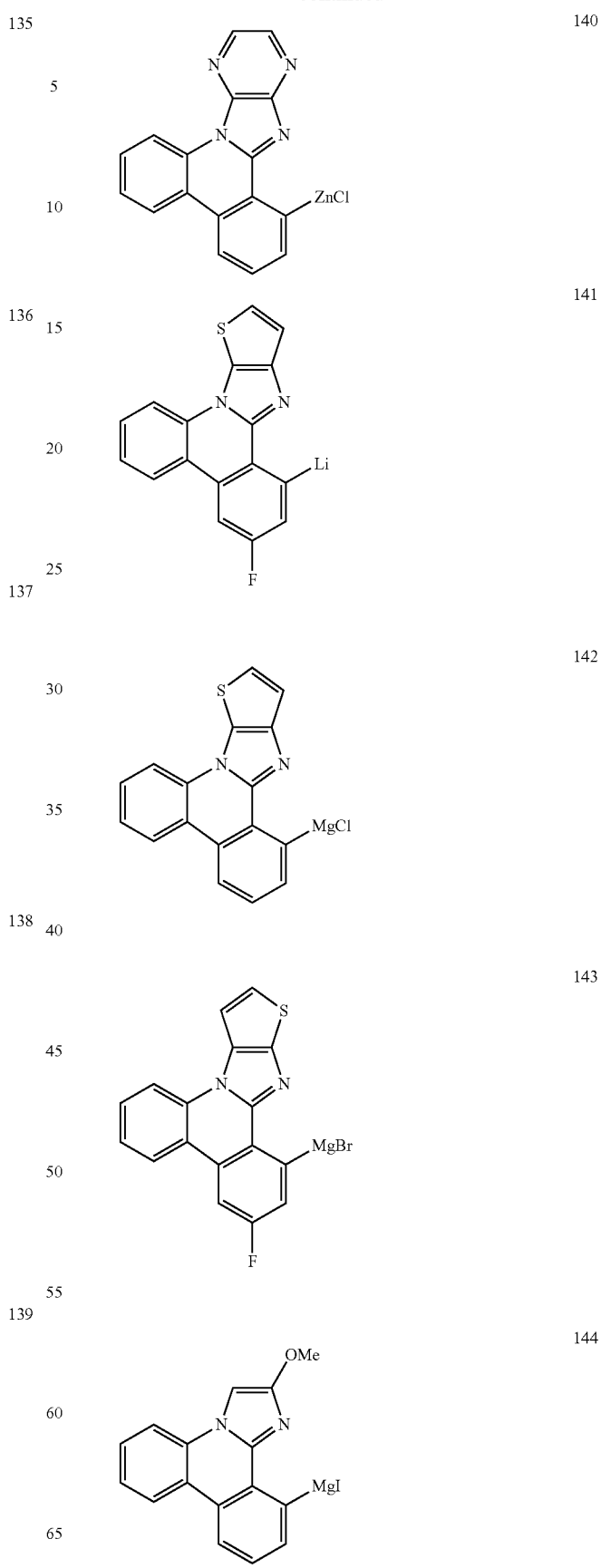

145 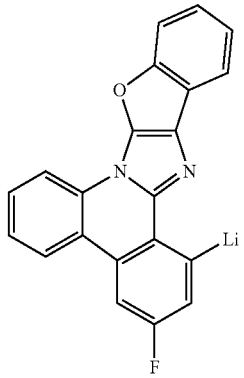
150 
146 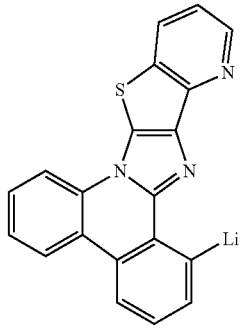
151 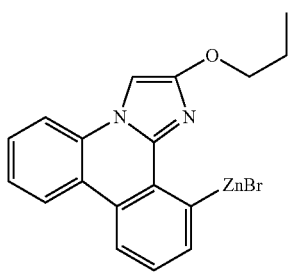
147 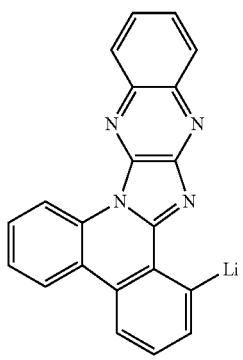
152 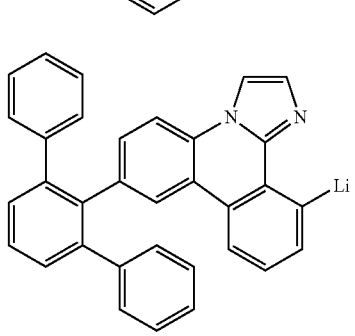
148 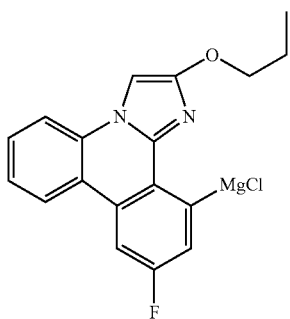
153 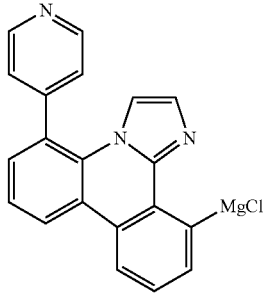
149 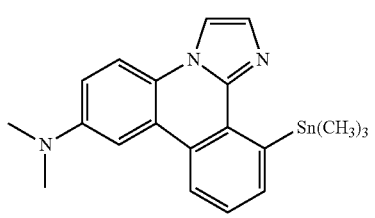
154 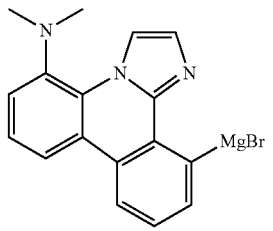

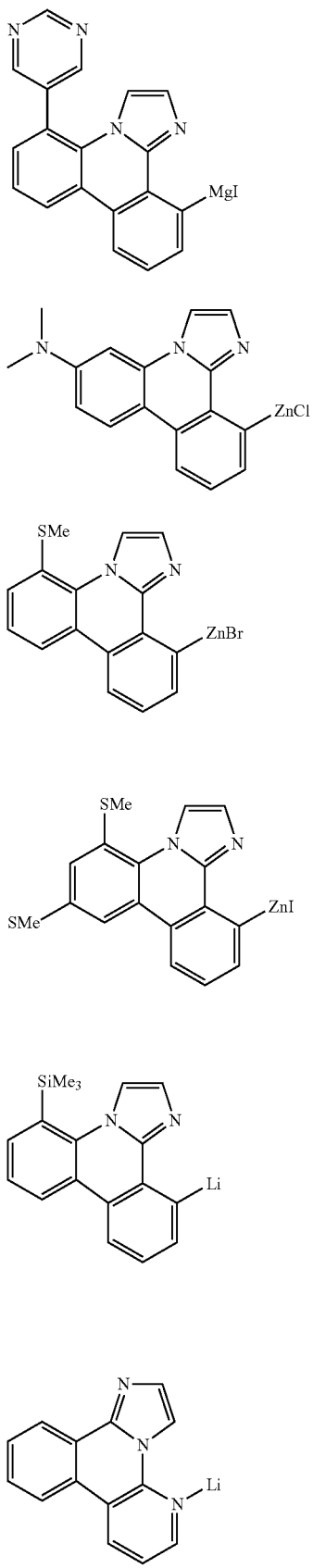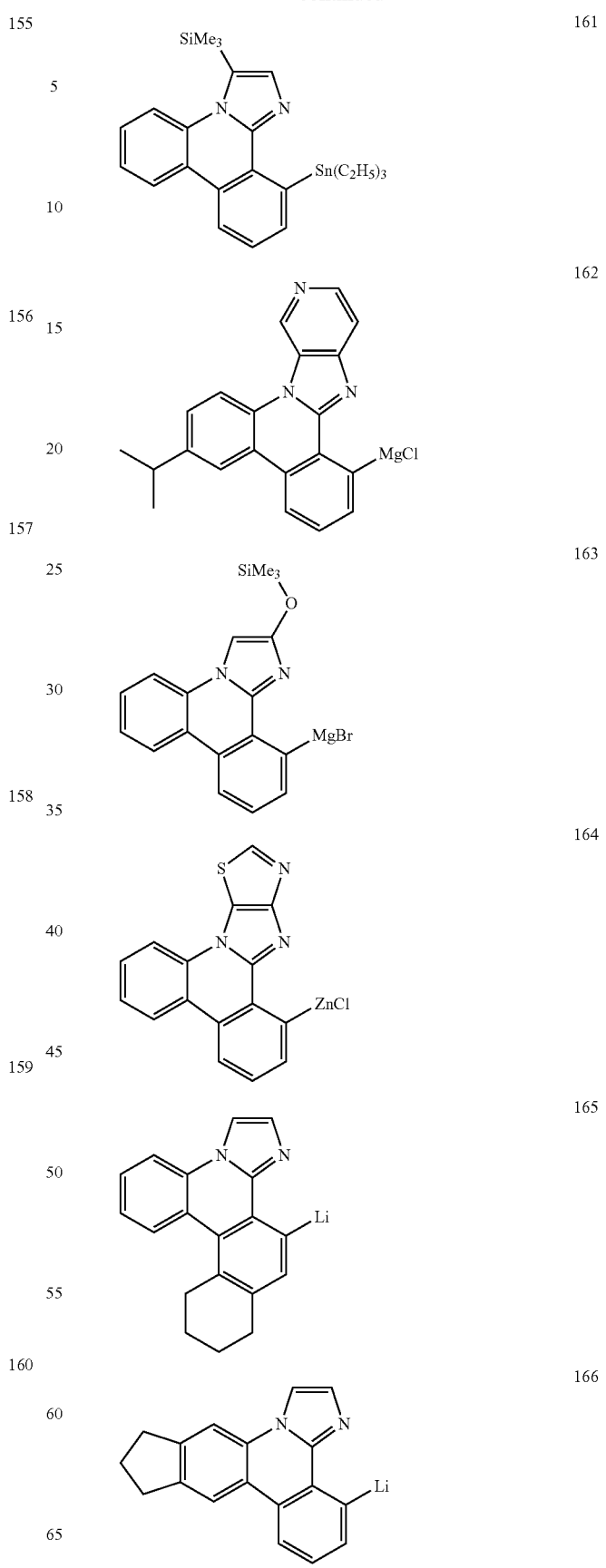

-continued
167
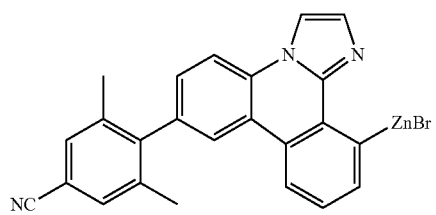
168
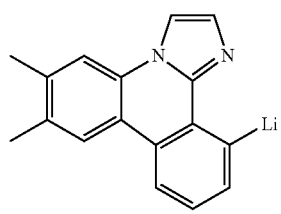
169
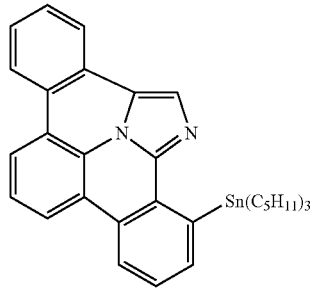
170
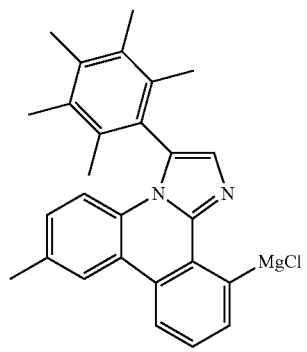
171
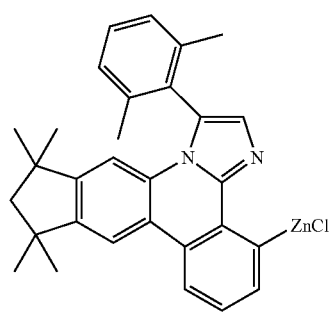
-continued
172
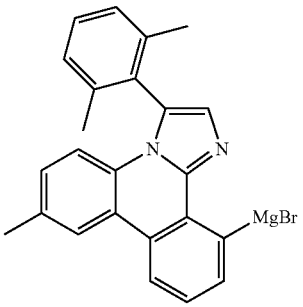
173
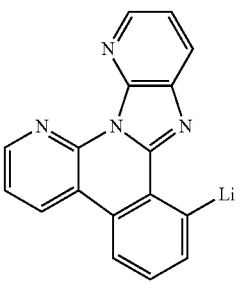
174
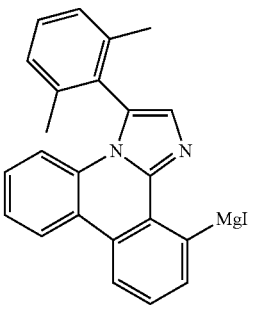
175
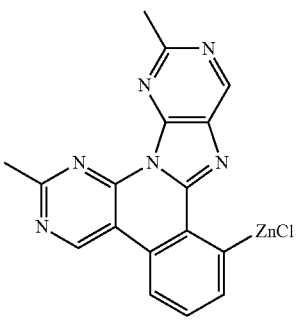
176
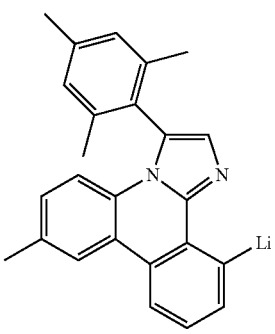

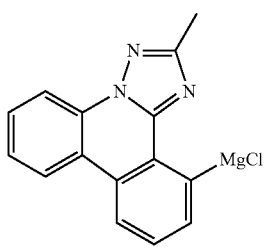
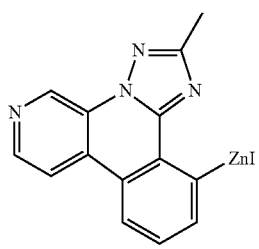
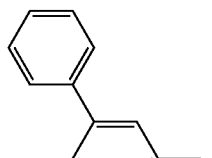
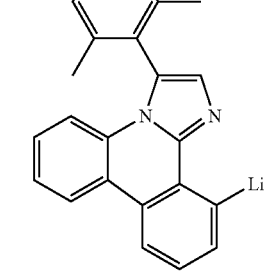
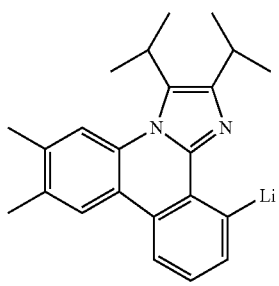
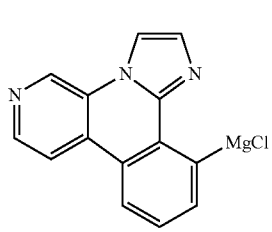
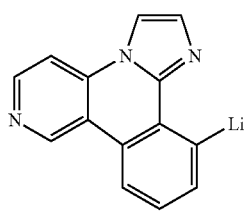
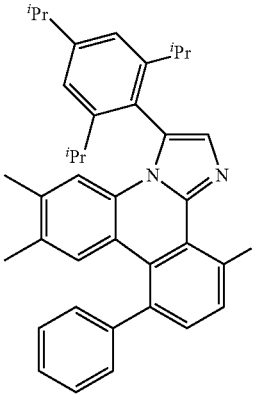
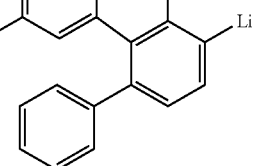
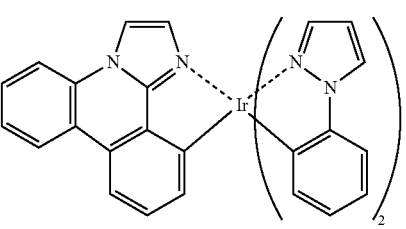
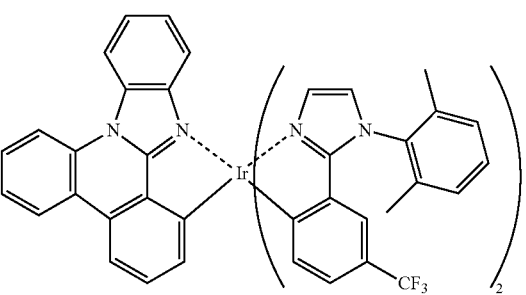
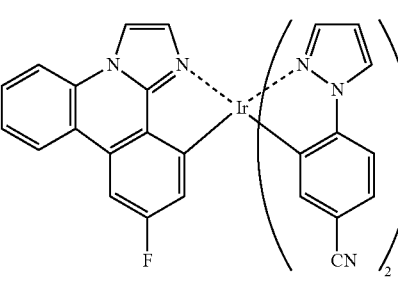
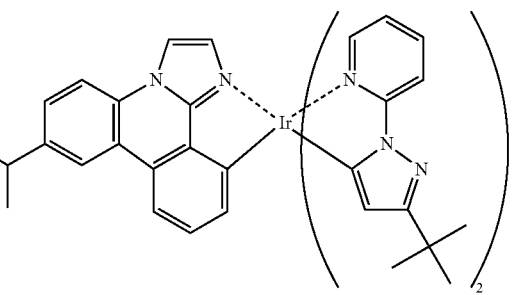

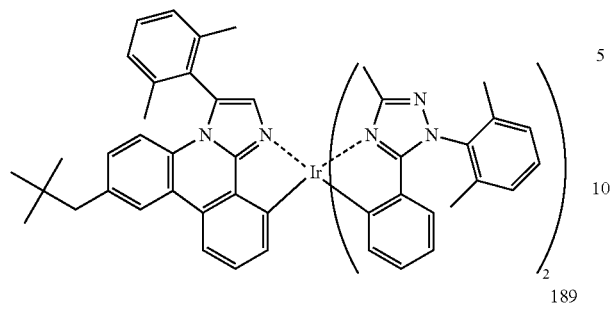
188
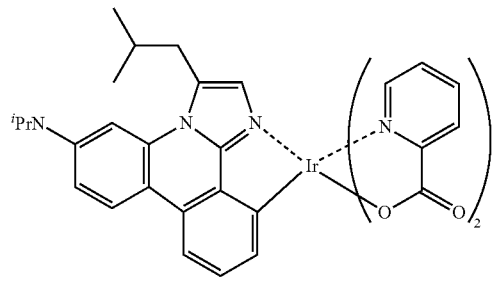
193
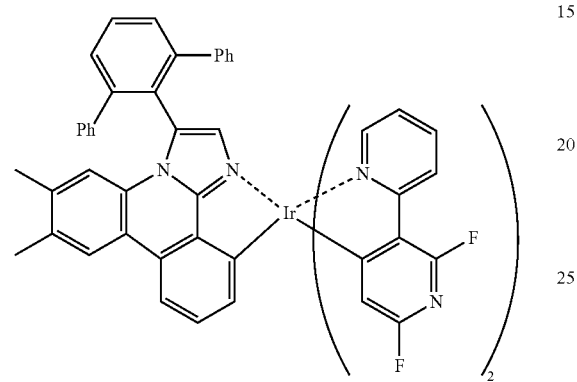
189
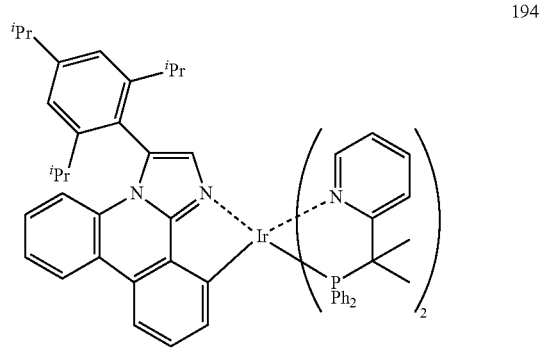
194
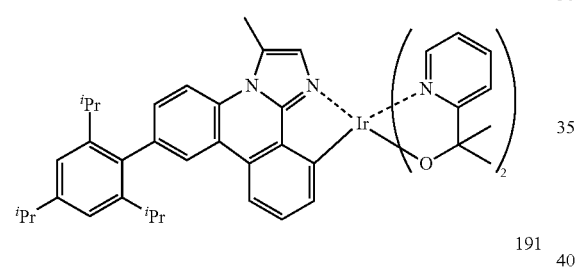
190
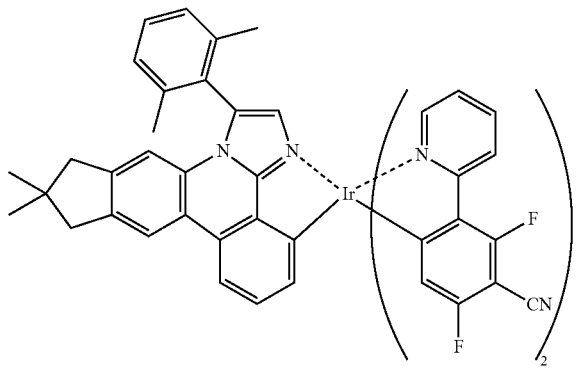
195
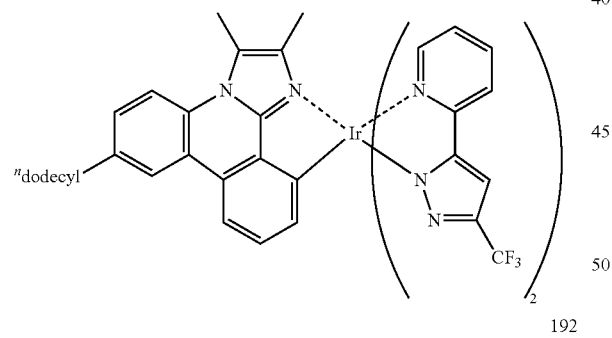
191
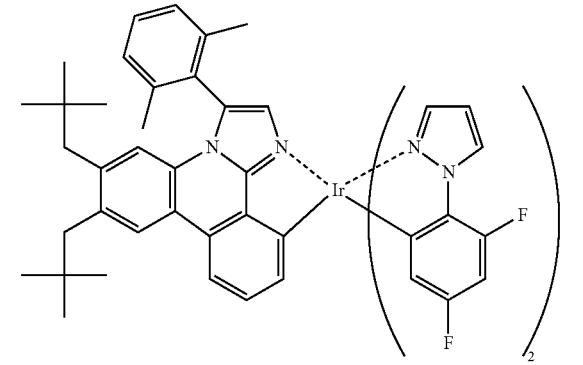
196
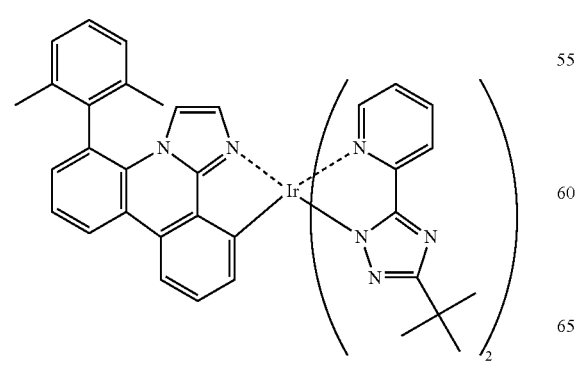
192
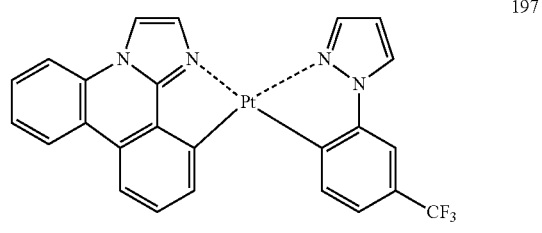
197

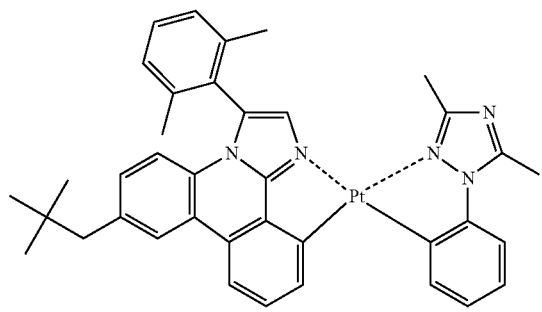
198
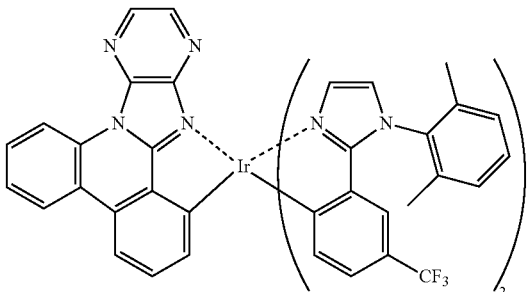
202
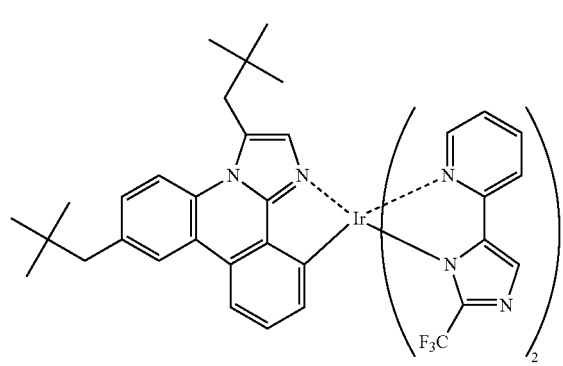
199
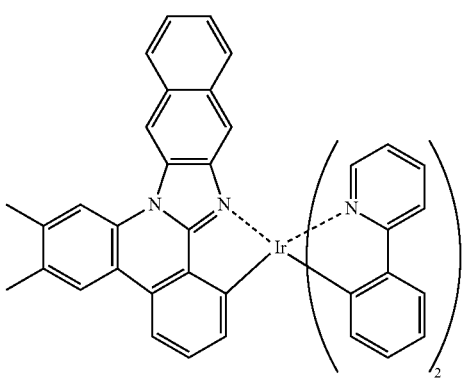
203
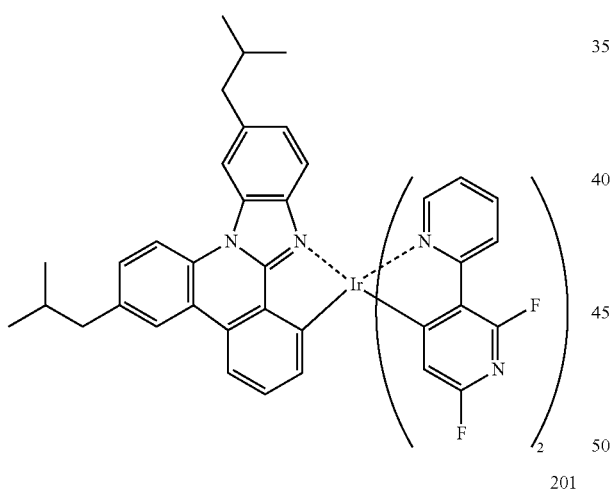
200
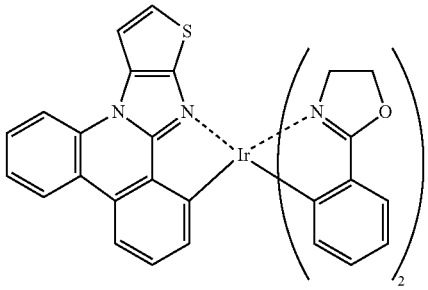
204
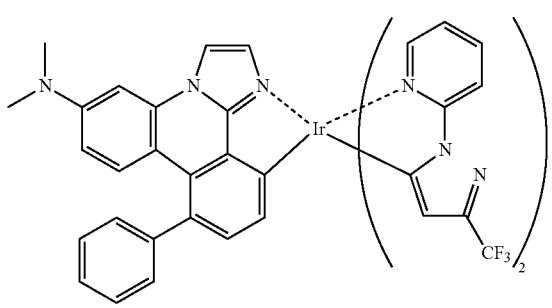
205
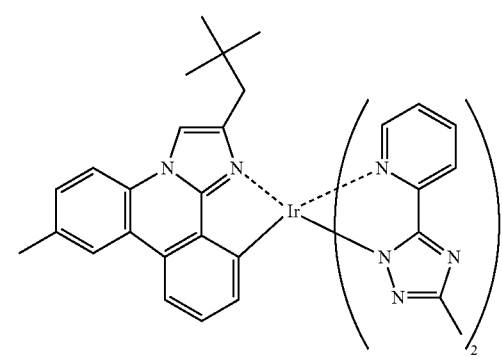
201
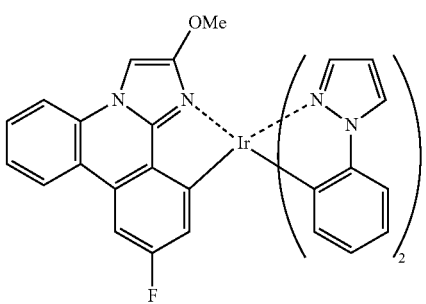
206

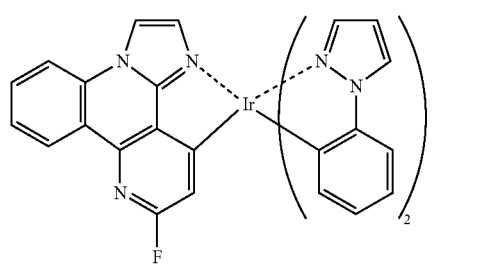
207
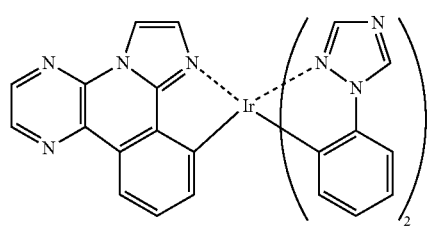
208
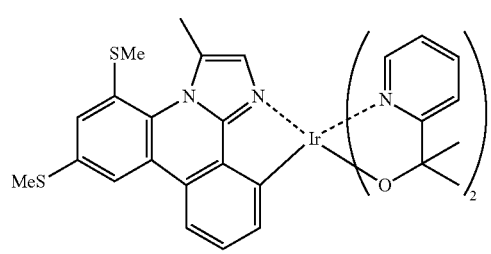
209
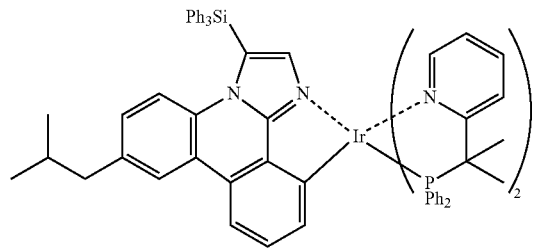
210
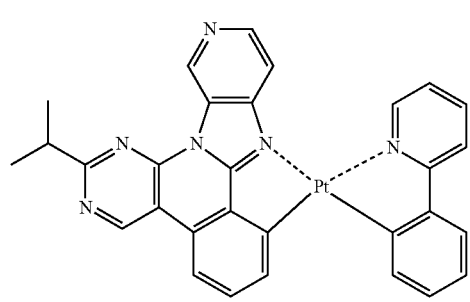
211
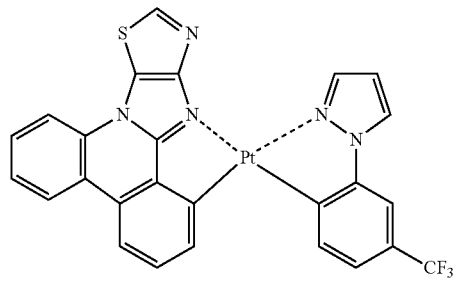
212
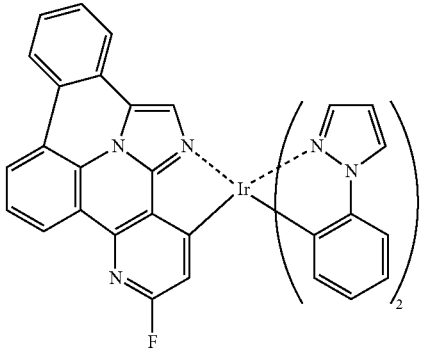
213
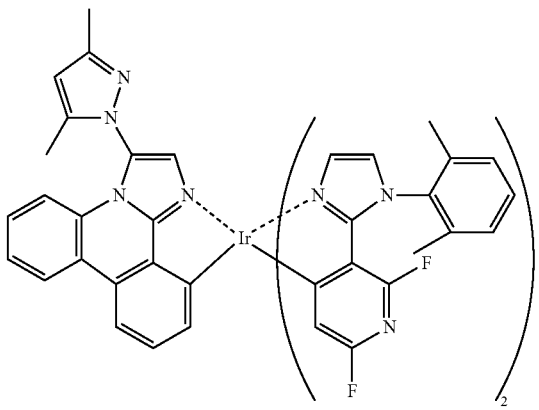
214
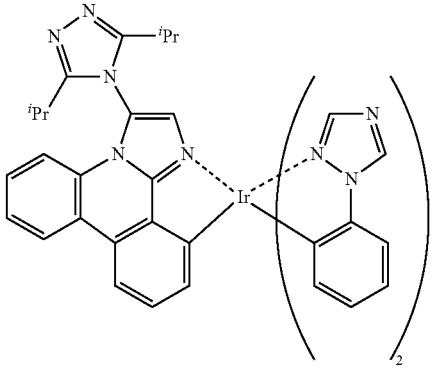
215
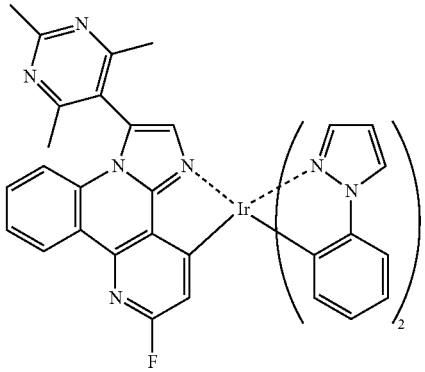
216

217
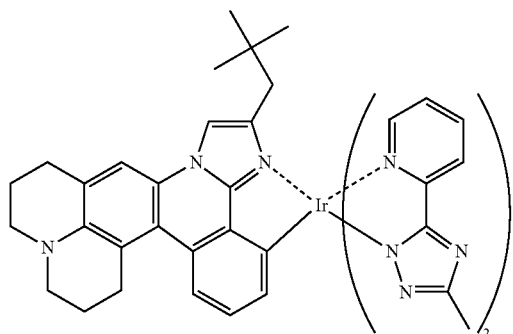
218
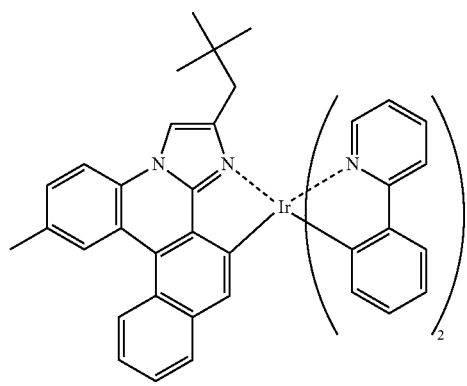
219
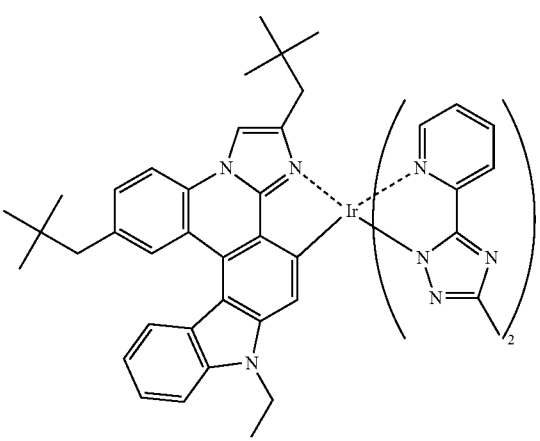
220
221
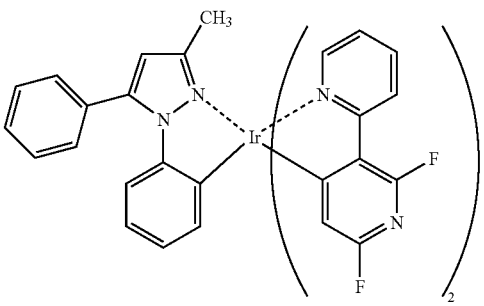
222
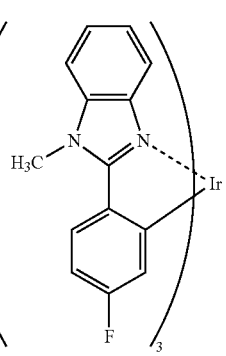
223
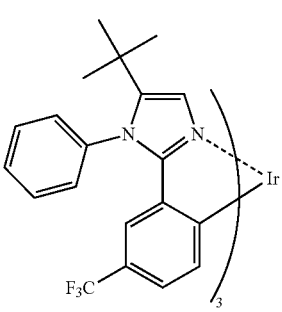
224
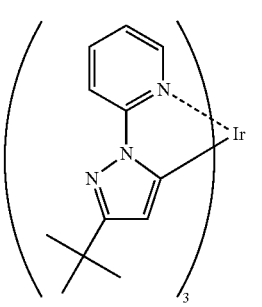
225
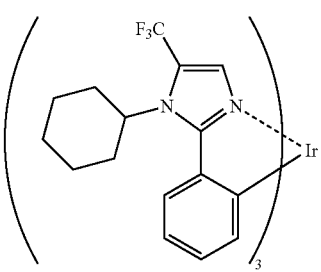

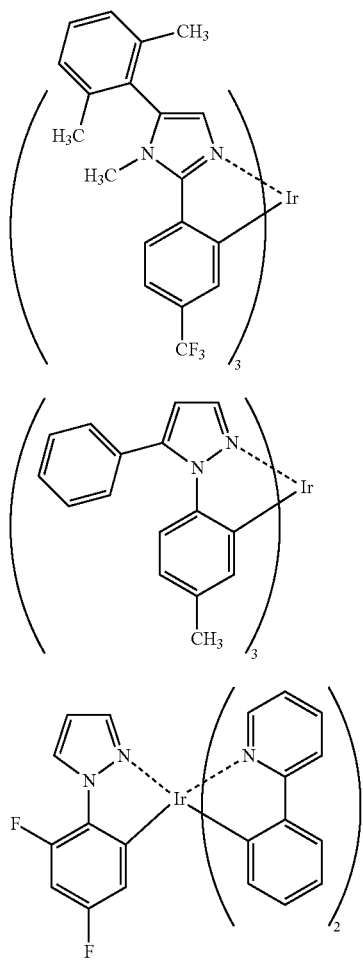

[Organic Electroluminescence Device Materials]

Organic electroluminescence device materials according to the invention are compounds which are formed by the present forming methods and represented by any of the formulae (1) to (8), and each of them is characterized by having a lithium atom and ion content of 0.1 ppm to 50 ppm.

In the compounds represented by any of the formulae (1) to (8), the Li atom and ion content is 50 ppm below, preferably from 0.1 ppm to 50 ppm.

Other organic electroluminescence device materials according to the invention are compounds represented by any of the formulae (1) to (8), and each of them has a magnesium atom and ion content of 50 ppm or below, preferably from 0.1 ppm to 50 ppm.

The organic electroluminescence device materials according to the invention can be obtained by use of the present forming methods.

In the thus obtained compounds of any of the formulae (1) to (8), the lithium atom and ion content is preferably from 0.1 ppm to 50 ppm, far preferably from 0.1 ppm to 10 ppm, further preferably from 1 ppm to 10 ppm. And the magnesium atom and ion content is preferably from 0.1 ppm to 50 ppm, far preferably from 0.1 ppm to 10 ppm, further preferably from 1 ppm to 10 ppm. When both the Li atom and ion content and the Mg atom and ion content are in the ranges specified above, high purity is maintained.

Light emitting materials reduced in impurity and decomposed-matter contents are restrained from causing photoemission quench traceable to impurities and decomposed matter, and therefore they can deliver improved durability.

Furthermore, light emitting materials synthesized from halogen-free ligands allow further improvement of device durability. It has been suggested that halogen impurities constitute a factor in degrading device durability, therefore the use of light emitting materials prepared in the invention makes it possible to restrain photoemission quench traceable to halogen impurities, and to improve device durability.

[Organic Electroluminescence Devices]

In addition, the invention provides organic electroluminescence devices which each have at least one organic layer, including a light emitting layer, between a pair of electrodes and contain in at least one of the organic layers a compound prepared in accordance with any of the present forming methods and represented by any of the formulae (1) to (8). Additionally, each of the compounds represented by the formulae (1) to (8) is preferably incorporated into the light emitting layer. In forming organic electroluminescence devices, the compounds represented by the formulae (1) to (8) may be utilized together with other ingredients. Such ingredients may be organic substances or they may be inorganic substances. As the organic substances, materials recited below as host materials, fluorescent materials, phosphorescent materials or hydrocarbon materials can be adopted, and the preferred ones are host materials or hydrocarbon materials.

The devices according to the invention are described below in detail.

The organic electroluminescence devices according to the invention are organic electroluminescence devices each having on a substrate a pair of electrodes between which a light emitting layer is sandwiched, preferably containing in the light emitting layer a compound represented by any of the formulae (1) to (8) in the invention.

In the organic electroluminescence device of the present invention, the light emitting layer is an organic layer, and the device may have a plurality of organic layers.

In view of property of the luminescence device, at least one electrode of the anode and the cathode is preferably transparent or translucent.

FIG. 1 shows one example of the configuration of the organic electroluminescence device of the present invention. In the organic electroluminescence device 10 of the present invention shown in FIG. 1, a light emitting layer 6 is sandwiched between an anode 3 and a cathode 9 on a supporting substrate 2. More specifically, a hole injection layer 4, a hole transporting layer 5, a light emitting layer 6, a hole blocking layer 7 and an electron transporting layer 8 are stacked in this order between an anode 3 and a cathode 9.

<Configuration of Organic Layer>

The layer configuration of the organic layer is not particularly limited and may be appropriately selected according to the use and purpose of the organic electroluminescence device but is preferably formed on the transparent electrode or back plate. In this case, the organic layer is formed on the front surface or one surface of the transparent electrode or back plate.

The shape, size, thickness and the like of the organic layer are not particularly limited and may be appropriately selected according to the purpose.

Specific examples of the layer configuration include the following configurations, but the present invention is not limited thereto.

Anode/hole transporting layer/light emitting layer/electron transporting layer/cathode Anode/hole transporting layer/light emitting layer/blocking layer/electron transporting layer/cathode Anode/hole transporting layer/light emitting layer/blocking layer/electron transporting layer/electron injection layer/cathode Anode/hole injection layer/hole transporting layer/light emitting layer/blocking layer/electron transporting layer/cathode Anode/hole injection layer/hole transporting layer/light emitting layer/blocking layer/electron transporting layer/electron injection layer/cathode The device configuration, substrate, cathode and anode of an organic electroluminescence device are described in detail, for example, in JP-A-2008-270736, and the matters described therein can be applied to the present invention.

<Substrate>

The substrate for use in the present invention is preferably a substrate which does not scatter or attenuate the light emitted from the organic layer. When the substrate is made from an organic material, it is preferable that the organic material has excellent heat resistance, dimensional stability, solvent resistance, electrical insulation and workability.

<Anode>

The anode is usually sufficient if it has a function as an electrode of supplying a hole to the organic layer. The shape, structure, size and the like thereof are not particularly limited, and the anode material may be appropriately selected from known electrode materials according to the use or purpose of the luminescence device. As described above, the anode is usually provided as a transparent anode.

<Cathode>

The cathode is usually sufficient if it has a function as an electrode of injecting an electron in the organic layer. The shape, structure, size and the like thereof are not particularly limited, and the cathode material may be appropriately selected from known electrode materials according to the use or purpose of the luminescence device.

As for the substrate, anode and cathode, the matters described in JP-A-2008-270736, paragraphs [0070] to [0089] can be applied to the present invention.

<Organic Layer>

The organic layer for use in the present invention is described below.

—Formation of Organic Layer—

In the organic electroluminescence device of the present invention, each organic layer may be suitably formed by any of a dry deposition method such as vapor deposition and sputtering, a transfer method, a printing method and the like.

(Light Emitting Layer)

<Light Emitting Material>

The light emitting material for use in the present invention is compounds represented by formulae (1) to (8).

The light emitting material in the light emitting layer is generally contained in the light emitting layer, based on the mass of all compounds forming the light emitting layer, in an amount of 0.1 to 50 mass %, and in view of durability and external quantum efficiency, preferably in an amount of from 1 to 50 mass %, still more preferably from 2 to 40 mass %.

The thickness of the light emitting layer is not particularly limited but usually, the thickness is preferably from 2 to 500 nm, and in view of external quantum efficiency, more preferably from 3 to 200 nm, still more preferably from 5 to 100 nm.

In the device of the present invention, the light emitting layer may be composed of only a light emitting material or may have a mixed layer configuration of a host material and a light emitting material. The light emitting material may be either a fluorescent material or a phosphorescent material and as for the dopant, one kind of a dopant or two or more kinds of dopants may be used. The host material is preferably a charge transport material. As for the host material, one kind of a host material or two or more kinds of host materials may be used, and examples of this configuration include a configuration where an electron transporting host material and a hole transporting host material are mixed. Also, the light emitting layer may contain a material having no charge transport property and being incapable of producing luminescence.

Furthermore, the light emitting layer may be a single layer or a multilayer composed of two or more layers. In the case of a plurality of light emitting layers, the compounds represented by formulae (1) to (8) in the present invention may be contained in two or more light emitting layers. Also, respective light emitting layers may produce luminescence in different colors.

<Host Material>

Examples of the host material in the present invention may include the following compounds. For example, pyrrole, indole, carbazole, CBP (4,4'-di(9-carbazoyl)biphenyl), azaindole, azacarbazole, triazole, oxazole, oxadiazole, pyrazole, imidazole, thiophene, polyarylalkane, pyrazoline, pyrazolone, phenylenediamine, arylamine, amino-substituted chalcone, styrylanthracene, fluorenone, hydrazone, stilbene, silazane, an aromatic tertiary amine compound, a styrylamine compound, a porphyrin-based compound, a polysilane-based compound, poly(N-vinylcarbazole), an aniline-base copolymer, an electrically conductive polymer oligomer such as thiophene oligomer and polythiophene, an organic silane, a carbon film, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, a fluorine-substituted aromatic compound, a heterocyclic tetracarboxylic anhydride such as naphthaleneperylene, various metal complexes typified by a metal complex of phthalocyanine or 8-quinolinol derivative and a metal complex having metal phthalocyanine, benzoxazole or benzothiazole as the ligand, and derivatives thereof (may have a substituent or form a condensed ring) are exemplified.

In the present invention, the content of the host compound is not particularly limited but in view of luminous efficiency and drive voltage, the content is preferably from 15 to 98 mass % based on the mass of all compounds forming the light emitting layer.

(Fluorescent Material)

Examples of a fluorescent material usable in the invention include benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyralidine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidyne derivatives, various kinds of complexes typified by complexes of 8-quinolinol derivatives and complexes of pyrromethene derivatives, polymeric compounds such as polythiophene, polyphenylene and polyphenylenevinylene, and compounds like organic silane derivatives.

(Phosphorescent Material)

Examples of the phosphorescent material which can be used in the present invention include, other than the compounds represented by formulae (1) to (8), phosphorescent compounds described in patent documents such as U.S. Pat.

No. 6,303,238B1, U.S. Pat. No. 6,097,147, WO 00/57676, WO 00/70655, WO 01/08230, WO 01/39234A2, WO 01/41512A1, WO 02/02714A2, WO 02/15645A1, WO 02/44189A1, WO 05/19373A2, JP-A-2001-247859, JP-A-2002-302671, JP-A-2002-117978, JP-A-2003-133074, JP-A-2002-235076, JP-A-2003-123982, JP-A-2002-170684, EP 1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635 and JP-A-2007-96259. Examples of luminescent dopants which are far preferred among those compounds include the Ir complexes, the Pt complexes, the Cu complexes, the Re complexes, the W complexes, the Rh complexes, the Ru complexes, the Pd complexes, the Os complexes, the Eu complexes, the Tb complexes, the Gd complexes, the Dy complexes and the Ce complexes. Of these complexes, Ir complexes, the Pt complexes and the Re complexes are particularly preferable, notably Ir complexes, the Pt complexes and the Re complexes each having at least one kind of coordination bond selected from metal-carbon, metal-nitrogen, metal-oxygen and metal-sulfur coordinate bonds. In terms of luminous efficiency, durability under driving, chromaticity and so on, the Ir complexes, the Pt complexes and the Re complexes each having a polydentate ligand, including a tridentate ligand or higher, are preferred over the others.

The content of the phosphorescent material in the light emitting layer is preferably from 0.1 to 50 mass %, more preferably from 0.2 to 50 mass %, still more preferably from 0.3 to 40 mass %, and most preferably from 20 to 30 mass %, based on the total mass of the light emitting layer.

The content of the phosphorescent material which can be used in the present invention is preferably from 0.1 to 50 mass %, more preferably from 1 to 40 mass %, and most preferably from 5 to 30 mass %, based on the total mass of the light emitting layer. In particular, within the range of 5 to 30 mass %, the chromaticity of luminescence of the organic electroluminescence device is small in the dependency on the concentration of the phosphorescent material added.

The organic electroluminescence device of the present invention most preferably contains at least one kind of the compound represented by formulae (1) to (8) in an amount of 5 to 30 mass % based on the total mass of the light emitting layer.

The organic electroluminescence device preferably further contains a hydrocarbon compound or a derivative thereof, and it is more preferred to contain a hydrocarbon compound in a light emitting layer.

The hydrocarbon compound is preferably a compound represented by the following formula (VI).

By appropriately using the compound represented by formula (VI) together with the light emitting material, the interaction between material molecules can be adequately controlled to make uniform the energy gap and interaction between adjacent molecules, whereby the drive voltage can be more lowered.

Also, the compound represented by formula (VI) for use in the organic electroluminescence device is excellent in chemical stability and less causes a deterioration such as decomposition of the material during driving of the device, so that the organic electroluminescence device can be prevented from reduction in the efficiency or life due to decomposition of the material.

The compound represented by formula (VI) is described below.

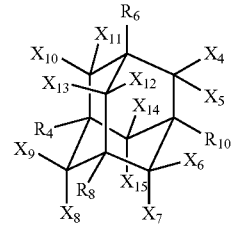

(VI)

In formula (VI), each of R4, R6, R8, R10 and X4 to X15 independently represents a hydrogen atom, an alkyl group or an aryl group.

In formula (VI), the alkyl group represented by $R_4$, $R_6$, $R_8$, $R_{10}$ and $X_4$ to $X_{15}$ may be substituted with an adamantane structure or an aryl structure and is preferably an alkyl group having a carbon number of 1 to 70, more preferably from 1 to 50, still more preferably from 1 to 30, yet still more preferably from 1 to 10, even yet still more preferably from 1 to 6, and most preferably a linear alkyl group having a carbon number of 2 to 6.

Examples of the alkyl group represented by each of $R_4$, $R_6$, $R_8$, $R_{10}$ and $X_4$ to $X_{15}$ in the formula (VI) include an n-$C_{50}H_{101}$ group, an n-$C_{30}H_{61}$ group, 3-(3,5,7-triphenyladamantane-1-yl)propyl group (number of carbon atoms: 31), a trityl group (number of carbon atoms: 19), 3-(adamantane-1-yl)propyl group (number of carbon atoms: 13), 9-decalyl group (number of carbon atoms: 10), a benzyl group (number of carbon atoms: 7), a cyclohexyl group (number of carbon atoms: 6), a n-hexyl group (number of carbon atoms: 6), an n-pentyl group (number of carbon atoms: 5), an n-butyl group (number of carbon atoms: 4), an n-propyl group (number of carbon atoms: 3), a cyclopropyl group (number of carbon atoms: 3), an ethyl group (number of carbon atoms: 2) and a methyl group (number of carbon atoms: 1).

The aryl group represented by each of $R_4$, $R_6$, $R_8$, $R_{10}$ and $X_4$ to $X_{15}$ in the formula (VI) may have as a substituent an adamantane structure or an alkyl structure, and the number of carbon atoms the aryl group has is preferably from 6 to 30, far preferably from 6 to 20, further preferably from 6 to 15, especially preferably from 6 to 10, the most preferably is 6.

Examples of the aryl group represented by each of $R_4$, $R_6$, $R_8$, $R_{10}$ and $X_4$ to $X_{15}$ in the formula (VI) include a 1-pyrenyl group (number of carbon atoms: 16), a 9-anthracenyl group (number of carbon atoms: 14), a 1-naphthyl group (number of carbon atoms: 10), a 2-natphthyl group (number of carbon atom: 10), a p-t-butylphenyl group (number of carbon atoms: 10), a 2-m-xylyl group (number of carbon atoms: 8), a 5-m-xylyl group (number of carbon atoms: 8), an o-tolyl group (number of carbon atoms: 7), a m-tolyl group (number of carbon atoms: 7), a p-tolyl group (number of carbon atoms: 7) and a phenyl group (number of carbon atoms: 6).

Although each of $R_4$, $R_6$, $R_8$ and $R_{10}$ in the formula (VI) may be either a hydrogen atom, or an alkyl group, or an aryl group, from the viewpoint that high glass transition temperatures are preferable, it is preferable that at least one of them is an aryl group, it is far preferable that at least two of them are aryl groups, and it is particularly preferable that 3 or 4 of them are aryl groups.

Although each of $X_4$ to $X_{15}$ in the formula (VI) may represent either a hydrogen atom, or an alkyl group, or an aryl group, it is preferable that each stands for a hydrogen atom or an aryl group, especially a hydrogen atom.

The organic electroluminescence devices are made using a vacuum deposition process or a solution coating process, and therefore, in terms of vacuum deposition suitability and solubility, the molecular weight of the compounds represented by the formula (VI) in the invention is preferably 2,000 or below, far preferably 1,200 or below, especially 1,000 or below. Also, from the viewpoint of vacuum deposition suitability, the molecular weight is preferably 250 or above, far preferably 350 or above, particularly preferably 400 or above. This is because, when the compounds have too low molecular weight, their vapor pressure becomes low and change from a vapor phase to a solid phase does not occur, and it is therefore difficult for the compounds to form organic layers.

The compound represented by the formula (VI) is preferably in solid phase at room temperature (25° C.), far preferably solid phase in a range from room temperature to 40° C., especially preferably solid phase in a range from room temperature to 60° C.

In the case of using the compound which, though represented by the formula (VI), is not in solid phase at room temperature, it is possible to form a solid phase at ordinary temperatures by combining the compound with other substances.

Uses of the compound represented by the formula (VI) are not limited, and the compound may be incorporated into any of the organic layers. The layer into which the compound represented by the formula (VI) in the invention is introduced is preferably a layer selected from a light emitting layer, a hole injection layer, a hole transporting layer, an electron transporting layer, an electron injection layer, an exciton block layer and a charge blocking layer, or a combination of two or more of these layers, far preferably a layer selected from the light emitting layer, the hole injection layer, the hole transporting layer, the electron transporting layer and the electron injection layer, or a combination of two or more of these layers, especially preferably a layer selected from the light emitting layer, the hole injection layer and the hole transporting layer, or a combination of at least two of these layers, the most preferably the light emitting layer.

When the compound represented by the formula (VI) is used in an organic layer, its content is required to be limited so as not to inhibit charge transportability, and therefore it is preferable from 0.1% to 70% by mass, far preferable from 0.1% to 30% by mass, especially preferable from 0.1% to 25% by mass.

When the compound represented by the formula (VI) is used in two or more organic layers, its content in each organic layer is preferably in the range specified above.

Only one kind of a compound represented by formula (VI) may be contained in any organic layer, or a plurality of kinds of compounds represented by formula (VI) may be contained in combination in an arbitrary ratio.

Specific preferred examples of the hydrocarbon compound and its derivative are illustrated below, but the present invention is not limited thereto.

(1-1)

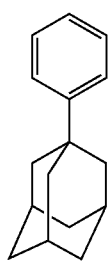

(1-2)

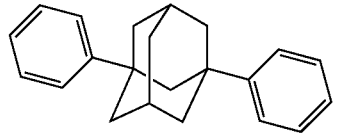

(1-3)

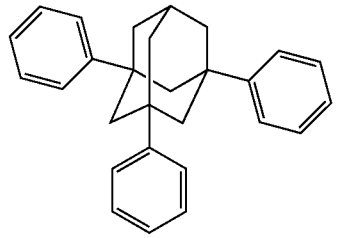

(1-4)

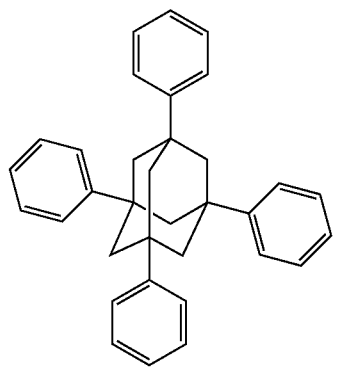

(1-5)

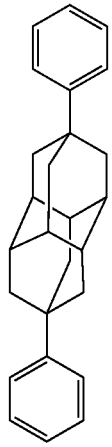

(1-6)

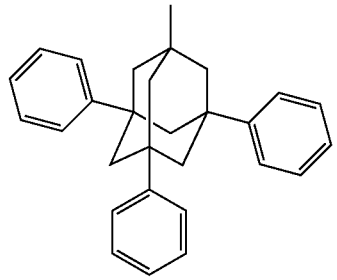

(1-7)
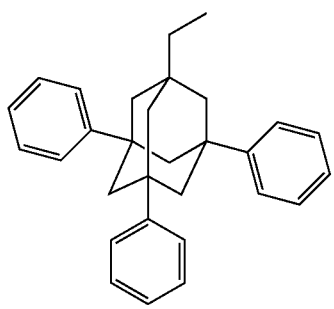
(1-8)
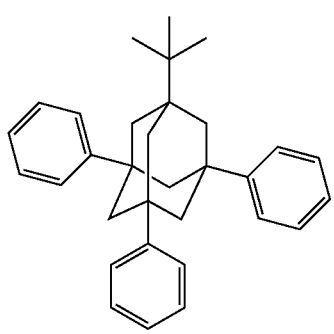
(1-9)
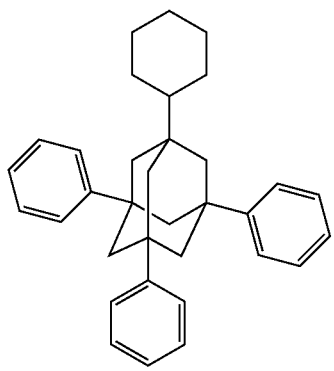
(1-10)
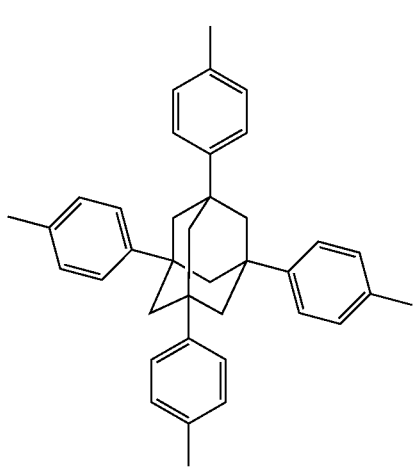
(1-11)
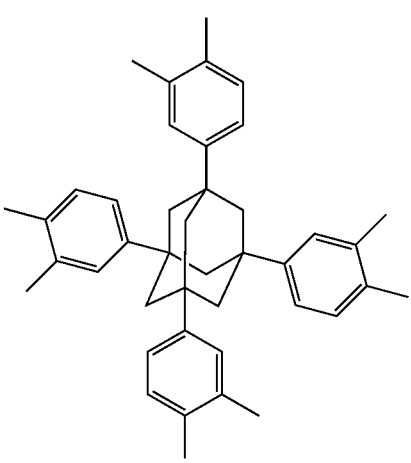
(1-12)
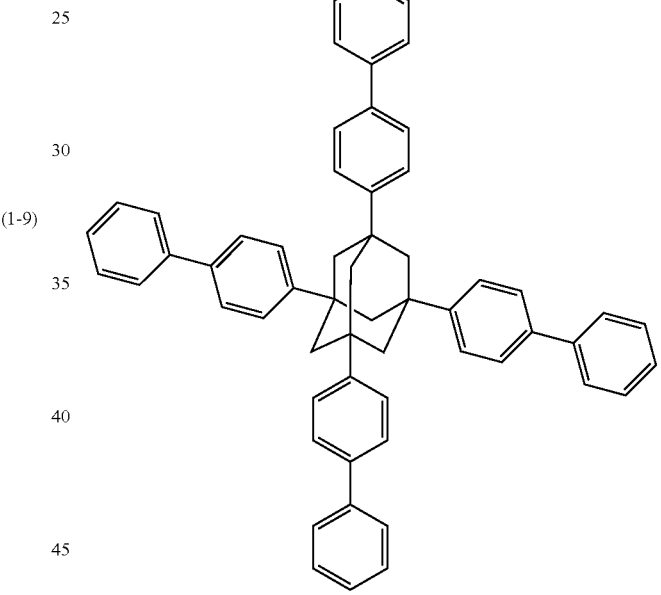
(1-13)
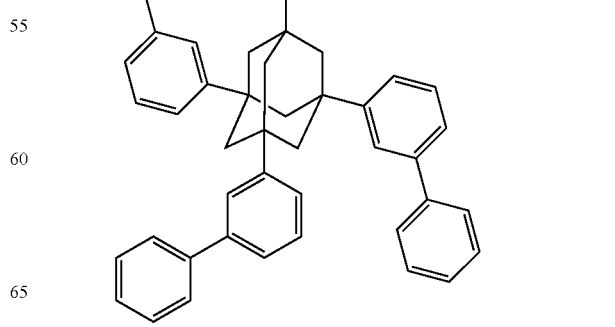

-continued
(1-14)
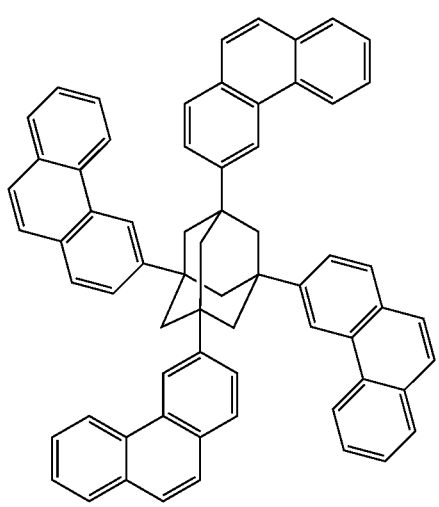
(1-15)
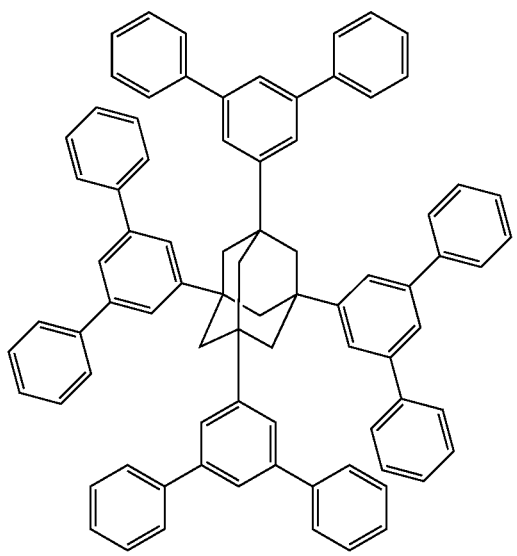
(1-16)
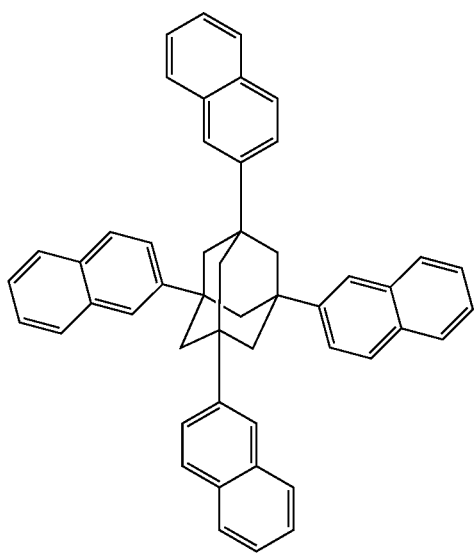
-continued
(1-17)
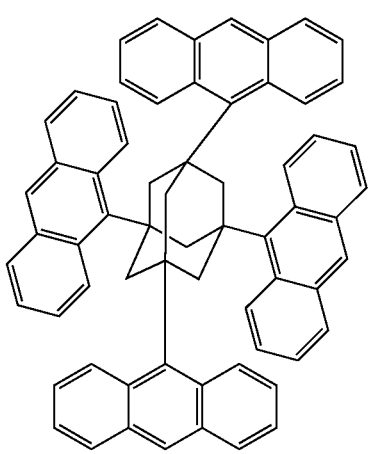
(1-18)
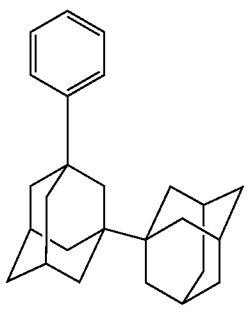
(1-19)
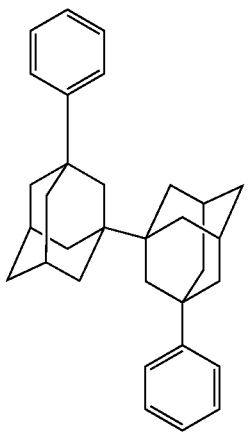

(1-20)
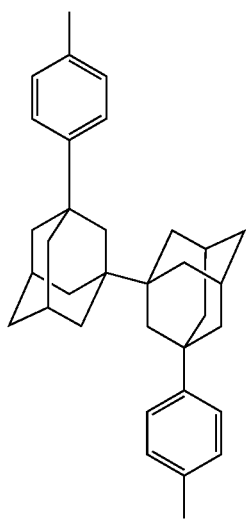
(1-21)
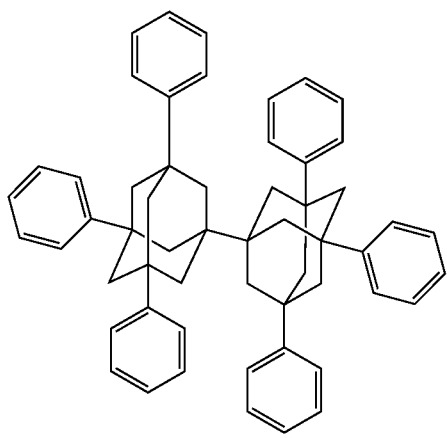
(1-22)
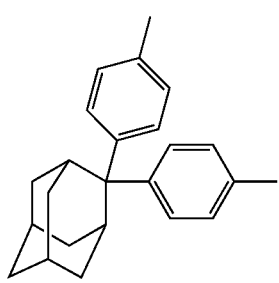
(1-23)
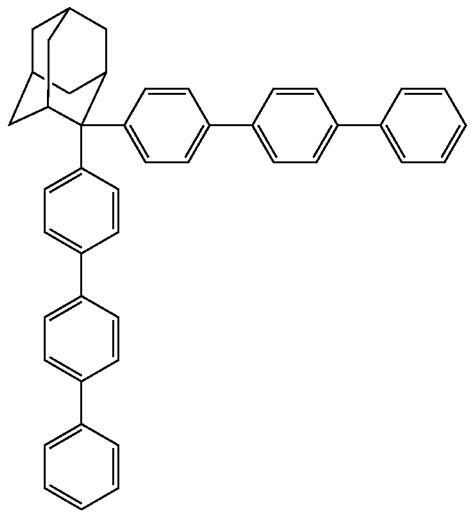
(1-24)
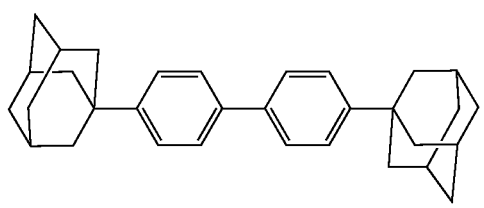
(1-25)
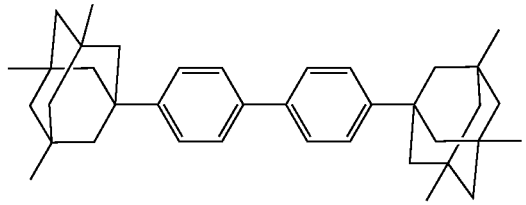
(1-26)
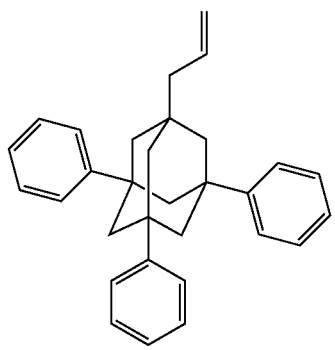

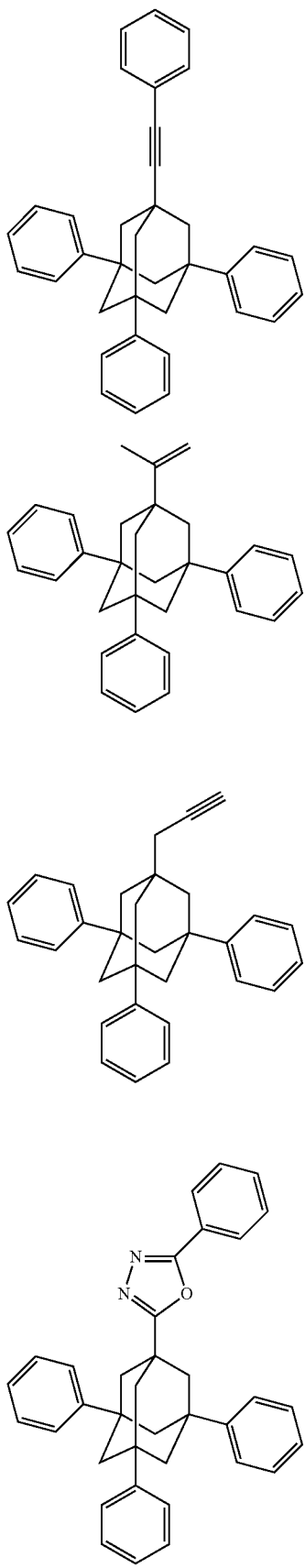
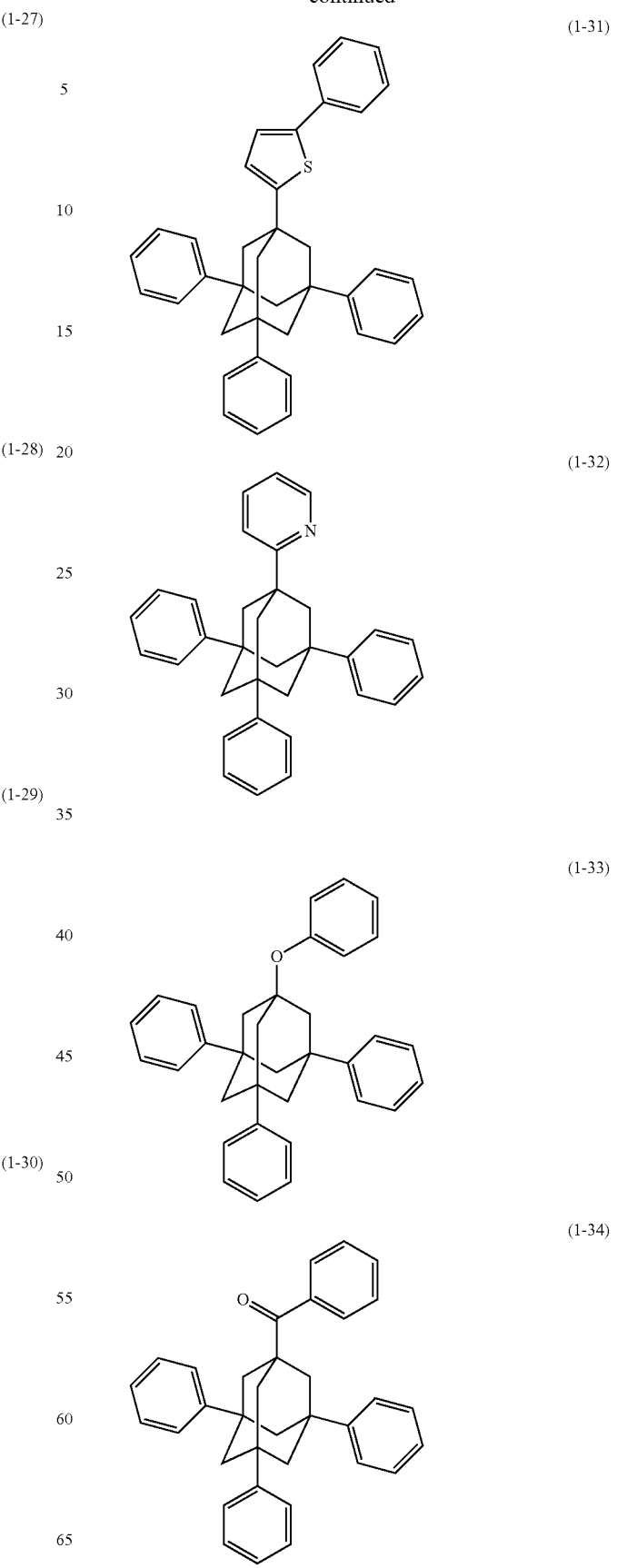

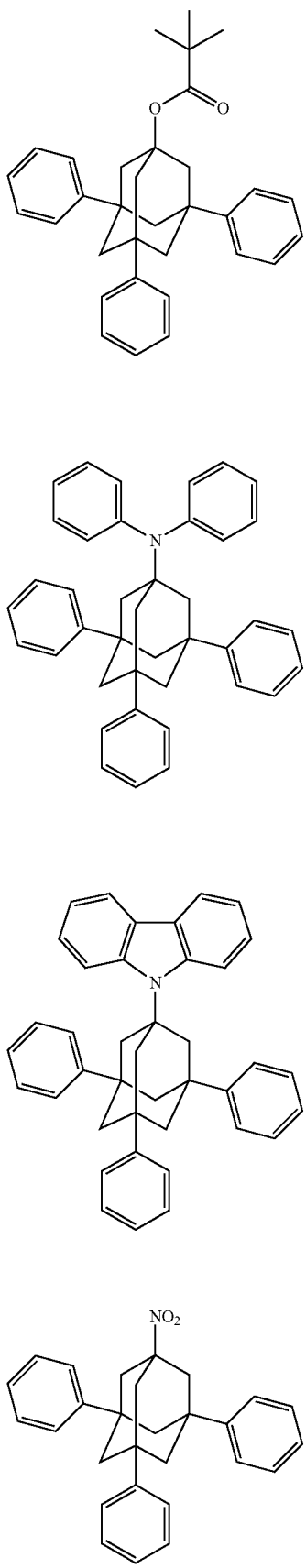
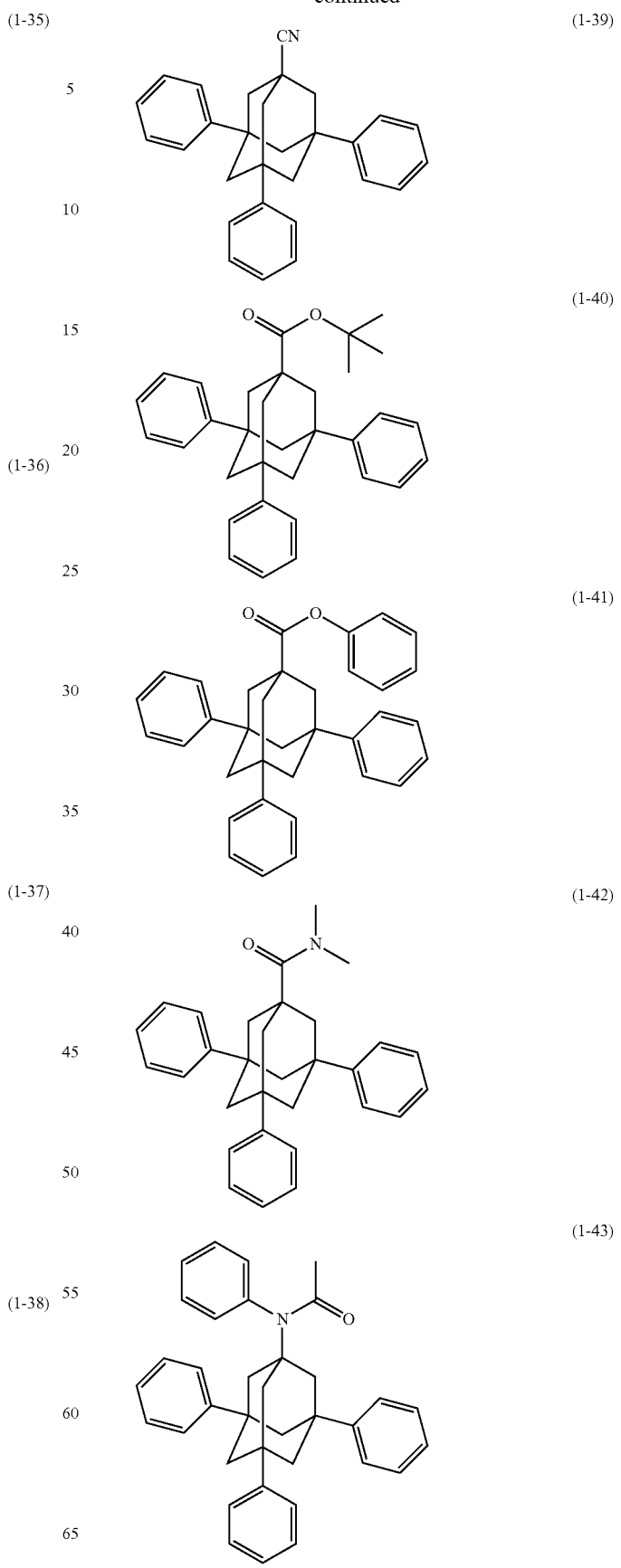

(1-44) 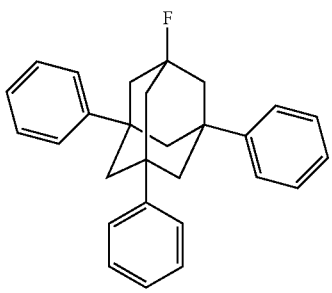

(1-45) 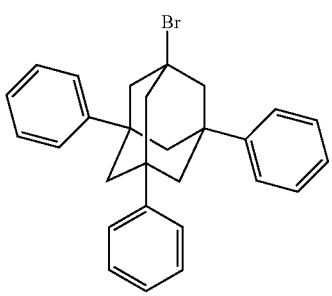

(1-46) 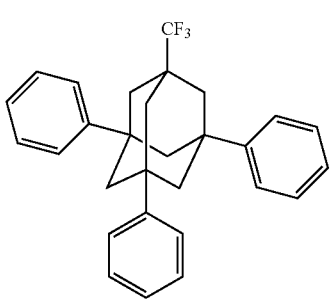

(1-47) 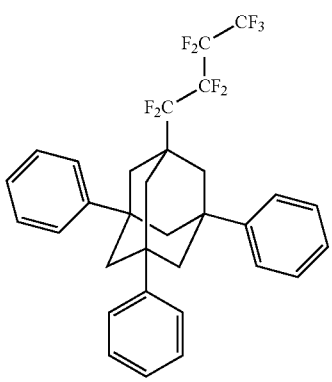

(1-48) 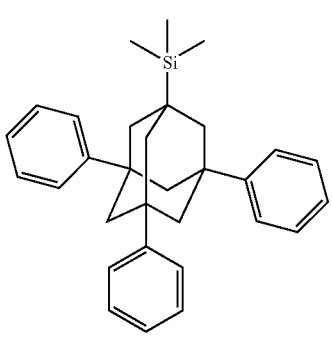

(1-49) 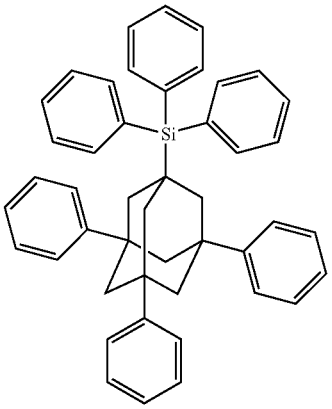

The compound represented by the formula (VI) can be synthesized by appropriately combining adamantane or haloadamantane with haloalkane or alkylmagnesium halide (Grignard reagent). For instance, it is possible to provide coupling between haloadamantane and haloalkane by use of indium (Reference 1). Alternatively, it is possible to convert haloalkane into an alkylcopper reagent and further to couple the reagent to Grignard reagent of an aromatic compound (Reference 2). Further, the coupling of haloalkane can also be performed using an appropriate arylboric acid and a palladium catalyst (Reference 3).

Reference 1: Tetrahedron Lett. 39, 9557-9558 (1998)
Reference 2: Tetrahedron Lett. 39, 2095-2096 (1998)
Reference 3: J. Am. Chem. Soc. 124, 13662-13663 (2002)

The adamantane structure having an aryl group can be synthesized by appropriately combining adamantane or haloadamantane with the corresponding arene or haloarene.

Additionally, even when defined substituents undergo changes under certain synthesis conditions in those production methods or they are unsuitable for carrying out those methods, the intended compounds can be produced with ease by adopting e.g. methods for protecting and deprotecting functional groups (T. W. Greene, Protective Groups in Organic Synthesis, John Wiley & Sons Inc. (1981)). Further, it is also possible to change the order of reaction steps, including a substituent introduction step, as appropriate, if needed.

The thickness of the light emitting layer is not particularly limited but usually, the thickness is preferably from 1 to 500 nm, more preferably from 5 to 200 nm, still more preferably from 10 to 100 nm.

—Hole Injection Layer, Hole Transporting Layer—

The hole injection layer and the hole transporting layer are a layer having a function of receiving a hole from the anode or anode side and transporting it to the cathode side.

—Electron Injection Layer, Electron Transporting Layer—

The electron injection layer and the electron transporting layer are a layer having a function of receiving an electron from the cathode or cathode side and transporting it to the anode side.

As regards the hole injection layer, hole transporting layer, electron injection layer and electron transporting layer, the matters described in JP-A-2008-270736, paragraphs [0165] to [0167] can be applied to the present invention.

—Hole Blocking Layer—

The hole blocking layer is a layer having a function of blocking the holes transported from an anode side to the light emitting layer from passing on through to the cathode side. In the invention, the hole blocking layer can be provided as an organic layer adjacent to the light emitting layer in the cathode side.

Examples of an organic compound which forms the hole blocking layer include aluminum complexes such as aluminum(III) bis(2-methyl-8-quinolinato) 4-phenylphenolate (abbreviated to BAlq), triazole derivatives, and phenanthroline derivatives such as 2,9-dimethyl-4,7-diphenyl-1,10-phenanthroline (abbreviated to BCP).

The thickness of the hole blocking layer is preferably from 1 nm to 500 nm, far preferably from 5 nm to 200 nm, further preferably from 10 nm to 100 nm.

The hole blocking layer may have either a single-layer structure made up of one or more than one material as recited above or a multiple-layer structure made up of two or more layers which are identical or different in composition.

—Electron Blocking Layer—

The electron blocking layer is a layer having a function of preventing the electrons transported from the cathode side to the light emitting layer from passing through to the anode side. In the invention, the electron blocking layer can be provided as an organic layer adjacent to the light emitting layer on the anode side.

As the examples of the compounds constituting the electron blocking layer, for instance, the hole transporting materials described above can be applied.

The thickness of the electron blocking layer is preferably from 1 nm to 500 nm, more preferably from 5 nm to 200 nm, still more preferably from 10 nm to 100 nm.

The electron blocking layer may have a single layer structure composed of one or more of the above materials or may be a multilayer structure composed of two or more layers having the same composition or different compositions.

<Protective Layer>

In the present invention, the entire organic EL device may be protected by a protective layer.

As for the protective layer, the matters described in JP-A-2008-270736, paragraphs [0169] and [0170] can be applied to the present invention.

<Sealing Enclosure>

The device of the present invention may be entirely sealed using a sealing container.

As for the sealing container, the matters described in JP-A-2008-270736, paragraph [0171] can be applied to the present invention.

[Film Formation Method]

The heating temperature at the time of film formation is preferably from 200° C. to 400° C., far preferably from 250° C. to 320° C.

The heating time is preferably from 0.1 hour to 350 hours, far preferably from 0.1 hour to 150 hours.

Luminescence of the organic electroluminescence device of the present invention can be obtained by applying a DC (if desired, an AC component may be contained) voltage (generally from 2 to 15 volts) or a DC current between the anode and the cathode.

As for the driving method of the organic electroluminescence device of the present invention, the driving methods described, for example, in JP-A-2-148687, JP-A-6-301355, JP-A-5-29080, JP-A-7-134558, JP-A-8-234685, JP-A-8-241047, Japanese Patent 2784615, and U.S. Pat. Nos. 5,828,429 and 6,023,308 can be applied.

The light collection efficiency of the luminescence device of the present invention can be enhanced by various known measures. For example, the light collection efficiency and the external quantum efficiency can be enhanced by processing the substrate surface shape (for example, forming a fine uneven pattern), by controlling the refractive index of the substrate, ITO layer or organic layer, or by controlling the film thickness of the substrate, ITO layer or organic layer.

The luminescence device of the present invention may be in a so-called top emission system of collecting light from the anode side.

The present organic EL devices may have resonator structure. For instance, each device has on a transparent substrate a multilayer film mirror made up of a plurality of laminated films that have different refractive indices, a transparent or translucent electrode, a light emitting layer and a metal electrode which are superposed on top of each other. Reflections of light produced in the light emitting layer occur repeatedly between the multilayer film mirror and the metal electrode which function as reflector plates, thereby producing resonance.

In another aspect, the transparent or translucent electrode and the metal electrode function as reflector plates, respectively, on the transparent substrate, and reflections of light produced in the light emitting layer occur repeatedly between the reflector plates, thereby producing resonance.

In order to form a resonance structure, the optical distance determined from effective refractive indices of the two reflector plates, and refractive indices and thicknesses of each layers sandwiched between the two reflector plates are adjusted to have optimum values for achieving the desired resonance wavelength. The calculating formula in the first aspect case is described in JP-A-9-180883, and that in the second aspect case is described in JP-A-2004-127795.

(Use of Luminescence Device of the Present Invention)

The present luminescence devices can be used suitably for light luminous apparatus, pixels, indication devices, displays, backlights, electrophotographic devices, illumination light sources, recording light sources, exposure light sources, readout light sources, sign, billboards, interior decorations or optical communications, especially preferably for devices driven in a region of high-intensity luminescence, such as illumination apparatus and display apparatus.

Next the present light luminous apparatus is explained by reference to FIG. 2.

The present light luminous apparatus incorporates any one of the present organic electroluminescence devices.

Figure 2:
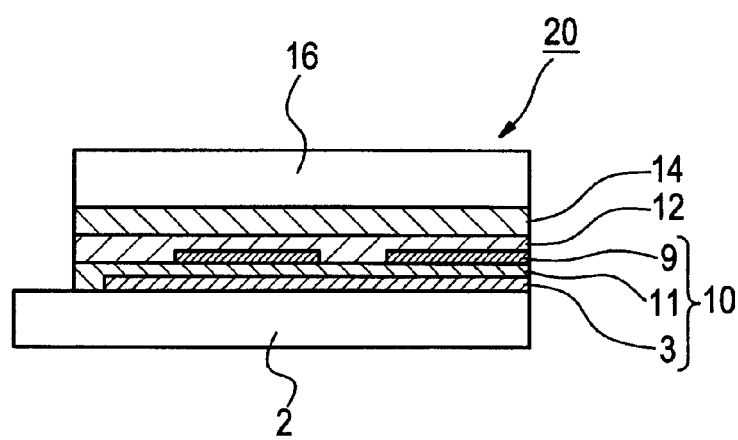
FIG. 2 is a schematic diagram showing one example of a light emission apparatus relating to the invention (a second embodiment of the invention)

FIG. 2 is a cross-sectional diagram schematically showing one example of the present light luminous apparatus.

The light luminous apparatus 20 in FIG. 2 includes a transparent substrate 2 (supporting substrate), an organic electroluminescence device 10, a sealing enclosure 16 and so on.

The organic electroluminescence device 10 is formed by stacking on the substrate 2 an anode 3 (first electrode), an organic layer 11 and a cathode 9 (second electrode) in the order of mention. In addition, a protective layer 12 is superposed on the cathode 9, and on the protective layer 12 a sealing enclosure 16 is further provided via an adhesive layer 14. Incidentally, part of each of the electrodes 3 and 9, a diaphragm and an insulating layer are omitted in FIG. 2.

Herein, a light cure adhesive such as epoxy resin, or a thermosetting adhesive can be used for the adhesive layer 14. Alternatively, a thermosetting adhesive sheet may be used as the adhesive layer 14.

The present light emission apparatus has no particular restrictions as to its uses, and specifically, it can be utilized e.g. as not only illumination apparatus but also display apparatus of a television set, a personal computer, a mobile phone, an electronic paper or the like.

The illumination apparatus according to an embodiment of the present invention is described below by referring to FIG. 3.

Figure 3:
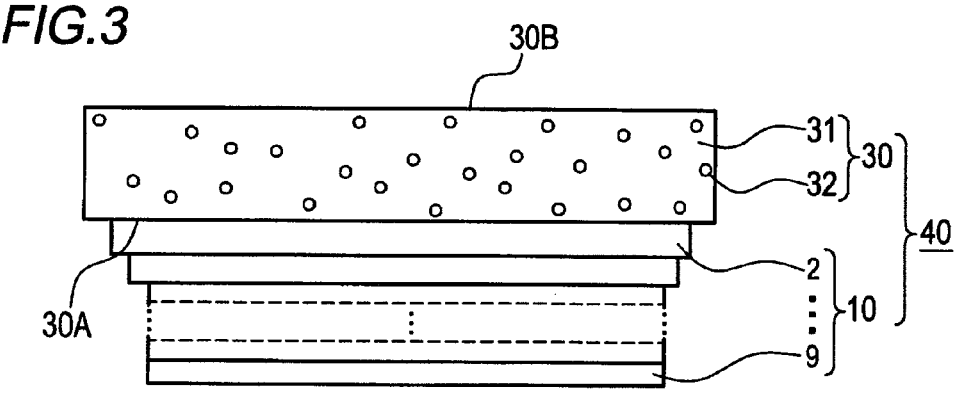
FIG. 3 is a schematic diagram showing one example of an illumination apparatus relating to the invention (a third embodiment of the invention).

The illumination apparatus 40 according to an embodiment of the present invention contains, as shown in FIG. 3, the above-described organic electroluminescence device 10 and a light scattering member 30. More specifically, the illumination apparatus 40 is configured such that the substrate 2 of the organic electroluminescence device 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particle 32 include a transparent resin fine particle. As the glass substrate and the transparent resin fine particle, a known product can be used for both. In such an illumination apparatus 40, when light emitted from the organic electroluminescence device 10 is incident on the light incident surface 30A of the scattering member 30, the incident light is scattered by the light scattering member and the scattered light is output as illuminating light from the light output surface 30B.

EXAMPLES

The invention will now be illustrated in further detail by reference to the following examples and comparative examples, but the invention should not be construed as being limited to the following examples in any way.

Synthesis Examples

Synthesis of Exemplified Compound 1

Exemplified Compound 1 was synthesized in accordance with the following reaction scheme (Synthesis Method 12).

At a temperature of −78° C. under an atmosphere of nitrogen, a pentane solution of n-BuLi (2.6 ml, 4.2 mmol) was added dropwise to 10 ml of a dehydrated THF solution of the compound 1a (744 mg, 4 mmol), and stirred for 30 minutes. Thereto, a diethyl ether solution of anhydrous zinc(II) chloride (4 ml, 4 mmol) was further added dropwise, and stirring was continued until the temperature of the reaction solution was restored to room temperature.

To the reaction solution containing the zinc complex, the bromine-bridged complex 2a (2.57 g, 2 mmol) and 20 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with MgSO₄ and removal of the solvent under reduced pressure. After isomerization and subsequent washing (12 hours) in boiling glycerol, a precipitate formed was filtered off, dissolved in dichloromethane, and purified by recrystallization. Thus, 1.85 g of Exemplified Compound 1 (2.48 mmol, 62%) was obtained. And it was found by HPLC that the thus obtained Exemplified Compound 1 had a purity of 99.5%. In addition, in ICP optical emission spectroscopy of the compound obtained, the content of Li and Li ion was found to be 7.2 ppm and the content of Mg and Mg ion was found to be below 1 ppm.

In addition, Exemplified Compound 1 was synthesized in accordance with the following reaction scheme (Synthesis Method 13) also.

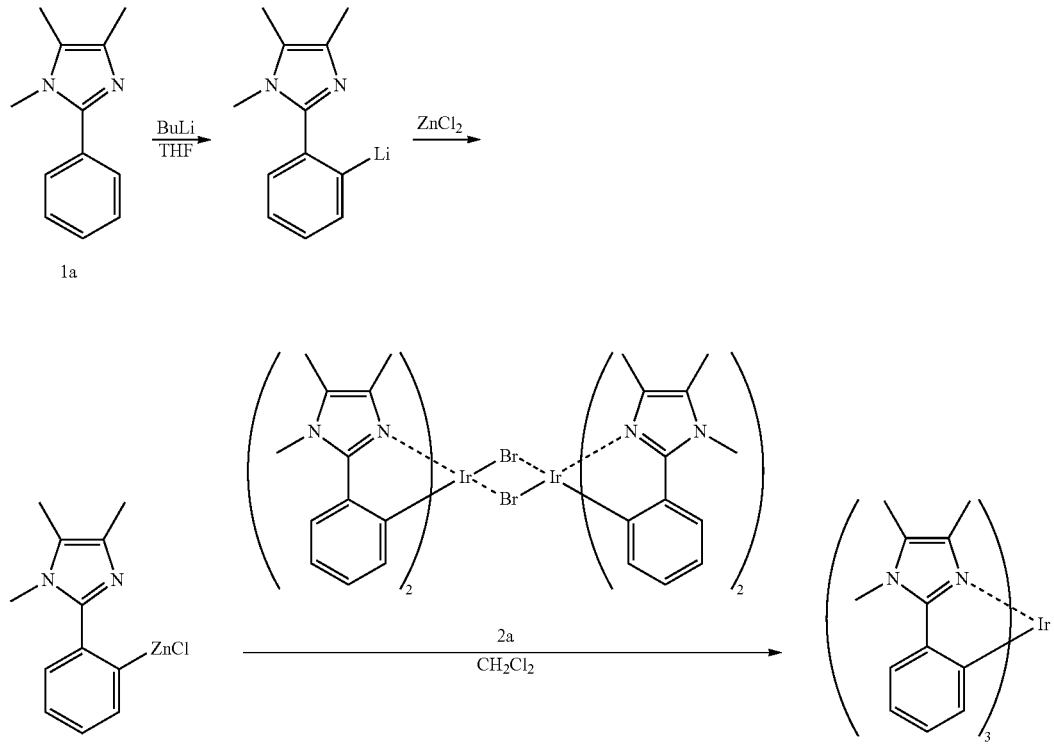

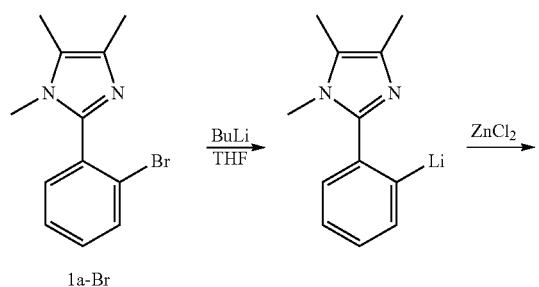

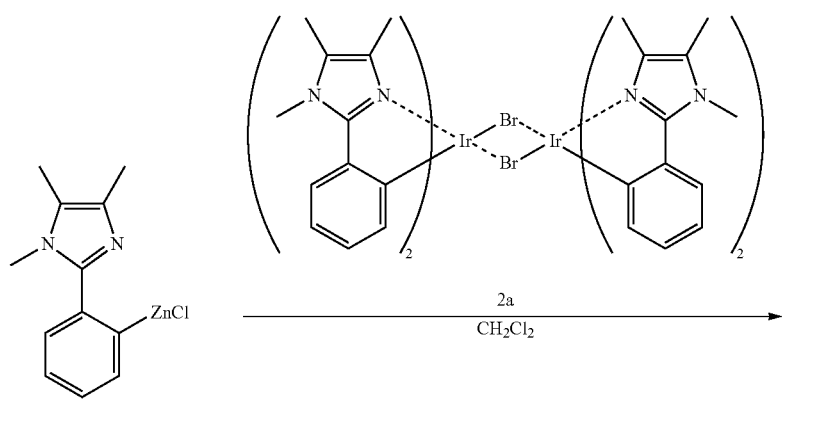

At a temperature of −78° C. under an atmosphere of nitrogen, a pentane solution of n-BuLi (2.6 ml, 4.2 mmol) was added dropwise to 10 ml of a dehydrated THF solution of the compound 1a-Br (744 mg, 4 mmol), and stirred for 30 minutes. Thereto, a diethyl ether solution of anhydrous zinc(II) chloride (4 ml, 4 mmol) was further added dropwise, and stirring was continued until the temperature of the reaction solution was restored to room temperature.

To the reaction solution containing the zinc complex, the bromine-bridged complex 2a (2.57 g, 2 mmol) and 20 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with MgSO$_4$ and removal of the solvent under reduced pressure. After isomerization and subsequent washing (12 hours) in boiling glycerol, a precipitate formed was filtered off, dissolved in dichloromethane, and purified by recrystallization. Thus, 2.08 g of Exemplified Compound 1 (2.80 mmol, 70%) was obtained. And it was found by HPLC that the thus obtained Exemplified Compound 1 had a purity of 99.2%. In addition, in ICP optical emission spectroscopy of the compound obtained, the content of Li and Li ion was found to be 9.2 ppm and the content of Mg and Mg ion was found to be below 1 ppm.

Further, Exemplified Compound 1 was synthesized in accordance with the following reaction scheme (Synthesis Method 14) also.

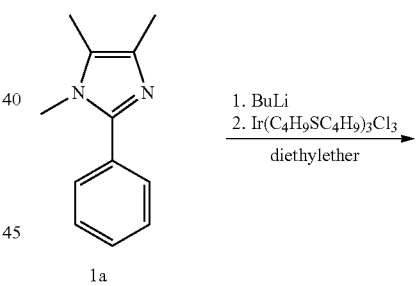

At a temperature of −78° C. under an atmosphere of nitrogen, a pentane solution of n-BuLi (5.0 ml, 8 mmol) was added dropwise to 60 ml of a dehydrated diethyl ether solution of the compound 1a (1.49 g, 8 mmol), and stirred for 30 minutes. Thereto, a diethyl ether solution of tris(dibutylsulfide)iridium chloride (15 ml, 2 mmol) was further added dropwise, and stirred for 1 hour at −78° C. Thereafter, stirring was further continued for 6 hours or more until the temperature of the reaction mixture was restored to room temperature. After the reaction mixture was quenched with dilute hydrochloric acid, extraction with dichloromethane, washing with water, drying with MgSO$_4$ and removal of the solvent under reduced pressure were carried out in sequence. The thus obtained reaction product was purified by column chromatography (developing solvent: dichloromethane), and recrystallized from a dichloromethane solution. Thus, 507 mg of Exemplified Compound 1 (0.68 mmol, 34%) was obtained. And it was found by HPLC that the thus obtained Exemplified Compound 1 had a purity of 99.2%. Further, in ICP optical emission spectroscopy of the compound obtained, the content of Li and Li ion was found to be 2.3 ppm and the content of Mg and Mg ion was found to be below 1 ppm.

Furthermore, Exemplified Compound 1 was synthesized by the method disclosed in US 2006/0008670 [0134] (a traditional method). And in ICP optical emission spectroscopy, the thus obtained Exemplified Compound 1 was found to be below 1 ppm in both the content of Li and Li ion and the content of Mg and Mg ion.

Synthesis of Exemplified Compound 62

Exemplified Compound 62 was synthesized in accordance with the following reaction scheme (Synthesis Method 6).

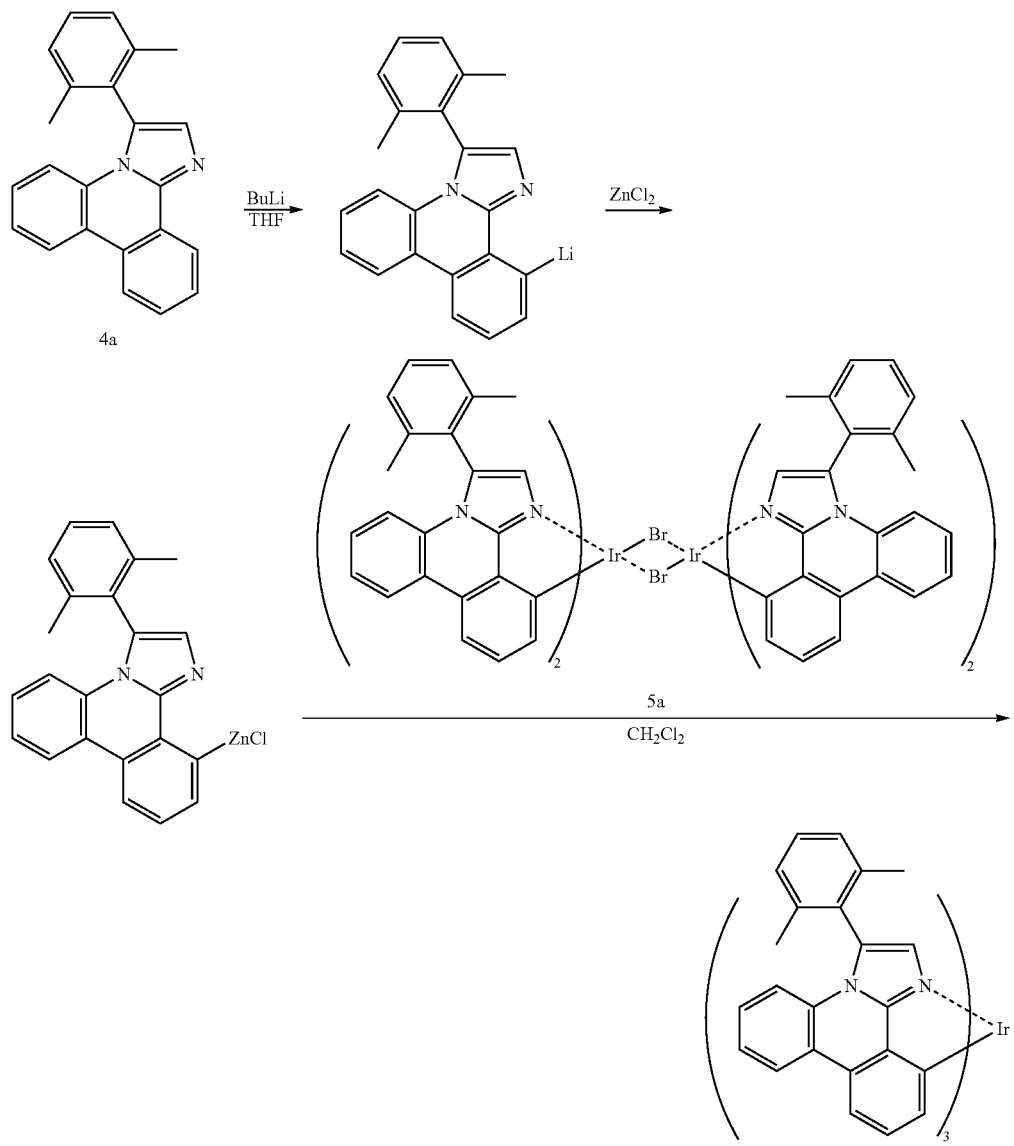

At a temperature of −78° C. under an atmosphere of nitrogen, a pentane solution of n-BuLi (1.8 ml, 2.9 mmol) was added dropwise to 15 ml of a dehydrated THF solution of the compound 4a (903 mg, 2.8 mmol), and stirred for 30 minutes. Thereto, a diethyl ether solution of anhydrous zinc(II) chloride (3 ml, 2.8 mmol) was further added dropwise, and stirring was continued until the temperature of the reaction solution was restored to room temperature. To the reaction solution containing the zinc complex, the bromine-bridged complex 5a (2.56 g, 1.4 mmol) and 15 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with MgSO₄ and removal of the solvent under reduced pressure. After isomerization and subsequent washing (12 hours) in boiling glycerol, a precipitate formed was filtered off, dissolved in dichloromethane, and purified by recrystallization. Thus, 1.64 g of Exemplified Compound 62 (1.43 mmol, 51%) was obtained. And it was found by HPLC that the thus obtained Exemplified Compound 62 had a purity of 99.3%. In addition, in ICP optical emission spectroscopy of the compound obtained, the content of Li and Li ion was found to be 3.3 ppm and the content of Mg and Mg ion was found to be below 1 ppm.

¹H-NMR (300 MHz, in CDCl₃): δ (ppm)=1.93 (s, 9H), 2.09 (s, 9H), 6.92 (s, 3H), 7.14-7.23 (m, 18H), 7.35 (t, 3H), 7.45 (t, 3H), 7.76 (d, J=7.6, 3H), 8.51 (d, J=8.2, 3H)

In addition, Exemplified Compound 62 was synthesized in accordance with the following reaction scheme (Synthesis Method 7) also.

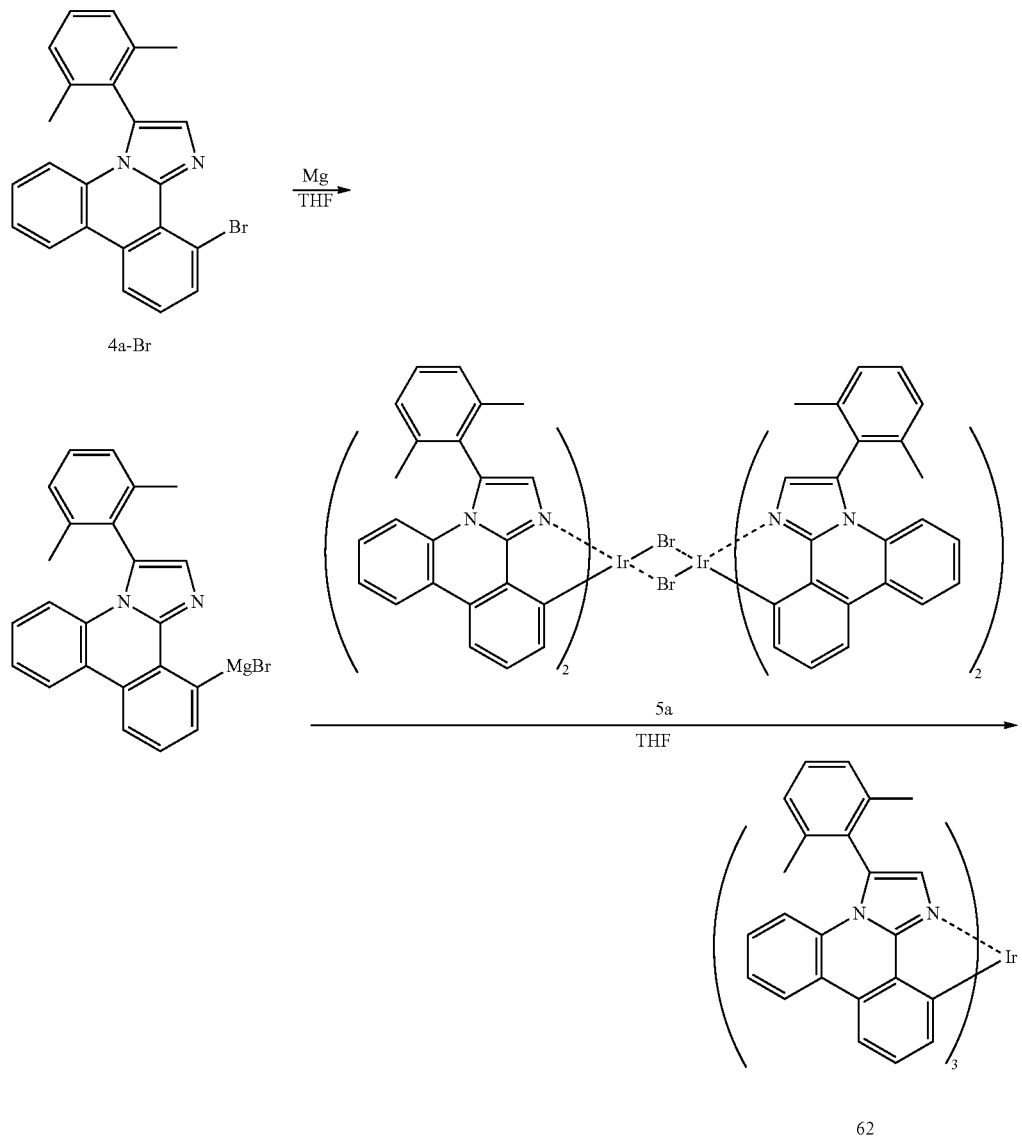

At room temperature under an atmosphere of nitrogen, 25 ml of a dehydrated THF solution of the compound 4a-Br (2.01 g, 5 mmol) and 1,2-dichloroethane (0.40 ml, 0.5 mmol) was added dropwise to a suspension of magnesium (121 mg, 5 mmol) in 2.5 ml of dehydrated THF. The reaction solution was refluxed for 2 hours at its boiling temperature, thus a Grignard reagent solution was prepared. In a separate vessel, the bromine-bridged complex 5a (2.29 g, 1.25 mmol) was dissolved in 50 ml of dehydrated THF, and cooled to 0° C. in an atmosphere of nitrogen. Thereto, the Grignard reagent prepared was added dropwise, and stirred for 1 hour. After the temperature of the reaction mixture was restored to room temperature, reflux at boiling temperature was carried out for 6 hours. The resulting reaction mixture was quenched with H₂O and alcohol, and then subjected successively to extraction with dichloromethane, washing with water, drying with MgSO₄ and removal of the solvent under reduced pressure.

After isomerization and subsequent washing (12 hours) in boiling glycerol, a precipitate formed was filtered off, dissolved in dichloromethane, and purified by recrystallization. Thus, 1.60 g of Exemplified Compound 62 (1.38 mmol, 55%) was obtained. And it was found by HPLC that the thus obtained Exemplified Compound 62 had a purity of 99.4%. In addition, in ICP optical emission spectroscopy of the compound obtained, the content of Li and Li ion was found to be below 1 ppm and the content of Mg and Mg ion was found to be 6.5 ppm.

Further, Exemplified Compound 62 was synthesized in accordance with the following reaction scheme (Synthesis Method 8) also.

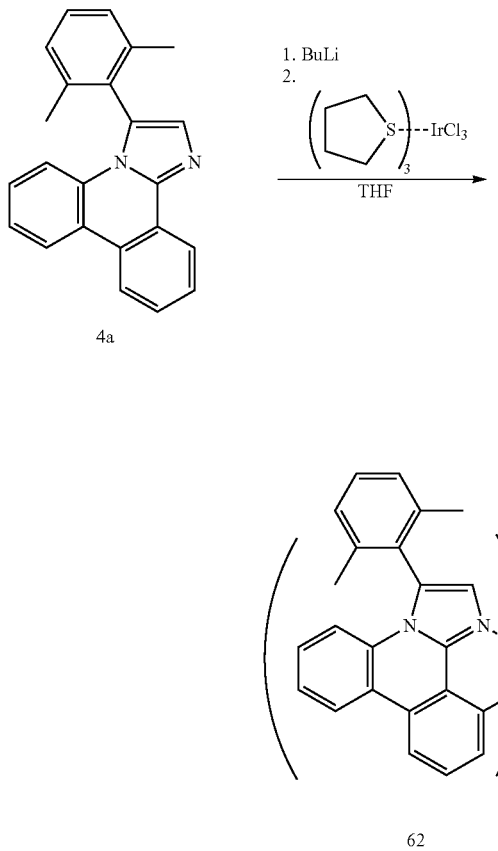

At a temperature of −78° C. under an atmosphere of nitrogen, a pentane solution of n-BuLi (3.9 ml, 6.3 mmol) was added dropwise to 30 ml of a dehydrated THF solution of the compound 4a (1.93 g, 6 mmol), and stirred for 30 minutes. Thereto, a THF solution of tris(tetrahydrothiophene)iridium chloride (7 ml, 1.5 mmol) was further added dropwise, and stirred for 1 hour at −78° C. Thereafter, stirring was further continued for 6 hours or more until the temperature of the reaction mixture was restored to room temperature. After the reaction mixture was quenched with dilute hydrochloric acid, extraction with dichloromethane, washing with water, drying with MgSO$_4$ and removal of the solvent under reduced pressure were carried out in sequence. The thus obtained reaction product was purified by column chromatography (developing solvent: dichloromethane), and recrystallized from a dichloromethane solution. Thus, 438 mg of Exemplified Compound 62 (0.38 mmol, 25%) was obtained. And it was found by HPLC that the thus obtained Exemplified Compound 62 had a purity of 99.1%. Further, in ICP optical emission spectroscopy of the compound obtained, the content of Li and Li ion was found to be 6.9 ppm and the content of Mg and Mg ion was found to be below 1 ppm.

Furthermore, Exemplified Compound 62 was synthesized in accordance with the following reaction scheme (a method devised by reference to US 2006/0008670) too.

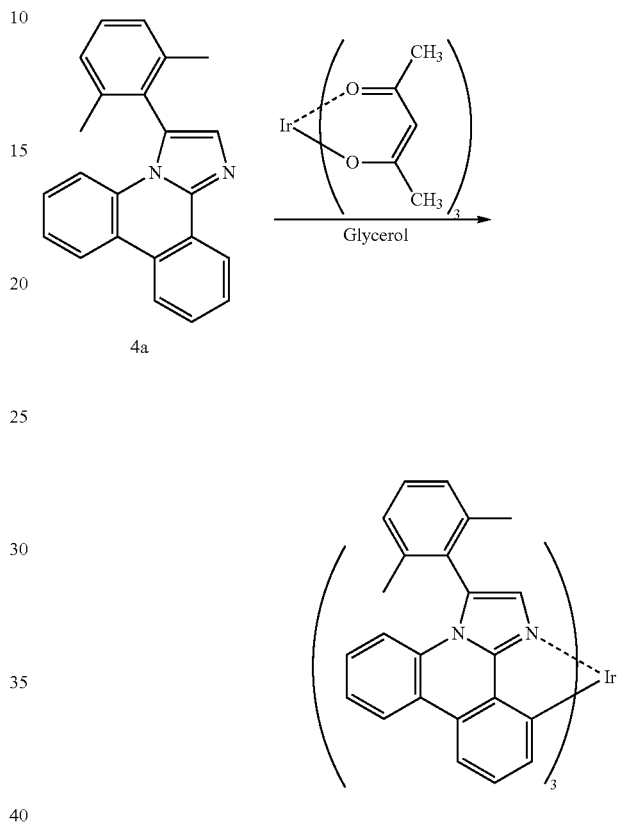

In an atmosphere of nitrogen, tris(acetylacetonato)iridium (587 mg, 1.2 mmol) was added to the compound 4a (1.93 g, 6 mmol), and these compounds were made to react with each other for 48 hours at 240° C. The reaction mixture was allowed to stand for cooling, and then subjected successively to extraction with dichloromethane, washing with water, drying with MgSO$_4$ and removal of the solvent under reduced pressure. The thus obtained reaction product was purified by column chromatography (developing solvent: dichloromethane), and recrystallized from a dichloromethane solution. Thus, 300 mg of Exemplified Compound 62 (0.26 mmol, 22%) was obtained. And it was found by HPLC that the thus obtained Exemplified Compound 62 had a purity of 99.1%. Further, in ICP optical emission spectroscopy of the compound obtained, the content of Li and Li ion was found to be below 1 ppm and the content of Mg and Mg ion was found to be below 1 ppm.

Synthesis of Exemplified Compound 63

Exemplified Compound 63 was synthesized in accordance with the following reaction scheme (Synthesis Method 1).

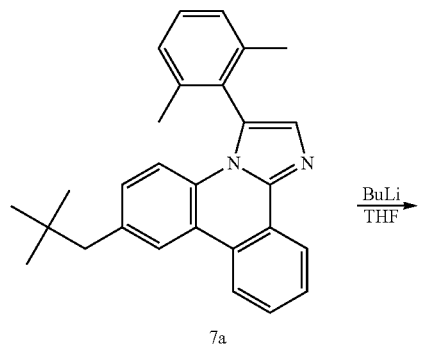

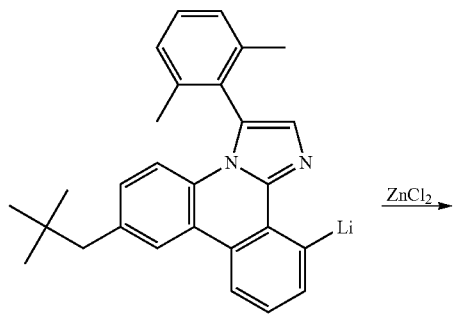

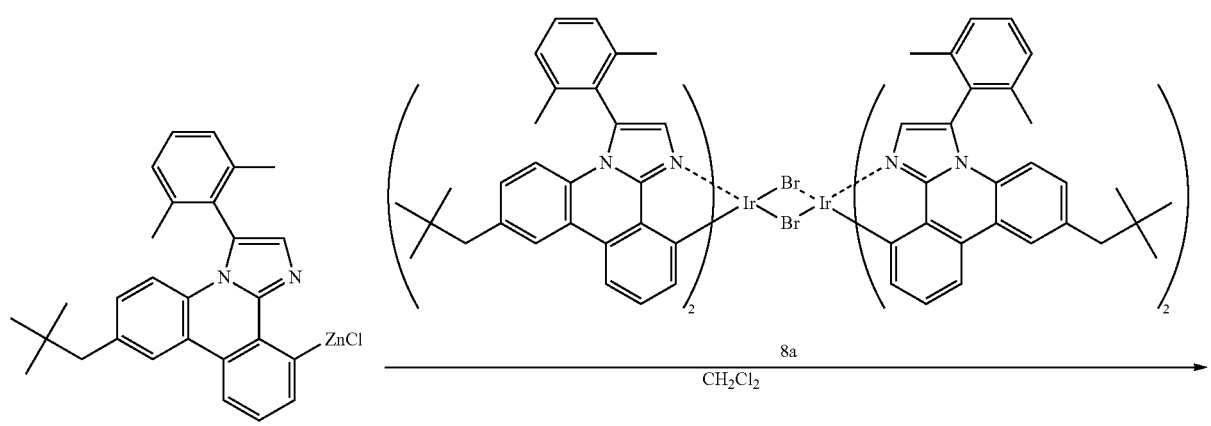

At a temperature of −78° C. under an atmosphere of nitrogen, a pentane solution of n-BuLi (1.3 ml, 2.1 mmol) was added dropwise to 10 ml of a dehydrated THF solution of the compound 7a (785 mg, 2 mmol), and stirred for 30 minutes. Thereto, a diethyl ether solution of anhydrous zinc(II) chloride (2 ml, 2 mmol) was further added dropwise, and stirring was continued until the temperature of the reaction solution was restored to room temperature. To the reaction solution containing the zinc complex, a bromine-bridged complex 8a (2.11 g, 1 mmol) and 10 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with MgSO$_4$ and removal of the solvent under reduced pressure. After isomerization and subsequent washing (12 hours) in boiling glycerol, a precipitate formed was filtered off, dissolved in dichloromethane, and purified by recrystallization. Thus, 1.53 g of Exemplified Compound 63 (1.12 mmol, 56%) was obtained. And it was found by HPLC that the thus obtained Exemplified Compound 63 had a purity of 99.5%. In addition, in ICP optical emission spectroscopy of the compound obtained, the content of Li and Li ion was found to be 5.8 ppm and the content of Mg and Mg ion was found to be below 1 ppm.

In addition, Exemplified Compound 63 was synthesized in accordance with the following reaction scheme (Synthesis Method 2) also.

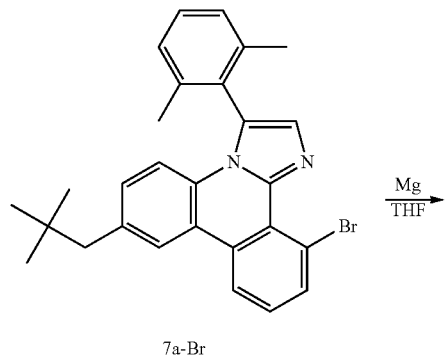

7a-Br

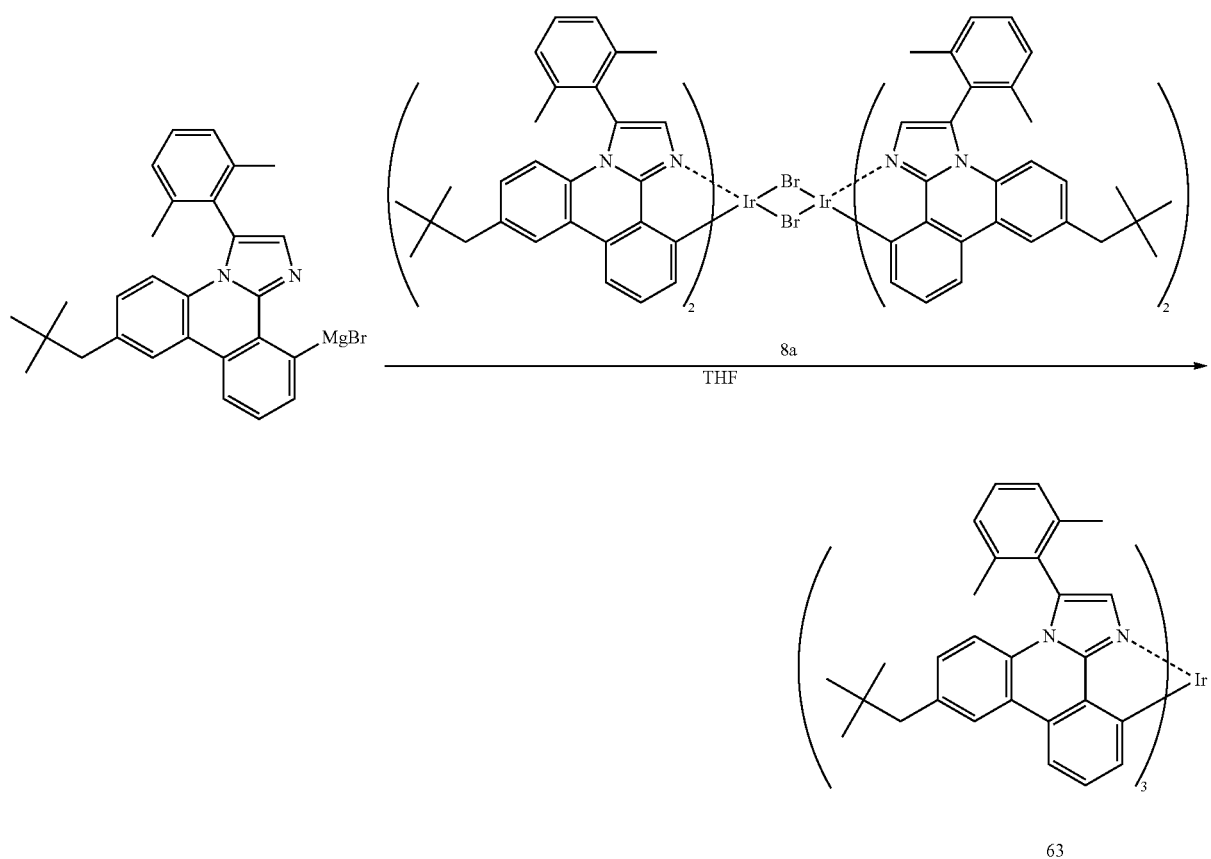

63

At room temperature under an atmosphere of nitrogen, 20 ml of a dehydrated THF solution of the compound 7a-Br (1.88 g, 4 mmol) and 1,2-dichloroethane (0.32 ml, 0.4 mmol) was added dropwise to a suspension of magnesium (121 mg, 5 mmol) in 2 ml of dehydrated THF. The reaction solution was refluxed for 2 hours at its boiling temperature, thus a Grignard reagent solution was prepared. In a separate vessel, the bromine-bridged complex 8a (2.11 g, 1 mmol) was dissolved in 40 ml of dehydrated THF, and cooled to 0° C. in an atmosphere of nitrogen. Thereto, the Grignard reagent prepared was added dropwise, and stirred for 1 hour. After the temperature of the reaction mixture was restored to room temperature, reflux at boiling temperature was carried out for 6 hours. The resulting reaction mixture was quenched with $H_2O$ and alcohol, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 1.36 g of Exemplified Compound 63 (1.02 mmol, 51%) was obtained. And it was found by HPLC that the thus obtained Exemplified Compound 63 had a purity of 99.3%. In addition, in ICP optical emission spectroscopy of the compound obtained, the content of Li and Li ion was found to be 5.2 ppm and the content of Mg and Mg ion was found to be 3.1 ppm.

Further, Exemplified Compound 63 was synthesized in accordance with the following reaction scheme (Synthesis Method 3) also.

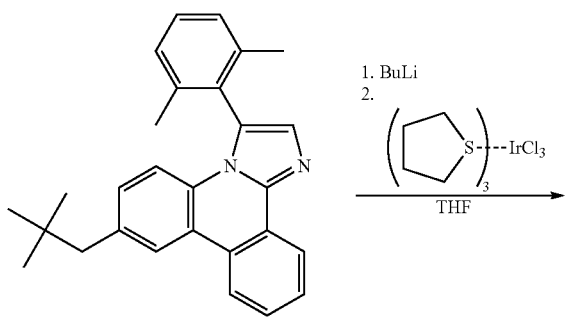
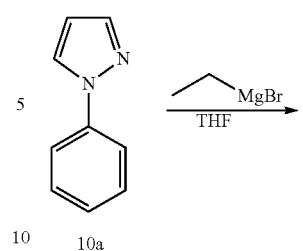

7a

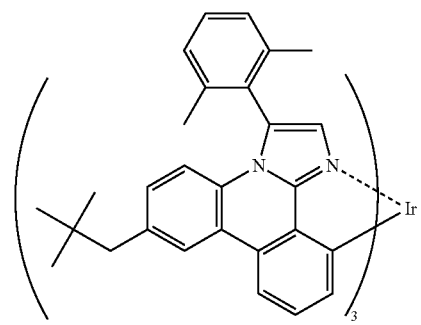
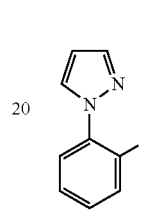
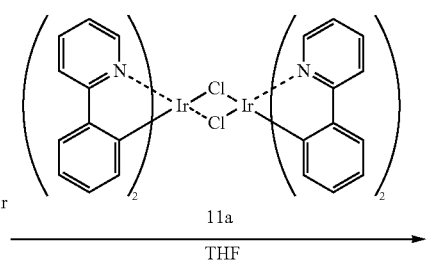

63

10a

11a

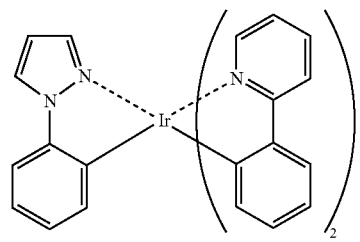

64

At a temperature of −78° C. under an atmosphere of nitrogen, a pentane solution of n-BuLi (3.9 ml, 6.3 mmol) was added dropwise to 30 ml of a dehydrated THF solution of the compound 7a (2.36 g, 6 mmol), and stirred for 30 minutes. Thereto, a THF solution of tris(tetrahydrothiophene)iridium chloride (7 ml, 1.5 mmol) was further added dropwise, and stirred for 1 hour at −78° C. Thereafter, stirring was further continued for 6 hours or more until the temperature of the reaction mixture was restored to room temperature. After the reaction mixture was quenched with dilute hydrochloric acid, extraction with dichloromethane, washing with water, drying with $MgSO_4$ and removal of the solvent under reduced pressure were carried out in sequence. The thus obtained reaction product was purified by column chromatography (developing solvent: dichloromethane), and recrystallized from a dichloromethane solution. Thus, 533 mg of Exemplified Compound 63 (0.39 mmol, 27%) was obtained. And it was found by HPLC that the thus obtained Exemplified Compound 63 had a purity of 99.1%. Further, in ICP optical emission spectroscopy of the compound obtained, the content of Li and Li ion was found to be 5.1 ppm and the content of Mg and Mg ion was found to be below 1 ppm.

Furthermore, Exemplified Compound 63 was also synthesized in accordance with a reaction scheme devised by reference to the method disclosed in US 2008/0297033, [0281] to [0287] (a traditional method). And in ICP optical emission spectroscopy, the thus obtained Exemplified Compound 63 was found to be below 1 ppm in both the content of Li and Li ion and the content of Mg and Mg ion.

Synthesis of Exemplified Compound 64

Exemplified Compound 64 was synthesized in accordance with the following reaction scheme (Synthesis Method 4).

At a temperature of 0° C. under an atmosphere of nitrogen, a THF solution of ethylmagnesium bromide (3.3 ml, 10 mmol) was added dropwise to 25 ml of a dehydrated THF solution of the compound 10a (1.44 g, 10 mmol), and stirred for 30 minutes, thus a Grignard reagent solution was prepared. In a separate vessel, the chlorine-bridged complex 11a (2.68 g, 2.5 mmol) was dissolved in 75 ml of dehydrated THF, and cooled to 0° C. in an atmosphere of nitrogen. Thereto, the Grignard reagent prepared was added dropwise, and stirred for 1 hour. The temperature of the reaction mixture was restored to room temperature over 6 hours or more with stirring. The resulting reaction mixture was quenched with $H_2O$ and alcohol, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 2.19 g of Exemplified Compound 64 (3.4 mmol, 68%) was obtained. And it was found by HPLC that the thus obtained Exemplified Compound 64 had a purity of 99.1%. In addition, in ICP optical emission spectroscopy of the compound obtained, the content of Li and Li ion was found to be 3.1 ppm and the content of Mg and Mg ion was found to be 6.3 ppm.

In addition, Exemplified Compound 64 was synthesized in accordance with the following reaction scheme (Synthesis Method 5) also.

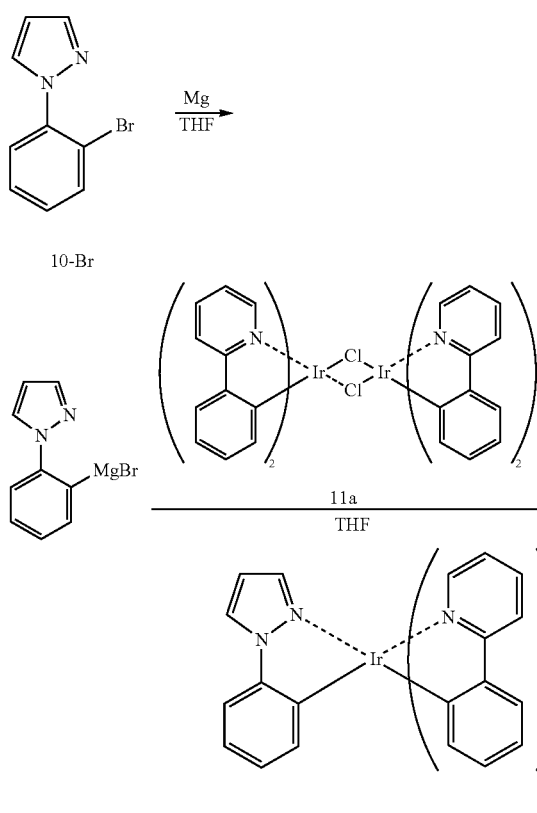

64

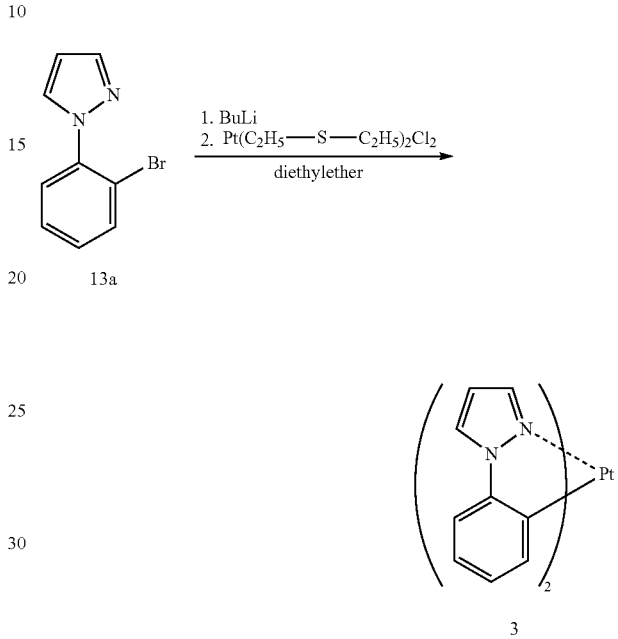

3

At room temperature under an atmosphere of nitrogen, 50 ml of a dehydrated THF solution of the compound 10a-Br (2.23 g, 10 mmol) and 1,2-dichloroethane (0.79 ml, 1 mmol) was added dropwise to a suspension of magnesium (243 mg, 10 mmol) in 5 ml of dehydrated THF. The reaction solution was refluxed for 2 hours at its boiling temperature, thus a Grignard reagent solution was prepared. In a separate vessel, the chlorine-bridged complex 11a (2.68 g, 2.5 mmol) was dissolved in 75 ml of dehydrated THF, and cooled to 0° C. in an atmosphere of nitrogen. Thereto, the Grignard reagent prepared was added dropwise, and stirred for 1 hour. After the temperature of the reaction mixture was restored to room temperature, reflux at boiling temperature was carried out for 6 hours. The resulting reaction mixture was quenched with $H_2O$ and alcohol, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 2.45 g of Exemplified Compound 64 (3.8 mmol, 75%) was obtained. And it was found by HPLC that the thus obtained Exemplified Compound 64 had a purity of 99.3%. In addition, in ICP optical emission spectroscopy of the compound obtained, the content of Li and Li ion was found to be 2.3 ppm and the content of Mg and Mg ion was found to be 6.5 ppm.

$^1$H-NMR (300 MHz, in $CDCl_3$): δ (ppm)=6.36-6.38 (m, 1H), 6.76-6.92 (m, 12H), 7.20 (d, J=8.0 Hz, 1H), 7.50-7.60 (m, 2H), 7.60-7.65 (m, 4H), 7.83-7.88 (m, 2H), 7.98-7.99 (m, 1H).

Further, Exemplified Compound 64 was also synthesized by reference to the method described in *Inorg. Chem.*, 2005, 44, 4445 to 4447 (a traditional method). And in ICP optical emission spectroscopy, the thus obtained Exemplified Compound 64 was found to be below 1 ppm in both the content of Li and Li ion and the content of Mg and Mg ion.

Synthesis of Exemplified Compound 3

Exemplified Compound 3 was synthesized in accordance with the following reaction scheme.

At a temperature of −78° C. under an atmosphere of nitrogen, a pentane solution of n-BuLi (3.4 ml, 5.5 mmol) was added dropwise to 30 ml of a dehydrated diethyl ether solution of the compound 13a (1.12 g, 5 mmol), and stirred for 30 minutes. Thereto, a diethyl ether solution of tris(diethylsulfide)platinum chloride (5 ml, 1.25 mmol) was further added dropwise, and stirred for 1 hour at −78° C. Thereafter, stirring was further continued for 6 hours or more until the temperature of the reaction mixture was restored to room temperature. After the reaction mixture was quenched with dilute hydrochloric acid, extraction with dichloromethane, washing with water, drying with $MgSO_4$ and removal of the solvent under reduced pressure were carried out in sequence. The thus obtained reaction product was purified by column chromatography (developing solvent: dichloromethane), and recrystallized from a dichloromethane solution. Thus, 212 mg of Exemplified Compound 3 (0.44 mmol, 35%) was obtained. And it was found by HPLC that the thus obtained Exemplified Compound 3 had a purity of 99.4%. Further, in ICP optical emission spectroscopy of the compound obtained, the content of Li and Li ion was found to be 6.8 ppm and the content of Mg and Mg ion was found to be below 1 ppm.

$^1$H-NMR (300 MHz, in $CDCl_3$): δ (ppm)=6.61 (dd, J=2.1, 2.6 Hz, 2H), 7.12-7.22 (m, 4H), 7.22-7.28 (m, 2H), 7.92 (d, J=2.1 Hz, 2H), 8.04 (d, J=2.6 Hz, 2H), 8.09-8.30 (m, 2H)

Synthesis of Exemplified Compound 65

Exemplified Compound 65 was synthesized in accordance with the following reaction scheme (Synthesis Method 25).

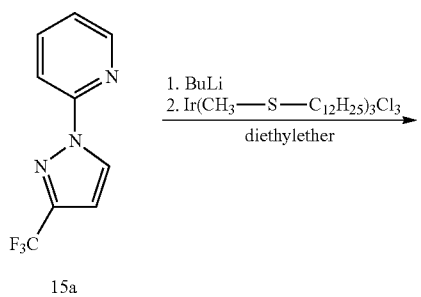

15a

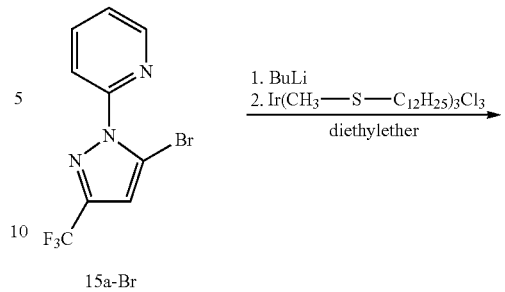

15a-Br

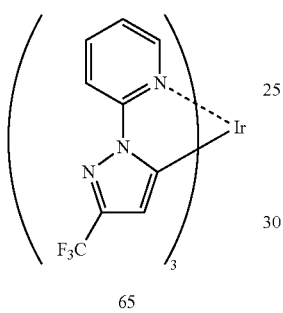

65

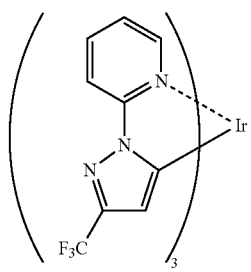

65

At a temperature of −78° C. under an atmosphere of nitrogen, a pentane solution of n-BuLi (4.7 ml, 7.5 mmol) was added dropwise to 50 ml of a dehydrated diethyl ether solution of the compound 15a (1.60 g, 7.5 mmol), and stirred for 30 minutes. Thereto, a diethyl ether solution of tris(dodecylmethylsulfide)iridium chloride (15 ml, 1.88 mmol) was further added dropwise, and stirred for 1 hour at −78° C. Then, stirring was further continued for 6 hours or more until the temperature of the reaction mixture was restored to room temperature. After the reaction mixture was quenched with dilute hydrochloric acid, extraction with dichloromethane, washing with water, drying with MgSO$_4$ and removal of the solvent under reduced pressure were carried out in sequence. The thus obtained reaction product was purified by column chromatography (developing solvent: dichloromethane), and recrystallized from a dichloromethane solution. Thus, 282 mg of Exemplified Compound 65 (0.34 mmol, 18%) was obtained. And it was found by HPLC that the thus obtained Exemplified Compound 65 had a purity of 99.4%. Further, in ICP optical emission spectroscopy of the compound obtained, the content of Li and Li ion was found to be 6.9 ppm and the content of Mg and Mg ion was found to be below 1 ppm.

$^1$H-NMR (300 MHz, in CDCl$_3$): δ (ppm)=0.32 (s, 18H), 7.13 (m, 2H), 7.49 (m, 2H), 7.73-7.97 (m, 4H), 8.51-8.73 (m, 2H)

In addition, Exemplified Compound 65 was synthesized in accordance with the following reaction scheme (Synthesis Method 26) also.

At a temperature of −78° C. under an atmosphere of nitrogen, a pentane solution of n-BuLi (4.7 ml, 7.5 mmol) was added dropwise to 50 ml of a dehydrated diethyl ether solution of the compound 15a-Br (2.19 g, 7.5 mmol), and stirred for 30 minutes. Thereto, a diethyl ether solution of tris(dodecylmethylsulfide)iridium chloride (15 ml, 1.88 mmol) was further added dropwise, and stirred for 1 hour at −78° C. Then, stirring was further continued for 6 hours or more until the temperature of the reaction mixture was restored to room temperature. After the reaction mixture was quenched with dilute hydrochloric acid, extraction with dichloromethane, washing with water, drying with MgSO$_4$ and removal of the solvent under reduced pressure were carried out in sequence. The thus obtained reaction product was purified by column chromatography (developing solvent: dichloromethane), and recrystallized from a dichloromethane solution. Thus, 312 mg of Exemplified Compound 65 (0.38 mmol, 20%) was obtained. And it was found by HPLC that the thus obtained Exemplified Compound 65 had a purity of 99.2%. Further, in ICP optical emission spectroscopy of the compound obtained, the content of Li and Li ion was found to be 4.8 ppm and the content of Mg and Mg ion was found to be below 1 ppm.

Synthesis of Exemplified Compound 66

Exemplified Compound 66 was synthesized in accordance with the following reaction scheme (Synthesis Method 9).

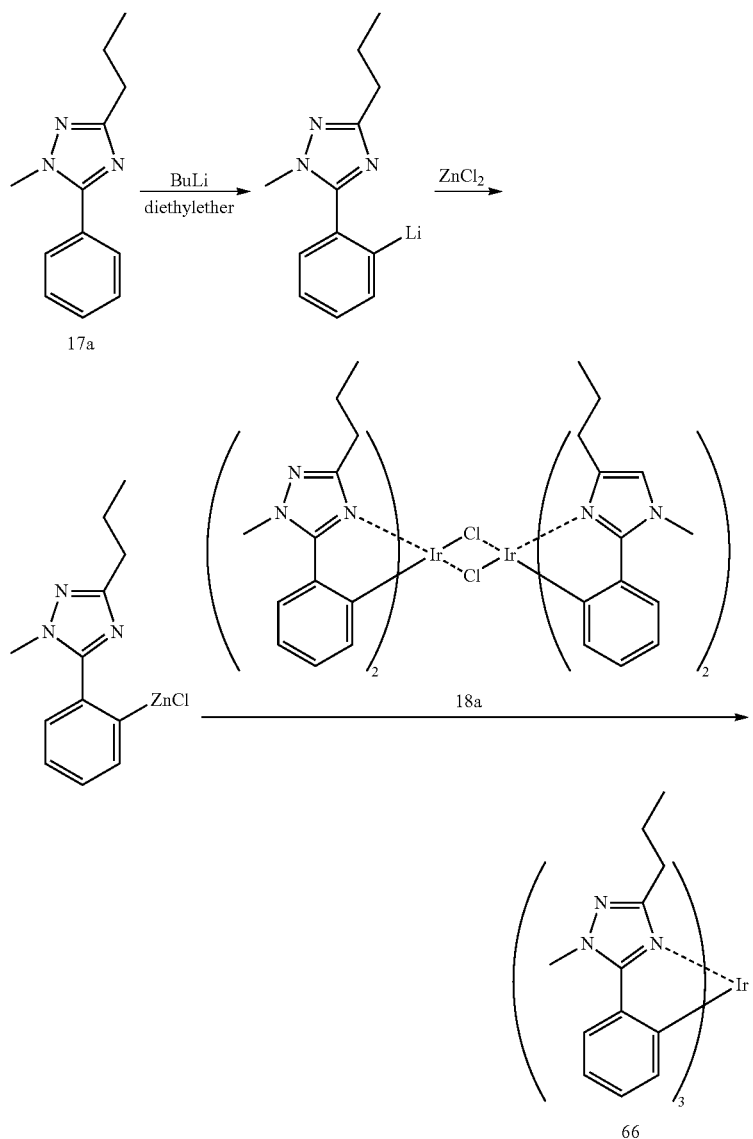

At a temperature of −78° C. under an atmosphere of nitrogen, a pentane solution of n-BuLi (4.5 ml, 7.2 mmol) was added dropwise to 30 ml of a dehydrated diethyl ether solution of the compound 17a (1.32 g, 6.6 mmol), and stirred for 30 minutes. Thereto, a diethyl ether solution of anhydrous zinc(II) chloride (6.6 ml, 6.6 mmol) was further added dropwise, and stirring was continued until the temperature of the reaction solution was restored to room temperature. To the reaction solution containing the zinc complex, the chlorine-bridged complex 18a (2.50 g, 2 mmol) and 10 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with $MgSO_4$ and removal of the solvent under reduced pressure. After isomerization and subsequent washing (12 hours) in boiling glycerol, a precipitate formed was filtered off, dissolved in dichloromethane, and purified by recrystallization. Thus, 1.36 g of Exemplified Compound 66 (1.76 mmol, 44%) was obtained.

And it was found by HPLC that the thus obtained Exemplified Compound 66 had a purity of 99.5%. In addition, in ICP optical emission spectroscopy of the compound obtained, the content of Li and Li ion was found to be 5.1 ppm and the content of Mg and Mg ion was found to be below 1 ppm.

$^1$H-NMR (300 MHz, in $CDCl_3$): δ (ppm)=0.68 (t, 9H), 1.06-1.22 (m, 3H), 1.27-1.41 (m, 3H), 1.80-1.92 (m, 3H), 2.12-2.24 (m, 3H), 4.15 (s, 9H), 6.61 (d, J=7, 4 Hz, 3H), 6.74-6.82 (m, 3H), 6.83-6.91 (m, 3H), 7.51 (d, J=7.4 Hz, 3H)

Alternatively, Exemplified Compound 66 can also be synthesized by using Synthesis Method (2) or (3).

Synthesis of Exemplified Compound 66

In addition, Exemplified Compound 66 was synthesized in accordance with the following reaction scheme (Synthesis Method 10) also.

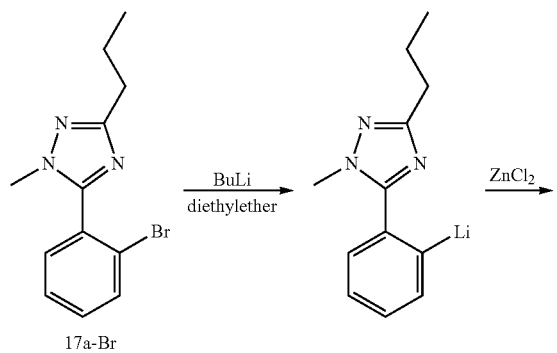

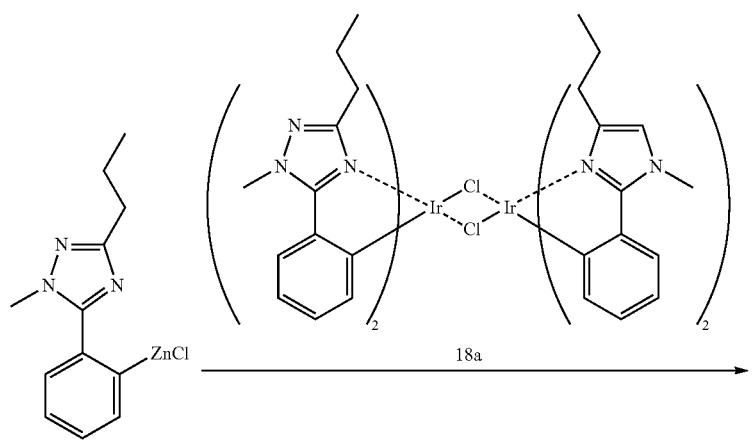

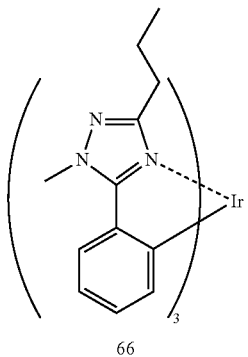

At a temperature of −78° C. under an atmosphere of nitrogen, a pentane solution of n-BuLi (4.5 ml, 7.2 mmol) was added dropwise to 30 ml of a dehydrated diethyl ether solution of the compound 17a-Br (1.85 g, 6.6 mmol), and stirred for 30 minutes. Thereto, a diethyl ether solution of anhydrous zinc(II) chloride (6.6 ml, 6.6 mmol) was further added dropwise, and stirring was continued until the temperature of the reaction solution was restored to room temperature. To the reaction solution containing the zinc complex, the chlorine-bridged complex 18a (2.50 g, 2 mmol) and 10 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with MgSO$_4$ and removal of the solvent under reduced pressure. After isomerization and subsequent washing (12 hours) in boiling glycerol, a precipitate formed was filtered off, dissolved in dichloromethane, and purified by recrystallization. Thus, 1.55 g of Exemplified Compound 66 (2.00 mmol, 50%) was obtained. And it was found by HPLC that the thus obtained Exemplified Compound 66 had a purity of 99.3%. In addition, in ICP optical emission spectroscopy of the compound obtained, the content of Li and Li ion was found to be 5.1 ppm and the content of Mg and Mg ion was found to be below 1 ppm.

Synthesis of Exemplified Compound 66

Further, Exemplified Compound 66 was synthesized in accordance with the following reaction scheme (Synthesis Method 11) also.

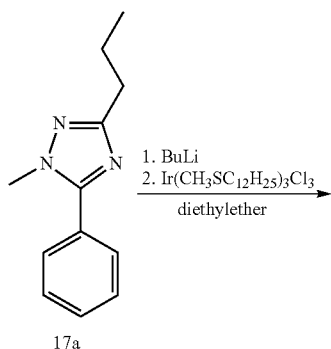

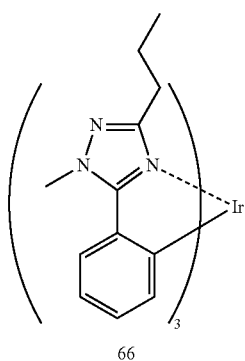

At a temperature of −78° C. under an atmosphere of nitrogen, a pentane solution of n-BuLi (4.7 ml, 7.5 mmol) was added dropwise to 50 ml of a dehydrated diethyl ether solution of the compound 17a (1.51 g, 7.5 mmol), and stirred for 30 minutes. Thereto, a diethyl ether solution of tris(dodecylmethylsulfide)iridium chloride (15 ml, 1.88 mmol) was further added dropwise, and stirred for 1 hour at −78° C. Thereafter, stirring was further continued for 6 hours or more until the temperature of the reaction mixture was restored to room temperature. After the reaction mixture was quenched with dilute hydrochloric acid, extraction with dichloromethane, washing with water, drying with $MgSO_4$ and removal of the solvent under reduced pressure were carried out in sequence. The thus obtained reaction product was purified by column chromatography (developing solvent: dichloromethane), and recrystallized from a dichloromethane solution. Thus, 450 mg of Exemplified Compound 66 (0.58 mmol, 31%) was obtained. And it was found by HPLC that the thus obtained Exemplified Compound 66 had a purity of 99.2%. Further, in ICP optical emission spectroscopy of the compound obtained, the content of Li and Li ion was found to be 3.5 ppm and the content of Mg and Mg ion was found to be below 1 ppm.

Furthermore, Exemplified Compound 66 was also synthesized by reference to the method described in *Chem. Mater.*, 2006, 18, 5119-5129, [0281] to [0282] (a traditional method). And in ICP optical emission spectroscopy, the thus obtained Exemplified Compound 66 was found to be below 1 ppm in both the content of Li and Li ion and the content of Mg and Mg ion.

Synthesis of Exemplified Compound 220

Exemplified Compound 220 was synthesized in accordance with the following reaction scheme.

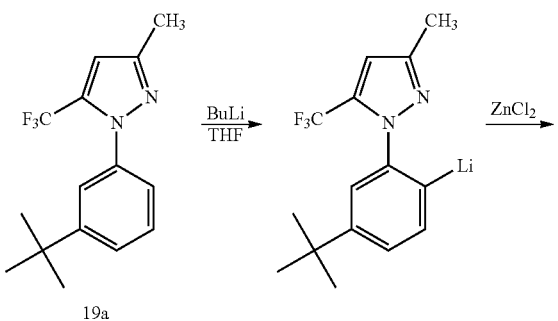

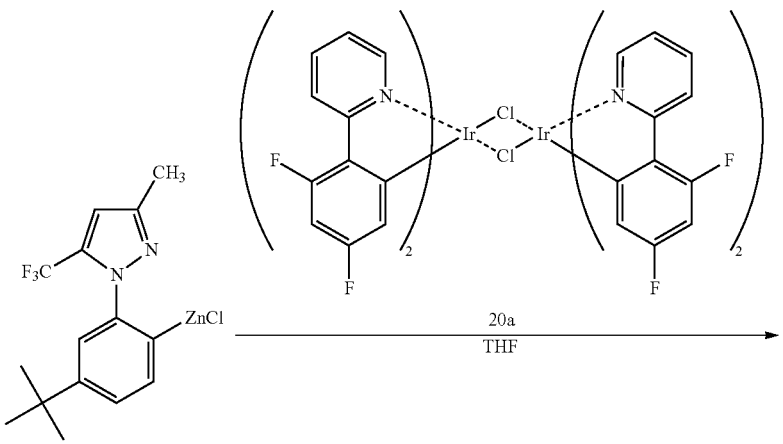

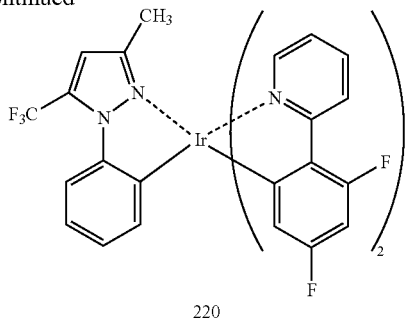

220

At a temperature of −78° C. under an atmosphere of nitrogen, a pentane solution of n-BuLi (3.3 ml, 5.2 mmol) was added dropwise to 13 ml of a dehydrated THF solution of the compound 19a (1.41 g, 5 mmol), and stirred for 30 minutes. Thereto, a diethyl ether solution of anhydrous zinc(II) chloride (5 ml, 5 mmol) was further added dropwise, and stirring was continued until the temperature of the reaction solution was restored to room temperature.

To the reaction solution containing the zinc complex, the chlorine-bridged complex 20a (3.04 g, 2.5 mmol) and 25 ml of dehydrated THF were added. And the resulting mixture was refluxed for 1 hour at its boiling temperature. The thus obtained reaction mixture was allowed to stand for cooling, and then subjected successively to extraction with dichloromethane, washing with water, drying with MgSO$_4$ and removal of the solvent under reduced pressure. After washing in boiling glycerol (12 hours), a precipitate formed was filtered off, dissolved in dichloromethane, and purified by recrystallization. Thus, 2.05 g of Exemplified Compound 220 (2.40 mmol, 45%) was obtained. And it was found by HPLC that the thus obtained Exemplified Compound 220 had a purity of 99.1%. In addition, in ICP optical emission spectroscopy of the compound obtained, the content of Li and Li ion was found to be 8.3 ppm and the content of Mg and Mg ion was found to be below 1 ppm.

MS (ESI, m/z) 855.2 (MH$^+$). Anal. Calcd. for C$_{37}$H$_{28}$F$_7$IrN$_4$: C, 52.05; H, 3.31; N, 6.56. Found: C, 52.3; H, 3.41; N, 6.45.

Synthesis of Exemplified Compound 220

In addition, Exemplified Compound 220 was synthesized in accordance with the following reaction scheme also.

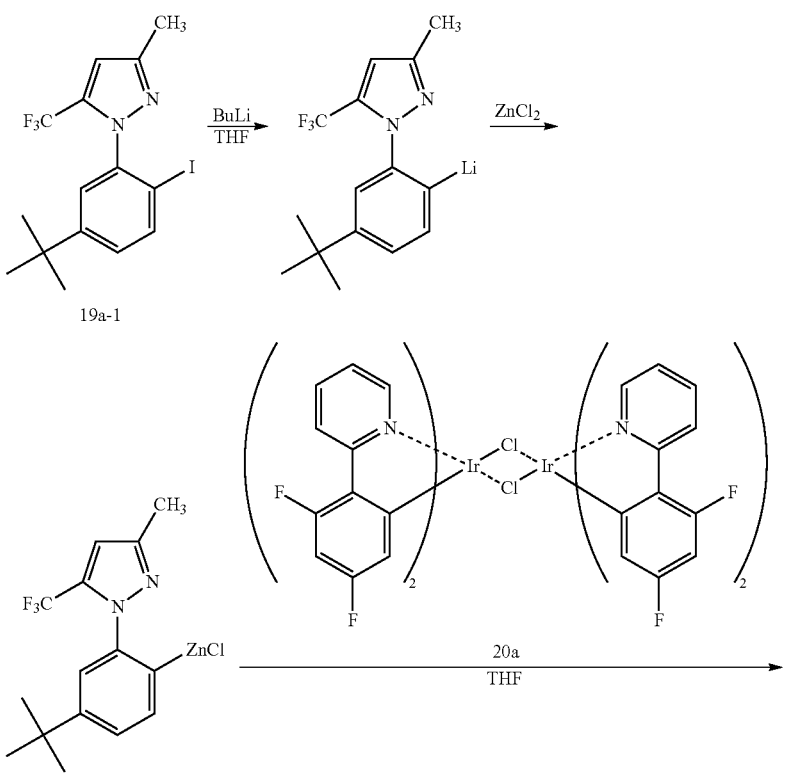

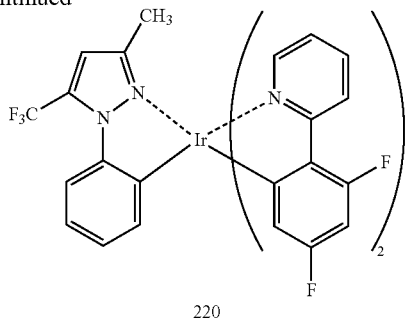

220

At a temperature of −78° C. under an atmosphere of nitrogen, a pentane solution of n-BuLi (3.3 ml, 5.2 mmol) was added dropwise to 13 ml of a dehydrated THF solution of the compound 19a-I (2.04 g, 5 mmol), and stirred for 30 minutes. Thereto, a diethyl ether solution of anhydrous zinc(II) chloride (5 ml, 5 mmol) was further added dropwise, and stirring was continued until the temperature of the reaction solution was restored to room temperature.

To the reaction solution containing the zinc complex, the chlorine-bridged complex 20a (3.04 g, 2.5 mmol) and 25 ml of dehydrated THF were added. And the resulting mixture was refluxed for 1 hour at its boiling temperature. The thus obtained reaction mixture was allowed to stand for cooling, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 2.17 g of Exemplified Compound 220 (2.55 mmol, 51%) was obtained. And it was found by HPLC that the thus obtained Exemplified Compound 220 had a purity of 99.2%. In addition, in ICP optical emission spectroscopy of the compound obtained, the content of Li and Li ion was found to be 6.1 ppm and the content of Mg and Mg ion was found to be below 1 ppm.

Synthesis of Exemplified Compound 221

Exemplified Compound 221 was synthesized in accordance with the following reaction scheme.

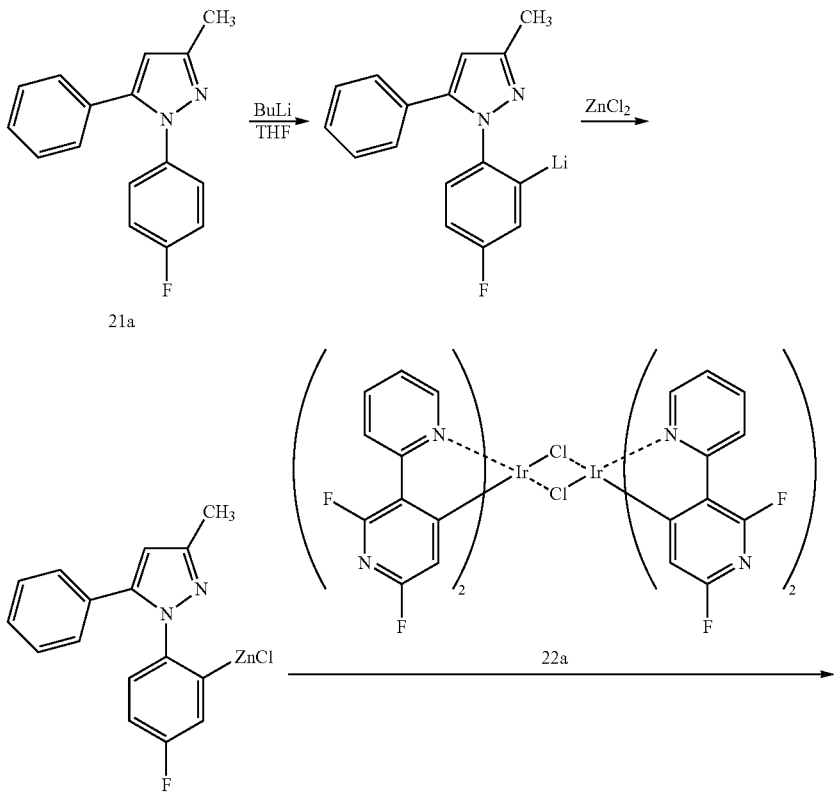

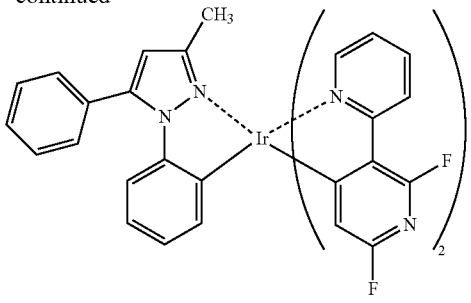

221

At a temperature of −78° C. under an atmosphere of nitrogen, a pentane solution of n-BuLi (3.3 ml, 5.2 mmol) was added dropwise to 13 ml of a dehydrated THF solution of the compound 21a (1.26 g, 5 mmol), and stirred for 30 minutes. Thereto, a diethyl ether solution of anhydrous zinc(II) chloride (5 ml, 5 mmol) was further added dropwise, and stirring was continued until the temperature of the reaction solution was restored to room temperature.

To the reaction solution containing the zinc complex, the chlorine-bridged complex 22a (3.05 g, 2.5 mmol) and 25 ml of dehydrated dichloromethane were added. And the resulting mixture was refluxed for 3 hours at its boiling temperature. The thus obtained reaction mixture was allowed to stand for cooling, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 1.45 g of Exemplified Compound 221 (1.80 mmol, 36%) was obtained. And it was found by HPLC that the thus obtained Exemplified Compound 221 had a purity of 99.2%. In addition, in ICP optical emission spectroscopy of the compound obtained, the content of Li and Li ion was found to be 9.1 ppm and the content of Mg and Mg ion was found to be below 1 ppm.

MS (ESI, m/z) 809.2 (MH$^+$). Anal. Calcd. for $C_{36}H_{23}F_4IrN_6$: C, 53.53; H, 2.87; N, 10.40. Found: C, 53.4; H, 2.92; N, 10.2.

Synthesis of Exemplified Compound 221

In addition, Exemplified Compound 221 was synthesized in accordance with the following reaction scheme also.

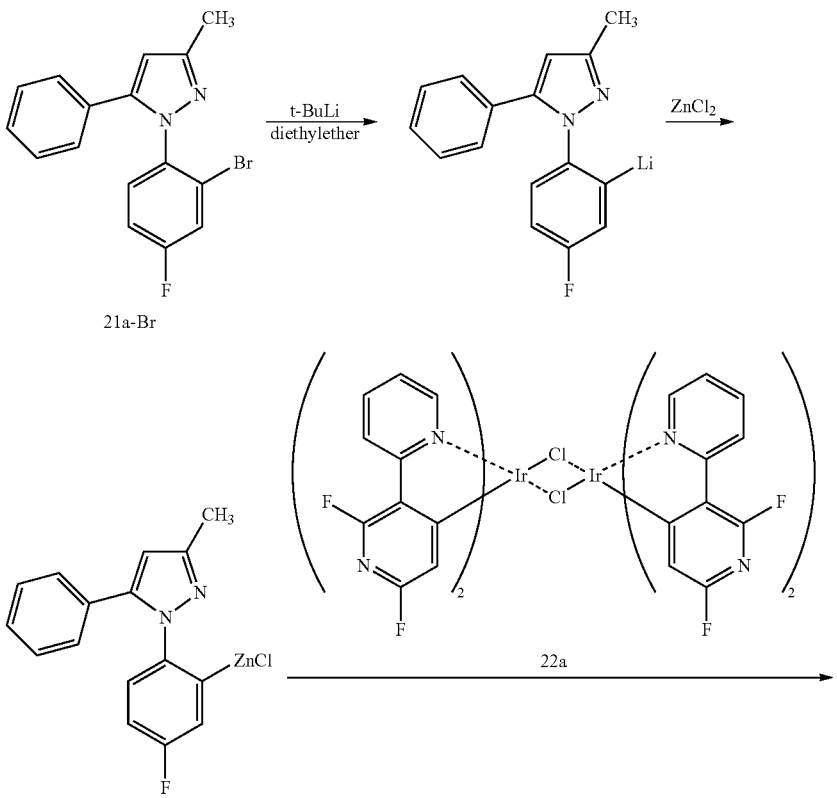

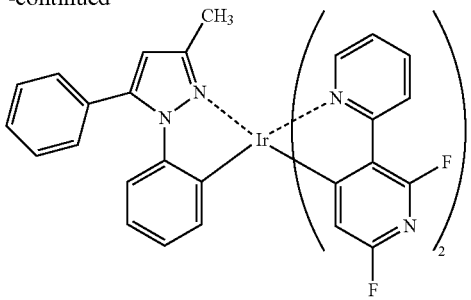

221

At a temperature of −78° C. under an atmosphere of nitrogen, a pentane solution of tert-BuLi (6.7 ml, 10 mmol) was added dropwise to 13 ml of a dehydrated diethyl ether solution of the compound 21a-Br (1.66 g, 5 mmol), and stirred for 30 minutes. Thereto, a diethyl ether solution of anhydrous zinc(II) chloride (5 ml, 5 mmol) was further added dropwise, and stirring was continued until the temperature of the reaction solution was restored to room temperature.

To the reaction solution containing the zinc complex, the chlorine-bridged complex 22a (3.05 g, 2.5 mmol) and 25 ml of dehydrated dichloromethane were added. And the resulting mixture was refluxed for 3 hours at its boiling temperature. The thus obtained reaction mixture was allowed to stand for cooling, and then subjected successively to extraction with dichloromethane, washing with water, drying with MgSO₄ and removal of the solvent under reduced pressure. After washing in boiling glycerol (12 hours), a precipitate formed was filtered off, dissolved in dichloromethane, and purified by recrystallization. Thus, 1.61 g of Exemplified Compound 221 (2.00 mmol, 40%) was obtained. And it was found by HPLC that the thus obtained Exemplified Compound 221 had a purity of 99.3%. In addition, in ICP optical emission spectroscopy of the compound obtained, the content of Li and Li ion was found to be 4.4 ppm and the content of Mg and Mg ion was found to be below 1 ppm.

Synthesis of Exemplified Compound 222

Exemplified Compound 222 was synthesized in accordance with the following reaction scheme.

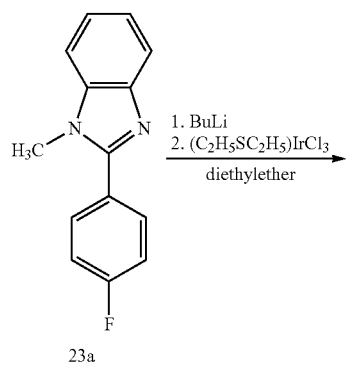

23a

-continued

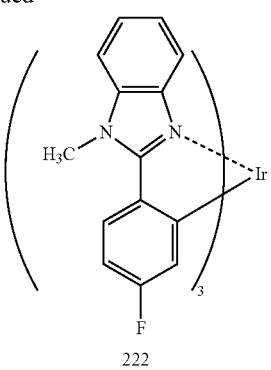

222

At a temperature of −78° C. under an atmosphere of nitrogen, a pentane solution of n-BuLi (3.8 ml, 6 mmol) was added dropwise to 50 ml of a dehydrated diethyl ether solution of the compound 23a (1.60 g, 6 mmol), and stirred for 30 minutes. Thereto, a diethyl ether solution of tris(diethylsulfide)iridium chloride (12 ml, 1.5 mmol) was further added dropwise, and stirred for 1 hour at −78° C. Then, stirring was further continued for 6 hours or more until the temperature of the reaction mixture was restored to room temperature. After the reaction mixture was quenched with dilute hydrochloric acid, extraction with dichloromethane, washing with water, drying with MgSO₄ and removal of the solvent under reduced pressure were carried out in sequence. The thus obtained reaction product was purified by column chromatography (developing solvent: dichloromethane), and recrystallized from a dichloromethane solution. Thus, 277 mg of Exemplified Compound 222 (0.48 mmol, 32%) was obtained. And it was found by HPLC that the thus obtained Exemplified Compound 222 had a purity of 99.5%. Further, in ICP optical emission spectroscopy of the compound obtained, the content of Li and Li ion was found to be 6.6 ppm and the content of Mg and Mg ion was found to be below 1 ppm.

MS (ESI, m/z) 869.2 (MH$^+$). Anal. Calcd. for $C_{42}H_{30}F_3IrN_6$: C, 58.12; H, 3.48; N, 9.68. Found: C, 58.0; H, 3.53; N, 9.53.

Synthesis of Exemplified Compound 222

In addition, Exemplified Compound 222 was synthesized in accordance with the following reaction scheme also.

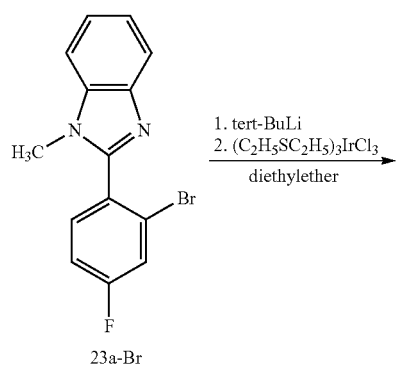

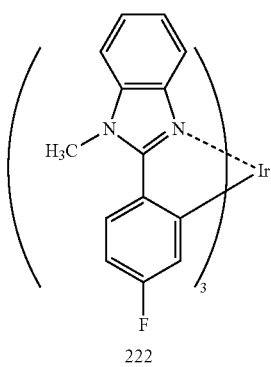

At a temperature of −78° C. under an atmosphere of nitrogen, a pentane solution of tert-BuLi (8.0 ml, 12 mmol) was added dropwise to 50 ml of a dehydrated diethyl ether solution of the compound 23a-Br (1.82 g, 6 mmol), and stirred for 30 minutes. Thereto, a diethyl ether solution of tris(diethylsulfide)iridium chloride (12 ml, 1.5 mmol) was further added dropwise, and stirred for 1 hour at −78° C. Then, stirring was further continued for 6 hours or more until the temperature of the reaction mixture was restored to room temperature. After the reaction mixture was quenched with dilute hydrochloric acid, extraction with dichloromethane, washing with water, drying with MgSO$_4$ and removal of the solvent under reduced pressure were carried out in sequence. The thus obtained reaction product was purified by column chromatography (developing solvent: dichloromethane), and recrystallized from a dichloromethane solution. Thus, 303 mg of Exemplified Compound 222 (0.53 mmol, 35%) was obtained. And it was found by HPLC that the thus obtained Exemplified Compound 222 had a purity of 99.2%. Further, in ICP optical emission spectroscopy of the compound obtained, the content of Li and Li ion was found to be 5.6 ppm and the content of Mg and Mg ion was found to be below 1 ppm.

Synthesis of Exemplified Compound 222

Further, Exemplified Compound 222 was synthesized in accordance with the following reaction scheme also.

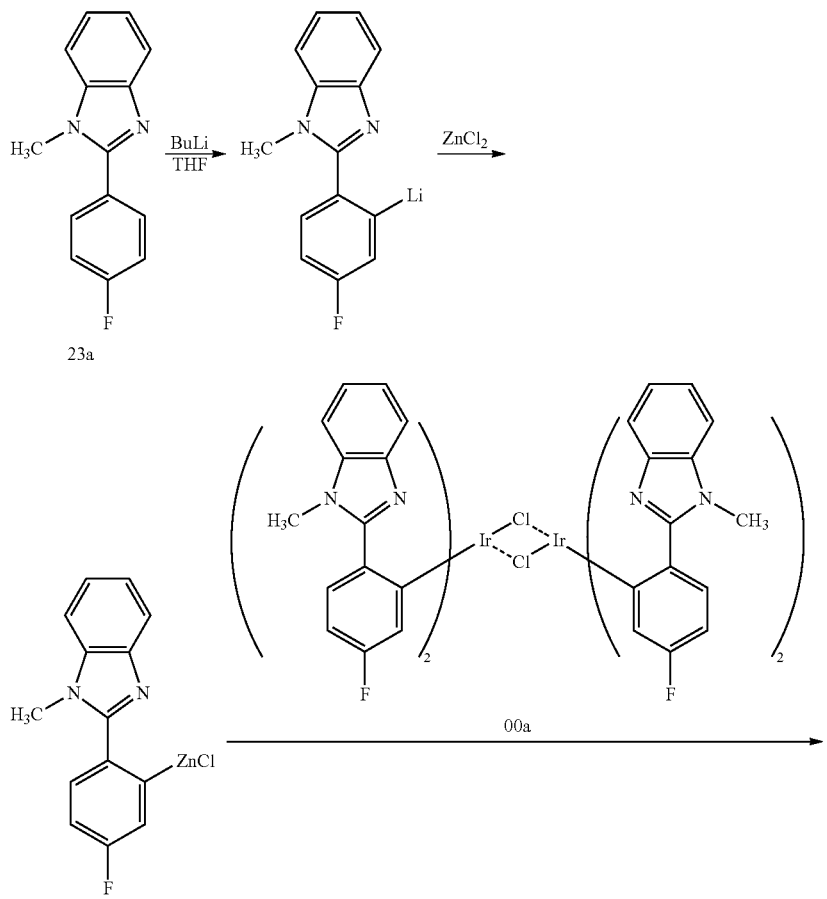

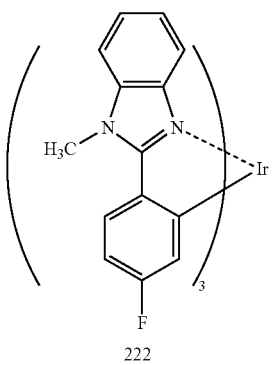

222

At a temperature of −78° C. under an atmosphere of nitrogen, a pentane solution of n-BuLi (4.5 ml, 7.2 mmol) was added dropwise to 30 ml of a dehydrated THF solution of the compound 23a (1.49 g, 6.6 mmol), and stirred for 30 minutes. Thereto, a diethyl ether solution of anhydrous zinc(II) chloride (6.6 ml, 6.6 mmol) was further added dropwise, and stirring was continued until the temperature of the reaction solution was restored to room temperature. To the reaction solution containing the zinc complex, the chlorine-bridged complex 00a (4.48 g, 3.3 mmol) and 20 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with $MgSO_4$ and removal of the solvent under reduced pressure. After isomerization and subsequent washing in boiling glycerol (12 hours), a precipitate formed was filtered off, dissolved in dichloromethane, and purified by recrystallization. Thus, 3.37 g of Exemplified Compound 222 (3.89 mmol, 59%) was obtained. And it was found by HPLC that the thus obtained Exemplified Compound 222 had a purity of 99.4%. In addition, in ICP optical emission spectroscopy of the compound obtained, the content of Li and Li ion was found to be 6.6 ppm and the content of Mg and Mg ion was found to be below 1 ppm.

Synthesis of Exemplified Compound 222

Furthermore, Exemplified Compound 222 was synthesized in accordance with the following reaction scheme also.

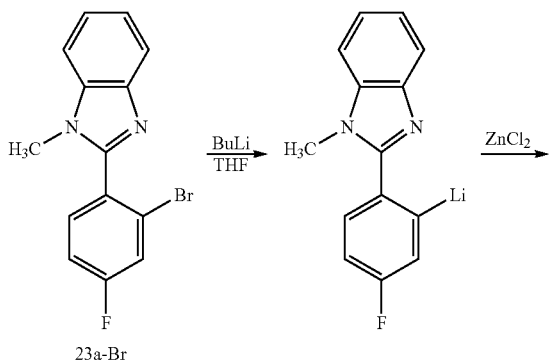

23a-Br

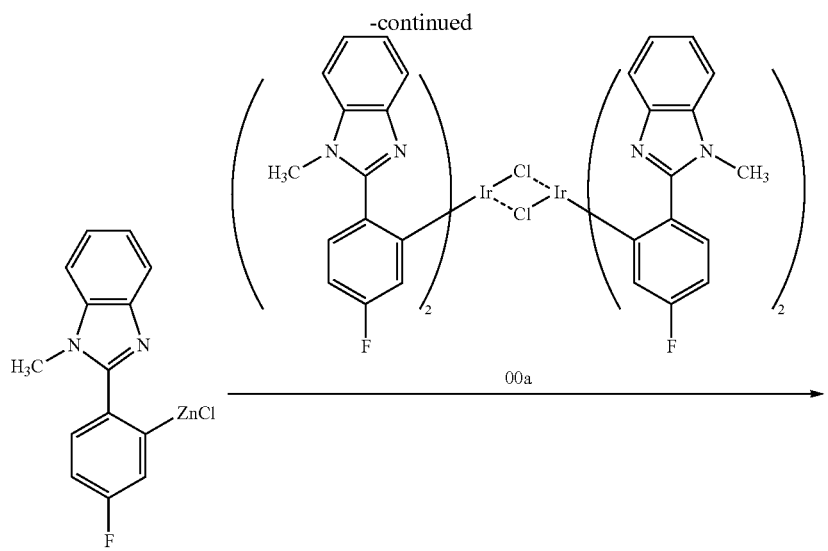

At a temperature of −78° C. under an atmosphere of nitrogen, a pentane solution of n-BuLi (4.5 ml, 7.2 mmol) was added dropwise to 30 ml of a dehydrated THF solution of the compound 23a-Br (2.01 g, 6.6 mmol), and stirred for 30 minutes. Thereto, a diethyl ether solution of anhydrous zinc (II) chloride (6.6 ml, 6.6 mmol) was further added dropwise, and stirring was continued until the temperature of the reaction solution was restored to room temperature. To the reaction solution containing the zinc complex, the chlorine-bridged complex 00a (4.48 g, 3.3 mmol) and 20 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with $MgSO_4$ and removal of the solvent under reduced pressure. After isomerization and subsequent washing in boiling glycerol (12 hours), a precipitate formed was filtered off, dissolved in dichloromethane, and purified by recrystallization. Thus, 3.60 g of Exemplified Compound 222 (3.89 mmol, 63%) was obtained. And it was found by HPLC that the thus obtained Exemplified Compound 222 had a purity of 99.5%. In addition, in ICP optical emission spectroscopy of the compound obtained, the content of Li and Li ion was found to be 5.7 ppm and the content of Mg and Mg ion was found to be below 1 ppm.

Synthesis of Exemplified Compound 223

Exemplified Compound 223 was synthesized in accordance with the following reaction scheme.

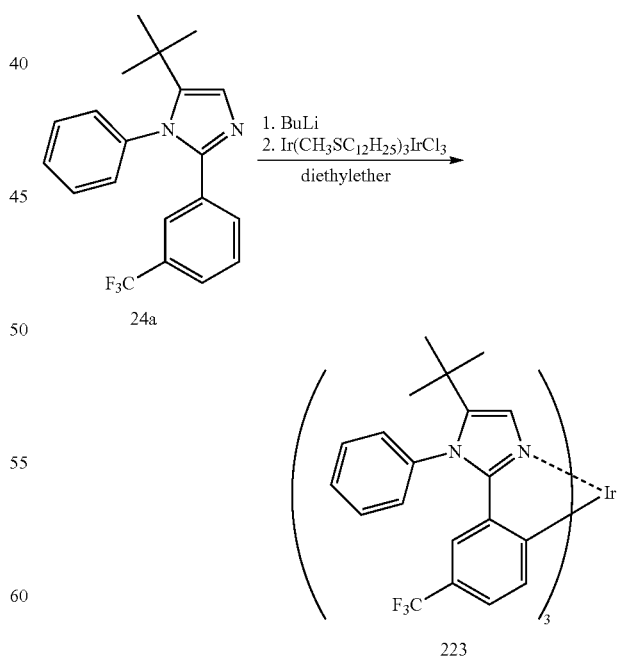

At a temperature of −78° C. under an atmosphere of nitrogen, a pentane solution of n-BuLi (4.4 ml, 7 mmol) was added dropwise to 50 ml of a dehydrated diethyl ether solution of the compound 24a (2.41 g, 7 mmol), and stirred for 30 minutes. Thereto, a diethyl ether solution of tris(dodecylmethylsulfide)iridium chloride (15 ml, 1.75 mmol) was further added dropwise, and stirred for 1 hour at −78° C. Then, stirring was further continued for 6 hours or more until the temperature of the reaction mixture was restored to room temperature. After the reaction mixture was quenched with dilute hydrochloric acid, extraction with dichloromethane, washing with water, drying with MgSO$_4$ and removal of the solvent under reduced pressure were carried out in sequence. The thus obtained reaction product was purified by column chromatography (developing solvent: dichloromethane), and recrystallized from a dichloromethane solution. Thus, 795 mg of Exemplified Compound 223 (0.65 mmol, 37%) was obtained. And it was found by HPLC that the thus obtained Exemplified Compound 223 had a purity of 99.2%. Further, in ICP optical emission spectroscopy of the compound obtained, the content of Li and Li ion was found to be 7.8 ppm and the content of Mg and Mg ion was found to be below 1 ppm.

MS (ESI, m/z) 1223.4 (MH$^+$). Anal. Calcd. for C$_{60}$H$_{54}$F$_9$IrN$_6$: C, 58.96; H, 4.45; N, 6.88. Found: C, 59.0; H, 3.45; N, 6.78.

Synthesis of Exemplified Compound 223

In addition, Exemplified Compound 223 was synthesized in accordance with the following reaction scheme also.

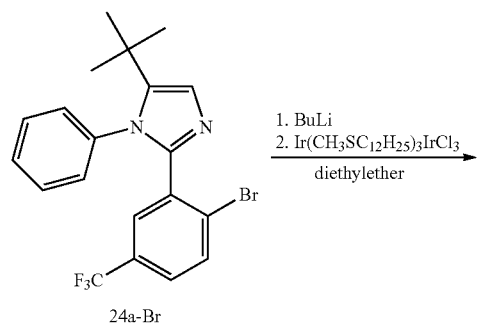

24a-Br

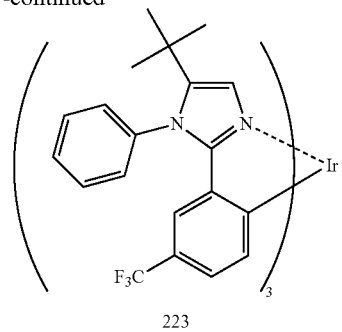

223

At a temperature of −78° C. under an atmosphere of nitrogen, a pentane solution of n-BuLi (4.4 ml, 7 mmol) was added dropwise to 50 ml of a dehydrated diethyl ether solution of the compound 24a-Br (2.96 g, 7 mmol), and stirred for 30 minutes. Thereto, a diethyl ether solution of tris(dodecylmethylsulfide)iridium chloride (15 ml, 1.75 mmol) was further added dropwise, and stirred for 1 hour at −78° C. Then, stirring was further continued for 6 hours or more until the temperature of the reaction mixture was restored to room temperature. After the reaction mixture was quenched with dilute hydrochloric acid, extraction with dichloromethane, washing with water, drying with MgSO$_4$ and removal of the solvent under reduced pressure were carried out in sequence. The thus obtained reaction product was purified by column chromatography (developing solvent: dichloromethane), and recrystallized from a dichloromethane solution. Thus, 856 mg of Exemplified Compound 223 (0.70 mmol, 40%) was obtained. And it was found by HPLC that the thus obtained Exemplified Compound 223 had a purity of 99.5%. Further, in ICP optical emission spectroscopy of the compound obtained, the content of Li and Li ion was found to be 2.8 ppm and the content of Mg and Mg ion was found to be below 1 ppm.

Synthesis of Exemplified Compound 223

Further, Exemplified Compound 223 was synthesized in accordance with the following reaction scheme also.

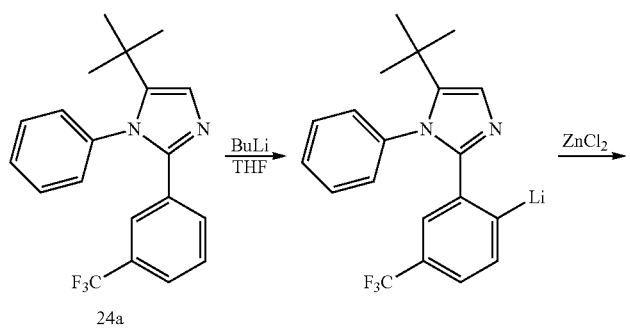

24a

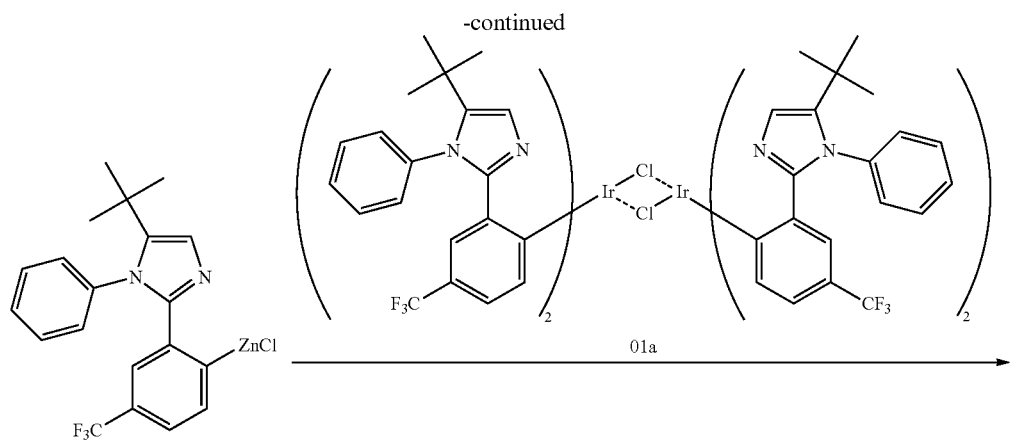

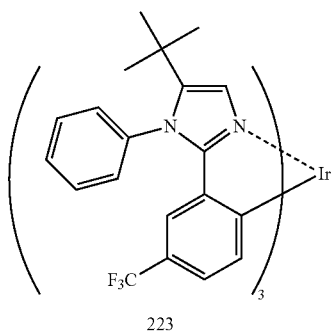

223

At a temperature of −78° C. under an atmosphere of nitrogen, a pentane solution of n-BuLi (3.6 ml, 5.7 mmol) was added dropwise to 30 ml of a dehydrated THF solution of the compound 24a (1.79 g, 5.2 mmol), and stirred for 30 minutes. Thereto, a diethyl ether solution of anhydrous zinc(II) chloride (5.2 ml, 5.2 mmol) was further added dropwise, and stirring was continued until the temperature of the reaction solution was restored to room temperature. To the reaction solution containing the zinc complex, the chlorine-bridged complex 01a (4.75 g, 2.6 mmol) and 20 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with $MgSO_4$ and removal of the solvent under reduced pressure. After isomerization and subsequent washing in boiling glycerol (12 hours), a precipitate formed was filtered off, dissolved in dichloromethane, and purified by recrystallization. Thus, 3.06 g of Exemplified Compound 223 (2.50 mmol, 48%) was obtained. And it was found by HPLC that the thus obtained Exemplified Compound 223 had a purity of 99.3%. In addition, in ICP optical emission spectroscopy of the compound obtained, the content of Li and Li ion was found to be 9.7 ppm and the content of Mg and Mg ion was found to be below 1 ppm.

Synthesis of Exemplified Compound 223

Furthermore, Exemplified Compound 223 was synthesized in accordance with the following reaction scheme also.

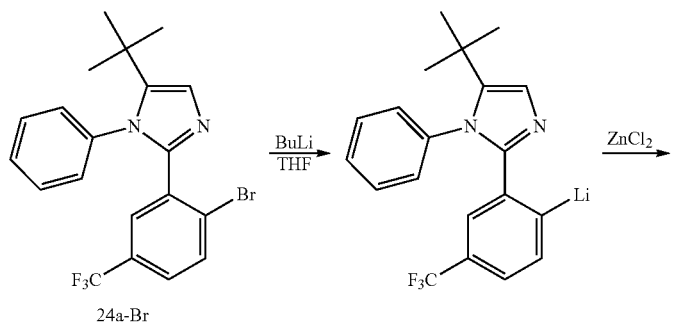

24a-Br

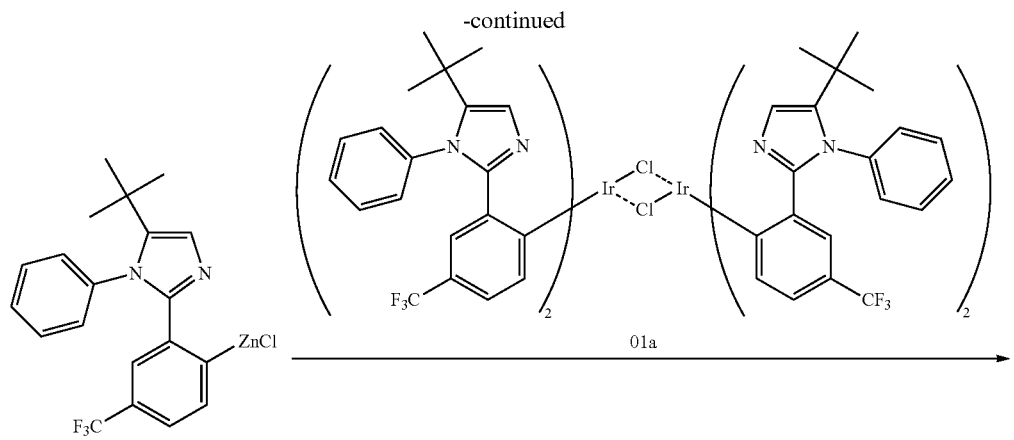

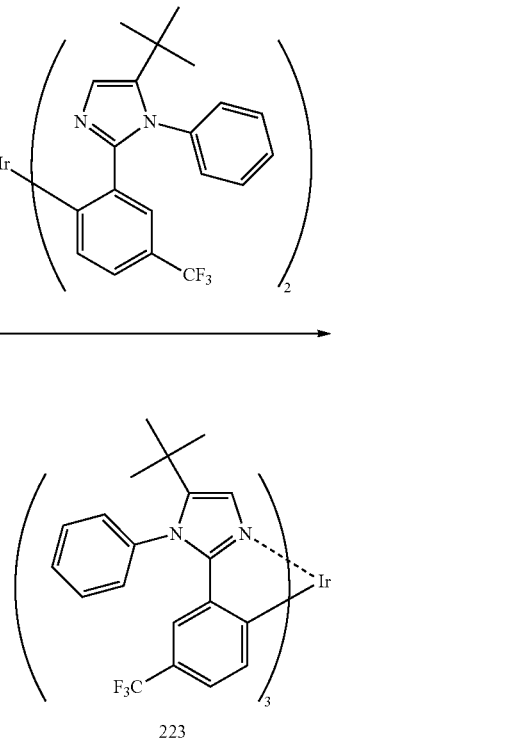

223

At a temperature of −78° C. under an atmosphere of nitrogen, a pentane solution of n-BuLi (3.6 ml, 5.7 mmol) was added dropwise to 30 ml of a dehydrated THF solution of the compound 24a-Br (2.20 g, 5.2 mmol), and stirred for 30 minutes. Thereto, a diethyl ether solution of anhydrous zinc (II) chloride (5.2 ml, 5.2 mmol) was further added dropwise, and stirring was continued until the temperature of the reaction solution was restored to room temperature. To the reaction solution containing the zinc complex, the chlorine-bridged complex 01a (4.75 g, 2.6 mmol) and 20 ml of dehydrated dichloromethane were added. And the resulting mixture was refluxed for 1 hour at its boiling temperature. The thus obtained reaction mixture was allowed to stand for cooling, and then subjected successively to extraction with dichloromethane, washing with water, drying with $MgSO_4$ and removal of the solvent under reduced pressure. After isomerization and subsequent washing in boiling glycerol (12 hours), a precipitate formed was filtered off, dissolved in dichloromethane, and purified by recrystallization. Thus, 3.37 g of Exemplified Compound 223 (2.76 mmol, 53%) was obtained. And it was found by HPLC that the thus obtained Exemplified Compound 223 had a purity of 99.3%. In addition, in ICP optical emission spectroscopy of the compound obtained, the content of Li and Li ion was found to be 9.7 ppm and the content of Mg and Mg ion was found to be below 1 ppm.

Synthesis of Exemplified Compound 224

Exemplified Compound 224 was synthesized in accordance with the following reaction scheme (Synthesis Method 27).

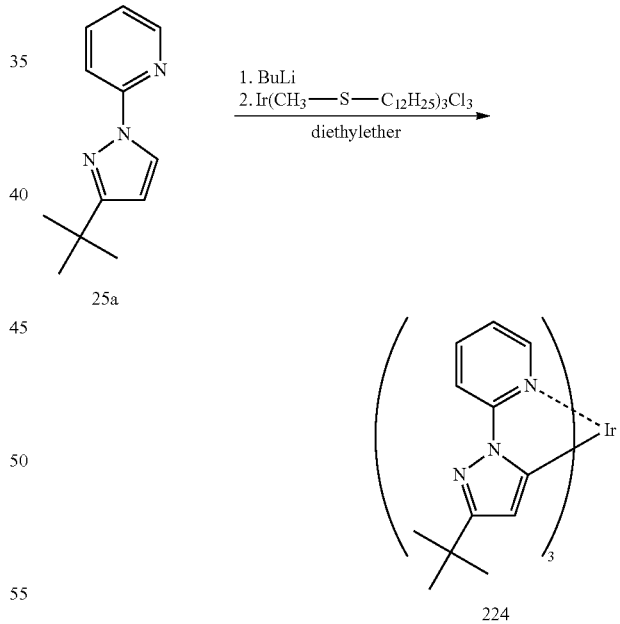

224

At a temperature of −78° C. under an atmosphere of nitrogen, a pentane solution of n-BuLi (4.7 ml, 7.5 mmol) was added dropwise to 50 ml of a dehydrated diethyl ether solution of the compound 25a (1.51 g, 7.5 mmol), and stirred for 30 minutes. Thereto, a diethyl ether solution of tris(dodecylmethylsulfide)iridium chloride (15 ml, 1.88 mmol) was further added dropwise, and stirred for 1 hour at −78° C. Thereafter, stirring was further continued for 6 hours or more until the temperature of the reaction mixture was restored to room temperature. The reaction mixture was quenched with dilute hydrochloric acid, and then extraction with dichloromethane, washing with water, drying with MgSO₄ and removal of the solvent under reduced pressure were carried out in sequence. The thus obtained reaction product was purified by column chromatography (developing solvent: dichloromethane), and recrystallized from a dichloromethane solution. Thus, 492 mg of Exemplified Compound 224 (0.62 mmol, 33%) was obtained. And it was found by HPLC that the thus obtained Exemplified Compound 224 had a purity of 99.4%. Further, in ICP optical emission spectroscopy of the compound obtained, the content of Li and Li ion was found to be 7.5 ppm and the content of Mg and Mg ion was found to be below 1 ppm.

MS (ESI, m/z) 794.3 (MH⁺). Anal. Calcd. for $C_{36}H_{42}IrN_9$: C, 54.53; H, 5.34; N, 15.90. Found: C, 54.1; H, 5.52; N, 15.7.

Synthesis of Exemplified Compound 224

In addition, Exemplified Compound 224 was synthesized in accordance with the following reaction scheme (Synthesis Method 28) also.

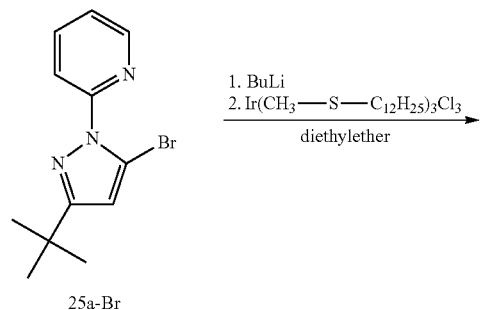

25a-Br

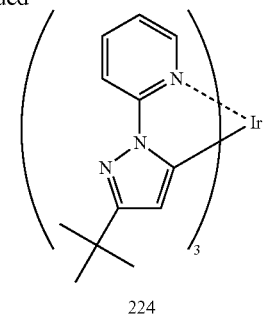

224

At a temperature of −78° C. under an atmosphere of nitrogen, a pentane solution of n-BuLi (4.7 ml, 7.5 mmol) was added dropwise to 50 ml of a dehydrated diethyl ether solution of the compound 25a-Br (2.10 g, 7.5 mmol), and stirred for 30 minutes. Thereto, a diethyl ether solution of tris(dodecylmethylsulfide)iridium chloride (15 ml, 1.88 mmol) was further added dropwise, and stirred for 1 hour at −78° C. Thereafter, stirring was further continued for 6 hours or more until the temperature of the reaction mixture was restored to room temperature. The reaction mixture was quenched with dilute hydrochloric acid, and then extraction with dichloromethane, washing with water, drying with MgSO₄ and removal of the solvent under reduced pressure were carried out in sequence. The thus obtained reaction product was purified by column chromatography (developing solvent: dichloromethane), and recrystallized from a dichloromethane solution. Thus, 522 mg of Exemplified Compound 224 (0.66 mmol, 35%) was obtained. And it was found by HPLC that the thus obtained Exemplified Compound 224 had a purity of 99.4%. Further, in ICP optical emission spectroscopy of the compound obtained, the content of Li and Li ion was found to be 7.5 ppm and the content of Mg and Mg ion was found to be below 1 ppm.

Synthesis of Exemplified Compound 225

Exemplified Compound 225 was synthesized in accordance with the following reaction scheme (Synthesis Method 15).

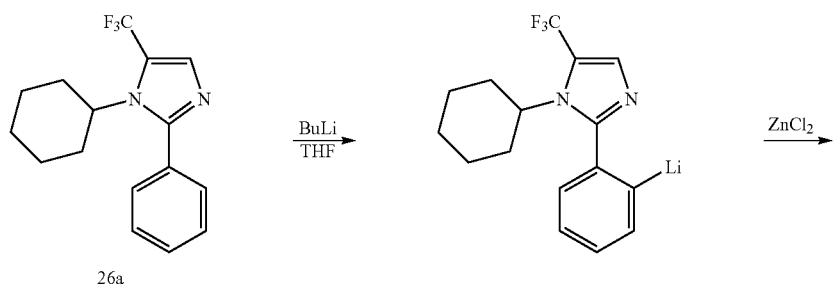

26a

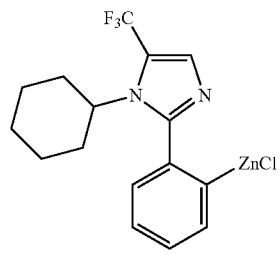

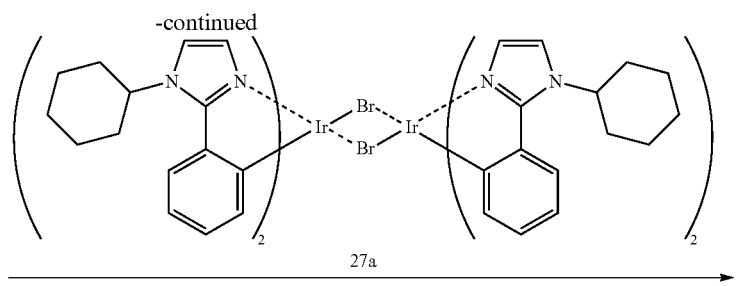

27a

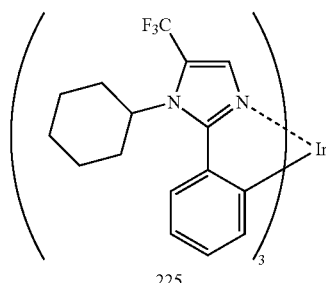

225

At a temperature of −78° C. under an atmosphere of nitrogen, a pentane solution of n-BuLi (4.4 ml, 7 mmol) was added dropwise to 17 ml of a dehydrated THF solution of the compound 26a (1.88 g, 6.4 mmol), and stirred for 30 minutes. Thereto, a diethyl ether solution of anhydrous zinc(II) chloride (6.4 ml, 6.4 mmol) was further added dropwise, and stirring was continued until the temperature of the reaction solution was restored to room temperature.

To the reaction solution containing the zinc complex, the bromine-bridged complex 27a (4.61 g, 3.2 mmol) and 40 ml of dehydrated dichloromethane were added. And the resulting mixture was refluxed for 3 hours at its boiling temperature. The thus obtained reaction mixture was allowed to stand for cooling, and then subjected successively to extraction with dichloromethane, washing with water, drying with MgSO$_4$ and removal of the solvent under reduced pressure. After washing in boiling glycerol (12 hours), a precipitate formed was filtered off, dissolved in dichloromethane, and purified by recrystallization. Thus, 2.93 g of Exemplified Compound 225 (3.39 mmol, 53%) was obtained. And it was found by HPLC that the thus obtained Exemplified Compound 225 had a purity of 99.3%. In addition, in ICP optical emission spectroscopy of the compound obtained, the content of Li and Li ion was found to be 8.2 ppm and the content of Mg and Mg ion was found to be below 1 ppm.

MS (ESI, m/z) 1070.2 (MH$^+$). Anal. Calcd. for C$_{48}$H$_{45}$F$_9$IrN$_6$: C, 54.3; H, 4.22; N, 7.76. Found: C, 53.9; H, 4.24; N, 7.86.

In addition, Exemplified Compound 225 was synthesized in accordance with the following reaction scheme (Synthesis Method 16) also.

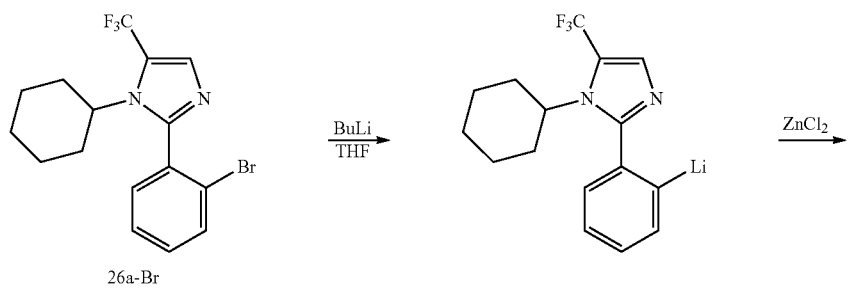

26a-Br

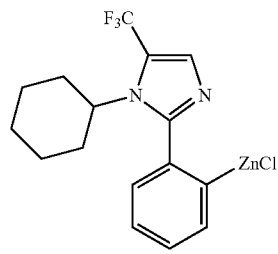

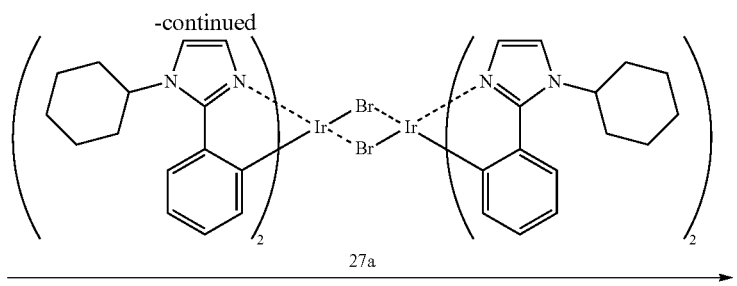

Under a temperature of −78° C. in an atmosphere of nitrogen, a pentane solution of n-BuLi (4.4 ml, 7 mmol) was added dropwise to 17 ml of a dehydrated THF solution of the compound 26a-Br (2.39 g, 6.4 mmol), and stirred for 30 minutes. Thereto, a diethyl ether solution of anhydrous zinc(II) chloride (6.4 ml, 6.4 mmol) was further added dropwise, and stirring was continued until the temperature of the reaction solution was restored to room temperature.

To the reaction solution containing the zinc complex, the bromine-bridged complex 27a (4.61 g, 3.2 mmol) and 40 ml of dehydrated dichloromethane were added. And the resulting mixture was refluxed for 3 hours at its boiling temperature. The thus obtained reaction mixture was allowed to stand for cooling, and then subjected successively to extraction with dichloromethane, washing with water, drying with MgSO$_4$ and removal of the solvent under reduced pressure. After washing in boiling glycerol (12 hours), a precipitate formed was filtered off, dissolved in dichloromethane, and purified by recrystallization. Thus, 3.27 g of Exemplified Compound 225 (3.78 mmol, 59%) was obtained. And it was found by HPLC that the thus obtained Exemplified Compound 225 had a purity of 99.3%. In addition, in ICP optical emission spectroscopy of the compound obtained, the content of Li and Li ion was found to be 7.5 ppm and the content of Mg and Mg ion was found to be below 1 ppm.

Further, Exemplified Compound 225 was synthesized in accordance with the following reaction scheme (Synthesis Method 17) also.

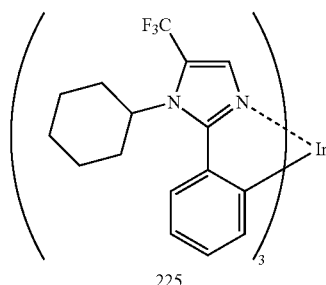

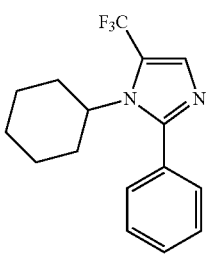

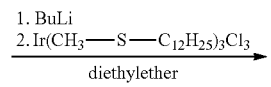

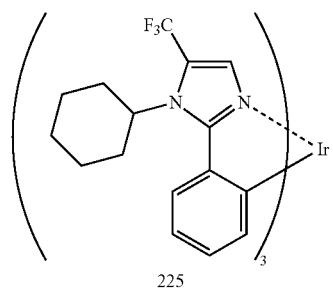

At a temperature of −78° C. under an atmosphere of nitrogen, a pentane solution of n-BuLi (4.8 ml, 7.7 mmol) was added dropwise to 50 ml of a dehydrated diethyl ether solution of the compound 26a (2.06 g, 7 mmol), and stirred for 30 minutes. Thereto, a diethyl ether solution of tris(dodecylmethylsulfide)iridium chloride (15 ml, 1.75 mmol) was further added dropwise, and stirred for 1 hour at −78° C. Thereafter, stirring was further continued for 6 hours or more until the temperature of the reaction mixture was restored to room temperature. The reaction mixture was quenched with dilute hydrochloric acid, and then extraction with dichloromethane, washing with water, drying with $MgSO_4$ and removal of the solvent under reduced pressure were carried out in sequence. The thus obtained reaction product was purified by column chromatography (developing solvent: dichloromethane), and recrystallized from a dichloromethane solution. Thus, 459 mg of Exemplified Compound 225 (0.53 mmol, 30%) was obtained. And it was found by HPLC that the thus obtained Exemplified Compound 225 had a purity of 99.2%. Further, in ICP optical emission spectroscopy of the compound obtained, the content of Li and Li ion was found to be 5.5 ppm and the content of Mg and Mg ion was found to be below 1 ppm.

Furthermore, Exemplified Compound 225 was also synthesized in accordance with the following reaction scheme devised by reference to the descriptions in JP-A-2009-21336, [0117] and [0122] (a traditional method).

In 5 ml of glycerol under an atmosphere of nitrogen, the compound 26a (706 mg, 2.4 mmol) and the bromine-bridged complex 27a (1.72 g, 1.2 mmol) were heated at 200° C. with stirring for 8 hours. The resulting reaction mixture was subjected successively to extraction with dichloromethane, washing with water, drying with $MgSO_4$ and removal of the solvent under reduced pressure. The thus obtained reaction product was purified by column chromatography (developing solvent: dichloromethane), and recrystallized from a dichloromethane solution. Thus, 1.04 g of Exemplified Compound 225 (1.20 mmol, 50%) was obtained. And it was found by HPLC that the thus obtained Exemplified Compound 225 had a purity of 99.3%. Further, it was found in ICP optical emission spectroscopy that the content of Li and Li ion was below 1 ppm and the content of Mg and Mg ion was also below 1 ppm.

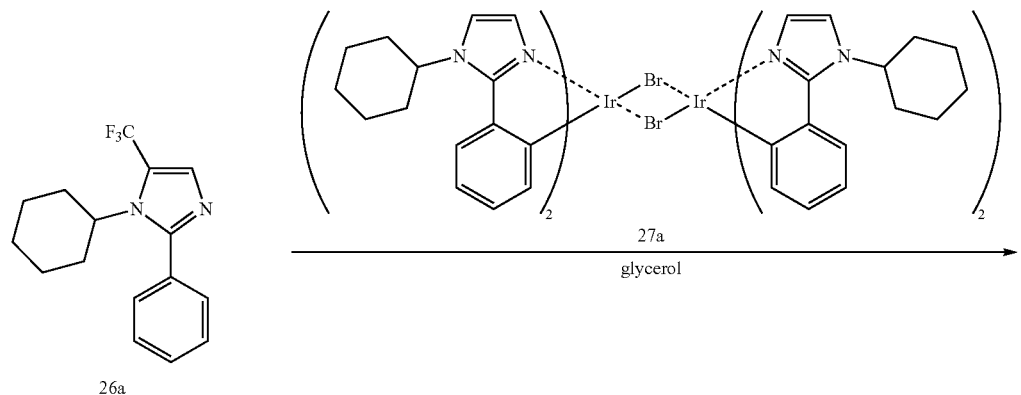

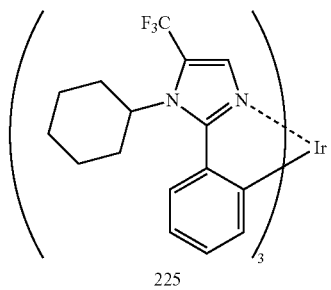

189
Synthesis of Exemplified Compound 226

Exemplified Compound 226 was synthesized in accordance with the following reaction scheme (Synthesis Method 18).

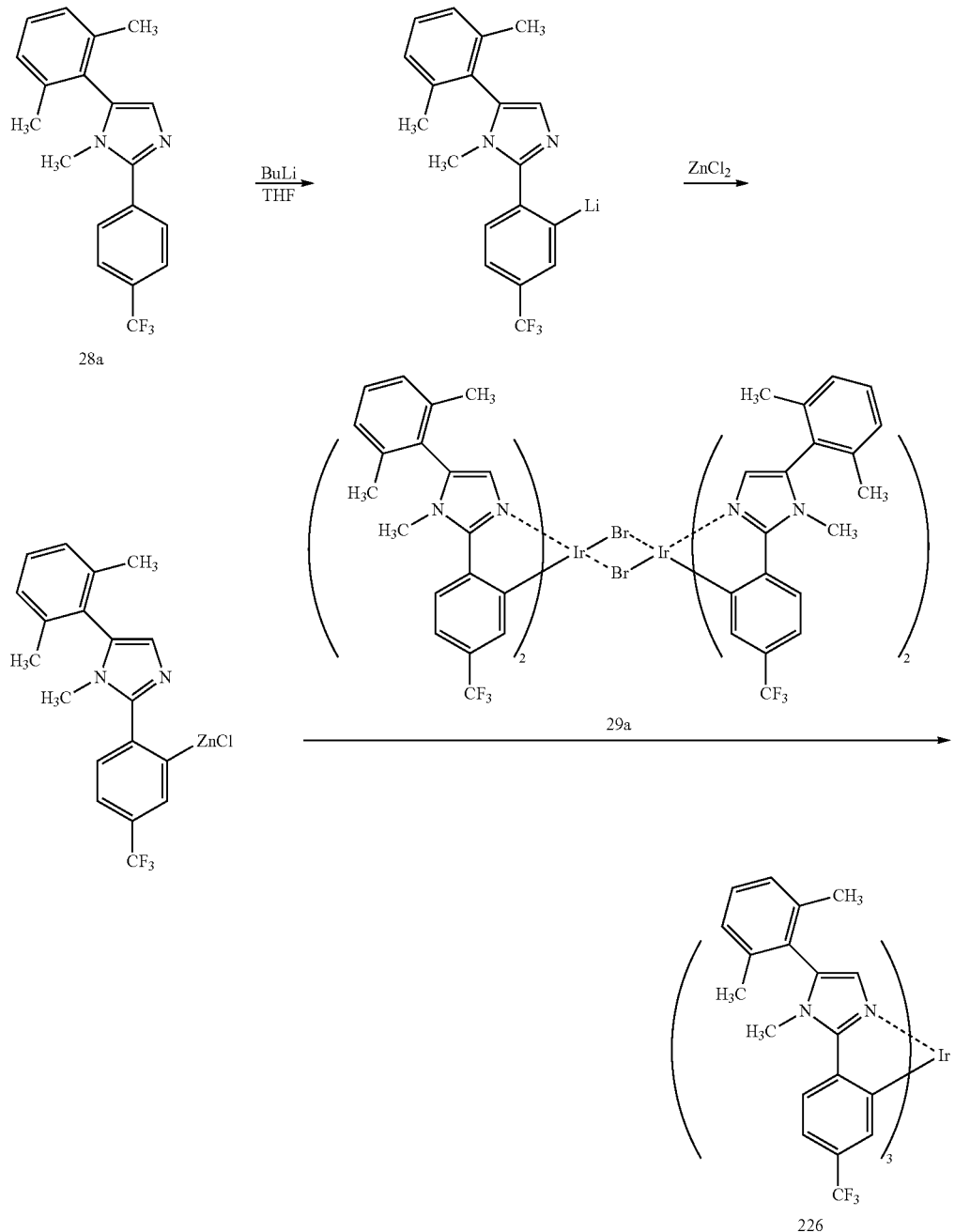

At a temperature of −78° C. under an atmosphere of nitrogen, a pentane solution of n-BuLi (2.8 ml, 4.4 mmol) was added dropwise to 12 ml of a dehydrated THF solution of the compound 28a (1.32 g, 4.0 mmol), and stirred for 30 minutes. Thereto, a diethyl ether solution of anhydrous zinc(II) chloride (4.0 ml, 4.0 mmol) was further added dropwise, and stirring was continued until the temperature of the reaction solution was restored to room temperature.

190

To the reaction solution containing the zinc complex, the bromine-bridged complex 29a (3.72 g, 2.0 mmol) and 30 ml of dehydrated dichloromethane were added. And the resulting mixture was refluxed for 3 hours at its boiling temperature. The thus obtained reaction mixture was allowed to stand for cooling, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 1.01 g of Exemplified Compound 226 (0.86 mmol, 43%) was obtained. And it was found by HPLC that the thus obtained Exemplified Compound 226 had a purity of 99.1%. In addition, in ICP optical emission spectroscopy of the compound obtained, the content of Li and Li ion was found to be 9.8 ppm and the content of Mg and Mg ion was found to be below 1 ppm.

MS (ESI, m/z) 1181.2 (MH$^+$). Anal. Calcd. for $C_{57}H_{48}F_9IrN_6$: C, 58.01; H, 4.10; N, 7.12. Found: C, 57.8; H, 7.32; N, 7.05.

In addition, Exemplified Compound 226 was synthesized in accordance with the following reaction scheme (Synthesis Method 19) also.

compound 28a (1.32 g, 4.0 mmol), and stirred for 30 minutes. Thereto, a diethyl ether solution of anhydrous zinc(II) chloride (4.0 ml, 4.0 mmol) was further added dropwise, and stirring was continued until the temperature of the reaction solution was restored to room temperature.

To the reaction solution containing the zinc complex, the bromine-bridged complex 29a (3.72 g, 2.0 mmol) and 30 ml of dehydrated dichloromethane were added. And the resulting mixture was refluxed for 3 hours at its boiling temperature. The thus obtained reaction mixture was allowed to stand

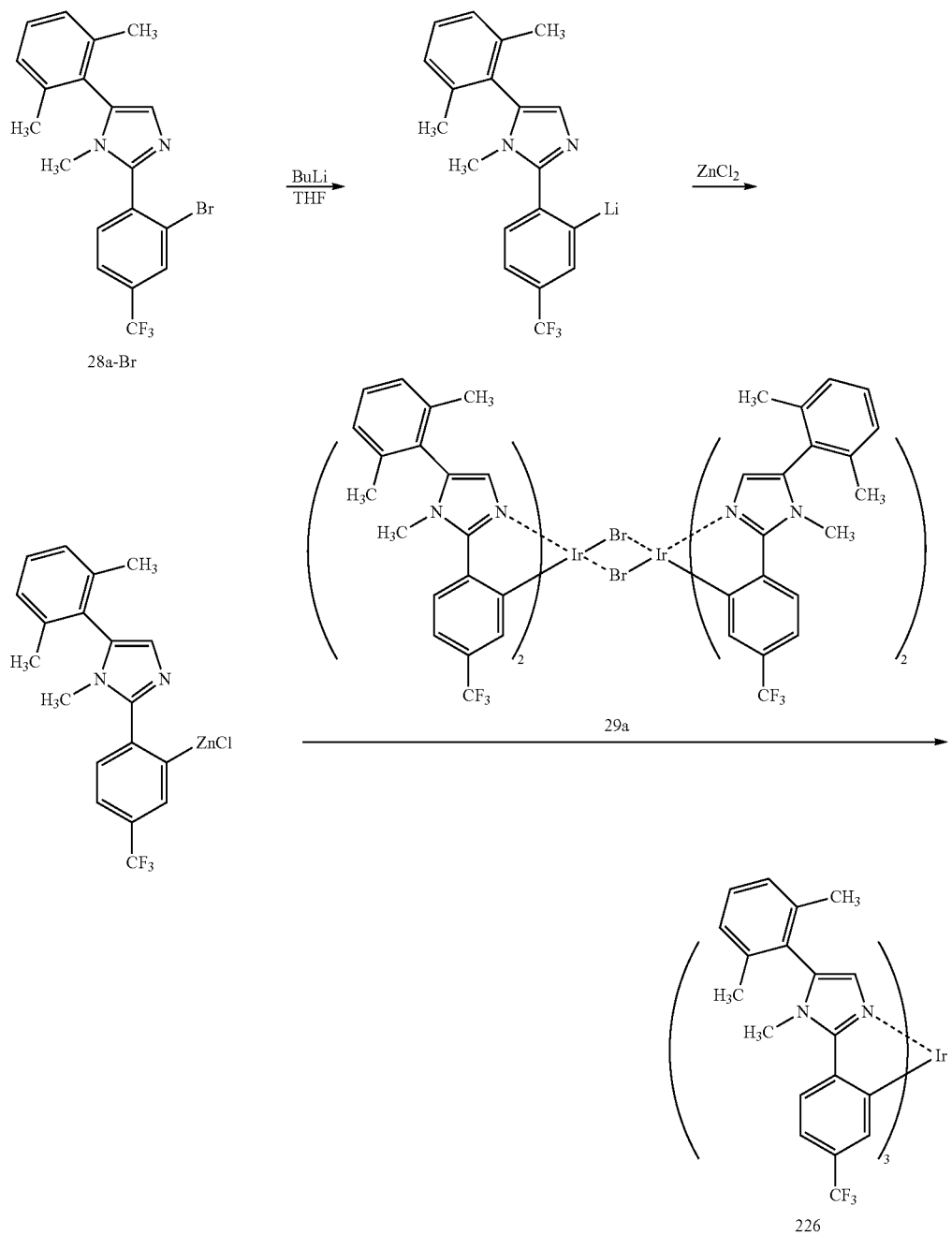

At a temperature of −78° C. under an atmosphere of nitrogen, a pentane solution of n-BuLi (2.8 ml, 4.4 mmol) was added dropwise to 12 ml of a dehydrated THF solution of the for cooling, and then subjected successively to extraction with dichloromethane, washing with water, drying with $MgSO_4$ and removal of the solvent under reduced pressure.

After washing in boiling glycerol (12 hours), a precipitate formed was filtered off, dissolved in dichloromethane, and purified by recrystallization. Thus, 1.08 g of Exemplified Compound 226 (0.92 mmol, 46%) was obtained. And it was found by HPLC that the thus obtained Exemplified Compound 226 had a purity of 99.4%. In addition, in ICP optical emission spectroscopy of the compound obtained, the content of Li and Li ion was found to be 7.5 ppm and the content of Mg and Mg ion was found to be below 1 ppm.

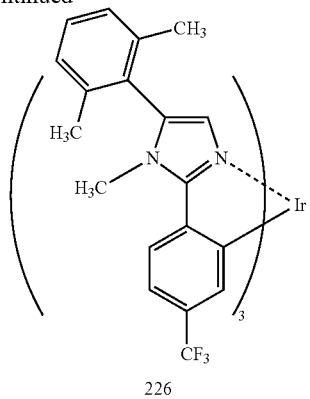

226

Further, Exemplified Compound 226 was synthesized in accordance with the following reaction scheme (Synthesis Method 20) also.

At a temperature of −78° C. under an atmosphere of nitrogen, a pentane solution of n-BuLi (5.5 ml, 8.8 mmol) was added dropwise to 60 ml of a dehydrated diethyl ether solution of the compound 28a-Br (3.27 g, 8 mmol), and stirred for 30 minutes. Thereto, a diethyl ether solution of tris(ethylhexylsulfide)iridium chloride (18 ml, 2 mmol) was further added dropwise, and stirred for 1 hour at −78° C. Thereafter, stirring was further continued for 6 hours or more until the temperature of the reaction mixture was restored to room temperature. The reaction mixture was quenched with dilute hydrochloric acid, and then extraction with dichloromethane, washing with water, drying with $MgSO_4$ and removal of the solvent under reduced pressure were carried out in sequence. The thus obtained reaction product was purified by column chromatography (developing solvent: dichloromethane), and recrystallized from a dichloromethane solution. Thus, 614 mg of Exemplified Compound 226 (0.52 mmol, 26%) was obtained. And it was found by HPLC that the thus obtained Exemplified Compound 226 had a purity of 99.5%. Further, in ICP optical emission spectroscopy of the compound obtained, the content of Li and Li ion was found to be 2.5 ppm and the content of Mg and Mg ion was found to be below 1 ppm.

Furthermore, Exemplified Compound 226 was also synthesized in accordance with the following reaction scheme devised by reference to the method disclosed in WO 2006/126389, [0103] and [0113] (a traditional method).

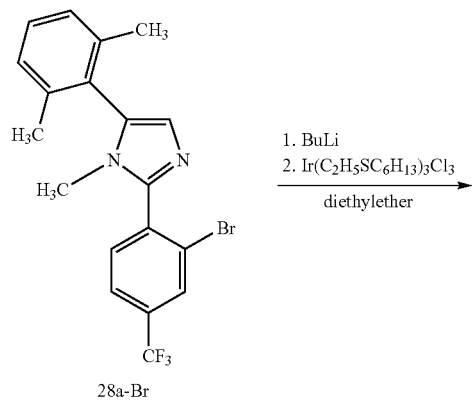

28a-Br

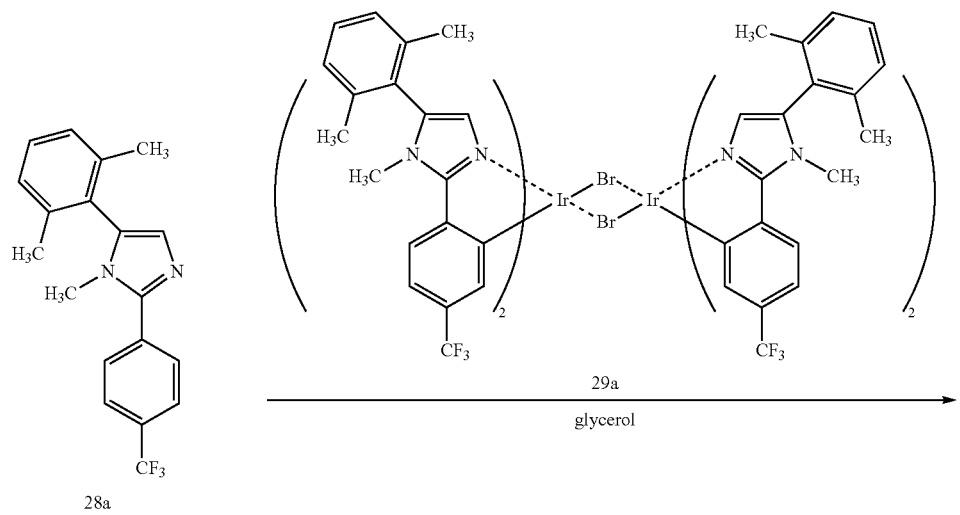

28a

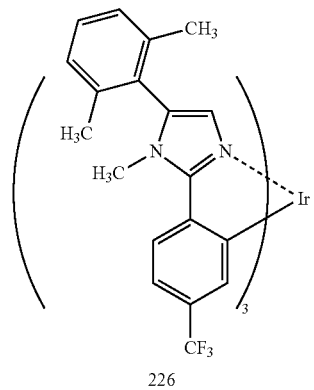

226

In 6 ml of glycerol under an atmosphere of nitrogen, the compound 28a (991 mg, 3.0 mmol) and the bromine-bridged complex 29a (2.79 g, 1.5 mmol) were heated at 220° C. with stirring for 8 hours. The resulting reaction mixture was subjected successively to extraction with dichloromethane, washing with water, drying with $MgSO_4$ and removal of the solvent under reduced pressure. The thus obtained reaction product was purified by column chromatography (developing solvent: dichloromethane), and recrystallized from a dichloromethane solution. Thus, 1.45 g of Exemplified Compound 226 (1.23 mmol, 41%) was obtained. And it was found by HPLC that the thus obtained Exemplified Compound 226 had a purity of 99.7%. Further, it was found in ICP optical emission spectroscopy that the content of Li and Li ion was below 1 ppm and the content of Mg and Mg ion was also below 1 ppm.

Synthesis of Exemplified Compound 227

Exemplified Compound 227 was synthesized in accordance with the following reaction scheme (Synthesis Method 21).

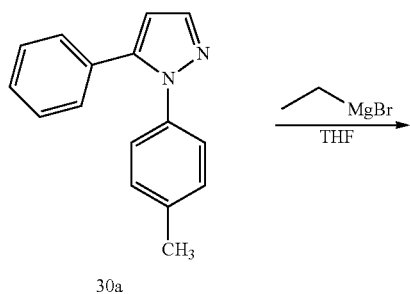

30a

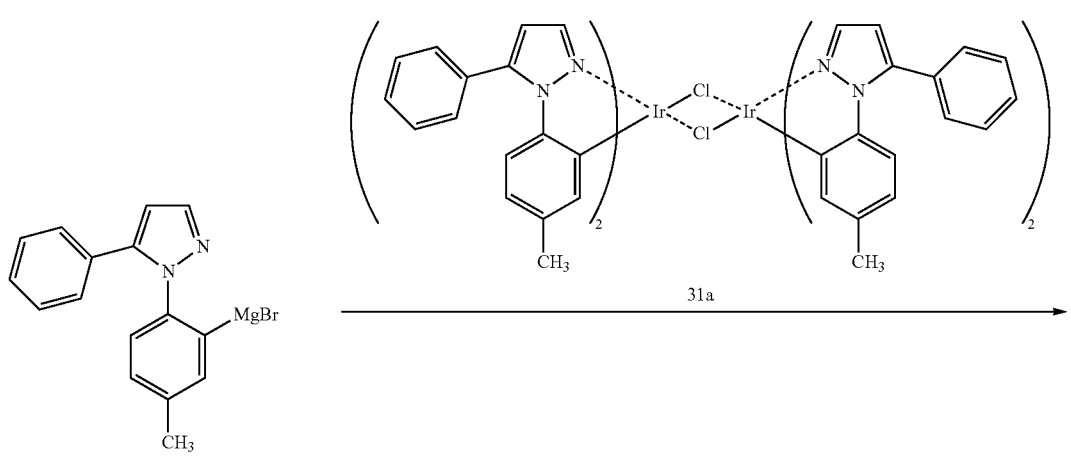

31a

-continued

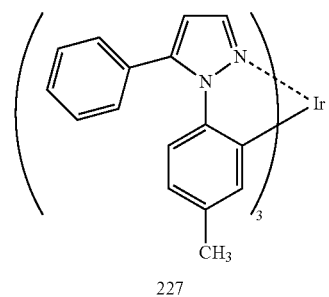
227

At a temperature of 0° C. under an atmosphere of nitrogen, a THF solution of ethylmagnesium bromide (2.0 ml, 6.00 mmol) was added dropwise to 20 ml of a dehydrated THF solution of the compound 30a (1.41 g, 6.00 mmol), and stirred for 30 minutes, thus a Grignard reagent solution was prepared. In a separate vessel, the chlorine-bridged complex 31a (2.08 g, 1.5 mmol) was dissolved in 70 ml of dehydrated THF, and cooled to 0° C. in an atmosphere of nitrogen. Thereto, the Grignard reagent prepared was added dropwise, and stirred for 1 hour. The temperature of the reaction mixture was restored to room temperature over 6 hours or more with stirring. The resulting reaction mixture was quenched with H$_2$O and alcohol, and then subjected successively to extraction with dichloromethane, washing with water, drying with MgSO$_4$ and removal of the solvent under reduced pressure. After washing in boiling glycerol (12 hours), a precipitate formed was filtered off, dissolved in dichloromethane, and purified by recrystallization. Thus, 1.42 g of Exemplified Compound 227 (1.59 mmol, 53%) was obtained. And it was found by HPLC that the thus obtained Exemplified Compound 227 had a purity of 99.3%. In addition, in ICP optical emission spectroscopy of the compound obtained, the content of Li and Li ion was found to below 1 ppm and the content of Mg and Mg ion was found to be 9.6 ppm.

MS (ESI, m/z) 893.3 (MH$^+$). Anal. Calcd. for C$_{48}$H$_{39}$IrN$_6$: C, 64.63; H, 4.41; N, 9.42. Found: C, 64.8; H, 4.51; N, 9.50.

In addition, Exemplified Compound 227 was synthesized in accordance with the following reaction scheme (Synthesis Method 22) also.

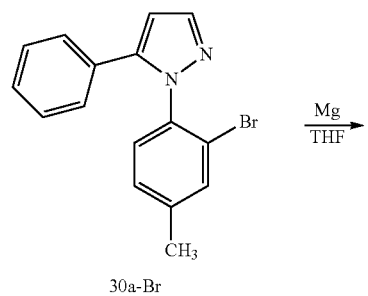
30a-Br

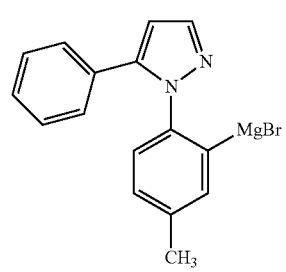

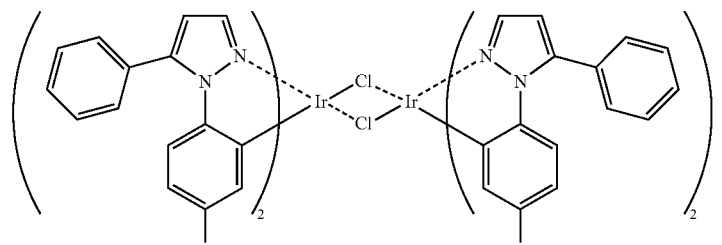
31a

-continued

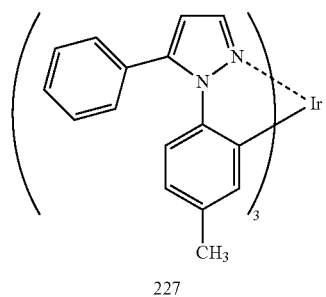
227

At room temperature under an atmosphere of nitrogen, 30 ml of a dehydrated THF solution of the compound 30a-Br (1.88 g, 6.00 mmol) and 1,2-dichloroethane (0.24 ml, 0.30 mmol) was added dropwise to a suspension of magnesium (146 mg, 6 mmol) in 5 ml of dehydrated THF. The reaction solution was refluxed for 2 hours at its boiling temperature, thus a Grignard reagent solution was prepared. In a separate vessel, the chlorine-bridged complex 31a (2.08 g, 1.5 mmol) was dissolved in 60 ml of dehydrated THF, and cooled to 0° C. in an atmosphere of nitrogen. Thereto, the Grignard reagent prepared was added dropwise, and stirred for 1 hour. After the temperature of the reaction mixture was restored to room temperature, reflux at boiling temperature was carried out for 6 hours. The resulting reaction mixture was quenched with $H_2O$ and alcohol, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 1.58 g of Exemplified Compound 227 (3.8 mmol, 59%) was obtained. And it was found by HPLC that the thus obtained Exemplified Compound 227 had a purity of 99.5%. In addition, in ICP optical emission spectroscopy of the compound obtained, the content of Li and Li ion was found to be below 1 ppm and the content of Mg and Mg ion was found to be 2.3 ppm.

Further, Exemplified Compound 227 was also synthesized in accordance with the following scheme devised by reference to the descriptions in JP-A-2007-51243, [0064] and [0070] to [0073] (a traditional method).

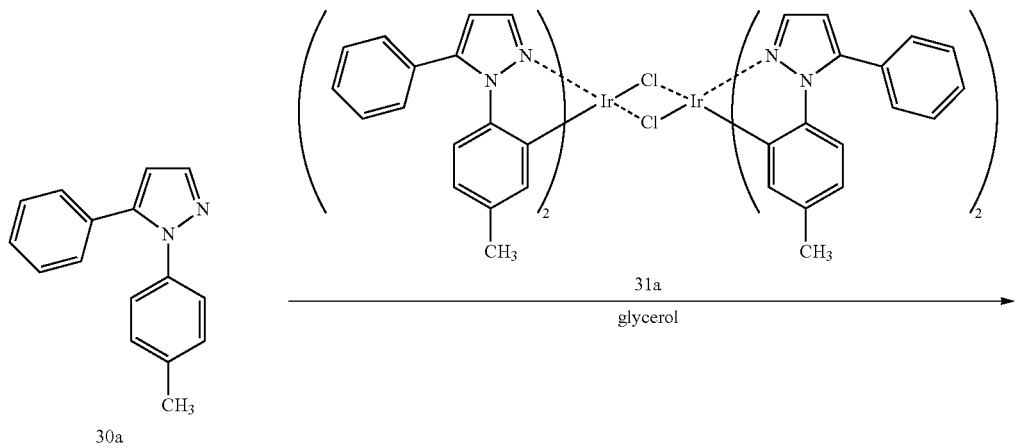

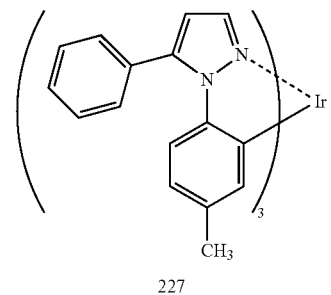
227

Thus, Exemplified Compound 227 was obtained in a 45% yield. And the purity of Exemplified Compound 227 thus obtained was found to be 99.4% by HPLC. Further, in ICP optical emission spectroscopy, the compound obtained was found to be below 1 ppm in both the content of Li and Li ion and the content of Mg and Mg ion.

Synthesis of Exemplified Compound 228

Exemplified Compound 228 was synthesized in accordance with the following reaction scheme (Synthesis Method 23).

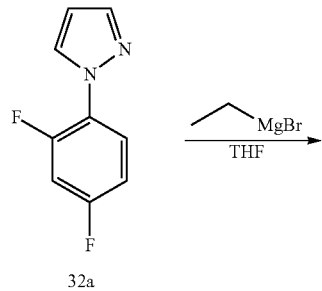

32a

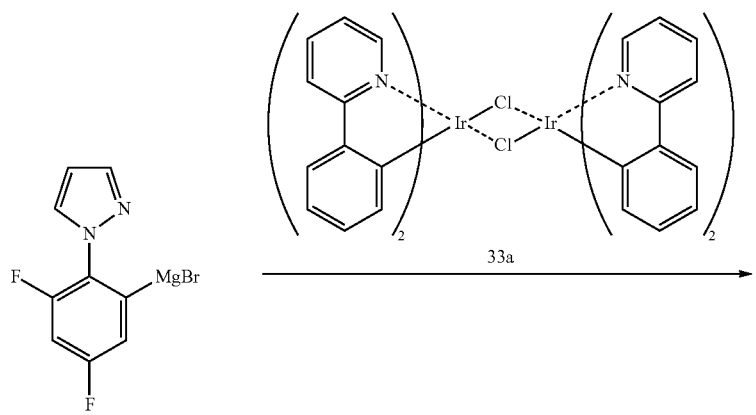

33a

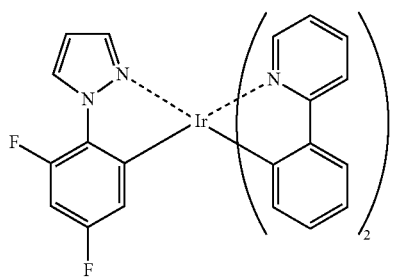

228

At a temperature of 0° C. under an atmosphere of nitrogen, a THF solution of ethylmagnesium bromide (2.3 ml, 7.00 mmol) was added dropwise to 20 ml of a dehydrated THF solution of the compound 32a (1.26 g, 7.00 mmol), and stirred for 30 minutes, thus a Grignard reagent solution was prepared. In a separate vessel, the chlorine-bridged complex 33a (1.87 g, 1.75 mmol) was dissolved in 80 ml of dehydrated THF, and cooled to 0° C. in an atmosphere of nitrogen. Thereto, the Grignard reagent prepared was added dropwise, and stirred for 1 hour. The temperature of the reaction mixture was restored to room temperature over 6 hours or more with stirring. The resulting reaction mixture was quenched with $H_2O$ and alcohol, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 1.22 g of Exemplified Compound 228 (1.79 mmol, 51%) was obtained. And it was found by HPLC that the thus obtained Exemplified Compound 228 had a purity of 99.5%. In addition, in ICP optical emission spectroscopy of the compound obtained, the content of Li and Li ion was found to below 1 ppm and the content of Mg and Mg ion was found to be 6.6 ppm.

MS (ESI, m/z) 681.1 (MH$^+$). Anal. Calcd. for $C_{31}H_{21}F_2IrN_4$: C, 54.78; H, 3.11; N, 8.24. Found: C, 54.8; H, 3.31; N, 8.33.

In addition, Exemplified Compound 228 was synthesized in accordance with the following reaction scheme (Synthesis Method 24) also.

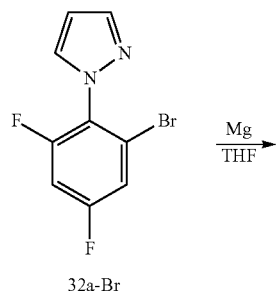

32a-Br

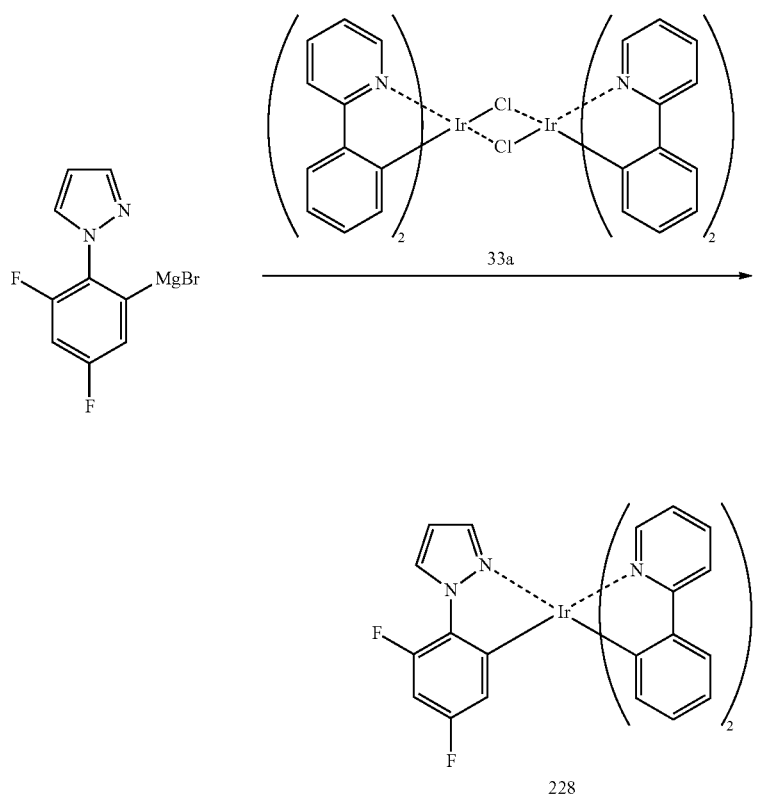

228

At room temperature under an atmosphere of nitrogen, 35 ml of a dehydrated THF solution of the compound 32a-Br (1.81 g, 7.00 mmol) and 1,2-dichloroethane (0.24 ml, 0.30 mmol) was added dropwise to a suspension of magnesium (191 mg, 7 mmol) in 5 ml of dehydrated THF. The reaction solution was refluxed for 2 hours at its boiling temperature, thus a Grignard reagent solution was prepared. In a separate vessel, the chlorine-bridged complex 33a (1.87 g, 1.75 mmol) was dissolved in 60 ml of dehydrated THF, and cooled to 0° C. in an atmosphere of nitrogen. Thereto, the Grignard reagent prepared was added dropwise, and stirred for 1 hour. After the temperature of the reaction mixture was restored to room temperature, reflux at boiling temperature was carried out for 6 hours. The resulting reaction mixture was quenched with $H_2O$ and alcohol, and then subjected successively to extraction with dichloromethane, washing with water, drying with $MgSO_4$ and removal of the solvent under reduced pressure. After washing in boiling glycerol (12 hours), a precipitate formed was filtered off, dissolved in dichloromethane, and purified by recrystallization. Thus, 1.38 g of Exemplified Compound 228 (2.03 mmol, 58%) was obtained. And it was found by HPLC that the thus obtained Exemplified Compound 228 had a purity of 99.7%. In addition, in ICP optical emission spectroscopy of the compound obtained, the content of Li and Li ion was found to be below 1 ppm and the content of Mg and Mg ion was found to be 3.1 ppm.

Further, Exemplified Compound 228 was synthesized by reference to the method described in Inorg. Chem., 2005, 44, 4445-4447 (a traditional method), and the yield thereof was 45%. The purity of the compound obtained was found to be 99.5% by HPLC. Further, in ICP optical emission spectroscopy, the compound obtained was found to be below 1 ppm in both the content of Li and Li ion and the content of Mg and Mg ion.

Compounds used in Examples according to the invention are illustrated below.

Exemplified Compound 62
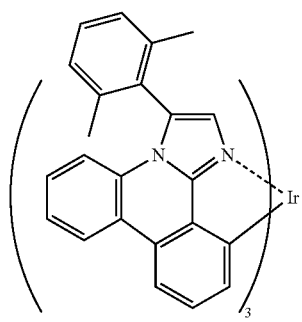
Exemplified Compound 225
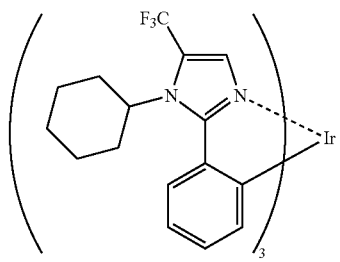
Exemplified Compound 63
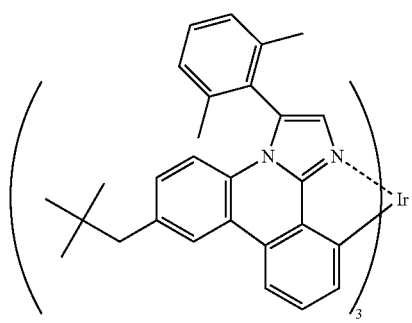
Exemplified Compound 226
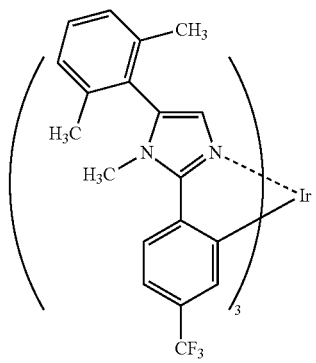
Exemplified Compound 64
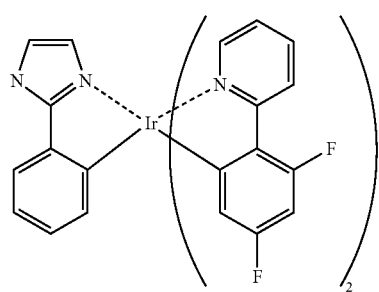
Exemplified Compound 227
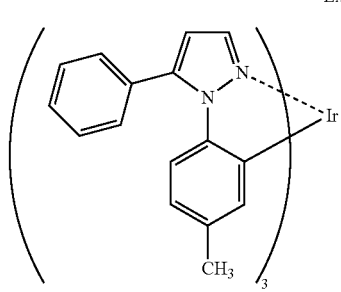
Exemplified Compound 66
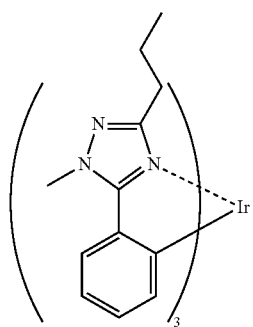
Exemplified Compound 228
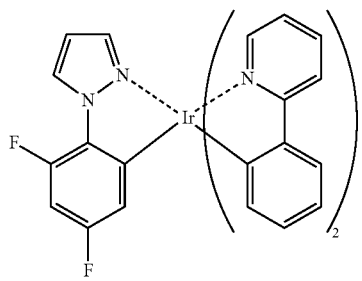
Exemplified Compound 1
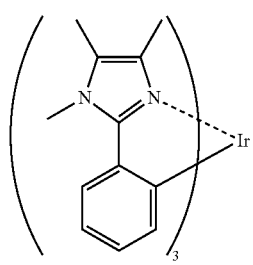
Exemplified Compound 65
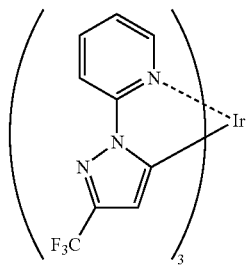

Exemplified Compound 224
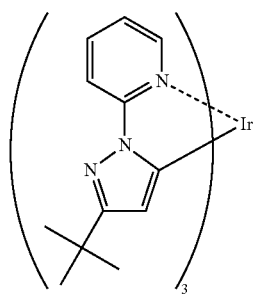
Exemplified Compound 220
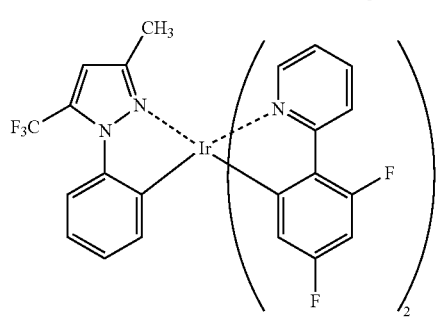
Exemplified Compound 221
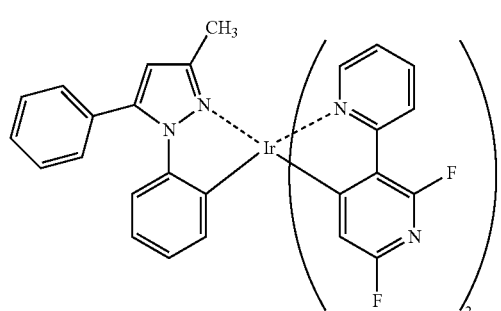
Exemplified Compound 222
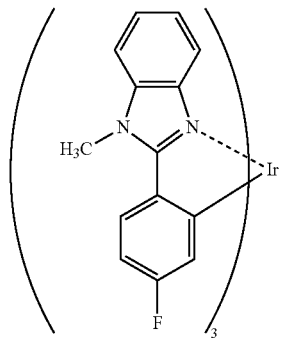
Exemplified Compound 223
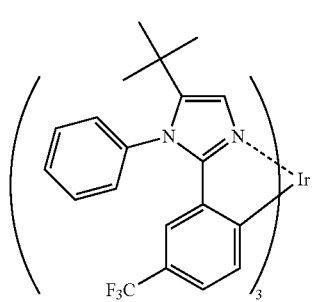
Exemplified Compound 3
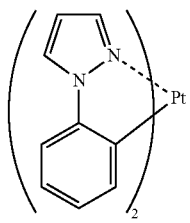
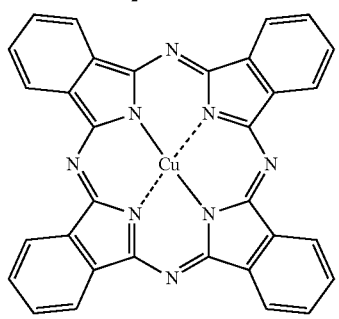
Copper phthalocyanine
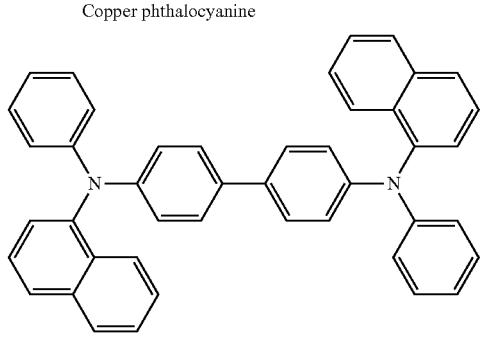
NPD
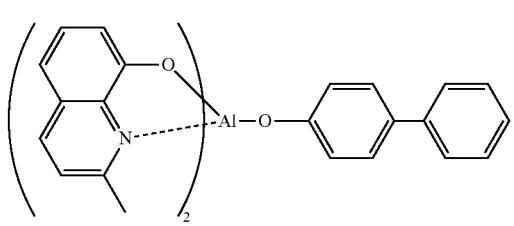
BAlq
H-1
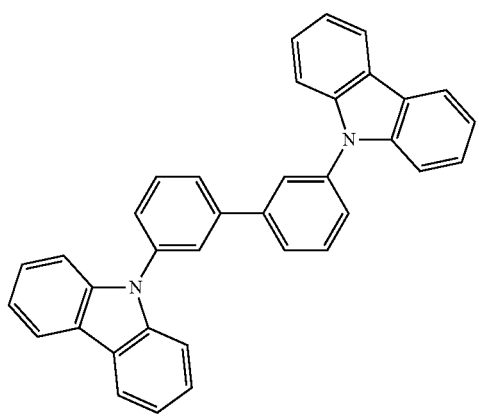

-continued

H-2

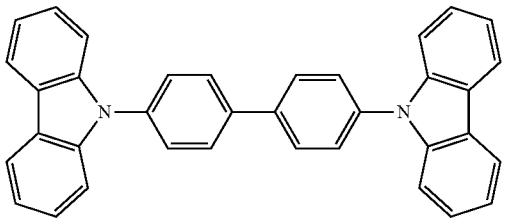

EXAMPLES

Example 1-1

An indium tin oxide (ITO) film-coated glass substrate having an area of 2.5 square centimeters and a thickness of 0.5 mm (made by GEOMATEC Corporation, surface resistivity: 10 Ω/sq) was placed in a cleaning vessel and subjected to ultrasonic cleaning in 2-propanol, and the thus cleaned substrate is further subjected to UV-ozone treatment of 30 minutes. Onto this transparent anode (ITO film), the following organic layers (organic compound layers) were evaporated in sequence by using a vacuum evaporation method.

The evaporation speed in each of Examples relating to the invention was 0.2 nm/sec unless otherwise specified. Evaporation speed measurements were made with a quartz resonator. And the following film thicknesses were also measured with a quartz resonator.

The ITO substrate cleaned in the foregoing manner was placed in a vacuum evaporator, and copper phthalocyanine was evaporated onto this substrate in the form of a 10 nm-thick film (first layer). Onto the first layer, NPD [(N,N'-di-α-naphthyl-N,N'-diphenyl)-benzidine] was evaporated in the form of a 40 nm-thick film (second layer). Onto the second layer, H-1 and the Exemplified Compound 63 synthesized in accordance with one of the present reaction schemes were evaporated at a ratio of 95:5 (by mass) in the form of a 30 nm-thick film (third layer/light emitting layer). Onto the third layer, BAlq [bis(2-methyl-8-quinolato)-4-phenylphenolatoaluminum] was evaporated in the form of a 40 nm-thick film (fourth layer). Onto the fourth layer, a 3 nm-thick film of lithium fluoride and a 60 nm-thick film of aluminum were evaporated in the order of mention. The thus formed laminate was placed in a glove box having undergone argon gas displacement without exposure to the air, and sealed by means of a sealing can made of stainless steel and a UV cure adhesive (XNR5516HV, produced by Nagase-Chiba, Ltd.), thereby making an organic EL Device of Example 1-1. A direct-current constant voltage was applied to this device through the use of Source Measure Unit 2400 made by TOYO Corporation, and thereby luminescence from the present Exemplified Compound 63 was produced.

Examples 1-2 and 1-3, and Comparative Example 1-1

Devices of Examples 1-2 and 1-3 and a device of Comparative Example 1-1 were made in the same manner as the device of Example 1-1, except that the method used for preparing Exemplified Compound 63 in Example 1-1 was changed to the methods entered in Table 1, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

<Measurement of Drive Voltage>

Each of the organic EL devices made in Examples 1-1 to 1-3 and Comparative Example 1-1, respectively, was mounted in an emission spectrum measuring system made by Shimadzu Corporation (ELS-1500), and thereon measurement of an impressed voltage at which the emission spectral intensity of each device reached 1,000 cd/m² was made.

<Evaluation of Drive Durability>

Each of the organic EL devices made in Examples 1-1 to 1-3 and Comparative Example 1-1, respectively, was mounted in an OLED Test System Model STD made by Tokyo System Development Co., Ltd., and made to drive in a constant-current mode under a condition of attaining an initial luminance of 1,000 cd/m². Under such drive, time taken to reduce the luminance in half to 500 cd/m² was determined.

<Evaluation of External Quantum Efficiency>

Each of the organic EL devices made in Examples 1-1 to 1-3 and Comparative Example 1-1, respectively, was made to produce luminescence by applying thereto a direct-current constant voltage through the use of Source Measure Unit 2400 made by TOYO Corporation. The external quantum efficiency (%) was calculated from the frontal luminance at 1,000 cd/m².

TABLE 1

| | Method of forming light emitting material (Exemplified Compound 63) | Drive voltage (V) at 1,000 cd/m² | External quantum efficiency (%) at 1,000 cd/m² | Half luminance time at 1,000 cd/m² (relative value) |
|---|---|---|---|---|
| Example 1-1 | Synthesis Method 1 | 12.3 | 5.8 | 100 |
| Example 1-2 | Synthesis Method 2 | 12.5 | 5.7 | 65 |
| Example 1-3 | Synthesis Method 3 | 12.3 | 5.8 | 84 |
| Comparative Example 1-1 | Method disclosed in U.S. 2008/02,97,033, [0281] to [0287] | 12.4 | 5.8 | 53 |

As is clear from comparisons of Examples 1-1 to 1-3 and Comparative Example 1-1, improvements in durability were achieved by using the light emitting material prepared in accordance with the present methods. Additionally, the time taken to reduce by half the luminance was expressed in relative value, with Example 1-1 being taken as 100.

Example 2-1

An organic EL device of Example 2-1 was made in the same manner as in Example 1-1, except that the Exemplified Compound 64 obtained as a light emitting material by Synthesis Method 4 was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in the Exemplified Compound 64 was produced.

Example 2-2 and Comparative Example 2-1

Devices of Example 2-2 and Comparative Example 2-1 were made in the same manner as the device of Example 2-1, except that the method used for preparing Exemplified Compound 64 in Example 2-1 was changed to the methods entered in Table 2, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

TABLE 2

|  | Method of forming light emitting material (Exemplified Compound 64) | Drive voltage (V) at 1,000 cd/m$^2$ | External quantum efficiency (%) at 1,000 cd/m$^2$ | Half luminance time at 1,000 cd/m$^2$ (relative value) |
|---|---|---|---|---|
| Example 2-1 | Synthesis Method 4 | 11.5 | 5.7 | 100 |
| Example 2-2 | Synthesis Method 5 | 11.8 | 5.9 | 72 |
| Comparative Example 2-1 | Method described in Inorg. Chem., 2005, 44, 4445-4447 | 11.6 | 5.8 | 58 |

As is clear from comparison of Examples 2-1 to 2-2 and Comparative Example 2-1, improvements in durability were achieved by using the light emitting material prepared in accordance with the present methods. Additionally, the time taken to reduce by half the luminance was expressed in relative value, with Example 2-1 being taken as 100.

Example 3-1

An organic EL device of Example 3-1 was made in the same manner as in Example 1-1, except that the Exemplified Compound 62 obtained as a light emitting material by Synthesis Method 6 was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in the Exemplified Compound 62 was produced.

Examples 3-2 to 3-3 and Comparative Example 3-1

Devices of Examples 3-2 to 3-3 and Comparative Example 3-1 were made in the same manner as the device of Example 3-1, except that the method of preparing Exemplified Compound 62 used in Example 3-1 was changed to the methods entered in Table 3, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

TABLE 3

|  | Method of forming light emitting material (Exemplified Compound 62) | Drive voltage (V) at 1,000 cd/m$^2$ | External quantum efficiency (%) at 1,000 cd/m$^2$ | Half luminance time at 1,000 cd/m$^2$ (relative value) |
|---|---|---|---|---|
| Example 3-1 | Synthesis Method 6 | 10.8 | 4.5 | 100 |
| Example 3-2 | Synthesis Method 7 | 10.7 | 4.5 | 75 |
| Example 3-3 | Synthesis Method 8 | 10.6 | 4.6 | 89 |
| Comparative Example 3-1 | Synthesis Method A (Method devised by reference to U.S. 2008/0,297,033) | 10.8 | 4.5 | 61 |

As is clear from comparisons of Examples 3-1 to 3-3 and Comparative Example 3-1, improvements in durability were achieved by using the light emitting material prepared in accordance with the present methods. Additionally, the time taken to reduce by half the luminance was expressed in relative value, with Example 3-1 being taken as 100.

Example 4-1

An organic EL device of Example 4-1 was made in the same manner as in Example 1-1, except that the Exemplified Compound 66 obtained as a light emitting material by Synthesis Method 9 was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in the Exemplified Compound 66 was produced.

Examples 4-2 to 4-3 and Comparative Example 4-1

Devices of Examples 4-2 to 4-3 and Comparative Example 4-1 were made in the same manner as the device of Example 4-1, except that the method used for preparing Exemplified Compound 66 in Example 4-1 was changed to the methods entered in Table 4, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

TABLE 4

|  | Method of forming light emitting material (Exemplified Compound 66) | Drive voltage (V) at 1,000 cd/m$^2$ | External quantum efficiency (%) at 1,000 cd/m$^2$ | Half luminance time at 1,000 cd/m$^2$ (relative value) |
|---|---|---|---|---|
| Example 4-1 | Synthesis Method 9 | 9.5 | 6.6 | 100 |
| Example 4-2 | Synthesis Method 10 | 9.5 | 6.5 | 68 |
| Example 4-3 | Synthesis Method 11 | 9.6 | 6.6 | 82 |
| Comparative Example 4-1 | Method described in Chem. Mater., 2006, 18, 5119-5129 | 9.7 | 6.5 | 41 |

As is clear from comparisons of Examples 4-1 to 4-3 and Comparative Example 4-1, improvements in durability were achieved by using the light emitting material prepared in accordance with the present methods. Additionally, the time taken to reduce by half the luminance was expressed in relative value, with Example 4-1 being taken as 100.

Example 5-1

An organic EL device of Example 5-1 was made in the same manner as in Example 1-1, except that the Exemplified Compound 1 obtained as a light emitting material by Synthesis Method 12 was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in Exemplified Compound 1 was produced.

Examples 5-2 to 5-3 and Comparative Example 5-1

Devices of Examples 5-2 to 5-3 and Comparative Example 5-1 were made in the same manner as the device of Example 5-1, except that the method used for preparing Exemplified Compound 1 in Example 5-1 was changed to the methods entered in Table 5, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

TABLE 5

|  | Method of forming light emitting material (Exemplified Compound 1) | Drive voltage (V) at 1,000 cd/m$^2$ | External quantum efficiency (%) at 1,000 cd/m$^2$ | Half luminance time at 1,000 cd/m$^2$ (relative value) |
| --- | --- | --- | --- | --- |
| Example 5-1 | Synthesis Method 12 | 8.9 | 7.3 | 100 |
| Example 5-2 | Synthesis Method 13 | 8.8 | 7.4 | 71 |
| Example 5-3 | Synthesis Method 14 | 8.7 | 7.3 | 92 |
| Comparative Example 5-1 | Method disclosed in U.S. 2006/0,008,670 [0134] | 8.8 | 7.2 | 55 |

As is clear from comparisons of Examples 5-1 to 5-3 and Comparative Example 5-1, improvements in durability were achieved by using the light emitting material prepared in accordance with the present methods. Additionally, the time taken to reduce by half the luminance was expressed in relative value, with Example 5-1 being taken as 100.

Example 6-1

An organic EL device of Example 6-1 was made in the same manner as in Example 1-1, except that the Exemplified Compound 225 obtained as a light emitting material by Synthesis Method 15 was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in the Exemplified Compound 225 was produced.

Examples 6-2 to 6-3 and Comparative Example 6-1

Devices of Examples 6-2 to 6-3 and Comparative Example 6-1 were made in the same manner as the device of Example 6-1, except that the method used for preparing Exemplified Compound 225 in Example 6-1 was changed to the methods entered in Table 6, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

achieved by using the light emitting material prepared in accordance with the present methods. Additionally, the time taken to reduce by half the luminance was expressed in relative value, with Example 6-1 being taken as 100.

Example 7-1

An organic EL device of Example 7-1 was made in the same manner as in Example 1-1, except that the Exemplified Compound 226 obtained as a light emitting material by Synthesis Method 15 was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in the Exemplified Compound 226 was produced.

Examples 7-2 to 7-3 and Comparative Example 7-1

Devices of Examples 7-2 to 7-3 and Comparative Example 7-1 were made in the same manner as the device of Example 7-1, except that the method used for preparing Exemplified Compound 226 in Example 7-1 was changed to the methods entered in Table 7, respectively. A direct-current constant voltage was applied to these devices, respectively, through the use of Source Measure Unit 2400 made by TOYO Corporation, and thereby the devices produced luminescence in col-

TABLE 6

|  | Method of forming light emitting material (Exemplified Compound 225) | Drive voltage (V) at 1,000 cd/m$^2$ | External quantum efficiency (%) at 1,000 cd/m$^2$ | Half luminance time at 1,000 cd/m$^2$ (relative value) |
| --- | --- | --- | --- | --- |
| Example 6-1 | Synthesis Method 15 | 9.9 | 5.1 | 100 |
| Example 6-2 | Synthesis Method 16 | 9.9 | 5.0 | 67 |
| Example 6-3 | Synthesis Method 17 | 9.7 | 5.0 | 88 |
| Comparative Example 6-1 | Method disclosed in JP-A-2009-21336 | 9.8 | 4.9 | 44 |

As is clear from comparisons of Examples 6-1 to 6-3 and Comparative Example 6-1, improvements in durability were ors originating in the light emitting materials incorporated, respectively.

TABLE 7

|  | Method of forming light emitting material (Exemplified Compound 226) | Drive voltage (V) at 1,000 cd/m$^2$ | External quantum efficiency (%) at 1,000 cd/m$^2$ | Half luminance time at 1,000 cd/m$^2$ (relative value) |
| --- | --- | --- | --- | --- |
| Example 7-1 | Synthesis Method 18 | 10.3 | 6.2 | 100 |
| Example 7-2 | Synthesis Method 19 | 10.2 | 6.3 | 77 |
| Example 7-3 | Synthesis Method 20 | 10.4 | 6.1 | 93 |

TABLE 7-continued

|  | Method of forming light emitting material (Exemplified Compound 226) | Drive voltage (V) at 1,000 cd/m$^2$ | External quantum efficiency (%) at 1,000 cd/m$^2$ | Half luminance time at 1,000 cd/m$^2$ (relative value) |
|---|---|---|---|---|
| Comparative Example 7-1 | Method disclosed in WO 2006/126389 | 10.2 | 6.2 | 63 |

As is clear from comparisons of Examples 7-1 to 7-3 and Comparative Example 7-1, improvements in durability were achieved by using the light emitting material prepared in accordance with the present methods. Additionally, the time taken to reduce by half the luminance was expressed in relative value, with Example 7-1 being taken as 100.

Example 8-1

An organic EL device of Example 8-1 was made in the same manner as in Example 1-1, except that the Exemplified Compound 227 as a light emitting material was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in Exemplified Compound 227 was produced.

Example 8-2 and Comparative Example 8-1

Devices of Example 8-2 and Comparative Example 8-1 were made in the same manner as the device of Example 8-1, except that the method used for preparing Exemplified Compound 227 in Example 8-1 was changed to the methods entered in Table 8, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

TABLE 8

|  | Method of forming light emitting material (Exemplified Compound 227) | Drive voltage (V) at 1,000 cd/m$^2$ | External quantum efficiency (%) at 1,000 cd/m$^2$ | Half luminance time at 1,000 cd/m$^2$ (relative value) |
|---|---|---|---|---|
| Example 8-1 | Synthesis Method 21 | 11.4 | 4.5 | 100 |
| Example 8-2 | Synthesis Method 22 | 11.2 | 4.6 | 86 |
| Comparative Example 8-1 | Method disclosed in JP-A-2007-51243 | 11.2 | 4.6 | 55 |

As is clear from comparisons of Examples 8-1 to 8-2 and Comparative Example 8-1, improvements in durability were achieved by using the light emitting material prepared in accordance with the present methods. Additionally, the time taken to reduce by half the luminance was expressed in relative value, with Example 8-1 being taken as 100.

Example 9-1

An organic EL device of Example 9-1 was made in the same manner as in Example 1-1, except that the Exemplified Compound 228 obtained as a light emitting material by Synthesis Method 23 was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in the Exemplified Compound 228 was produced.

Example 9-2 and Comparative Example 9-1

Devices of Example 9-2 and Comparative Example 9-1 were made in the same manner as the device of Example 9-1, except that the method used for preparing Exemplified Compound 228 in Example 9-1 was changed to the methods entered in Table 9, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

TABLE 9

|  | Method of forming light emitting material (Exemplified Compound 228) | Drive voltage (V) at 1,000 cd/m$^2$ | External quantum efficiency (%) at 1,000 cd/m$^2$ | Half luminance time at 1,000 cd/m$^2$ (relative value) |
|---|---|---|---|---|
| Example 9-1 | Synthesis Method 23 | 9.9 | 6.4 | 100 |
| Example 9-2 | Synthesis Method 24 | 9.9 | 6.6 | 89 |
| Comparative Example 9-1 | Method described in *Inorg. Chem.*, 2005, 44, 4445-4447 | 9.8 | 6.5 | 58 |

As is clear from comparisons of Examples 9-1 to 9-2 and Comparative Example 9-1, improvements in durability were achieved by using the light emitting material prepared in accordance with the present methods. Additionally, the time taken to reduce by half the luminance was expressed in relative value, with Example 9-1 being taken as 100.

Example 10-1

An organic EL device of Example 10-1 was made in the same manner as in Example 1-1, except that the Exemplified Compound 65 obtained as a light emitting material by Synthesis Method 25 was evaporated into film (thickness: 50 nm) in place of the Exemplified Compound 63 used in Example 1-1. A direct-current constant voltage was applied to this device through the use of Source Measure Unit 2400 made by TOYO Corporation, and thereby luminescence originating in the Exemplified Compound 65 was produced.

Examples 10-2 to 10-4

Devices of Examples 10-2 to 10-4 were made in the same manner as the device of Example 10-1, except that the light emitting material and its preparation method used in Example 10-1 were changed to those entered in Table 10, respectively. A direct-current constant voltage was applied to these devices, respectively, through the use of Source Measure Unit 2400 made by TOYO Corporation, and thereby the devices produced luminescence in colors originating in the light emitting materials incorporated, respectively.

TABLE 10

|  | Light emitting material and preparation method | Drive voltage (V) at 360 cd/m² | External quantum efficiency (%) at 360 cd/m² | Half luminance time at 360 cd/m² (relative value) |
|---|---|---|---|---|
| Example 10-1 | Exemplified Compound 65 (Synthesis Method 25) | 9.6 | 4.4 | 100 |
| Example 10-2 | Exemplified Compound 65 (Synthesis Method 26) | 9.5 | 4.6 | 79 |
| Example 10-3 | Exemplified Compound 224 (Synthesis Method 27) | 10.3 | 5.2 | 187 |
| Example 10-4 | Exemplified Compound 224 (Synthesis Method 28) | 10.3 | 5.3 | 165 |

As is clear from Examples 10-1 to 10-4, luminescence was produced by using the light emitting materials prepared in accordance with the present methods. Additionally, the time taken to reduce by half the luminance was expressed in relative value, with Example 10-1 being taken as 100.

While the present invention has been shown and described with reference to certain exemplary embodiments thereof, it will be understood by those skilled in the art that various changes modifications may be made therein without departing from the spirit and scope of the present invention as defined by the appended claims.

What is claimed is:

1. A method of forming a compound having a nitrogen-containing heterocyclic 5-membered ring as a partial structure of a ligand through the use of metal-metal exchange reaction, wherein the compound is represented by the following formula (2) and formed by allowing a compound represented by the following formula (2a) to react with a compound represented by the following formula (2b):

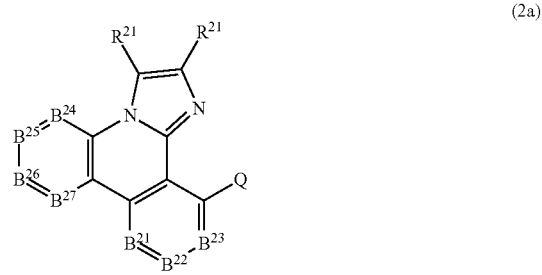

(2a)

wherein Q represents an alkali metal, an alkaline earth metal, an alkaline earth metal halide, a trialkyltin, zinc or a zinc halide, which each may further have an arbitrary organic group as a substituent;

$R^{21}$ and $B^{21}$ to $B^{27}$ have the same meanings as $R^{21}$ and $B^{21}$ to $B^{27}$ in the formula (2), respectively;

(2b)

wherein the formula (2b) stands for a bridged metal dimer;

Y is F, Cl, Br, I, $OR^{23}$, $R^{23}COO$, $SR^{23}$ or $N(R^{23})_2$, each of $R^{23}$s is independently a hydrogen atom, an aliphatic hydrocarbon group having 1 to 20 carbon atoms or an aromatic hydrocarbon group;

k is 2 when $M^{21}$ is Ir, while k is 1 when $M^{21}$ is Pt;

$L^{21}$ and $M^{21}$ have the same meanings as $L^{21}$ and $M^{21}$ in the formula (2), respectively;

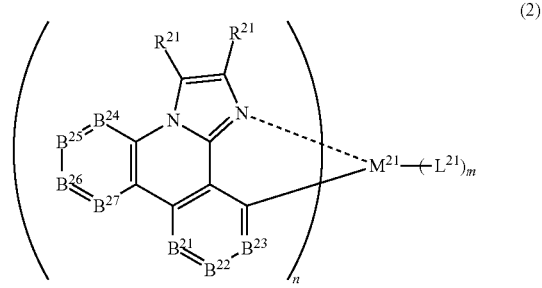

(2)

wherein $M^{21}$ represents Ir or Pt;

$L^{21}$ is a substituted or unsubstituted phenylpyridine, phenylpyrazole, phenylimidazole, pyridylimidazole, phenyltriazole, phenyltetrazole, pyridylpyridine, imidazolylpyridine, pyrazolylpyridine, triazolylpyridine,

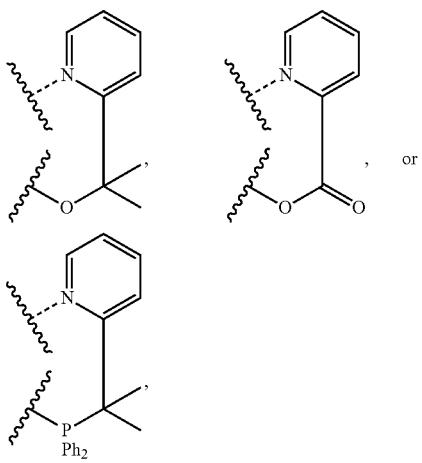

wherein the substituted phenylpyridine, phenylpyrazole, phenylimidazole, pyridylimidazole, phenyltriazole, phenyltetrazole, pyridylpyridine, imidazolylpyridine, pyrazolylpyridine, or triazolylpyridine is substituted with at least one substituent selected from the group consisting of an alkyl group, a cycloalkyl group, an alkenyl group, an alkynyl group, an aryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio, an arylthio group, a heterocyclic thio group, a sulfonyl group, a sulfinyl group, an ureido group, a phosphoric acid amido group, a hydroxy group, a mercapto group, a halogen atom, a cyano group, a sulfo group, a carboxyl group, a nitro group, a hydroxamic acid group, a sulfino group, a hydrazino group, an imino group, a heterocyclic group, a silyl group, and a silyloxy group, wherein the substituent may be further substituted, with the proviso that the phenylimidazole is not substituted with an aryl group;

$R^{21}$ represents a hydrogen atom or a substituent selected from the group consisting of an alkyl group, a cycloalkyl group, an alkenyl group, an alkynyl group, an aryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio, an arylthio group, a sulfonyl group, a sulfonyl group, an ureido group, a phosphoric acid amido group, a hydroxy group, a mercapto group, a halogen atom, a cyano group, a sulfo group, a carboxyl group, a nitro group, a hydroxamic acid group, a sulfino group, a hydrazino group, an imino group, a heterocyclic group which includes at least one nitrogen atom or oxygen atom, a silyl group, and a silyloxy group, wherein the substituent may be further substituted, wherein two or more of the substituents may combine with each other to form a ring, and wherein two or more of the substituents may combine with each other and complete a condensed ring; neighboring $R^{21}$s may combine with each other and complete a condensed ring; and each $R^{21}$ may be the same as or different from every other $R^{21}$;

each of $B^{21}$ to $B^{27}$ independently represents a nitrogen atom or C—$R^{22}$, $R^{22}$ represents a hydrogen atom or a substituent and each $R^{22}$ may be the same as or different from every other $R^{22}$ and neighboring $R^{22}$s may combine with each other and complete a condensed ring; and n represents an integer of 1 and m represents an integer of 0 to 2, provided that n+m is 2 or 3.

2. An organic electroluminescence device material comprising a compound formed according to claim 1, wherein the compound has a Li atom and ion content of 0.1 ppm to 50 ppm.

3. An organic electroluminescence device material comprising a compound formed according to claim 1, wherein the compound has an Mg atom and ion content of 0.1 ppm to 50 ppm.

4. An organic electroluminescence device comprising:

a pair of electrodes; and at least one organic layer provided between the pair of electrodes, which includes a light emitting layer, wherein at least one layer included in the organic layer contains a compound formed by the following formula (2) and formed by allowing a compound represented by the following formula (2a) to react with a compound represented by the following formula (2b):

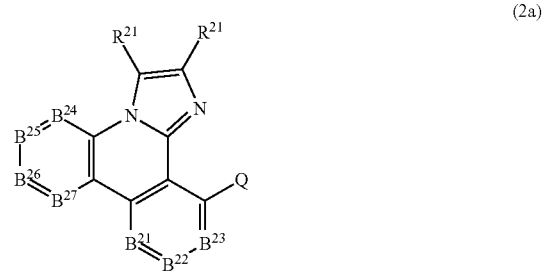

(2a)

wherein Q represents an alkali metal, an alkaline earth metal, an alkaline earth metal halide, a trialkyltin, zinc or a zinc halide, which each may further have an arbitrary organic group as a substituent;

$R^{21}$ and $B^{21}$ to $B^{27}$ have the same meanings as $R^{21}$ and $B^{21}$ to $B^{27}$ in the formula (2), respectively;

$$[L^{21}{}_kM^{21}(\mu\text{-}Y)]_2 \qquad (2b)$$

wherein the formula (2b) stands for a bridged metal dimer;

Y is F, Cl, Br, I, $OR^{23}$, $R^{23}COO$, $SR^{23}$ or $N(R^{23})_2$, each of $R^{23}$s is independently a hydrogen atom, an aliphatic hydrocarbon group having 1 to 20 carbon atoms or an aromatic hydrocarbon group;

k is 2 when $M^{21}$ is Ir, while k is 1 when $M^{21}$ is Pt;

$L^{21}$ and $M^{21}$ have the same meanings as $L^{21}$ and $M^{21}$ in the formula (2), respectively;

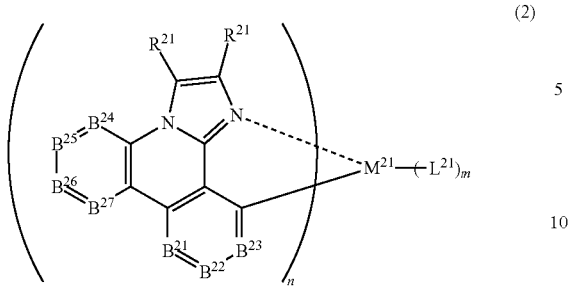
(2)

(L$^a$)

(L$^b$)

wherein M$^{21}$ represents Ir or Pt;

L$^{21}$ is a substituted or unsubstituted phenylpyridine, phenylpyrazole, phenylimidazole, pyridylimidazole, phenyltriazole, phenyltetrazole, pyridylpyridine, imidazolylpyridine, pyrazolylpyridine, or triazolylpyridine, with the proviso that the phenylimidazole is not substituted with an aryl group;

R$^{21}$ represents a hydrogen atom or a substituent; neighboring R$^{21}$s may combine with each other and complete a condensed ring; and each R$^{21}$ may be the same as or different from every other R$^{21}$;

each of B$^{21}$ to B$^{27}$ independently represents a nitrogen atom or C—R$^{22}$, R$^{22}$ represents a hydrogen atom or a substituent and each R$^{22}$ may be the same as or different from every other R$^{22}$ and neighboring R$^{22}$s may combine with each other and complete a condensed ring; and n represents an integer of 1 and m represents an integer of 0 to 2, provided that n+m is 2 or 3.

5. A light emission apparatus using the organic electroluminescence devices according to claim 4.

6. A display apparatus using the organic electroluminescence devices according to claim 4.

7. An illumination apparatus using the organic electroluminescence devices according to claim 4.

8. A compound formed by the method of claim 1, wherein each R$^{21}$ is a substituent independently chosen from an alkyl group, a cycloalkyl group, an alkenyl group, an alkynyl group, an aryl group, an amino, an alkoxy, an acyloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio, an arylthio group, a sulfonyl group, a sulfinyl group, an ureido group, a phosphoric acid amido group, a hydroxy group, a mercapto group, a halogen atom, a cyano group, a sulfo group, a carboxyl group, a nitro group, a hydroxamic acid group, a sulfino group, a hydrazino group, an imino group, a heterocyclic group which includes at least one nitrogen atom or oxygen atom, a silyl group, and a silyloxy group, wherein the substituent may be further substituted, wherein two or more of the substituents may combine with each other to form a ring, and wherein two or more of the substituents may combine with each other and complete a condensed ring.

9. The compound according to claim 8, wherein the alkyl group has a carbon number of 1 to 30.

10. The compound according to claim 8, wherein the alkyl group has a carbon number of 1 to 20.

11. The compound according to claim 8, wherein the alkyl group has a carbon number of 1 to 10.

12. A compound formed by the method of claim 1, wherein L$^{21}$ has a structure chosen from the following structures L$^a$-L$^f$:

(L$^c$)

(L$^d$)

(L$^e$)

-continued

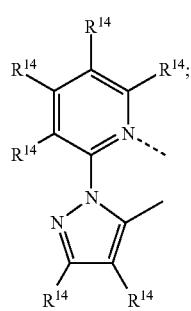

(L<sup>f</sup>)

wherein each of R¹⁴s independently represents a hydrogen atom or a substituent; and
wherein each of R¹⁵s represents a hydrogen atom or a substituent, wherein the substituent is selected from the group consisting of an alkyl group, a cycloalkyl group, an alkenyl group, an alkynyl group, an aryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio, an arylthio group, a heterocyclic thio group, a sulfonyl group, a sulfonyl group, an ureido group, a phosphoric acid amido group, a hydroxy group, a mercapto group, a halogen atom, a cyano group, a sulfo group, a carboxyl group, a nitro group, a hydroxamic acid group, a sulfino group, a hydrazino group, an imino group, a heterocyclic group, a silyl group, and a silyloxy group, wherein the substituent may be further substituted, with the proviso that when L²¹ is L^d, then none of L¹⁴ or L¹⁵ are an aryl group.

13. The compound according to claim 12 having the structure (184):

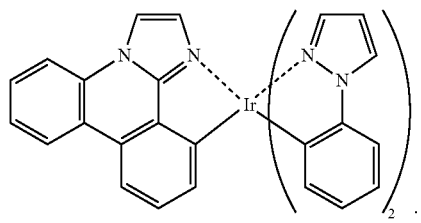

(184)

14. A compound formed by the method of claim 1, wherein L²¹ is a bidentate ligand selected from the group consisting of:

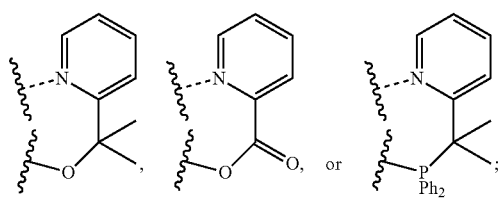

wherein a covalent bond is formed between M²¹ and either an oxygen atom or a phosphorus atom of L²¹, and wherein a covalent bond is formed between M²¹ and an N atom of L²¹.

15. The compound according to claim 14 having the structure (190):

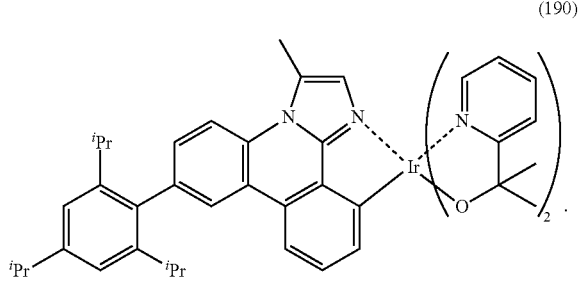

(190)

16. The compound according to claim 14 having the structure (193):

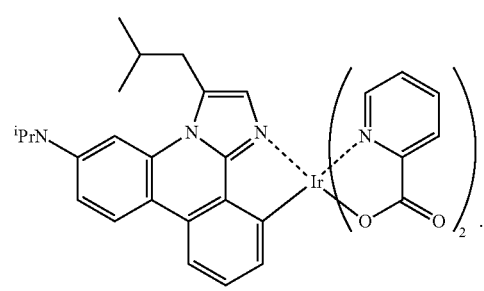

(193)

17. The compound according to claim 14 having the structure (209):

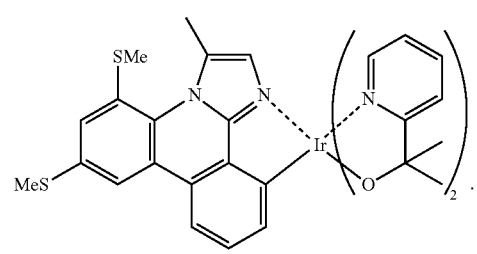

(209)

18. The compound according to claim 14 having the structure (194):
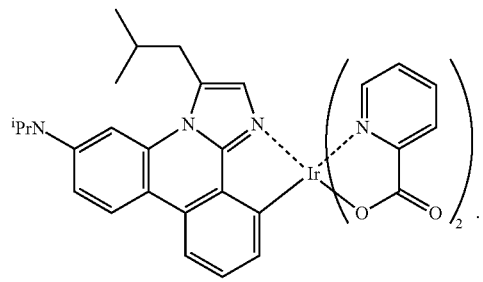
(194)
19. The compound according to claim 14 having the structure (210):
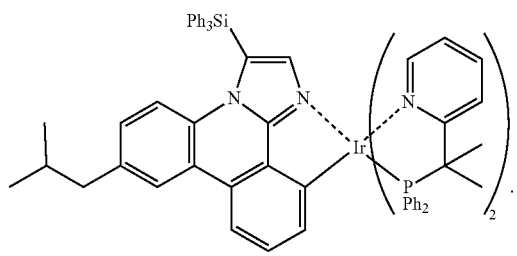
(210)
* * * * *